(12) United States Patent
Rabuka et al.

(10) Patent No.: US 12,102,689 B2
(45) Date of Patent: Oct. 1, 2024

(54) ANTI-CD22 ANTIBODY-MAYTANSINE CONJUGATES AND METHODS OF USE THEREOF

(71) Applicant: R.P. Scherer Technologies, LLC, Carson City, NV (US)

(72) Inventors: David Rabuka, Kensington, CA (US); Jesse M. Mcfarland, Berkeley, CA (US); Penelope M. Drake, Castro Valley, CA (US); Robyn M. Barfield, Emeryville, CA (US)

(73) Assignee: R.P. Scherer Technologies, LLC, Carson City, NV (US)

( * ) Notice: Subject to any disclaimer, the term of this patent is extended or adjusted under 35 U.S.C. 154(b) by 215 days.

(21) Appl. No.: 15/774,384

(22) PCT Filed: Nov. 8, 2016

(86) PCT No.: PCT/US2016/060996
§ 371 (c)(1),
(2) Date: May 8, 2018

(87) PCT Pub. No.: WO2017/083306
PCT Pub. Date: May 18, 2017

(65) Prior Publication Data
US 2020/0246480 A1 Aug. 6, 2020

Related U.S. Application Data

(60) Provisional application No. 62/252,985, filed on Nov. 9, 2015.

(51) Int. Cl.
*A61K 47/68* (2017.01)
*A61P 35/00* (2006.01)
*C07D 498/18* (2006.01)
*C07K 16/28* (2006.01)

(52) U.S. Cl.
CPC ...... *A61K 47/6849* (2017.08); *A61K 47/6809* (2017.08); *A61P 35/00* (2018.01); *C07D 498/18* (2013.01); *C07K 16/2803* (2013.01)

(58) Field of Classification Search
CPC ............ A61K 47/6849; A61K 47/6809; A61K 47/6851; A61K 2039/505; A61K 47/6817; A61K 31/5365; A61K 31/537; A61P 35/00; A61P 35/02; C07D 498/18; C07D 471/14; C07D 487/04; C07D 405/12; C07K 16/2803; C07K 16/44; C07K 2317/21
See application file for complete search history.

(56) References Cited

U.S. PATENT DOCUMENTS

| 4,179,337 A | 12/1979 | Davis et al. |
| 4,352,795 A | 10/1982 | Cook |
| 4,352,995 A | 10/1982 | Yoshida et al. |
| 4,802,655 A | 2/1989 | Bates |
| 4,816,567 A | 3/1989 | Cabilly et al. |
| 4,935,496 A | 6/1990 | Kudo et al. |
| 5,075,046 A | 12/1991 | Stoll |
| 5,089,261 A | 2/1992 | Nitecki et al. |
| 5,100,992 A | 3/1992 | Cohn et al. |
| 5,134,192 A | 7/1992 | Feijen et al. |
| 5,166,309 A | 11/1992 | Maj et al. |
| 5,171,264 A | 12/1992 | Merrill |
| 5,204,449 A | 4/1993 | Puri |
| 5,213,891 A | 5/1993 | Maj et al. |
| 5,219,564 A | 6/1993 | Zalipsky et al. |
| 5,225,539 A | 7/1993 | Winter |
| 5,275,838 A | 1/1994 | Merrill |
| 5,281,698 A | 1/1994 | Nitecki |
| 5,298,643 A | 3/1994 | Greenwald |
| 5,312,808 A | 5/1994 | Shorr et al. |
| 5,321,095 A | 6/1994 | Greenwald |
| 5,324,844 A | 6/1994 | Zalipsky |
| 5,349,001 A | 9/1994 | Greenwald et al. |
| 5,352,756 A | 10/1994 | Meldal |
| 5,405,877 A | 4/1995 | Greenwald et al. |
| 5,446,090 A | 8/1995 | Harris |
| 5,455,027 A | 10/1995 | Zalipsky et al. |
| 5,470,829 A | 11/1995 | Prisell et al. |
| 5,478,805 A | 12/1995 | Shorr et al. |
| 5,484,892 A | 1/1996 | Tedder et al. |
| 5,502,167 A | 3/1996 | Waldmann et al. |
| 5,530,101 A | 6/1996 | Queen et al. |
| 5,558,864 A | 9/1996 | Bendig et al. |
| 5,565,332 A | 10/1996 | Hoogenboom et al. |
| 5,567,422 A | 10/1996 | Greenwald |

(Continued)

FOREIGN PATENT DOCUMENTS

| CN | 101010106 A | 8/2007 |
| CN | 101272783 A | 9/2008 |

(Continued)

OTHER PUBLICATIONS

Sela-Culang, et al., Frontiers in Immunology 2013 vol. 4, Article 302 (Year: 2013).*
Agarwal, P. "A Pictet-Spengler ligation for protein chemical modification." Proc Natl Acad Sci U S A. Jan. 2, 2013;110(1):46-51. doi: 10.1073/pnas.1213186110.
Drake, PM. "Aldehyde tag coupled with HIPS chemistry enables the production of ADCs conjugated site-specifically to different antibody regions with distinct in vivo efficacy and PK outcomes." Bioconjug Chem. Jul. 16, 2014;25(7):1331-41. doi: 10.1021/bc500189z.

(Continued)

*Primary Examiner* — Julie Wu
*Assistant Examiner* — Sydney Van Druff
(74) *Attorney, Agent, or Firm* — Rudy J. Ng; Bozicevic, Field & Francis LLP

(57) ABSTRACT

The present disclosure provides anti-CD22 antibody-maytansine conjugate structures. The disclosure also encompasses methods of production of such conjugates, as well as methods of using the same.

32 Claims, 38 Drawing Sheets
Specification includes a Sequence Listing.

(56) References Cited

U.S. PATENT DOCUMENTS

| | | |
|---|---|---|
| 5,585,089 A | 12/1996 | Queen et al. |
| 5,605,976 A | 2/1997 | Martinez et al. |
| 5,612,460 A | 3/1997 | Zalipsky |
| 5,614,549 A | 3/1997 | Greenwald et al. |
| 5,618,528 A | 4/1997 | Cooper et al. |
| 5,637,749 A | 6/1997 | Greenwald |
| 5,643,575 A | 7/1997 | Martinez et al. |
| 5,650,388 A | 7/1997 | Shorr et al. |
| 5,672,662 A | 9/1997 | Harris et al. |
| 5,681,567 A | 10/1997 | Martinez et al. |
| 5,686,072 A | 11/1997 | Uhr et al. |
| 5,686,110 A | 11/1997 | Greenwald et al. |
| 5,693,493 A | 12/1997 | Robinson et al. |
| 5,698,417 A | 12/1997 | Robinson et al. |
| 5,705,154 A | 1/1998 | Dalie et al. |
| 5,730,990 A | 3/1998 | Greenwald et al. |
| 5,739,208 A | 4/1998 | Harris |
| 5,750,078 A | 5/1998 | Shitara et al. |
| 5,756,593 A | 5/1998 | Martinez et al. |
| 5,770,403 A | 6/1998 | Dalie et al. |
| 5,789,554 A | 8/1998 | Leung et al. |
| 5,808,096 A | 9/1998 | Zalipsky |
| 5,824,778 A | 10/1998 | Ishikawa et al. |
| 5,824,784 A | 10/1998 | Kinstler et al. |
| 5,840,900 A | 11/1998 | Greenwald et al. |
| 5,874,500 A | 2/1999 | Rhee et al. |
| 5,880,131 A | 3/1999 | Greenwald et al. |
| 5,900,461 A | 5/1999 | Harris |
| 5,902,588 A | 5/1999 | Greenwald et al. |
| 5,919,442 A | 7/1999 | Yin et al. |
| 5,919,455 A | 7/1999 | Greenwald et al. |
| 5,932,462 A | 8/1999 | Harris et al. |
| 5,965,119 A | 10/1999 | Greenwald et al. |
| 5,965,566 A | 10/1999 | Greenwald et al. |
| 5,980,895 A | 11/1999 | Pastan et al. |
| 5,985,263 A | 11/1999 | Lee et al. |
| 5,990,237 A | 11/1999 | Bentley et al. |
| 6,011,042 A | 1/2000 | Greenwald et al. |
| 6,013,283 A | 1/2000 | Greenwald et al. |
| 6,077,939 A | 6/2000 | Wei et al. |
| 6,113,906 A | 9/2000 | Greenwald et al. |
| 6,127,355 A | 10/2000 | Greenwald et al. |
| 6,177,087 B1 | 1/2001 | Greenwald et al. |
| 6,180,095 B1 | 1/2001 | Greenwald et al. |
| 6,183,744 B1 | 2/2001 | Goldenberg |
| 6,187,287 B1 | 2/2001 | Leung et al. |
| 6,194,580 B1 | 2/2001 | Greenwald et al. |
| 6,214,966 B1 | 4/2001 | Harris |
| 6,254,868 B1 | 7/2001 | Leung et al. |
| 6,395,276 B1 | 5/2002 | Ryback et al. |
| 6,570,040 B2 | 5/2003 | Saxon et al. |
| 6,653,104 B2 | 11/2003 | Goldenberg |
| 6,900,304 B2 | 5/2005 | Tsien et al. |
| 7,037,498 B2 | 5/2006 | Cohen et al. |
| 7,049,311 B1 | 5/2006 | Thurston et al. |
| 7,067,511 B2 | 6/2006 | Thurston et al. |
| 7,255,012 B2 | 8/2007 | Hedtke |
| 7,321,026 B2 | 1/2008 | Leung |
| 7,338,659 B2 | 3/2008 | Leung |
| 7,355,011 B2 | 4/2008 | Popplewell et al. |
| 7,355,012 B2 | 4/2008 | Pastan et al. |
| 7,456,260 B2 | 11/2008 | Ryback et al. |
| 7,517,903 B2 | 4/2009 | Chen et al. |
| 7,521,541 B2 | 4/2009 | Eigenbrot et al. |
| 7,534,427 B2 | 5/2009 | Goldenberg et al. |
| 7,541,034 B1 | 6/2009 | Fitzgerald et al. |
| 7,598,257 B2 | 10/2009 | Rodgers et al. |
| 7,754,884 B2 | 7/2010 | Bornhop et al. |
| 7,777,019 B2 | 8/2010 | Pastan et al. |
| 7,829,086 B2 | 11/2010 | Hilbert et al. |
| 7,837,995 B2 | 11/2010 | Goldenberg |
| 7,855,275 B2 | 12/2010 | Eigenbrot et al. |
| 7,985,783 B2 | 7/2011 | Carrico et al. |
| 8,097,701 B2 | 1/2012 | Carrico et al. |
| 8,226,945 B2 | 7/2012 | Ebens, Jr. et al. |
| 8,343,928 B2 | 1/2013 | Doronina et al. |
| 8,349,910 B2 | 1/2013 | Carrico et al. |
| 8,729,232 B2 | 5/2014 | Rush et al. |
| 8,846,866 B2 | 9/2014 | Carrico et al. |
| 9,181,343 B2 | 11/2015 | Rabuka et al. |
| 9,310,374 B2 | 4/2016 | Kudirka et al. |
| 9,447,390 B2 | 9/2016 | Carrico et al. |
| 9,540,438 B2 | 1/2017 | Barfield et al. |
| 9,833,515 B2 | 12/2017 | Kudirka et al. |
| 9,873,730 B2 | 1/2018 | Torikai et al. |
| 9,951,367 B2 | 4/2018 | Rabuka et al. |
| 10,150,806 B2 | 12/2018 | Carrico et al. |
| 10,259,871 B2 | 4/2019 | Rabuka et al. |
| 10,745,464 B2 | 8/2020 | Carrico et al. |
| 2002/0146504 A1 | 10/2002 | Schwartz |
| 2003/0069430 A1 | 4/2003 | Davis et al. |
| 2003/0186229 A1 | 10/2003 | Tsien et al. |
| 2004/0086979 A1 | 5/2004 | Zhang et al. |
| 2004/0229250 A1 | 11/2004 | Figura et al. |
| 2005/0026234 A1 | 2/2005 | Violin et al. |
| 2005/0033031 A1 | 2/2005 | Cuoto |
| 2005/0153989 A1 | 7/2005 | Grotzfeld et al. |
| 2005/0201981 A1 | 9/2005 | Liu et al. |
| 2005/0276812 A1 | 12/2005 | Ebens, Jr. et al. |
| 2006/0035305 A1 | 2/2006 | Bertozzi |
| 2006/0116417 A1 | 6/2006 | Chen et al. |
| 2007/0135485 A1 | 6/2007 | Gillig et al. |
| 2007/0275962 A1 | 11/2007 | Koul et al. |
| 2008/0031823 A1 | 2/2008 | Bornhop et al. |
| 2008/0118505 A1 | 5/2008 | Tedder |
| 2008/0187956 A1 | 8/2008 | Carrico et al. |
| 2009/0305411 A1 | 12/2009 | Fitzgerald et al. |
| 2010/0210543 A1 | 8/2010 | Rabuka et al. |
| 2011/0117621 A1 | 5/2011 | Rush et al. |
| 2011/0182887 A1 | 7/2011 | Hilbert et al. |
| 2012/0329094 A1 | 12/2012 | Ebensn, Jr. et al. |
| 2013/0028881 A1 | 1/2013 | von Figura et al. |
| 2014/0004097 A1 | 1/2014 | Zhang et al. |
| 2014/0011871 A1 | 1/2014 | Rockhill |
| 2014/0141025 A1 | 5/2014 | Kurdirka et al. |
| 2015/0079088 A1 | 3/2015 | Lowman et al. |
| 2015/0157736 A1 | 6/2015 | Rabuka et al. |
| 2016/0229911 A1 | 8/2016 | Rabuka et al. |
| 2017/0014403 A1 | 1/2017 | Govindan et al. |
| 2017/0049906 A1 | 2/2017 | Liao et al. |
| 2017/0106097 A1 | 4/2017 | Blattler et al. |
| 2018/0223322 A1 | 8/2018 | Rabuka et al. |
| 2019/0201541 A1 | 7/2019 | Maclaren |
| 2020/0246480 A1 | 8/2020 | Rabuka et al. |
| 2020/0317610 A1 | 10/2020 | Rabuka et al. |
| 2021/0024614 A1 | 1/2021 | Carrico et al. |

FOREIGN PATENT DOCUMENTS

| | | |
|---|---|---|
| EP | 0 239 400 A2 | 9/1987 |
| EP | 0 519 596 A1 | 12/1992 |
| EP | 0 592 106 A1 | 4/1994 |
| EP | 1391213 A1 | 2/2004 |
| EP | 1 731 506 A1 | 12/2006 |
| ES | 324 609 A1 | 12/1966 |
| JP | 2005-503138 | 2/2005 |
| JP | 2006-517412 | 7/2006 |
| JP | 2008-528668 | 7/2008 |
| JP | 2010-504095 | 2/2010 |
| JP | 2013-506653 A | 2/2013 |
| RU | 2013137868 A | 1/2012 |
| RU | 2018120696 A | 11/2016 |
| WO | WO 1990/13540 A1 | 11/1990 |
| WO | WO 1991/09967 A1 | 7/1991 |
| WO | WO 1992/00748 A1 | 1/1992 |
| WO | WO 1992/16555 A1 | 10/1992 |
| WO | WO 1994/04193 A1 | 3/1994 |
| WO | WO 1994/14758 A1 | 7/1994 |
| WO | WO 1994/17039 A1 | 8/1994 |
| WO | WO 1994/18247 A1 | 8/1994 |
| WO | WO 1994/28937 A1 | 12/1994 |
| WO | WO 1995/11924 A1 | 5/1995 |
| WO | WO 1995/13312 A1 | 5/1995 |
| WO | WO 1996/00080 A1 | 1/1996 |

(56) References Cited

FOREIGN PATENT DOCUMENTS

| | | | |
|---|---|---|---|
| WO | WO 1996/21469 A1 | 7/1996 | |
| WO | WO 1996/23794 A1 | 8/1996 | |
| WO | WO 1997/03106 A1 | 1/1997 | |
| WO | WO 1998/07713 A1 | 2/1998 | |
| WO | WO 1998/41562 A1 | 9/1998 | |
| WO | WO 1998/45331 A2 | 10/1998 | |
| WO | WO 1998/45332 A2 | 10/1998 | |
| WO | WO 1998/48837 A1 | 11/1998 | |
| WO | WO 98/59244 | 12/1998 | |
| WO | WO 1999/30727 A1 | 6/1999 | |
| WO | WO 1999/32134 A1 | 7/1999 | |
| WO | WO 1999/33483 A1 | 7/1999 | |
| WO | WO 1999/45964 A1 | 9/1999 | |
| WO | WO 1999/53951 A1 | 10/1999 | |
| WO | WO 2000/074718 | 12/2000 | |
| WO | WO 2001/26692 A1 | 4/2001 | |
| WO | WO 2003/002607 | 1/2003 | |
| WO | WO 2003/072736 | 9/2003 | |
| WO | WO 2003/105782 | 12/2003 | |
| WO | WO 2004/072275 | 8/2004 | |
| WO | WO 2005/113765 | 12/2005 | |
| WO | WO 2006/082406 | 8/2006 | |
| WO | WO 2006/085518 | 8/2006 | |
| WO | WO 2006/121820 A1 | 11/2006 | |
| WO | WO 2007/023143 A1 | 3/2007 | |
| WO | WO 2007/027248 A2 | 3/2007 | |
| WO | WO 2007/103470 | 9/2007 | |
| WO | WO 2007/140371 | 12/2007 | |
| WO | WO 2008/008398 A2 | 1/2008 | |
| WO | WO 2008/019303 A2 | 2/2008 | |
| WO | WO 2008/036350 | 3/2008 | |
| WO | WO 2008/070569 | 6/2008 | |
| WO | WO 2009/120611 | 10/2009 | |
| WO | WO 2010/081110 | 7/2010 | |
| WO | WO 2010/096394 | 8/2010 | |
| WO | WO 2010/117939 A1 | 10/2010 | |
| WO | WO 2011/039721 A1 | 4/2011 | |
| WO | WO 2011/076684 | 6/2011 | |
| WO | WO 2011/099718 A1 | 8/2011 | |
| WO | WO 2012/051734 | 4/2012 | |
| WO | WO 2012/078777 A1 | 6/2012 | |
| WO | WO-2012097333 A2 * | 7/2012 | ............ C07K 1/1077 |
| WO | WO 2014/074218 A1 | 5/2014 | |
| WO | WO-2014078566 A1 * | 5/2014 | ......... A61K 49/0058 |
| WO | WO-2015081282 A1 * | 6/2015 | .............. A61P 35/02 |
| WO | WO 2015/187428 A1 | 12/2015 | |
| WO | WO 2016/210108 A1 | 12/2016 | |
| WO | WO 2017/083306 A1 | 5/2017 | |

OTHER PUBLICATIONS

Adams, et al., (2002) "New Biarsenical Ligands and Tetracysteine Labeling in Vitro and in Vivo: Synthesis Applications" *J. Amer. Chem. Soc.* 124(21):6063-6076.
Agarwal et al., (2012) "A pictet-Spengler ligation for protein chemical modification," *PNAS* 110(1):46-51.
Albers (2014) "Hydrazinyl-Iso-Pictet-Spengler (HIPS) ligation as a novel method for the generation of highly stable, site-specifically modified antibody drug conjugates," *Abstracts of papers American Chemical Society* 247:19-BIOT.
Amlot et al. (1993) "A phase I study of an anti-CD22-deglycosylated ricin A chain immunotoxin in the treatment of B-cell lymphomas resistant to conventional therapy" *Blood* 82(9):2624-2633.
Banghart, et al., (2004) "Light-Activated Ion Channels for Remote Control of Neuronal Firing" *Nat. Neurosci.* 7(12): 1381-6.
Berteau, et al., (2006) "A New Type Of Bacterial Sulfatase Reveals A Novel Maturation Pathway In Prokaryotes" *J. Biol. Chem.* 281 (32):22464-70.
Campana et al. (1985) "Human B cell development. I. Phenotypic differences of B lymphocytes in the bone marrow and peripheral lymphoid tissue" *J. Immunol.* 134(3):1524-1530.

Carnahan et al, (2007) "Epratuzumab, a CD22-targeting recombinant humanized antibody with a different mode of action from rituximab", *Mol. Immunol.* 44(6):1331-1341.
Chen et al., (2005) "Synthetic Erythropoietic Proteins: Tuning Biological Performance by Site-Specific Polymer Attachment" *Chem. Biol.* 12(3):371-383.
Cosma, et al., (2003) "The Multiple Sulfatase Deficiency Gene Encodes an Essential and Limiting Factor for the Activity of Sulfatases" *Cell* 113(4):445-56.
Dierks, et al., "Conversion of Cysteine to Formylglycine: A Protein Modification in the Endoplasmic Reticulum" *PNAS USA*, 94(22), (1997):11963-8.
Dierks, et al., (2005) "Molecular Basis for Multiple Sulfatase Deficiency and Mechanism for Formylglycine Generation of the Human Formylglycine-Generating Enzyme" *Cell* 121(4):541-52.
Dierks, et al., (2003) "Multiple Sulfatase Deficiency Is Caused by Mutations in the Gene Encoding the Human Cα-Formylglycine Generating Enzyme" *Cell* 113(4):435-44.
Dierks, et al., (1998) "Conversion of Cysteine to Formylglycine in Eukaryotic Sulfatases Occurs by a (Common Mechanism in the Endoplasmic Reticulum" *FEBS Lett.* 423(1):61-5.
Dierks, et al., (1998) "Posttranslational Formation of Formylglycine in Prokaryotic Sulfatases by Modification of Either Cysteine or Serine" *J. Biol. Chem*, 273(40):25560-25564.
Dierks, et al., (1999) "Sequence Determinants Directing Conversion of Cysteine to Formylglycine in Eukaryotic Sulfatases" *EMBO J.* 18(8):2084-91.
DMEM/F-12 product composition sheet from ThermoFisher Scientific [found online Jul. 5, 2016] at https://www.thermofisher.com/order/catalog/product/11320033.
Drake et al., (2014) "Aldehyde Tag Coupled with HIPS Chemistry Enables the Production of ADCs Conjugated Site-Specifically to Different Antibody Regions with Distinct in Vivo Efficacy and PK Outcomes," *Bioconjugate Chemistry* 25:1331-1341.
Fang, et al., (2004) "Post-Translational Formylglycine Modification of Bacterial Sulfatases by the Radical S-Adenosylmethionine Protein AtsB" *J. Biol. Chem.* 279(15):14570-8.
Figura, et al. (1998) "A Novel Protein Modification Generating an Aldehyde Group in Sulfatases: It's (Role in Catalysis and Disease" *Bioessays.* 20(6):505-10.
Garofalo et al., (2014) "Variation of linker composition in ADCs generated from aldehyde-tagged antibodies impacts both efficacy and PK," *Abstracts of papers American Chemical Society* 248(489).
GenBank Acc. No. NP_215226 (Jan. 6, 2005).
GenBank Acc. No. NP_215226 (May 24, 2007).
Gen 2002. Bank Accession No. BAC01670 "immunoglobulin kappa light chain VLJ region [*Homo sapiens*]" dated Jul. 2, 2002.
Gen Bank Accession No. CAA75032 "immunoglobulin lambda heavy chain [*Homo sapiens*]" dated Aug. 19, 1998.
George, et al. (2004) "Specific Labeling of Cell Surface Proteins with Chemically Diverse Compounds" *J. Amer. Chem. Soc.* 126(29):8896-8897.
Ghetie et al. (1991) "Antitumor activity of Fab' and IgG-anti-CD22 immunotoxins in disseminated human B lymphoma grown in mice with severe combined immunodeficiency disease: effect on turnor cells in extranodal sites" *Cancer Res.* 51(21):5876-5880.
Griffin, et al., (1998) "Specific Covalent Labeling of Recombinant Protein Molecules Inside Live Cells" *Science* 281 (5374):269-272.
Guignet, et al., (2004) "Reversible Site-Selective Labeling of Membrane Proteins in Live Cells" *Nature Biotechnol.* 22(4):440-444.
Holder et al. (2015) "Reconstitution of formylglycine-generating enzyme with copper(II) for aldehyde tag conversion." *J Biol. Chem.* 290(25):15730-15745. abstract.
International Search Report & Written Opinion dated Jun. 3, 2016, for PCT/US2015/066878, 19 pages.
Knaust et al., (1998) "Residues Critical for Formylglycine Formation and/or Catalytic Activity of Arylsulfatase A," *Biochemistry*, 37(40):13941-13946.
Kreitman et al. (2011) "Antibody-fusion proteins: anti-CD22 recombinant immunotoxin Moxetumomab Pasudotox." *Clin. Cancer Res.* vol. 17(20):6398-6405.

(56) References Cited

OTHER PUBLICATIONS

Landgrebe, et al., (2003) "The Human SUMF1 Gene, Required for Posttranslational Sulfatase Modification, Defines a New Gene Family Which Is Conserved from Pro-to Eukaryotes" *Gene* 316:47-56.

Lemieux, et al., (1998) "Chemoselective Ligation Reactions with Proteins, Oligosaccharides and Cells" *Trends Biotechnol.* 16 (12):506-13.

Liu and Li, (2006) "Anti CD22 Monoclonal Antibody and Therapy of Lymphomas", *Medical Recapitulate*, 12(6):339-341, English Abstract.

Lisenbee, et al., (2003) "Overexpression and Mislocalization of a Tail-Anchored GFP Redefines the Identity of Peroxisomal ER" *Traffic* 4(7):491-501.

Lukatela, et al., (1998) "Crystal Structure of Human Arylsulfatase A: the Aldehyde Function and the Metal ion at the Active Site Suggest a Novel Mechanism for Sulfate Ester Hydrolysis" *Biochemistry* 37(11):3654-3664.

Mansfield E et al: (1997) "Recombinant RFB4 immunotoxins exhibit potent cytotoxic activity for CD22-bearing cells and tumors", *Blood*90(5): 2020-2026.

Mariappan, et al., (2005) "Expression, Localization, Structural, and Functional Characterization of pFGE, the Paralog of the Cα-Formylglycine-generating Enzyme" *J. Biol. Chem.* 280(15):15173-9.

Mariappan et al. (2008) "The Non-catalytic N-terminal Extension of Formylglycine-generating Enzyme Is Required for Its Biological Activity and Retention in the Endoplasmic Reticulum." *J. Biol. Chem.* 283(17):11556-11564.

Mougous et al., (2004) "Identification, Function and Structure of the Mycobacterial Sulfotransferase that Initiates Sulfolipid-1 Biosynthesis" *Nat. Struc. Mol. Biol.* 11(8):721-729.

Prescher, et al., (2005) "Chemistry in Living Systems" *Nat. Chem. Biol.* 1(1):13-21.

Preusser, et al., (2005) "Molecular Characterization of the Human Cα-formylglycine-generating Enzyme" *J. Biol. Chem.* 280(15):14900-10.

Rabuka (2014) "Abstract 2662: Site Specific ADC generation using SMARTag technology with programmable payload placement," *Cancer Research* 74(19):2662.

Roeser, et al., (2006) "A General Binding Mechanism for All Human Sulfatases by the Formylglycine-Generating Enzyme" *PNAS* 103(1):81-6.

Rush, et al., (2006) "An α-Formylglycine Building Block for Fmoc-Based Solid-Phase Peptide Synthesis" *Org Lett.* 8(1):131-4.

Samuel, et al., (2004) "Chemical Tools for the Study of Polysialic Acid", (2004) *Trends In Glycoscience and Technology* 16 (91):305-318.

Sardiello et al., (2005) "Sulfatases and Sulfatase Modifying Factors: An Exclusive and Promiscuous Relationship" *Human Mol. Genet.* 14(21):3203-3217.

Schirmer, et al., (1998) "Computational Analysis of Bacterial Sulfatases and Their Modifying Enzymes", *Chem. Biol.* 5(8):R181-R186.

Schmidt, et al., (1995) "A Novel Amino Acid Modification in Sulfatases that Is Defective in Multiple Sulfatase Deficiency" *Cell* 82(2):271-8.

Stimmel et al. (2000) "Site-specific conjugation on serine → cysteine variant monoclonal antibodies" *J. Biol. Chem* 275(39):30445-30450.

Stroffekova, et al. (2001) "The Protein-Labeling Reagent FLASH-EDT2 Binds Not Only to CCXXCC Motifs but Also Non-Specifically to Endogenous Cysteine-Rich Proteins" *Archiv-Europ. J. Physiol.* 442(6):859-866.

Szameit, et al., (1999) "The Iron Sulfur Protein AtsB Is Required for Posttranslational Formation of Formylglycine in the Klebsiella Sulfatase" *J. Biol. Chem* 274(22),:15375-81.

Takakusaki et al. (2005) "Coexpression of Formylglycine-Generating Enzyme is Essential for Synthesis and Secretion of Functional Arylsulfatase A in a Mouse Model of Metachromatic Leukodystrophy" *Human Gene Ther.* 16(8):929-936.

Tirat et al., (2006) "Evaluation of Two Novel Tag-Based Labelling Technologies for Site-Specific modification of Proteins" *International Journal of Biological Macromolecules* 39(1-3):66-76.

Xiao, et al., (2009) "Identification and characterization of fully human anti-CD22 monoclonal antibodies", *MABS* 1(3): 297-303.

Villani, G. R. D. et al. (2000) "Expression of Five Iduronate-2-Sulfatase Site-Directed Mutations." *Biochimica et Biophysica Acta.* 1501(2-3):71-80: abstract.

Vitetta et al. (1991) "Phase I immunotoxin trial in patients with B-cell lymphoma" *Cancer Res.* 51(15):4052-4058.

Yin, et al., (2005) "Genetically Encoded Short Peptide Tag for Versatile Protein Labeling by Sfp Phosphopantetheinyl Transferase" *PNAS* 102(44):15815-15820.

"Triphase Accelerator to Present Investigational New Drug Enabling Data for TRPH-222", Presentation to the American Society of Hematology (ASH) 2017 Annual Meeting Coincides with Publication of Catalent Biologics Research Manuscript, Dec. 4, 2017, 2 pages. Retrieved from the Internet: URL:https://www.globenewswire.com/news-release/2017/12/04/1220328/0/en/Triphase-Accelerator-to-Present-Investigational-New-Drug-EnablingData-for-TRPH-222.html.

Adams, et al., "New Biarsenical Ligands and Tetracysteine Labeling in Vitro and in Vivo: Synthesis Applications" *J. Amer. Chem. Soc.*, vol. 124, No. 21, 2002, p. 6063-6076.

Drake et al. "CAT-02-106, a Site-Specifically Conjugated Anti-CD22 Antibody Bearing an MDR1-Resistant Maytansine Payload Yields Excellent Efficacy and Safety in Preclinical Models", Molecular Cancer Therapeutics, vol. 17, No. 1, 2017, p. 161-168.

Drake et al. Supplementary data of Article "CAT-02-106, a Site-Specifically Conjugated Anti-CD22 Antibody Bearing an MDR1-Resistant Maytansine Payload Yields Excellent Efficacy and Safety in Preclinical Models", Molecular Cancer Therapeutics, Supplementary Methods, part 2, Synthesis of RED-106, 2017, p. 3-20.

Maclaren Ann et al. "Trph-222, a Novel Anti-CD22 Antibody Drug Conjugate (ADC), Has Signficant Anti-Tumor Activity in NHL Xenografts and Is Well Tolerated in Non-Human Primates", Blood, vol. 130, 2017, p. 4105.

Melao Alice: "TRPH-222 Shows Significant Anti-tumor Activity in Lymphoma Preclinical Models", Lymphomanewstoday.com, 2017, 2 pages.

Mokhtari et al. "Combination therapy in combating cancer", Oncotarget, 2017, vol. 8, No. 23, p. 38022-38043.

O'Brien, S. & Jones, T. "Humanising Antibodies by CDR Grafting," Chapter 40: Antibody Engineering, Springer Lab Manuals, 2001, p. 567-590.

"Variable chain engineering—humanization and optimization approaches," Chapter 6: Therapeutic Antibody Engineering, Woodhead Publishing Series in Biomedicine, 2012, pp. 111-129 and 459-595.

Williams, D.G. et al. "Humanising Antibodies by CDR Grafting," Chapter 21: Antibody Engineering, 2010.

Albers (2014) "Exploring the effects of linker composition on site-specifically modified antibodyedrug conjugates", European Journal of Medicinal Chemistry, 88, 3-9.

Drake et al. (2017) "CAT-02-106, a Site-Specifically Conjugated Anti-CD22 Antibody Bearing an MDR1-Resistant Maytansine Payload Yields Excellent Efficacy and Safety in Preclinical Models", Molecular Cancer Therapeutics, vol. 17, No. 1 (with supplementary data and figures).

No. Author "Comparison of Anti-CD22 Antibody-Drug Conjugates (ADCs) with Two Different Payload-Linkers", Data submitted with response to Office Action dated Jul. 29, 2022, 4 pages (Data submitted with a response to Office Action).

Huang et al. (2018) "Antibody-drug conjugate library prepared by scanning insertion of the aldehyde tag into IgG1 constant regions", MABS vol. 10, No. 8, 1182-1189.

Young RM, Staudt LM (2013) "Targeting pathological B cell receptor signalling in lymphoid malignancies", Nat Rev Drug Discov, 12(3):229-243.

Agarwal, P. et al. (2013) "Hydrazino-Pictet-Spengler Ligation as a Biocompatible Method for the Generation of Stable Protein Conjugates" *Bioconjugate Chemistry*, 24(6):846-851.

Agarwal, P. et al. (May 28, 2013) "Supporting information for Hydrazino-Pictet-Spengler Ligation as a Biocompatible Method for

(56) References Cited

OTHER PUBLICATIONS the Generation of Stable Protein Conjugates" *Bioconjugate Chem*, p. S1-S18 [online]. Retrieved from the Internet: http://pubs.acs.org/doi/suppl/10.1021/bc400042a/suppl_file/bc400042a_si_001.pdf; retrieved on May 18, 2015.
Alam, J. et al. (2010) "Functionalization of Peptides and Proteins by Mukaiyama Aldol Reaction" *J Am Chem Soc*, 132(28):9546-9548.
Alam, J. et al. (2011) "Indium mediated allylation in peptide and protein functionalization" *Chem Commun*, 47(32):9066-9068.
Albers, A.E. et al. (Dec. 2014) "Exploring the effects of linker composition on site-specifically modified antibody-drug conjugates" *Eur J Med Chem*, 88:3-9.
Caplus Accession No. 1991:536605; Abstract of Seela et al., Synthesis of Pyrrolo[3,2-c]pyridine and Pyrazolo [3,4-d]pyrimidine beta-D-Arabinocucleosides via Nucleobase Anion Glycosylation, Nucleosides & Nucleotides, vol. No. 1-3, pp. 713-714; 2 pages.
Caplus Accession No. 1975:68021; Abstract of Smith et al., Improved Methods for the Study of Drug Effects of Purine Metabolism and Their Application to Nebularine and 7-Deazanebularine, Biochemical Pharmacology, vol. 23, No. 14, pp. 2023-2035; 1 page.
Carrico, I.S. et al. (2007) "Introducing genetically encoded aldehydes into proteins" *Nat. Chem. Biol.*, 3(6):321-322, including Supplementary Figures and Methods, 12 pages.
Chemical Abstract Service Registry No. 1438805-15-2, "Xanthylium, 3,6-diamino-9-[2-carboxy-4-[[[5-[[3-[2-[(1,2-dimethylhydrazinyl)methyl]-1H-indol-1-yl]-1-oxopropyl]amino]pentyl]amino]carbonyl]phenyl]-4,5-disulfo-, inner salt, sodium salt (1:1)" [Entered STN Jun. 18, 2013], 5 pages.
Chemical Abstract Service Registry No. 15566-04-8, 16576-11-6, and 16579-10-5, "Acetic acid, 2-[(1-methyl-1H-indol-2-yl)methyl]hydrazide" [Entered STN: Nov. 16, 1984], 8 pages.
Chemical Abstract Service Registry No. 1347337-54-5 [Entered STN: Dec. 2, 2011], 3 pages.
Chen, I. et al. (2005) "Site-specific labeling of cell surface proteins with biophysical probes using biotin ligase" *Nat. Methods*, 2(2):99-104.
Cho, H. et al. (2011) "Optimized clinical performance of growth hormone with an expanded genetic code" *Proc. Natl. Acad. Sci. USA*, 108(22):9060-9065.
Dirksen, A. et al. (2006) "Nucleophilic Catalysis of Oxime Ligation" *Angew. Chem. Int. Ed.*, 45:7581-7584.
Ducry, L. and B. Stump (2009) "Antibody-Drug Conjugates: Linking Cytotoxic Payloads to Monoclonal Antibodies" *Bioconjugate Chem.*, 21(1):5-13.
Esser-Kahn, A.P. and M.B. Francis (2008) "Protein-Cross-Linked Polymeric Materials through Site-Selective Bioconjugation" *Angew. Chem. Int. Ed.*, 47(20):3751-3754.
Gadaginamath, G.S. et al. (Jan. 1, 1997) "Synthesis and Antibacterial Activity of Novel 1-Butyl-2-phenoxy/2-Phenylthio/2-Aminomethyl-5-methoxyndole Derivatives" *Polish J Chem*, 71(7):923-928.
Geoghegan, K.F. and J.G. Stroh (1992) "Site-Directed Conjugation of Nonpeptide Groups to Peptides and Proteins Via Periodate-Oxidation of a 2-Amino Alcohol. Application to Modification at N-Terminal Serine" *Bioconjugate Chem*, 3(2):138-146.
Gilmore, J.M. et al. (2006) "N-Terminal Protein Modification through a Biomimetic Transamination Reaction" *Angew. Chem. Int. Ed.*, 45(32):5307-5311.
Glazer, A.N. (1970) "Specific Chemical Modification of Proteins" *Annu. Rev. Biochem.*, 39(1):101-130.
Hang, H.C. and C.R. Bertozzi (2001) "Ketone Isosteres of 2-N-Acetamidosugars as Substrates for Metabolic Cell Surface Engineering," *J. Am. Chem. Soc.*, 123(6):1242-1243.
Hermkens, P.H.H. et al. (1990) "Syntheses of 1,3-disubstituted N-oxy-β-carbolines by the Pictet-Spengler reactions of N-oxy-tryptophan and -tryptamine derivatives" *Tetrahedron*, 46(3):833-846.
Hudak, J.E. et al. (2011) "Protein Glycoengineering Enabled by the Versatile Synthesis of Aminooxy Glycans and the Genetically Encoded Aldehyde Tag" *J. Am. Chem. Soc.*, 133(40):16127-16135.

Hudak, J.E. et al., (2012) "Synthesis of Heterobifunctional Protein FUS ions US ing Copper-Free Click Chemistry and the Aldehyde Tag" *Angew. Chem. Int. Ed.*, 51(17):4161-4165.
Hutchins, B.M. et al. (2011) "Selective Formation of Covalent Protein Heterodimers with an Unnatural Amino Acid" *Chem. Biol.*, 18(3):299-303.
Ishikawa, T. et al. (2001) "Novel [2-3]-Sigmatropic Rearrangement for Carbon-Nitrogen Bond Formation" *J. Am. Chem. Soc.*, 123(31):7734-7735.
Jameson, D.M. and J.A. Ross (2010) "Fluorescence Polarization/Anisotropy in Diagnostics and Imaging" *Chem Rev*, 110 (5):2685-2708.
Jenks, W.P. (1964) "Mechanism and Catalysis of Simple Carbonyl Group Reactions" *Prog. Phys. Org. Chem.*, 2:63-128.
Kalia, J. and R.T. Raines (2008) "Hydrolytic Stability of Hydrazones and Oximes" *Angew. Chem. Int. Ed.*, 47(39):7523-7526.
Kim, C.H. et al. (2012) "Synthesis of Bispecific Antibodies using Genetically Encoded Unnatural Amino Acids" *J. Am. Chem. Soc.*, 134(24):9918-9921.
Kirkup, M.P. et al. (1989) "A concise route to the oxathiazepine containing eudistomin skeleton and some carba-analogs" *Tetrahedron Lett*, 30(49):6809-6812.
Krop, I.E. et al. (2012) "A Phase II Study of Trastuzumab Emtansine in Patients With Human Epidermal Growth Factor Receptor 2-Positive Metastatic Breast Cancer Who Were Previously Treated With Trastuzumab, Lapatin, an Anthracycline, a Taxane, and Capecitabine" *J Clin Oncol*, 30(26):3234-3241.
Lee, Y. et al. (2011) "Thiourea-Catalyzed Enantioselective Iso-Pictet-Spengler Reactions" *Org. Lett.*, 13(20):5564-5567.
Mahal, L.K. et al. (1997) "Engineering Chemical Reactivity on Cell Surfaces Through Oligosaccharide Biosynthesis" *Science*, 267:1125-1128.
Mahmoud, M.R. et al. (Sep. 13, 2007) "Utility of Nitriles in Synthesis of Pyrido[2,3-d]pyrimidines, Thiazolo[3,2-a]pyridines, Pyrano[2,3-b]benzopyrrole, and Pyrino[2,3-b]benzopyrroles" *Phosphorus, Sulfur and Silicon*, 182(11):2507-2521.
Maresh, J.J. et al. (2007) "Strictosidine Synthase: Mechanism of a Pictet-Spengler Catalyzing Enzyme" *J. Am. Chem. Soc.*, 130(2):710-723. NIH Public Access Author Manuscript, 32 pages.
Michalet, X. et al. (2006) "Single-Molecule Fluorescence Studies of Protein Folding and Conformational Dynamics" *Chem. Rev.*, 106(5):1785-1813.
Molina, P. et al. (1996) "Regiospecific preparation of γ-carbolines and pyrimido[3, 4-α]indole derivatives by intramolecular ring-closure of heterocumulene-substituted indoles" *Tetrahedron*, 52(16):5833-5844.
Mueller, B.M. et al. (1990) "Antibody conjugates with morpholinodoxorubicin and acid cleavable linkers" *Bioconjugate Chem.*, 1(5):325-330.
Nakagawa, M. et al. (1988) "New Evidence for the Presence of a Spiroindolenine Intermediate in Pictet-Spengler Reaction of Nb-Hydroxytryptamine" *J. Chem. Soc. Commun.*, p. 463-464.
Nystrom, T. (2005) "Role of oxidative carbonylation in protein quality control and senescence" *EMBO J*, 24(7):1311-1317.
O'Shannessy, D.J. et al. (1987) "Quantitation of Glycoproteins on Electroblots Using the Biotin-Streptavidin Complex" *Anal Biochem*, 163(1):204-209.
Padlan, E.A. (1991) "A possible procedure for reducing the immunogenicity of antibody variable domains while preserving their ligand-binding properties" *Mol Immunol*, 28(4-5):489-498.
Pandit, R.S. and S. Seshadri (1974) "Synthetic Studies in the Indole Series. Synthesis of Potential Pharmacological Agents" *Indian Journal of Chemistry*, 12(9):943-945.
Plate, R. et al. (1987) "Synthesis of 2-hydroxy-3-(ethoxycarbonyl)-1,2,3,4-tetrahydro-β-carbolines from N-hydroxytryptophans. An approach to the eudistomin series" *J. Org. Chem.*, 52(4):555-560.
Polson, A.G. et al. (Jul. 2010) "Anti-CD22-MCC-DMI: An antibody-drug conjugate with a stable linker for the treatment of non-Hodgkin's lymphoma" *Leukemia*, 24:1566-1573.
Pubchem Compound, "1H-Indole-2-carbohydrazide", Compound Summary for CID 231954. NCBI, U.S. National Library of Medicine. Create Date: Mar. 26, 2005 [online]. Retrieved from the Internet: http://pubchem.ncbi.nlm.nih.gov/compound/231954, 22 pages.

(56) References Cited

OTHER PUBLICATIONS

Pubchem Compound, "SCHEMBL743887", Substance Record for SID 227030170. NCBI, U.S. National Library of Medicine. Deposit Date: Feb. 12, 2015 [online]. Retrieved from the Internet: https://pubchem.ncbi.nlm.nih.gov/substance/227030170#section=Top, 7 pages.
Pubchem Compound, "CID 12343703", Compound Summary for CID 12343703. NCBI, U.S. National Library of Medicine. Create Date: Feb. 8, 2007 [online] [retrieved on Feb. 20, 2014]. Retrieved from the Internet: http://pubchem.ncbi.nlm.nih.gov/summary/summary.cgi?cid=12343703&loc=ec_rcs, 2 pages.
Pubchem Compound, "CTK2E1080", Compound Summary for CID 12343698. NCBI, U.S. National Library of Medicine. Create Date: Feb. 8, 2007 [online]. [retrieved on Feb. 6, 2014] Retrieved from the Internet: http://pubchem.ncbi.nlm.nih.gov/summary/summary.cgi?cid=1234698&loc=ec_rcs, 3 pages.
Pubchem Compound, "SureCN743887", Compound Summary for CID 66787168. NCBI, U.S. National Library of Medicine. [online]. Create Date: Nov. 30, 2012 [retrieved on Feb. 6, 2014]. Retrieved from the Internet: http://pubchem.ncbi.nlm.nih.gov/summary/summary.cgi?cid=66787168&loc=ec_rcs>; 2 pages.
Pudlo, J.S. et al. (1998) "Synthesis and Antiviral Activity of Certain 4- and 4,5-Disubstituted 7-[(2-Hydroxyethoxy)methyl]pyrrolo[2,3-d]pyrimidines" *J. Med. Chem.*, 31(11):2086-2092.
Rabuka, D. et al., (2012) "Site-specific chemical protein conjugation using genetically encoded aldehyde tags" *Nat. Protoc.*, 7(6):1052-1067.
Rashidian, M. et al. (2012) "Chemoenzymatic Reversible Immobilization and Labeling of Proteins without Prior Purification" *J. Am. Chem. Soc.*, 134(20):8455-8467.
Riechmann, L. et al. (1988) "Reshaping human antibodies for therapy" *Nature*, 332(6162):323-327.
Roguska, M.A. et al. (1994) "Humanization of murine monoclonal antibodies through variable domain resurfacing" *PNAS*, 91(3):969-973.
Sadamoto, R. et al. (2004) "Control of Bacteria Adhesion by Cell-Wall Engineering" *J. Am. Chem. Soc.*, 126(12):3755-3761.
Sasaki, T. et al. (2008) "N-terminal labeling of proteins by the Pictet-Spengler reaction" *Bioorg. Med. Chem. Lett.*, 18(16):4550-4553.
Scheck, R.A. et al. (2008) "Optimization of a Biomimetic Transamination Reaction" *J. Am. Chem. Soc.*, 130(35):11762-11770.
Seela, F. et al. (1994) "Synthesis of pyrrolo[3,2-c]pyridine and pyrazolo[3,4-d]pyrimidine beta-D- arabinonucleosides via nucleobase anion glycosylation" *Nucleosides & Nucleotides*, 10(1-3):713-714.
Shen, B-Q. et al. (2012) "Conjugation site modulates the in vivo stability and therapeutic activity of antibody-drug conjugates" *Nat. Biotechnol.*, 30(2):184-189.
Shi, X. et al. (2012) "Quantitative fluorescence labeling of aldehyde-tagged proteins for singlemolecule imaging" *Nat. Methods*, 9(5):499-503. HHS Public Access Author Manuscript; 21 pages.
Sletten, E.M. & C.R. Bertozzi (2009) "Bioorthogonal Chemistry: Fishing for Selectivity in a Sea of Functionality" *Agnew Chem. Soc.*, 48(38):6974-6998; NIH Public Access Author Manuscript; 54 pages.
Smith, C.D. et al. (1974) "Improved methods for the study of drug effects of purine metabolism and their application to nebularine and 7-deazanebularine" *Biotechnology Pharmacology*, 23(14) 2023-2035.
Smith, C.D. et al. (1991) "Excess brain protein oxidation and enzyme dysfunction in normal aging and in Alzheimer disease" *Proc. Natl. Acad. Sci. USA*, 88(23):10540-10543.
Stephanopoulos, N. and M.B. Francis (2011) "Choosing an effective protein bioconjugation strategy" *Nat. Chem. Biol.*, 7(12):876-884.
Stöckigt, J. et al. (2011) "The Pictet-Spengler Reaction in Nature and in Organic Chemistry" *Angew Chem Int Ed*, 50(37):8538-8564.
Studnicka, G.M. et al. (1994) "Human-engineered monoclonal antibodies retain full specific binding activity by preserving non-CDR complementarity-modulating residues" *Protein Eng*, 7(6):805-814.
Tai, H-C. et al. (2004) "Parallel Identification of O-GlcNAc-Modified Proteins from Cell Lysates" *J. Am. Chem. Soc.*, 126(34):10500-10501.
Teno, N. et al. (Oct. 12, 2007) "Novel scaffold for cathepsin K inhibitors" *Bioorg Med Chem Lett*, 17(22):6096-6100.
Tsunoda, T. et al. (1993) "1,1'-(azodicarbonyl)dipiperidine-tributylphosphine, a new reagent system for mitsunobu reaction" *Tetrahedron Lett.* 34(10):1639-1642.
Van Maarseveen, J.H. et al. (1993) "Intramolecular Pictet-Spengler Reaction of Nb-Alkoxytryptamines. 4. A Study towards Diastereocontrol in the Synthesis of Tetracyclic Eudistomins" *Tetrahedron*, 49(11):2325-2344.
Van Maarseveen, J.H. et al. (1995) "An Approach to Canthine Derivatives Using the Intramolecular Pictet-Spengler Condensation" *Tetrahedron*, 51(16):4841-4852.
Wang, L. et al. (2003) "Addition of the keto functional group to the genetic code of *Escherichia coli*" *Proc. Natl. Acad. Sci. USA*, 100(1):56-61.
Witus, L.S. et al. (2010) "Identification of Highly Reactive Sequences for PLP-Mediated Bioconjugation Using a Combinatorial Peptide Library" *J. Am. Chem. Soc.*, 132(47):16812-16817.
Wong, L.S. et al. (2009) "Selective Covalent Protein Immobilization: Strategies and Applications" *Chem. Rev.*, 109(9)4025-4053.
Wu, P. et al. (2009) "Site-specific chemical modification of recombinant proteins produced in mammalian cells by using the genetically encoded aldehyde tag" *Proc. Natl. Acad. Sci. USA*, 106:3000-3005.
Yeom, C-E. et al. (2007) "1,8-Diazabicylo[5.4.0]undec-7-ene (DBU)-promoted efficient and versatile aza-Michael addition" *Tetrahedron*, 63(4):904-909.
Yi, L. et al. (2010) "A Highly Efficient Strategy for Modification of Proteins at the C Terminus" *Angew. Chem. Int. Ed.*, 49:9417-9421.
Zeng, Y. et al. (2009) "High-efficiency labeling of glycoproteins on living cells" *Nat. Methods*, 6(3):207-209. NIH Public Access Author Manuscript; 7 pages.
Zheng, X. et al. (2008) "Synthesis of Indole Derivatives by Cyclization of Oxo N-Acyliminium Ions" *Synthesis*, 9:1345-1350.
Small GW, McLeod HL, Richards KL. "Analysis of Innate and Acquired Resistance to Anti-CD20 Antibodies in Malignant and Nonmalignant B cells." Peer J. Feb. 12, 2013. pp. 1-20.
Olejniczak Scott H, Hernandez-Illuzaliturri FJ, Clements JL, Czuczman MS. "Acquired Resistance to Rituximab is Associated with Chemotherapy Resistance Resulting from Decreased Bax and Bak Expression." Clinical Cancer Research. Mar. 1, 2008. pp. 1550-1560.

\* cited by examiner

FIG. 8A

```
isoform2   MHLLGPWLLLLLVLEYLAPSDSSKWVFEHPETLYAWEGACVWIPCTYRALDGDLESFILFH   60
isoform4   MHLLGPWLLLLLVLEYLAPSDSSKWVFEHPETLYAWEGACVWIPCTYRALDGDLESFILFH   60
isoform1   MHLLGPWLLLLLVLEYLAPSDSSKWVFEHPETLYAWEGACVWIPCTYRALDGDLESFILFH   60
isoform3   MHLLGPWLLLLLVLEYLAPSDSSKWVFEHPETLYAWEGACVWIPCTYRALDGDLESFILFH   60
           ************************************************************ isoform2   NPEYNKNTSKFDGTRLYESTKDGSKVPSEQKRVQFLGDRNKNCTLSIBPVHLMDSGQLGLR  120
isoform4   NPEYNKNTSKFDGTRLYESTKDGSKVPSEQKRVQFLGDRNKNCTLSIBPVHLMDSGQLGLR  120
isoform1   NPEYNKNTSKFDGTRLYESTKDGSKVPSEQKRVQFLGDRNKNCTLSIBPVHLMDSGQLGLR  120
isoform3   NPEYNKNTSKFDGTRLYESTKDGSKVPSEQKRVQFLGDRNKNEMCTLSIBPVHLMDSGQLGLR 120
           ************************************************************ isoform2   MESKTEKWMERIHLMVSERPFPPHIQLPPEIQESQEVTLTCLLNFSCYGYPIQLQWLLEG  180
isoform4   MESKTEKWMERIHLMVSERPFPPHIQLPPEIQESQEVTLTCLLNFSCYGYPIQLQWLLEG  180
isoform1   MESKTEKWMERIHLMVSERPFPPHIQLPPEIQESQEVTLTCLLNFSCYGYPIQLQWLLEG  180
isoform3   MESETEKWMERIHLMVSERPFPPHIQLPPEIQESQEVTLTCLLNFSCYGYPIQLQWLLEG  180
           ************************************************************ isoform2   VPMRQAAVTSTSLTIKSVFTRSELKFSPQWSHHGKIVTCQLQDADGKFLSNDTVQLMVKH  240
isoform4   VPMRQAAVTSTSLTIKSVFTRSELKFSPQWSHHGKIVTCQLQDADGKFLSNDTVQLMVKH  240
isoform1   VPMRQAAVTSTSLTIKSVFTRSELKFSPQWSHHGKIVTCQLQDADGKFLSNDTVQLMVKH  240
isoform3   VPMRQAAVTSTSLTIKSVFTRSELKFSPQWSHHGKIVTCQLQDADGKFLSNDTVQLMVKH  240
           ************************************************************ isoform2   TPKLEIKVTPSDAIVREGDSVTMTCEVSSSNPEYTTVSWLKDGTSLKKQNTFTLNLREVT  300
isoform4   ----------------------------------------------------------
isoform1   TPKLEIKVTPSDAIVREGDSVTMTCEVSSSNPEYTTVSWLKDGTSLKKQNTFTLNLREVT  300
isoform3   TPKLEIKVTPSDAIVREGDSVTMTCEVSSSNPEYTTVSWLKDGTSLKKQNTFTLNLREVT  300 isoform2   KDQSGKYCCQVSNDVGPGRSEEVFLQVQ-------------------------------  328
isoform4   ----------------------------------------------------------
isoform1   KDQSGKYCCQVSNDVGPGRSEEVFLQVQYAPEPSTVQILHSPAVEGSQVEFLCMSLANPL  360
isoform3   KDQSGKYCCQVSNDVGPGRSEEVFLQVQYAPEPSTVQILHSPAVEGSQVEFLCMSLANPL  360
```

FIG. 8B

```
isoform2  ------------------------------------------YPPK  332
isoform4  ------------------------------------------PPK   243
isoform1  FTNYTWYHNGKEMQGRTEEKVHIPKILPWHAGTYSCVAENILGTGQRGPGAELDVQYPPK  420
isoform3  FTNYTWYHNGKEMQGRTEEKVHIPKILPWHAGTYSCVAENILGTGQRGPGAELDVQYPPK  420
                                                    *** isoform2  KVTTVIQNPMPIREGDTVTLSCNYNSSMPSVTRYEWKPHGAWEEPSLGVLKIQNVGWDNT  392
isoform4  KVTTVIQNPMPIREGDTVTLSCNYNSSMPSVTRYEWKPHGAWEEPSLGVLKIQNVGWDNT  303
isoform1  KVTTVIQNPMPIREGDTVTLSCNYNSSMPSVTRYEWKPHGAWEEPSLGVLKIQNVGWDNT  480
isoform3  KVTTVIQNPMPIREGDTVTLSCNYNSSMPSVTRYEWKPHGAWEEPSLGVLKIQNVGWDNT  480
          ************************************************************ isoform2  TIACAACNSWCSWASPVALNVQYAPRDVRVRKIKPLSEIHSGNSVSLQCDFSSSHPKEVQ  452
isoform4  TIACAACNSWCSWASPVALNVQYAPRDVRVRKIKPLSEIHSGNSVSLQCDFSSSHPKEVQ  363
isoform1  TIACAACNSWCSWASPVALNVQYAPRDVRVRKIKPLSEIHSGNSVSLQCDFSSSHPKEVQ  540
isoform3  TIACAACNSWCSWASPVALNVQYAPRDVRVRKIKPLSEIHSGNSVSLQCDFSSSHPKEVQ  540
          ************************************************************ isoform2  FFWEKNGRLLGKESQLMFDSISPEDAGSYSCWVNNSIGQTASKAWTLEVLYAPRRLRVSM  512
isoform4  FFWEKNGRLLGKESQLMFDSISPEDAGSYSCWVNNSIGQTASKAWTLEVLYAPRRLRVSM  423
isoform1  FFWEKNGRLLGKESQLMFDSISPEDAGSYSCWVNNSIGQTASKAWTLEVLYAPRRLRVSM  600
isoform3  FFWEKNGRLLGKESQLMFDSISPEDAGSYSCWVNNSIGQTASKAWTLEVLYAPRRLRVSM  600
          ************************************************************ isoform2  SPGDQVMEGKSATLTCESDANPPVSHYTWFDWNNQSLPYHSQKLRLEPVKVQHSGAYWCQ  572
isoform4  SPGDQVMEGKSATLTCESDANPPVSHYTWFDWNNQSLPYHSQKLRLEPVKVQHSGAYWCQ  483
isoform1  SPGDQVMEGKSATLTCESDANPPVSHYTWFDWNNQSLPYHSQKLRLEPVKVQHSGAYWCQ  660
isoform3  SPGDQVMEGKSATLTCESDANPPVSHYTWFDWNNQSLPYHSQKLRLEPVKVQHSGAYWCQ  660
          ************************************************************ isoform2  GTNSVGKGRSPLSTLTVYYSPETIGRRVAVGLGSCLAILILAICGLKLQRRWKRTQSQQG  632
isoform4  GTNSVGKGRSPLSTLTVYYSPETIGRRVAVGLGSCLAILILAICGLKLQRRWKRTQSQQG  543
isoform1  GTNSVGKGRSPLSTLTVYYSPETIGRRVAVGLGSCLAILILAICGLKLQRRWKRTQSQQG  720
isoform3  GTNSVGKGRSPLSTLTVYYSPETIGRRVAVGLGSCLAILILAICGLKLQRRWKRTQSQQG  720
          ************************************************************
```

FIG. 8C

```
isoform2  LQENSSGQSFFVRNKKVRRAPLSEGPHSLGCYNPMMEDGISYTTLRFPEMNIPRTGDAES  692
isoform4  LQENSSGQSFFVRNKKVRRAPLSEGPHSLGCYNPMMEDGISYTTLRFPEMNIPRTGDAES  603
isoform1  LQENSSGQSFFVRNKKVRRAPLSEGPHSLGCYNPMMEDGISYTTLRFPEMNIPRTGDAES  780
isoform3  LQENSSGQSFFVRNKKKRCRVLR-------------------------------DAET  746
          ***********            *;

isoform2  SEMQRPPPDCDDTVTYSALHKRQVGDYENVIPDFPEDEGIHYSELIQFGVGERPQAQENV  752
isoform4  SEMQRPPPDCDDTVTYSALHKRQVGDYENVIPDFPEDEGIHYSELIQFGVGERPQAQENV  663
isoform1  SEMQRPPPDCDDTVTYSALHKRQVGDYENVIPDFPEDEGIHYSELIQFGVGERPQAQENV  840
isoform3  SPGLR-------------------------------------------------------  751
          * isoform2  DYVILKH  759
isoform4  DYVILKH  670
isoform1  DYVILK-  846
isoform3  -------
```

Light chain conserved region:

```
       140        150        160        170        180        189
     SVFI FPPSDEQLKS GTASVVCLLN NFYPREAKVQ WKVDNALQSG NSQESVTEQD
       200        210        220        230  236
     YSLSS TLTLSKADYE KHKVYACEVT HQGLSSPVTK SFNRGEC
```

Heavy chain conserved region:

```
       130        140        150        160        170        180
     SVFP LAPSSKSTSG GTAALGCLVK DYFPEPVTVS WNSGALTSGV HTFPAVLQSS
       190        200        210        220        230        240
     YSLSSVVT VPSSSLGTQT YICNVNHKPS NTKVDKKVEP KSCDKTHTCP PCPAPELLGG
       250        260        270        280        290        300
     PSVFLFPPKP KDTLMISRTP EVTCVVVDVS HEDPEVKFNW YVDGVEVHNA KTKPREEQYN
       310        320        330        340        350        360
     STYRVVSVLT VLHQDWLNGK EYKCKVSNKA LPAPIEKTIS KAKGQPREPQ VYTLPPSREE
       370        380        390        400        410        420
     MTKNQVSLTC LVKGFYPSDI AVEWESNGQP ENNYKTTPPV LDSDGSFFLY SKLTVDKSRW
       430        440        450
     QQGNVFSCSV MHEALHNHYT QKSLSLSPGK
```

FIG. 9A

*Homo sapiens* IgG1 constant region; GenBank P01857.1
*Homo sapiens* IgG3 constant region; GenBank P01859.2
*Homo sapiens* IgG2 constant region; GenBank P01860.2
*Homo sapiens* IgG4 constant region; GenBank AAB59394.1
*Homo sapiens* IgA constant region; GenBank AAAT74070

```
IgG1   --ASTKGPSVFPLAPSSKSTSGGTAALGCLVKDYFP-EPVTVSWNSGALTSGVHTFPAVL   178
IgG3   --ASTKGPSVFPLAPCSRSTSGGTAALGCLVKDYFP-EPVTVSWNSGALTSGVHTFPAVL
IgG2   --ASTKGPSVFPLAPCSRSTSESTAALGCLVKDYFP-EPVTVSWNSGALTSGVHTFPAVL
IgG4   STKGPSVFPLAPCSRSTSESTAALGCLVKDYFP-EPVTVSWNSGALTSGVHTFPAVL
IgA    --ASPTSPKVFPLSLCS-TQPDGNVVIACLVQGFFPQEPLSVTWSESGQGVTARNFPPSQ
         : .****.*****. : *   .:*****:**:::****.* . *:*.****

IgG1   QSSG-LYSLSSVVTVPS-SSLGTQTYICNVNHKPSNTKVDKKVE------------       220
IgG3   QSSG-LYSLSSVVTVPS-SSLGTQTYICNVNHKPSNTKVDKRVELKTPLGDTTHTCPRCP
IgG2   QSSG-LYSLSSVVTVPS-SNFGTQTYTCNVDHKPSNTKVDKTVER---------------
IgG4   QSSG-LYSLSSVVTVPS-SSLGTKTYTCNVDHKPSNTKVDKRVES---------------
IgA    DASGDLYTTSSQLTLPATQCLAGKSVTCHVKHY-TNPSQDVTVPCF--------------
         :**  ** .*:.* :*.:  : ::  *  ::: :::.:  * ::  .

IgG1   ------------PKSCDKTHTCPPCPAPELLGGPSVFLFPP                    249
IgG3   EPKSCDTPPPCPRCPEPKSCDTPPPCPRCPEPKSCDTPPPCPRCPEPKSCDTPPPCPRCP
IgG2   ------------KCCVE----CPPCPAPPVAG-PSVFLFPP
IgG4   ------------KYGPPCPSCPAPEFLGGPSVFLFPP
IgA    ------------VPSTPPTPSPSTPPTPSPSCCHPRLSLHR
                               :                   :.

IgG1   KPKDTLMISRTPEVTCVVVDVSHEDPEVKFNWYVDGVEVHNAKTKPREEQYNSTYRVVSV  309
IgG3   KPKDTLMISRTPEVTCVVVDVSHEDPEVQFKWYVDGVEVHNAKTKPREEQYNSTFRVVSV
IgG2   KPKDTLMISRTPEVTCVVVDVSHEDPEVQFNWYVDGVEVHNAKTKPREEQFNSTFRVVSV
IgG4   KPKDTLMISRTPEVTCVVVDVSQEDPEVQFNWYVDGVEVHNAKTKPREEQFNSTYRVVSV
IgA    PALEDLLLGSEANLTCTLTGLR-DASGVTFTWTPS--SGKSAVQGPPDRDLCGCYSVSSV
       : :**:::*.*: ** :: : .  .:.* * * .   :. . *:: .: * *:: **
```

FIG. 9B

```
IgG1  LTVLHQDWLNGKEYKCKVSNKALPAPIEKTISKAKGQPREPQVYTLPPSRDELTKNQVS-  368
IgG3  LTVLHQDWLNGKEYKCKVSNKALPAPIEKTISKTKGQPREPQVYTLPPSREEMTKNQVS-
IgG2  LTVVHQDWLNGKEYKCKVSNKGLPAPIEKTISKTKGQPREPQVYTLPPSREEMTKNQVS-
IgG4  LTVLHQDWLNGKEYKCKVSNKGLPSSIEKTISKAKGQPREPQVYTLPPSQEEMTKNQVS-
IgA   LSGCAEPWNHGKTFTCTAAYPESKTPLTATLSKS-GNTFRPEVHLLPPPSEELALNELVT
      *  *:  *  *  **:::   *  *:: *       *:**  *  :***:*  * *:

IgG1  LTCLVKGFYPSDIAVEWESNGQ---PENNYKTTPPVLDSDG----SFFLYSKLTVDKSRWQQ  423
IgG3  LTCLVKGFYPSDIAVEWESSGQ---PENNYNTTPPMLDSDG----SFFLYSKLTVDKSRWQQ
IgG2  LTCLVKGFYPSDISVEWESNGQ---PENNYKTTPPMLDSDG----SFFLYSKLTVDKSRWQQ
IgG4  LTCLVKGFYPSDIAVEWESNGQ---PENNYKTTPPVLDSDG----SFFLYSRLTVDKSRWQE
IgA   LTCLARGFSPKDVLVRWLQGSQELPREKYLTWASRQEPSQGTTTFAVTSILRVAAEDWKK
      *** . :** *.*:.*:*  . :     :* *:: : .       :* :*::****  :

IgG1  GNVFSCSVMHEALHNHYTQKSLSLSPGK----------------------- 451
IgG3  GNIFSCSVMHEALHNRFTQKSLSLSLSPGK
IgG2  GNVFSCSVMHEALHNHYTQKSLSLSLSPGK
IgG4  GNVFSCSVMHEALHNHYTQKSLSLSLSPGK
IgA   GDTFSCMVGHEALPLAFTQKTIDRLAGKPTHVNVSVVMAEVDGTCY
      *  *** * ****    **:: .
```

FIG. 9B, continued

```
Seq1 = Homo sapiens kappa light chain constant region; GenBank CAA75031.1
Seq2 = Homo sapiens kappa light chain constant region; GenBank BAC0168.1
Seq3 = Homo sapiens lambda light chain constant region; GenBank CAA75033
Seq4 = Mus musculus light chain constant region; GenBank AAB09710.1
Seq5 = Rattus norvegicus light chain constant region; GenBank AAD10133 seq1  RTVAAPSVFIFPPSDEQLKSGTASVVCLLNNFYPREAKVQWKVDNALQSGNSQESVTEQD  189
seq2  RTVAAPSVFIFPPSDEQLKSGTASVVCLLNNFYPREAKVQWKVDNALQSGNSQESVTEQD
seq3  RADAAPTVSIFPPSSEQLTSGGASVVCFLNNFYPKDINVKWKIDGSERQNGVLNSWTDQD
seq4  RADAAPTVSIFPPSMEQLTSGGATVVCFVNNFYPRDISVKWKIDGSEQRDGVLDSVTDQD
seq3  QPKAAPSVTLFPPSSEELQANKATLVCLISDFYPGAVTVAWKADSSPVKAGVETTTPSKQ
      :  :** * :.:***   * :  ** :*:*::;*.:  . *  ..     .  :: .::

seq1  SKDSTYSLSSTLTLSKADYEKHKVYACEVTHQGLSSPVTKSFNRGEC  236
seq2  SKDSTYSLSSTLTLSKADYEKHKLYACEVTHQGLSSPVTKSFNRGEC
seq4  SKDSTYSMSSTLTLTKDEYERHNSYTCEATHKTSTSPIVKSFNRGEC
seq5  SKDSTYSMSSTLTKVEYERHNLYTCEVVHKTSSSPVVKSFNRNEC
seq3  S-NNKYAASSYLSLTPEQWKSHKSYSCQVTHEG--STVEKTVAPTECS
      *  * :  ** :*::*  ::  *..:*  :*.    *     ** *
```

FIG. 9C

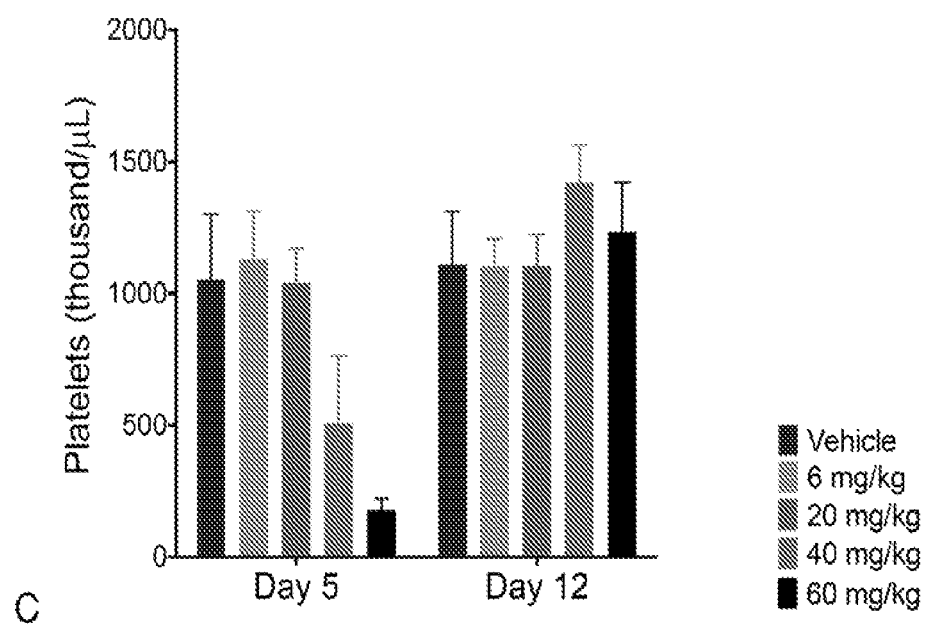
FIG. 20, continued

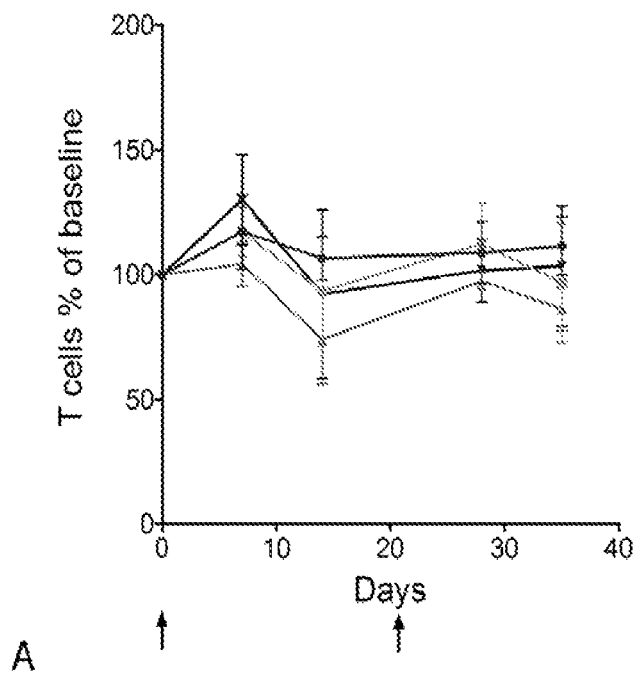
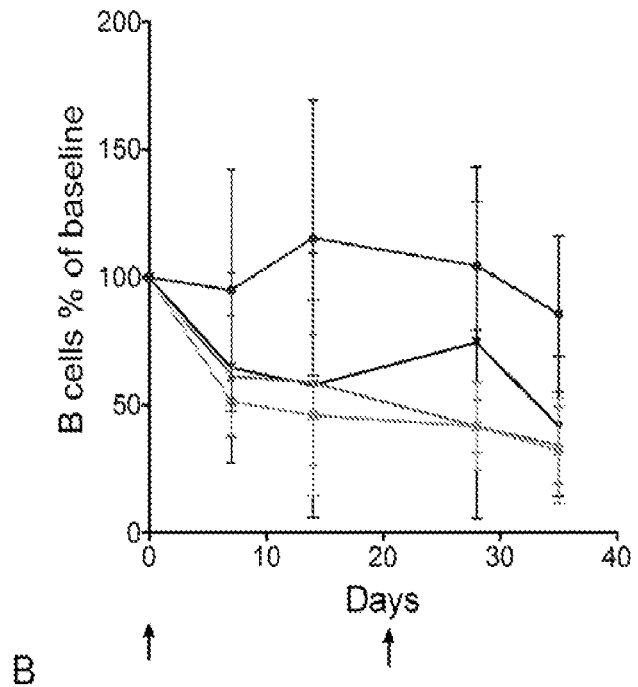
FIG. 24

Table 3. Summary of mean (± SD) pharmacokinetic (PK) and toxicokinetic (TK) parameters of total ADC values in animals dosed with Anti-CD22 ADC.

| Dose (mg/kg) | Mouse (q4d × 4)[a] | | Rat (single dose) | | Cynomolgus monkey (q3w × 2)[b] | |
|---|---|---|---|---|---|---|
| | $C_{max}$ first dose (µg/mL) | $AUC_{0\text{-}inf}$ (day·µg/mL) | $C_{max}$ (µg/mL) | $AUC_{0\text{-}inf}$ (day·µg/mL) | $C_{max}$ first dose (µg/mL) | $AUC_{0\text{-}inf}$ (day·µg/mL) |
| 3 | | | 83.9 (16) | 218 (18.4) | | |
| 5 | 74.4 (5.48) | 1500 (45.1) | | | | |
| 6 | | | 110 (38.5) | 660 (143) | | |
| 10 | 136 (4.57) | 2530 (131) | | | 318 (110) | 1360 (556) |
| 20 | | | 382 (63.0) | 2280 (325) | | |
| 30 | | | | | 1030 (57.4) | 4200 (768) |
| 40 | | | 687 (52.8) | 3740 (185) | | |
| 60 | | | 1020 (158) | 5201 (273) | 1630 (138) | 6140 (667) |

[a] AUC calculation includes all doses.
[b] AUC calculation from the first dose only.

SD, standard deviation; $AUC_{0\text{-}inf}$, area under the concentration versus time curve from time 0 to infinity; $C_{max}$, highest concentration observed at the first sampling time point from each study as follows: mouse and rat PK, 1 h; rat TK, 8 h; cynomolgus TK, 5 min.

FIG. 26

ANTI-CD22 ANTIBODY-MAYTANSINE CONJUGATES AND METHODS OF USE THEREOF

CROSS-REFERENCE TO RELATED APPLICATIONS

This application is a U.S. National Phase application, filed under 35 U.S.C. § 371, of International Application No. PCT/US2016/60996, filed on Nov. 8, 2016, which claims benefit pursuant to 35 U.S.C. § 119(e) of U.S. Provisional Application No. 62/252,985, filed Nov. 9, 2015, the disclosure of each of which is incorporated herein by reference in its entirety.

INCORPORATION—BY-REFERENCE OF SEQUENCE LISTING

The contents of the file named "TRPS-032-02US-SubSeqList-ST25.txt", which was created on Mar. 4, 2021, and is ~88.9 KB in size are hereby incorporated by reference in their entirety.

INTRODUCTION

The field of protein-small molecule therapeutic conjugates has advanced greatly, providing a number of clinically beneficial drugs with the promise of providing more in the years to come. Protein-conjugate therapeutics can provide several advantages, due to, for example, specificity, multiplicity of functions and relatively low off-target activity, resulting in fewer side effects. Chemical modification of proteins may extend these advantages by rendering them more potent, stable, or multimodal.

A number of standard chemical transformations are commonly used to create and manipulate post-translational modifications on proteins. There are a number of methods where one is able to modify the side chains of certain amino acids selectively. For example, carboxylic acid side chains (aspartate and glutamate) may be targeted by initial activation with a water-soluble carbodiimide reagent and subsequent reaction with an amine. Similarly, lysine can be targeted through the use of activated esters or isothiocyanates, and cysteine thiols can be targeted with maleimides and α-halo-carbonyls.

One significant obstacle to the creation of a chemically altered protein therapeutic or reagent is the production of the protein in a biologically active, homogenous form. Conjugation of a drug or detectable label to a polypeptide can be difficult to control, resulting in a heterogeneous mixture of conjugates that differ in the number of drug molecules attached and in the position of chemical conjugation. In some instances, it may be desirable to control the site of conjugation and/or the drug or detectable label conjugated to the polypeptide using the tools of synthetic organic chemistry to direct the precise and selective formation of chemical bonds on a polypeptide.

SUMMARY

The present disclosure provides anti-CD22 antibody-maytansine conjugate structures. The disclosure also encompasses methods of production of such conjugates, as well as methods of using the same.

Aspects of the present disclosure include a conjugate that includes at least one modified amino acid residue of formula (I):

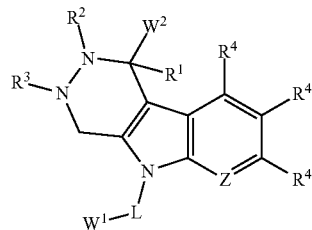

wherein
Z is $CR^4$ or N;
$R^1$ is selected from hydrogen, alkyl, substituted alkyl, alkenyl, substituted alkenyl, alkynyl, substituted alkynyl, aryl, substituted aryl, heteroaryl, substituted heteroaryl, cycloalkyl, substituted cycloalkyl, heterocyclyl, and substituted heterocyclyl;
$R^2$ and $R^3$ are each independently selected from hydrogen, alkyl, substituted alkyl, alkenyl, substituted alkenyl, alkynyl, substituted alkynyl, alkoxy, substituted alkoxy, amino, substituted amino, carboxyl, carboxyl ester, acyl, acyloxy, acyl amino, amino acyl, alkylamide, substituted alkylamide, sulfonyl, thioalkoxy, substituted thioalkoxy, aryl, substituted aryl, heteroaryl, substituted heteroaryl, cycloalkyl, substituted cycloalkyl, heterocyclyl, and substituted heterocyclyl, or $R^2$ and $R^3$ are optionally cyclically linked to form a 5 or 6-membered heterocyclyl;
each $R^4$ is independently selected from hydrogen, halogen, alkyl, substituted alkyl, alkenyl, substituted alkenyl, alkynyl, substituted alkynyl, alkoxy, substituted alkoxy, amino, substituted amino, carboxyl, carboxyl ester, acyl, acyloxy, acyl amino, amino acyl, alkylamide, substituted alkylamide, sulfonyl, thioalkoxy, substituted thioalkoxy, aryl, substituted aryl, heteroaryl, substituted heteroaryl, cycloalkyl, substituted cycloalkyl, heterocyclyl, and substituted heterocyclyl;
L is a linker comprising -$(T^1-V^1)_a$-$(T^2-V^2)_b$-$(T^3-V^3)_c$-$(T^4-V^4)_d$-, wherein a, b, c and d are each independently 0 or 1, where the sum of a, b, c and d is 1 to 4;
$T^1$, $T^2$, $T^3$ and $T^4$ are each independently selected from $(C_1-C_{12})$alkyl, substituted $(C_1-C_{12})$alkyl, $(EDA)_w$, $(PEG)_n$, $(AA)_p$, —$(CR^{13}OH)_h$—, piperidin-4-amino (4AP), an acetal group, a hydrazine, a disulfide, and an ester, wherein EDA is an ethylene diamine moiety, PEG is a polyethylene glycol or a modified polyethylene glycol, and AA is an amino acid residue, wherein w is an integer from 1 to 20, n is an integer from 1 to 30, p is an integer from 1 to 20, and h is an integer from 1 to 12;
$V^1$, $V^2$, $V^3$ and $V^4$ are each independently selected from the group consisting of a covalent bond, —CO—, —$NR^{15}$—, —$NR^{15}(CH_2)_q$—, —$NR^{15}(C_6H_4)$—, —$CONR^{15}$—, —$NR^{15}CO$—, —C(O)O—, —OC(O)—, —O—, —S—, —S(O)—, —$SO_2$—, —$SO_2NR^{15}$—, —$NR^{15}SO_2$— and —P(O)OH—, wherein q is an integer from 1 to 6;
each $R^{13}$ is independently selected from hydrogen, an alkyl, a substituted alkyl, an aryl, and a substituted aryl;
each $R^{15}$ is independently selected from hydrogen, alkyl, substituted alkyl, alkenyl, substituted alkenyl, alkynyl, substituted alkynyl, carboxyl, carboxyl ester, acyl, aryl, substituted aryl, heteroaryl, substituted heteroaryl, cycloalkyl, substituted cycloalkyl, heterocyclyl, and substituted heterocyclyl;

$W^1$ is a maytansinoid; and $W^2$ is an anti-CD22 antibody.

In certain embodiments, $T^1$ is selected from a $(C_1-C_{12})$alkyl and a substituted $(C_1-C_{12})$alkyl;

$T^2$, $T^3$ and $T^4$ are each independently selected from $(EDA)_w$, $(PEG)_n$, $(C_1-C_{12})$alkyl, substituted $(C_1-C_{12})$alkyl, $(AA)_p$, $-(CR^{13}OH)_h-$, piperidin-4-amino (4AP), an acetal group, a hydrazine, and an ester; and $V^1$, $V^2$, $V^3$ and $V^4$ are each independently selected from the group consisting of a covalent bond, $-CO-$, $-NR^{15}-$, $-NR^{15}(CH_2)_q-$, $-NR^{15}(C_6H_4)-$, $-CONR^{15}-$, $-NR^{15}CO-$, $-C(O)O-$, $-OC(O)-$, $-O-$, $-S-$, $-S(O)-$, $-SO_2-$, $-SO_2NR^{15}-$, $-NR^{15}SO_2-$, and $-P(O)OH-$;

wherein:

$(PEG)_n$ is

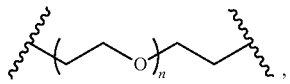

where n is an integer from 1 to 30;

EDA is an ethylene diamine moiety having the following structure:

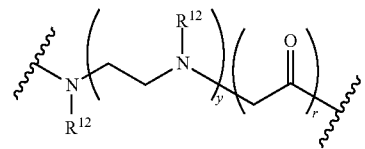

where y is an integer from 1 to 6 and r is 0 or 1;

piperidin-4-amino is

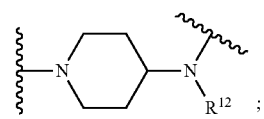

each $R^{12}$ and $R^{15}$ is independently selected from hydrogen, an alkyl, a substituted alkyl, a polyethylene glycol moiety, an aryl and a substituted aryl, wherein any two adjacent $R^{12}$ groups may be cyclically linked to form a piperazinyl ring; and $R^{13}$ is selected from hydrogen, an alkyl, a substituted alkyl, an aryl, and a substituted aryl.

In certain embodiments, $T^1$, $T^2$, $T^3$ and $T^4$, and $V^1$, $V^2$, $V^3$ and $V^4$ are selected from the following table:

| $T^1$ | $V^1$ | $T^2$ | $V^2$ | $T^3$ | $V^3$ | $T^4$ | $V^4$ |
|---|---|---|---|---|---|---|---|
| $(C_1-C_{12})$alkyl | $-CONR^{15}-$ | $(PEG)_n$ | $-CO-$ | — | — | — | — |
| $(C_1-C_{12})$alkyl | $-CO-$ | $(AA)_p$ | $-NR^{15}-$ | $(PEG)_n$ | $-CO-$ | — | — |
| $(C_1-C_{12})$alkyl | $-CO-$ | $(AA)_p$ | — | — | — | — | — |
| $(C_1-C_{12})$alkyl | $-CONR^{15}-$ | $(PEG)_n$ | $-NR^{15}-$ | — | — | — | — |
| $(C_1-C_{12})$alkyl | $-CO-$ | $(AA)_p$ | $-NR^{15}-$ | $(PEG)_n$ | $-NR^{15}-$ | — | — |
| $(C_1-C_{12})$alkyl | $-CO-$ | $(EDA)_w$ | $-CO-$ | — | — | — | — |
| $(C_1-C_{12})$alkyl | $-CONR^{15}-$ | $(C_1-C_{12})$alkyl | $-NR^{15}-$ | — | — | — | — |
| $(C_1-C_{12})$alkyl | $-CONR^{15}-$ | $(PEG)_n$ | $-CO-$ | $(EDA)_w$ | — | — | — |
| $(C_1-C_{12})$alkyl | $-CO-$ | $(EDA)_w$ | — | — | — | — | — |
| $(C_1-C_{12})$alkyl | $-CO-$ | $(EDA)_w$ | $-CO-$ | $(CR^{13}OH)_h$ | $-CONR^{15}-$ | $(C_1-C_{12})$alkyl | $-CO-$ |
| $(C_1-C_{12})$alkyl | $-CO-$ | $(AA)_p$ | $-NR^{15}-$ | $(C_1-C_{12})$alkyl | $-CO-$ | — | — |
| $(C_1-C_{12})$alkyl | $-CONR^{15}-$ | $(PEG)_n$ | $-CO-$ | $(AA)_p$ | — | — | — |
| $(C_1-C_{12})$alkyl | $-CO-$ | $(EDA)_w$ | $-CO-$ | $(CR^{13}OH)_h$ | $-CO-$ | $(AA)_p$ | — |
| $(C_1-C_{12})$alkyl | $-CO-$ | $(AA)_p$ | $-NR^{15}-$ | $(C_1-C_{12})$alkyl | $-CO-$ | $(AA)_p$ | — |
| $(C_1-C_{12})$alkyl | $-CO-$ | $(AA)_p$ | $-NR^{15}-$ | $(PEG)_n$ | $-CO-$ | $(AA)_p$ | — |
| $(C_1-C_{12})$alkyl | $-CO-$ | $(AA)_p$ | $-NR^{15}-$ | $(PEG)_n$ | $-SO_2-$ | $(AA)_p$ | — |
| $(C_1-C_{12})$alkyl | $-CO-$ | $(EDA)_w$ | $-CO-$ | $(CR^{13}OH)_h$ | $-CONR^{15}-$ | $(PEG)_n$ | $-CO-$ |
| $(C_1-C_{12})$alkyl | $-CO-$ | $(CR^{13}OH)_h$ | $-CO-$ | — | — | — | — |
| $(C_1-C_{12})$alkyl | $-CONR^{15}-$ | substituted $(C_1-C_{12})$alkyl | $-NR^{15}-$ | $(PEG)_n$ | $-CO-$ | — | — |
| $(C_1-C_{12})$alkyl | $-SO_2-$ | $(C_1-C_{12})$alkyl | $-CO-$ | — | — | — | — |
| $(C_1-C_{12})$alkyl | $-CONR^{15}-$ | $(C_1-C_{12})$alkyl | — | $(CR^{13}OH)_h$ | $-CONR^{15}-$ | — | — |
| $(C_1-C_{12})$alkyl | $-CO-$ | $(AA)_p$ | $-NR^{15}-$ | $(PEG)_n$ | $-CO-$ | $(AA)_p$ | $-NR^{15}-$ |
| $(C_1-C_{12})$alkyl | $-CO-$ | $(AA)_p$ | $-NR^{15}-$ | $(PEG)_n$ | $-P(O)OH-$ | $(AA)_p$ | — |
| $(C_1-C_{12})$alkyl | $-CO-$ | $(EDA)_w$ | — | $(AA)_p$ | — | — | — |
| $(C_1-C_{12})$alkyl | $-CONR^{15}-$ | $(C_1-C_{12})$alkyl | $-NR^{15}-$ | — | $-CO-$ | — | — |
| $(C_1-C_{12})$alkyl | $-CONR^{15}-$ | $(C_1-C_{12})$alkyl | $-NR^{15}-$ | — | $-CO-$ | $(C_1-C_{12})$alkyl | $-NR^{15}-$ |
| $(C_1-C_{12})$alkyl | $-CO-$ | 4AP | $-CO-$ | $(C_1-C_{12})$alkyl | $-CO-$ | $(AA)_p$ | — |
| $(C_1-C_{12})$alkyl | $-CO-$ | 4AP | $-CO-$ | $(C_1-C_{12})$alkyl | $-CO-$ | — | — |

In certain embodiments, L is selected from one of the following structures:
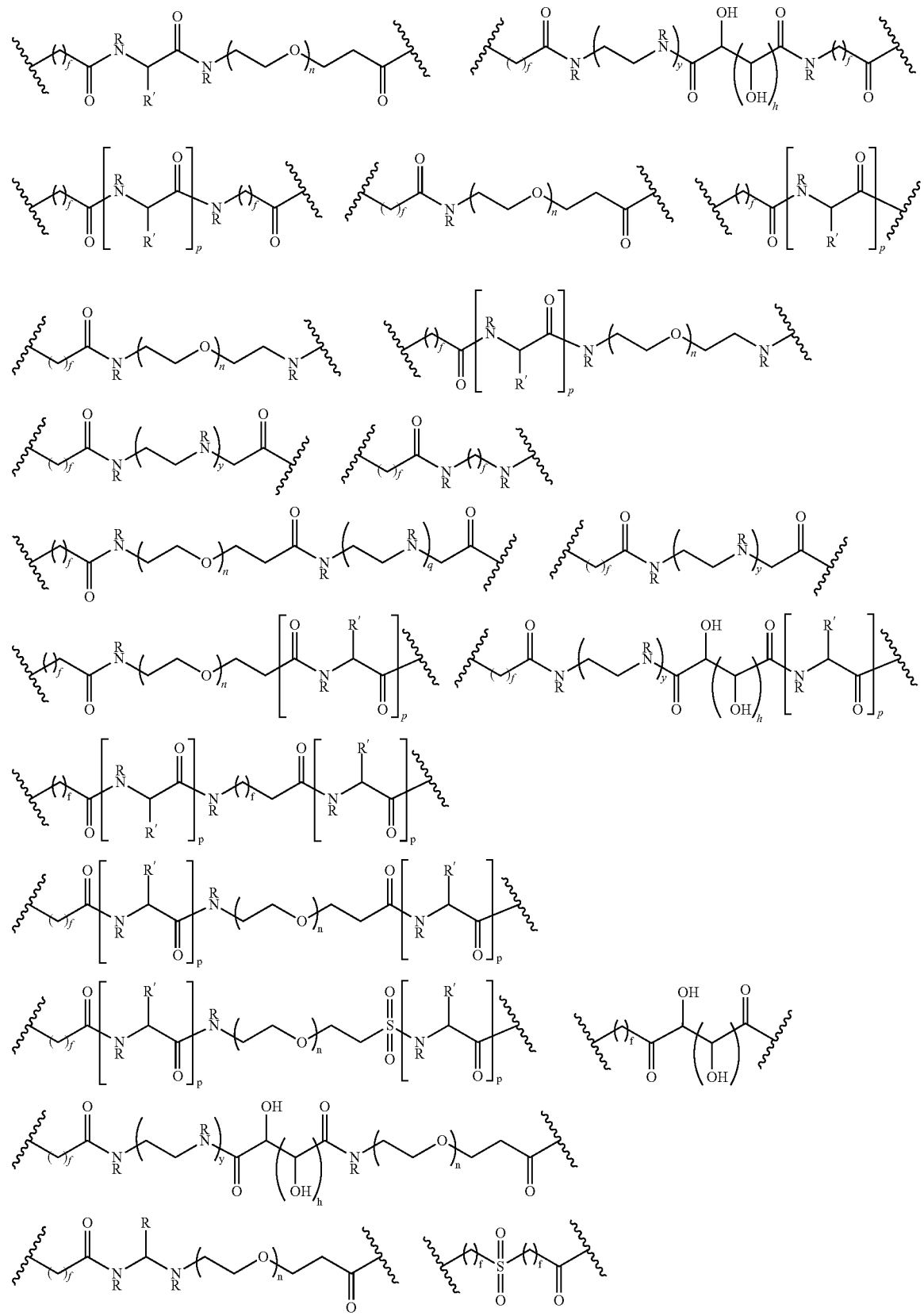

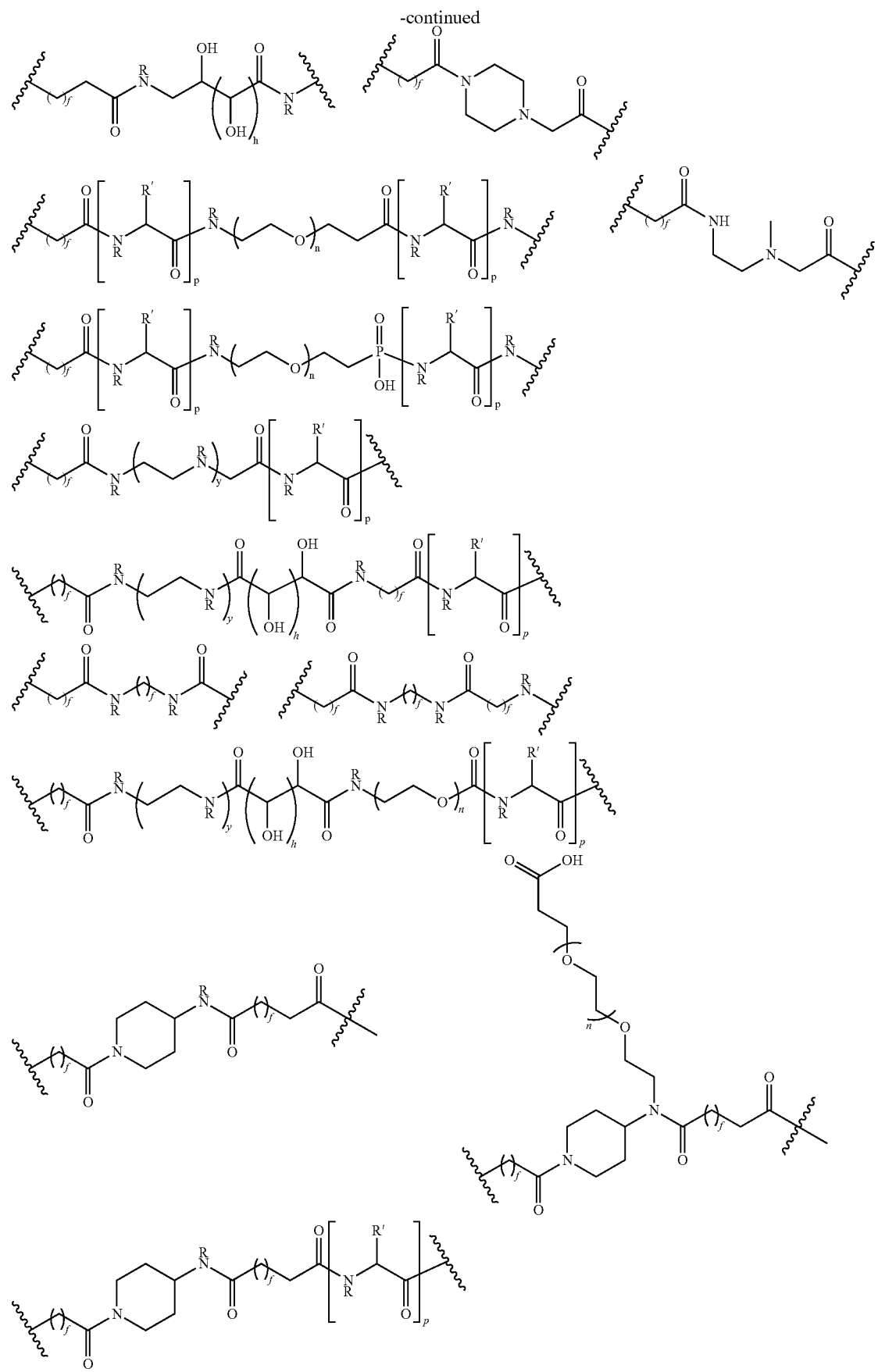

-continued

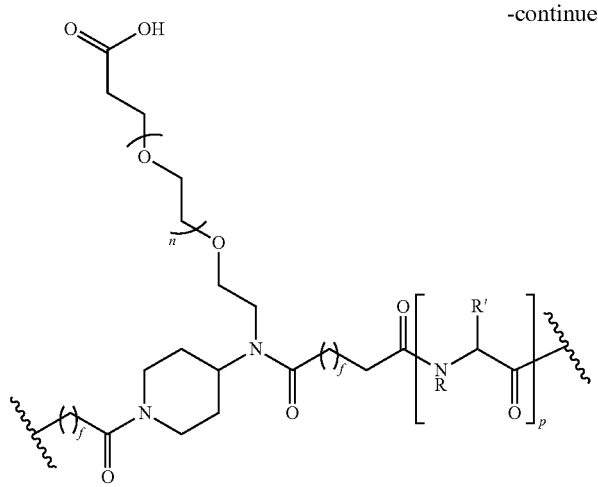

wherein
- each f is independently 0 or an integer from 1 to 12;
- each y is independently 0 or an integer from 1 to 20;
- each n is independently 0 or an integer from 1 to 30;
- each p is independently 0 or an integer from 1 to 20;
- each h is independently 0 or an integer from 1 to 12;
- each R is independently hydrogen, alkyl, substituted alkyl, alkenyl, substituted alkenyl, alkynyl, substituted alkynyl, alkoxy, substituted alkoxy, amino, substituted amino, carboxyl, carboxyl ester, acyl, acyloxy, acyl amino, amino acyl, alkylamide, substituted alkylamide, sulfonyl, thioalkoxy, substituted thioalkoxy, aryl, substituted aryl, heteroaryl, substituted heteroaryl, cycloalkyl, substituted cycloalkyl, heterocyclyl, and substituted heterocyclyl; and
- each R' is independently H, a sidechain group of an amino acid, alkyl, substituted alkyl, alkenyl, substituted alkenyl, alkynyl, substituted alkynyl, alkoxy, substituted alkoxy, amino, substituted amino, carboxyl, carboxyl ester, acyl, acyloxy, acyl amino, amino acyl, alkylamide, substituted alkylamide, sulfonyl, thioalkoxy, substituted thioalkoxy, aryl, substituted aryl, heteroaryl, substituted heteroaryl, cycloalkyl, substituted cycloalkyl, heterocyclyl, and substituted heterocyclyl.

In certain embodiments, the maytansinoid is of the formula:

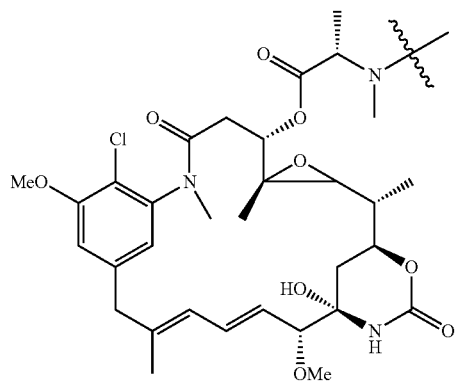

where ᴡᴡ indicates the point of attachment between the maytansinoid and L.

In certain embodiments, $T^1$ is $(C_1\text{-}C_{12})$alkyl, $V^1$ is —CO—, $T^2$ is 4AP, $V^2$ is —CO—, $T^3$ is $(C_1\text{-}C_{12})$alkyl, $V^3$ is —CO—, $T^4$ is absent and $V^4$ is absent.

In certain embodiments, the linker, L, includes the following structure:

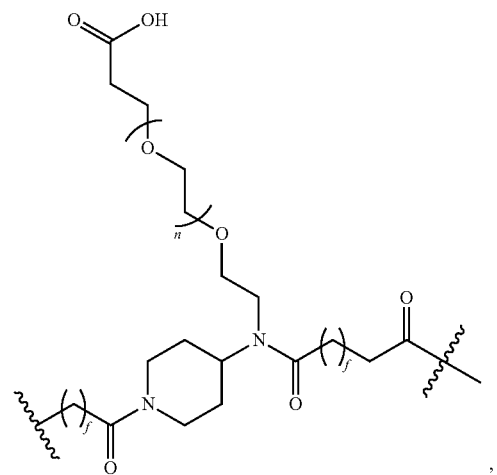

wherein
- each f is independently an integer from 1 to 12; and
- n is an integer from 1 to 30.

In certain embodiments, the anti-CD22 antibody binds an epitope within amino acids 1 to 846 (SEQ ID NO: 23), within amino acids 1-759 (SEQ ID NO: 21), within amino acids 1-751 (SEQ ID NO: 24), or within amino acids 1-670 (SEQ ID NO: 22), of a CD22 amino acid sequence depicted in FIG. 8A-8C.

In certain embodiments, the anti-CD22 antibody comprises a sequence of the formula (II):

$$X^1(FG1y')X^2Z^{20}X^3Z^{30}(SEQ\ ID\ NO{:}10) \quad (II)$$

wherein
- FG1y' is the modified amino acid residue of formula (I);
- $Z^{20}$ is either a proline or alanine residue;
- $Z^{30}$ is a basic amino acid or an aliphatic amino acid;
- $X^1$ may be present or absent and, when present, can be any amino acid, with the proviso that when the sequence is at the N-terminus of the conjugate, $X^1$ is present; and
- $X^2$ and $X^3$ are each independently any amino acid.

In certain embodiments, the sequence is L(FG1y')TPSR (SEQ ID NO: 11).

In certain embodiments, $Z^{30}$ is selected from R, K, H, A, G, L, V, I, and P; $X^1$ is selected from L, M, S, and V; and $X^2$ and $X^3$ are each independently selected from S, T, A, V, G, and C.

In certain embodiments, the modified amino acid residue is positioned at a C-terminus of a heavy chain constant region of the anti-CD22 antibody.

In certain embodiments, the heavy chain constant region comprises a sequence of the formula (II):

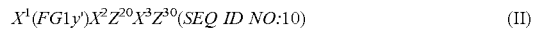

$$X^1(FG1y')X^2Z^{20}X^3Z^{30}(SEQ\ ID\ NO:10) \quad (II)$$

wherein

FG1y' is the modified amino acid residue of formula (I);

$Z^{20}$ is either a proline or alanine residue;

$Z^{30}$ is a basic amino acid or an aliphatic amino acid;

$X^1$ may be present or absent and, when present, can be any amino acid, with the proviso that when the sequence is at the N-terminus of the conjugate, $X^1$ is present; and $X^2$ and $X^3$ are each independently any amino acid, and wherein the sequence is C-terminal to the amino acid sequence SLSLSPG (SEQ ID NO: 12).

In certain embodiments, the heavy chain constant region comprises the sequence SPGSL(FG1y')TPSRGS. (SEQ ID NO: 13)

In certain embodiments, $Z^{30}$ is selected from R, K, H, A, G, L, V, I, and P; $X^1$ is selected from L, M, S, and V; and $X^2$ and $X^3$ are each independently selected from S, T, A, V, G, and C.

In certain embodiments, the modified amino acid residue is positioned in a light chain constant region of the anti-CD22 antibody.

In certain embodiments, the light chain constant region comprises a sequence of the formula (II):

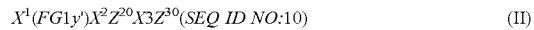

$$X^1(FG1y')X^2Z^{20}X^3Z^{30}(SEQ\ ID\ NO:10) \quad (II)$$

wherein

FG1y' is the modified amino acid residue of formula (I);

$Z^{20}$ is either a proline or alanine residue;

$Z^{30}$ is a basic amino acid or an aliphatic amino acid;

$X^1$ may be present or absent and, when present, can be any amino acid, with the proviso that when the sequence is at the N-terminus of the conjugate, $X^1$ is present; and $X^2$ and $X^3$ are each independently any amino acid, and wherein the sequence C-terminal to the sequence KVDNAL (SEQ ID NO: 14), and/or is N-terminal to the sequence QSGNSQ (SEQ ID NO: 15).

In certain embodiments, the light chain constant region comprises the sequence KVDNAL(FG1y')TPSRQSGNSQ (SEQ ID NO: 16).

In certain embodiments, $Z^{30}$ is selected from R, K, H, A, G, L, V, I, and P; $X^1$ is selected from L, M, S, and V; and $X^2$ and $X^3$ are each independently selected from S, T, A, V, G, and C.

In certain embodiments, the modified amino acid residue is positioned in a heavy chain CH1 region of the anti-CD22 antibody.

In certain embodiments, the heavy chain CH1 region comprises a sequence of the formula (II):

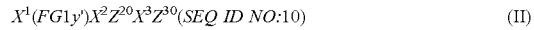

$$X^1(FG1y')X^2Z^{20}X^3Z^{30}(SEQ\ ID\ NO:10) \quad (II)$$

wherein

FG1y' is the modified amino acid residue of formula (I);

$Z^{20}$ is either a proline or alanine residue;

$Z^{30}$ is a basic amino acid or an aliphatic amino acid;

$X^1$ may be present or absent and, when present, can be any amino acid, with the proviso that when the sequence is at the N-terminus of the conjugate, $X^1$ is present; and $X^2$ and $X^3$ are each independently any amino acid, and wherein the sequence is C-terminal to the amino acid sequence SWNSGA (SEQ ID NO: 17) and/or is N-terminal to the amino acid sequence GVHTFP (SEQ ID NO: 18).

In certain embodiments, the heavy chain CH1 region comprises the sequence SWNSGAL(FG1y')TPSRGVHTFP (SEQ ID NO: 19).

In certain embodiments, $Z^{30}$ is selected from R, K, H, A, G, L, V, I, and P; $X^1$ is selected from L, M, S, and V; and $X^2$ and $X^3$ are each independently selected from S, T, A, V, G, and C.

In certain embodiments, the modified amino acid residue is positioned in a heavy chain CH2 region of the anti-CD22 antibody.

In certain embodiments, the modified amino acid residue is positioned in a heavy chain CH3 region of the anti-CD22 antibody.

Aspects of the present disclosure include a pharmaceutical composition that includes a conjugate as described herein, and a pharmaceutically acceptable excipient.

Aspects of the present disclosure include a method, where the method includes administering to a subject an effective amount of a conjugate as described herein.

Aspects of the present disclosure include a method of treating cancer in a subject. The method includes administering to the subject a therapeutically effective amount of a pharmaceutical composition that includes a conjugate as described herein, where the administering is effective to treat cancer in the subject.

Aspects of the present disclosure include a method of delivering a drug to a target site in a subject. The method includes administering to the subject a pharmaceutical composition that includes a conjugate as described herein, where the administering is effective to release a therapeutically effective amount of the drug from the conjugate at the target site in the subject.

BRIEF DESCRIPTION OF THE DRAWINGS

FIG. 1, panel B, shows antibodies carrying aldehyde moieties (2 per antibody) reacted with a Hydrazino-iso-Pictet-Spengler (HIPS) linker and payload to generate a site-specifically conjugated ADC. FIG. 1, panel C, shows HIPS chemistry, which proceeds through an intermediate hydrazonium ion followed by intramolecular alkylation with a nucleophilic indole to generate a stable C—C bond.

FIG. 8A-8C provide amino acid sequences of CD22 isoforms (Top to bottom: SEQ ID NOs:21-24).

FIG. 9A depicts a site map showing possible modification sites for generation of an aldehyde tagged Ig polypeptide. The upper sequence is the amino acid sequence of the conserved region of an IgG1 light chain polypeptide (SEQ ID NO:25) and shows possible modification sites in an Ig light chain; the lower sequence is the amino acid sequence of the conserved region of an Ig heavy chain polypeptide (SEQ ID NO:26; GenBank Accession No. AAG00909) and shows possible modification sites in an Ig heavy chain. The heavy and light chain numbering is based on the full-length heavy and light chains.

FIG. 9B depicts an alignment of immunoglobulin heavy chain constant regions for IgG1 (SEQ ID NO:27), IgG2 (SEQ ID NO:28), IgG3 (SEQ ID NO:29), IgG4 (SEQ ID NO:30), and IgA (SEQ ID NO:31), showing modification sites at which aldehyde tags can be provided in an immunoglobulin heavy chain. The heavy and light chain numbering is based on the full-heavy and light chains.

FIG. 9C depicts an alignment of immunoglobulin light chain constant regions (SEQ ID NOS:32-36), showing modification sites at which aldehyde tags can be provided in an immunoglobulin light chain.

FIG. 11, panel B) and reversed-phase (PLRP) chromatography (FIG. 11, panel C) to assess the drug-to-antibody ratio (DAR), which was 1.8.

(FIG. 17, panel C) Female CB17 ICR SCID mice (12/group) bearing Ramos xenografts were treated with vehicle alone, or with 5 or 10 mg/kg CAT-02-106 q4d×4. Dosing was initiatesd when tumors reached an average size of 246 $mm^3$. The data are presented as the mean±S.E.M.

(FIG. 19, panel A) Single dose WSU-DLCL2 study; (FIG. 19, panel B) Multidose WSU-DLCL2 study; (FIG. 19, panel C) Ramos study. Error bars indicate S.D.

(FIG. 20, panel A) Body weight was monitored at the times indicated. (FIG. 20, panel B) Alanine aminotransferase (ALT), and (FIG. 20, panel C) platelet counts were assessed at 5 and 12 days post-dose. The data are presented as the mean±S.D.

(FIG. 23, panel A) Aspartate transaminase (AST), (FIG. 23, panel B) alanine aminotransferase (ALT), (FIG. 23, panel C) platelets, and (FIG. 23, panel D) monocytes were monitored at the times indicated. The data are presented as the mean±S.D.

FIG. 24 (panel A and panel B)—Treatment with an anti-CD22 ADC according to the present disclosure reduced peripheral B cell populations in cynomolgus monkeys. Peripheral blood mononuclear cells from cynomolgus monkeys enrolled in the toxicity study were monitored by flow cytometry to detect the ratio of B cells (CD20+), T cells (CD3+), and NK cells (CD20−/CD3−) observed in animals pre-dose and at days 7, 14, 28, and 35. The data are presented as the mean±S.D.

FIG. 26 shows Table 3: summary of mean (±SD) pharmacokinetic and toxicokinetic (TK) parameters of total ADC values in animals dosed with an anti-CD22 ADC according to embodiments of the present disclosure.

DEFINITIONS

Figure 1:
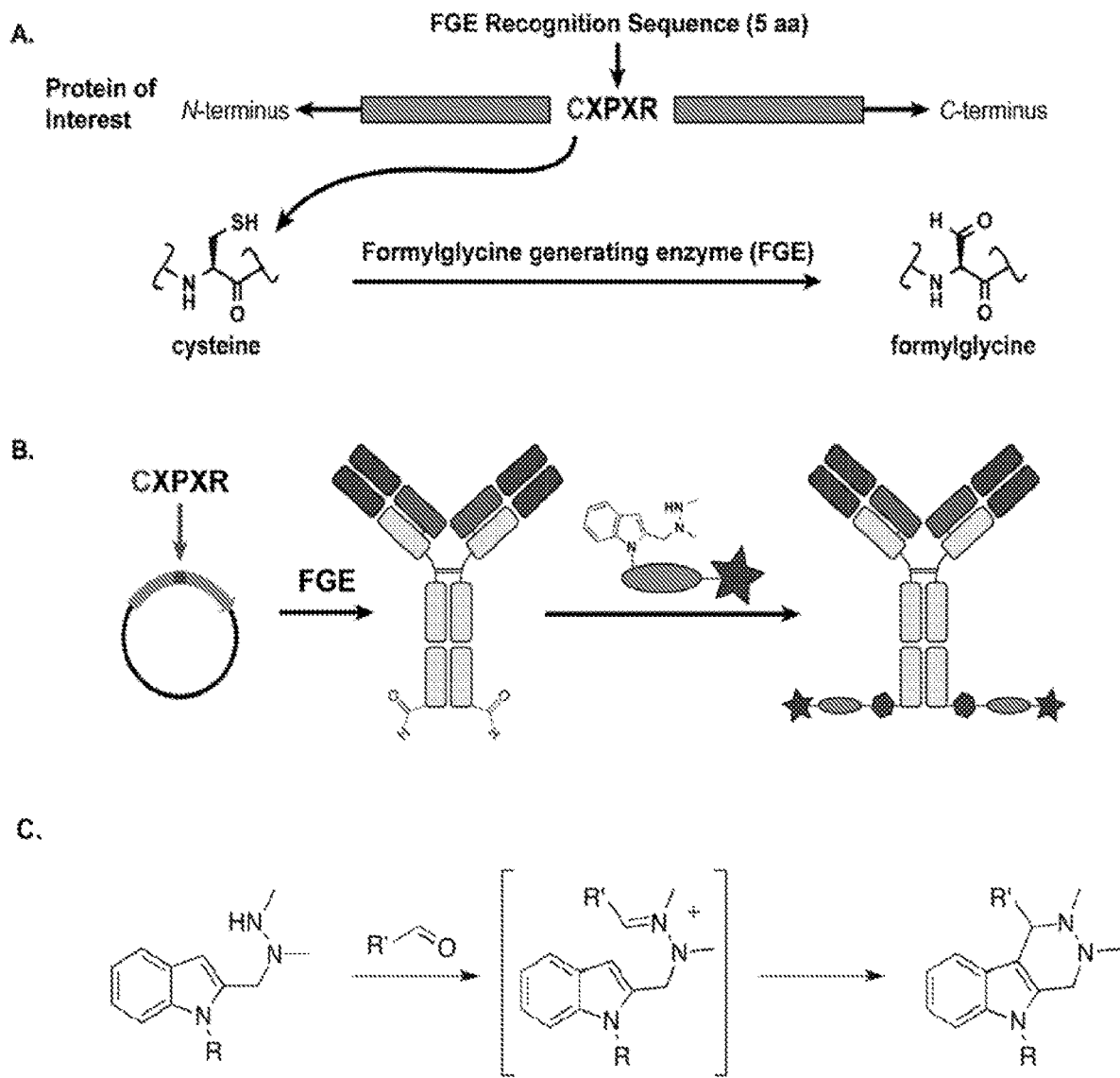
FIG. 1, panel A, shows a formylglycine-generating enzyme (FGE) recognition sequence (SEQ ID NO: 20) inserted at the desired location along the antibody backbone using standard molecular biology techniques. Upon expression, FGE, which is endogenous to eukaryotic cells, catalyzes the conversion of the Cys within the consensus sequence to a formylglycine residue (FG1y).

The following terms have the following meanings unless otherwise indicated. Any undefined terms have their art recognized meanings.

"Alkyl" refers to monovalent saturated aliphatic hydrocarbyl groups having from 1 to 10 carbon atoms and such as 1 to 6 carbon atoms, or 1 to 5, or 1 to 4, or 1 to 3 carbon atoms. This term includes, by way of example, linear and branched hydrocarbyl groups such as methyl ($CH_3$—), ethyl ($CH_3CH_2$—), n-propyl ($CH_3CH_2CH_2$—), isopropyl (($CH_3$)$_2$CH—), n-butyl ($CH_3CH_2CH_2CH_2$—), isobutyl (($CH_3$)$_2$CHCH$_2$—), sec-butyl (($CH_3$)($CH_3CH_2$)CH—), t-butyl (($CH_3$)$_3$C—), n-pentyl ($CH_3CH_2CH_2CH_2CH_2$—), and neopentyl (($CH_3$)$_3$CCH$_2$—).

The term "substituted alkyl" refers to an alkyl group as defined herein wherein one or more carbon atoms in the alkyl chain (except the $C_1$ carbon atom) have been optionally replaced with a heteroatom such as —O—, —N—, —S—, —S(O)$_n$— (where n is 0 to 2), —NR— (where R is hydrogen or alkyl) and having from 1 to 5 substituents selected from the group consisting of alkoxy, substituted alkoxy, cycloalkyl, substituted cycloalkyl, cycloalkenyl, substituted cycloalkenyl, acyl, acylamino, acyloxy, amino, aminoacyl, aminoacyloxy, oxyaminoacyl, azido, cyano, halogen, hydroxyl, oxo, thioketo, carboxyl, carboxylalkyl, thioaryloxy, thioheteroaryloxy, thioheterocyclooxy, thiol, thioalkoxy, substituted thioalkoxy, aryl, aryloxy, heteroaryl, heteroaryloxy, heterocyclyl, heterocyclooxy, hydroxyamino, alkoxyamino, nitro, —SO-alkyl, —SO-aryl, —SO-heteroaryl, —SO$_2$-alkyl, —SO$_2$-aryl, —SO$_2$-heteroaryl, and —NR$^a$R$^b$, wherein R' and R" may be the same or different and are chosen from hydrogen, optionally substituted alkyl, cycloalkyl, alkenyl, cycloalkenyl, alkynyl, aryl, heteroaryl and heterocyclic.

"Alkylene" refers to divalent aliphatic hydrocarbyl groups preferably having from 1 to 6 and more preferably 1 to 3 carbon atoms that are either straight-chained or branched, and which are optionally interrupted with one or more groups selected from —O—, —NR$^{10}$—, —NR$^{10}$C(O)—, —C(O)NR$^{10}$— and the like. This term includes, by way of example, methylene (—CH$_2$—), ethylene (—CH$_2$CH$_2$—), n-propylene (—CH$_2$CH$_2$CH$_2$—), iso-propylene (—CH$_2$CH(CH$_3$)—), (—C(CH$_3$)$_2$CH$_2$CH$_2$—), (—C(CH$_3$)$_2$CH$_2$C(O)—), (—C(CH$_3$)$_2$CH$_2$C(O)NH—), (—CH(CH$_3$)CH$_2$—), and the like.

"Substituted alkylene" refers to an alkylene group having from 1 to 3 hydrogens replaced with substituents as described for carbons in the definition of "substituted" below.

The term "alkane" refers to alkyl group and alkylene group, as defined herein.

The term "alkylaminoalkyl", "alkylaminoalkenyl" and "alkylaminoalkynyl" refers to the groups R'NHR"—where R' is alkyl group as defined herein and R' is alkylene, alkenylene or alkynylene group as defined herein.

The term "alkaryl" or "aralkyl" refers to the groups-alkylene-aryl and -substituted alkylene-aryl where alkylene, substituted alkylene and aryl are defined herein.

"Alkoxy" refers to the group —O-alkyl, wherein alkyl is as defined herein. Alkoxy includes, by way of example, methoxy, ethoxy, n-propoxy, isopropoxy, n-butoxy, t-butoxy, sec-butoxy, n-pentoxy, and the like. The term "alkoxy" also refers to the groups alkenyl-O—, cycloalkyl-O—, cycloalkenyl-O—, and alkynyl-O—, where alkenyl, cycloalkyl, cycloalkenyl, and alkynyl are as defined herein.

The term "substituted alkoxy" refers to the groups substituted alkyl-O—, substituted alkenyl-O—, substituted cycloalkyl-O—, substituted cycloalkenyl-O—, and substituted alkynyl-O— where substituted alkyl, substituted alkenyl, substituted cycloalkyl, substituted cycloalkenyl and substituted alkynyl are as defined herein.

The term "alkoxyamino" refers to the group —NH-alkoxy, wherein alkoxy is defined herein.

The term "haloalkoxy" refers to the groups alkyl-O— wherein one or more hydrogen atoms on the alkyl group have been substituted with a halo group and include, by way of examples, groups such as trifluoromethoxy, and the like.

The term "haloalkyl" refers to a substituted alkyl group as described above, wherein one or more hydrogen atoms on the alkyl group have been substituted with a halo group. Examples of such groups include, without limitation, fluoroalkyl groups, such as trifluoromethyl, difluoromethyl, trifluoroethyl and the like.

The term "alkylalkoxy" refers to the groups-alkylene-O-alkyl, alkylene-O-substituted alkyl, substituted alkylene-O-alkyl, and substituted alkylene-O-substituted alkyl wherein alkyl, substituted alkyl, alkylene and substituted alkylene are as defined herein.

The term "alkylthioalkoxy" refers to the group-alkylene-S-alkyl, alkylene-S-substituted alkyl, substituted alkylene-S-alkyl and substituted alkylene-S-substituted alkyl wherein alkyl, substituted alkyl, alkylene and substituted alkylene are as defined herein.

"Alkenyl" refers to straight chain or branched hydrocarbyl groups having from 2 to 6 carbon atoms and preferably 2 to 4 carbon atoms and having at least 1 and preferably from 1 to 2 sites of double bond unsaturation. This term includes, by way of example, bi-vinyl, allyl, and but-3-en-1-yl. Included within this term are the cis and trans isomers or mixtures of these isomers.

The term "substituted alkenyl" refers to an alkenyl group as defined herein having from 1 to 5 substituents, or from 1 to 3 substituents, selected from alkoxy, substituted alkoxy, cycloalkyl, substituted cycloalkyl, cycloalkenyl, substituted cycloalkenyl, acyl, acylamino, acyloxy, amino, substituted amino, aminoacyl, aminoacyloxy, oxyaminoacyl, azido, cyano, halogen, hydroxyl, oxo, thioketo, carboxyl, carboxylalkyl, thioaryloxy, thioheteroaryloxy, thioheterocyclooxy, thiol, thioalkoxy, substituted thioalkoxy, aryl, aryloxy, heteroaryl, heteroaryloxy, heterocyclyl, heterocyclooxy, hydroxyamino, alkoxyamino, nitro, —SO-alkyl, —SO— substituted alkyl, —SO-aryl, —SO-heteroaryl, —SO$_2$-alkyl, —SO$_2$-substituted alkyl, —SO$_2$-aryl and —SO$_2$-heteroaryl.

"Alkynyl" refers to straight or branched monovalent hydrocarbyl groups having from 2 to 6 carbon atoms and preferably 2 to 3 carbon atoms and having at least 1 and preferably from 1 to 2 sites of triple bond unsaturation. Examples of such alkynyl groups include acetylenyl (—C≡CH), and propargyl (—CH$_2$C≡CH).

The term "substituted alkynyl" refers to an alkynyl group as defined herein having from 1 to 5 substituents, or from 1 to 3 substituents, selected from alkoxy, substituted alkoxy, cycloalkyl, substituted cycloalkyl, cycloalkenyl, substituted cycloalkenyl, acyl, acylamino, acyloxy, amino, substituted amino, aminoacyl, aminoacyloxy, oxyaminoacyl, azido, cyano, halogen, hydroxyl, oxo, thioketo, carboxyl, carboxylalkyl, thioaryloxy, thioheteroaryloxy, thioheterocyclooxy, thiol, thioalkoxy, substituted thioalkoxy, aryl, aryloxy, heteroaryl, heteroaryloxy, heterocyclyl, heterocyclooxy, hydroxyamino, alkoxyamino, nitro, —SO-alkyl, —SO— substituted alkyl, —SO-aryl, —SO-heteroaryl, —SO$_2$-alkyl, —SO$_2$-substituted alkyl, —SO$_2$-aryl, and —SO$_2$-heteroaryl.

"Alkynyloxy" refers to the group —O-alkynyl, wherein alkynyl is as defined herein. Alkynyloxy includes, by way of example, ethynyloxy, propynyloxy, and the like.

"Acyl" refers to the groups H—C(O)—, alkyl-C(O)—, substituted alkyl-C(O)—, alkenyl-C(O)—, substituted alkenyl-C(O)—, alkynyl-C(O)—, substituted alkynyl-C(O)—, cycloalkyl-C(O)—, substituted cycloalkyl-C(O)—, cycloalkenyl-C(O)—, substituted cycloalkenyl-C(O)—, aryl-C(O)—, substituted aryl-C(O)—, heteroaryl-C(O)—, substituted heteroaryl-C(O)—, heterocyclyl-C(O)—, and substituted heterocyclyl-C(O)—, wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein. For example, acyl includes the "acetyl" group CH$_3$C(O)—

"Acylamino" refers to the groups —NR$^{20}$C(O)alkyl, —NR$^{20}$C(O)substituted alkyl, NR$^{20}$C(O)cycloalkyl, —NR$^{20}$C(O)substituted cycloalkyl, —NR$^{20}$C(O)cycloalkenyl, —NR$^{20}$C(O)substituted cycloalkenyl, —NR$^{20}$C(O)alkenyl, —NR$^{20}$C(O)substituted alkenyl, —NR$^{20}$C(O)alkynyl, —NR$^{20}$C(O)substituted alkynyl, —NR$^{20}$C(O)aryl, —NR$^{20}$C(O)substituted aryl, —NR$^{20}$C(O)heteroaryl, —NR$^{20}$C(O)substituted heteroaryl, —NR$^{20}$C(O)heterocyclic, and —NR$^{20}$C(O)substituted heterocyclic, wherein R$^{20}$ is hydrogen or alkyl and wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

"Aminocarbonyl" or the term "aminoacyl" refers to the group —C(O)NR$^{21}$R$^{22}$, wherein R$^{21}$ and R$^{22}$ independently are selected from the group consisting of hydrogen, alkyl, substituted alkyl, alkenyl, substituted alkenyl, alkynyl, substituted alkynyl, aryl, substituted aryl, cycloalkyl, substituted cycloalkyl, cycloalkenyl, substituted cycloalkenyl, heteroaryl, substituted heteroaryl, heterocyclic, and substituted heterocyclic and where R$^{21}$ and R$^{22}$ are optionally joined together with the nitrogen bound thereto to form a heterocyclic or substituted heterocyclic group, and wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

"Aminocarbonylamino" refers to the group —NR$^{21}$C(O) NR$^{22}$R$^{23}$ where R$^{21}$, R$^{22}$, and R$^{23}$ are independently selected from hydrogen, alkyl, aryl or cycloalkyl, or where two R groups are joined to form a heterocyclyl group.

The term "alkoxycarbonylamino" refers to the group —NRC(O)OR where each R is independently hydrogen, alkyl, substituted alkyl, aryl, heteroaryl, or heterocyclyl wherein alkyl, substituted alkyl, aryl, heteroaryl, and heterocyclyl are as defined herein.

The term "acyloxy" refers to the groups alkyl-C(O)O—, substituted alkyl-C(O)O—, cycloalkyl-C(O)O—, substituted cycloalkyl-C(O)O—, aryl-C(O)O—, heteroaryl-C(O) O—, and heterocyclyl-C(O)O— wherein alkyl, substituted alkyl, cycloalkyl, substituted cycloalkyl, aryl, heteroaryl, and heterocyclyl are as defined herein.

"Aminosulfonyl" refers to the group —SO$_2$NR$^{21}$R$^{22}$, wherein R$^{21}$ and R$^{22}$ independently are selected from the group consisting of hydrogen, alkyl, substituted alkyl, alkenyl, substituted alkenyl, alkynyl, substituted alkynyl, aryl, substituted aryl, cycloalkyl, substituted cycloalkyl, cycloalkenyl, substituted cycloalkenyl, heteroaryl, substituted heteroaryl, heterocyclic, substituted heterocyclic and where R$^{21}$ and R$^{22}$ are optionally joined together with the nitrogen bound thereto to form a heterocyclic or substituted heterocyclic group and alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic and substituted heterocyclic are as defined herein.

"Sulfonylamino" refers to the group —NR$^{21}$SO$_2$R$^{22}$, wherein R$^{21}$ and R$^{22}$ independently are selected from the group consisting of hydrogen, alkyl, substituted alkyl, alkenyl, substituted alkenyl, alkynyl, substituted alkynyl, aryl, substituted aryl, cycloalkyl, substituted cycloalkyl, cycloalkenyl, substituted cycloalkenyl, heteroaryl, substituted heteroaryl, heterocyclic, and substituted heterocyclic and where R$^{21}$ and R$^{22}$ are optionally joined together with the atoms bound thereto to form a heterocyclic or substituted heterocyclic group, and wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

"Aryl" or "Ar" refers to a monovalent aromatic carbocyclic group of from 6 to 18 carbon atoms having a single ring (such as is present in a phenyl group) or a ring system having multiple condensed rings (examples of such aromatic ring systems include naphthyl, anthryl and indanyl) which condensed rings may or may not be aromatic, provided that the point of attachment is through an atom of an aromatic ring. This term includes, by way of example, phenyl and naphthyl. Unless otherwise constrained by the definition for the aryl substituent, such aryl groups can optionally be substituted with from 1 to 5 substituents, or from 1 to 3 substituents, selected from acyloxy, hydroxy, thiol, acyl, alkyl, alkoxy, alkenyl, alkynyl, cycloalkyl, cycloalkenyl, substituted alkyl, substituted alkoxy, substituted alkenyl, substituted alkynyl, substituted cycloalkyl, substituted cycloalkenyl, amino, substituted amino, aminoacyl, acylamino, alkaryl, aryl, aryloxy, azido, carboxyl, carboxylalkyl, cyano, halogen, nitro, heteroaryl, heteroaryloxy, heterocyclyl, heterocyclooxy, aminoacyloxy, oxyacylamino, thioalkoxy, substituted thioalkoxy, thioaryloxy, thioheteroaryloxy, —SO-alkyl, —SO-substituted alkyl, —SO-aryl, —SO-heteroaryl, —SO$_2$-alkyl, —SO$_2$-substituted alkyl, —SO$_2$-aryl, —SO$_2$-heteroaryl and trihalomethyl.

"Aryloxy" refers to the group —O-aryl, wherein aryl is as defined herein, including, by way of example, phenoxy, naphthoxy, and the like, including optionally substituted aryl groups as also defined herein.

"Amino" refers to the group —NH$_2$.

The term "substituted amino" refers to the group —NRR where each R is independently selected from the group consisting of hydrogen, alkyl, substituted alkyl, cycloalkyl, substituted cycloalkyl, alkenyl, substituted alkenyl, cycloalkenyl, substituted cycloalkenyl, alkynyl, substituted alkynyl, aryl, heteroaryl, and heterocyclyl provided that at least one R is not hydrogen.

The term "azido" refers to the group —N$_3$.

"Carboxyl," "carboxy" or "carboxylate" refers to —CO$_2$H or salts thereof.

"Carboxyl ester" or "carboxy ester" or the terms "carboxyalkyl" or "carboxylalkyl" refers to the groups —C(O)O-alkyl, —C(O)O-substituted alkyl, —C(O)O-alkenyl, —C(O)O-substituted alkenyl, —C(O)O-alkynyl, —C(O)O-substituted alkynyl, —C(O)O-aryl, —C(O)O-substituted aryl, —C(O)O-cycloalkyl, —C(O)O-substituted cycloalkyl, —C(O)O-cycloalkenyl, —C(O)O-substituted cycloalkenyl, —C(O)O-heteroaryl, —C(O)O-substituted heteroaryl, —C(O)O-heterocyclic, and —C(O)O-substituted heterocyclic, wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

"(Carboxyl ester)oxy" or "carbonate" refers to the groups —O—C(O)O— alkyl, —O—C(O)O-substituted alkyl, —O—C(O)O-alkenyl, —O—C(O)O-substituted alkenyl, —O—C(O)O-alkynyl, —O—C(O)O-substituted alkynyl, —O—C(O)O-aryl, —O—C(O)O-substituted aryl, —O—C(O)O-cycloalkyl, —O—C(O)O-substituted cycloalkyl, —O—C(O)O-cycloalkenyl, —O—C(O)O— substituted cycloalkenyl, —O—C(O)O-heteroaryl, —O—C(O)O-substituted heteroaryl, —O—C(O)O-heterocyclic, and —O—C(O)O-substituted heterocyclic, wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

"Cyano" or "nitrile" refers to the group —CN.

"Cycloalkyl" refers to cyclic alkyl groups of from 3 to 10 carbon atoms having single or multiple cyclic rings including fused, bridged, and spiro ring systems. Examples of suitable cycloalkyl groups include, for instance, adamantyl, cyclopropyl, cyclobutyl, cyclopentyl, cyclooctyl and the like. Such cycloalkyl groups include, by way of example, single ring structures such as cyclopropyl, cyclobutyl, cyclopentyl, cyclooctyl, and the like, or multiple ring structures such as adamantanyl, and the like.

The term "substituted cycloalkyl" refers to cycloalkyl groups having from 1 to 5 substituents, or from 1 to 3 substituents, selected from alkyl, substituted alkyl, alkoxy, substituted alkoxy, cycloalkyl, substituted cycloalkyl, cycloalkenyl, substituted cycloalkenyl, acyl, acylamino, acyloxy, amino, substituted amino, aminoacyl, aminoacyloxy, oxyaminoacyl, azido, cyano, halogen, hydroxyl, oxo, thioketo, carboxyl, carboxylalkyl, thioaryloxy, thioheteroaryloxy, thioheterocyclooxy, thiol, thioalkoxy, substituted thioalkoxy, aryl, aryloxy, heteroaryl, heteroaryloxy, heterocyclyl, heterocyclooxy, hydroxyamino, alkoxyamino, nitro, —SO-alkyl, —SO-substituted alkyl, —SO-aryl, —SO-heteroaryl, —SO$_2$-alkyl, —SO$_2$-substituted alkyl, —SO$_2$-aryl and —SO$_2$-heteroaryl.

"Cycloalkenyl" refers to non-aromatic cyclic alkyl groups of from 3 to 10 carbon atoms having single or multiple rings and having at least one double bond and preferably from 1 to 2 double bonds.

The term "substituted cycloalkenyl" refers to cycloalkenyl groups having from 1 to 5 substituents, or from 1 to 3 substituents, selected from alkoxy, substituted alkoxy, cycloalkyl, substituted cycloalkyl, cycloalkenyl, substituted cycloalkenyl, acyl, acylamino, acyloxy, amino, substituted amino, aminoacyl, aminoacyloxy, oxyaminoacyl, azido, cyano, halogen, hydroxyl, keto, thioketo, carboxyl, carboxylalkyl, thioaryloxy, thioheteroaryloxy, thioheterocyclooxy, thiol, thioalkoxy, substituted thioalkoxy, aryl, aryloxy, heteroaryl, heteroaryloxy, heterocyclyl, heterocyclooxy, hydroxyamino, alkoxyamino, nitro, —SO-alkyl, —SO-substituted alkyl, —SO-aryl, —SO-heteroaryl, —SO$_2$-alkyl, —SO$_2$-substituted alkyl, —SO$_2$-aryl and —SO$_2$-heteroaryl.

"Cycloalkynyl" refers to non-aromatic cycloalkyl groups of from 5 to 10 carbon atoms having single or multiple rings and having at least one triple bond.

"Cycloalkoxy" refers to —O-cycloalkyl.

"Cycloalkenyloxy" refers to —O-cycloalkenyl.

"Halo" or "halogen" refers to fluoro, chloro, bromo, and iodo.

"Hydroxy" or "hydroxyl" refers to the group —OH.

"Heteroaryl" refers to an aromatic group of from 1 to 15 carbon atoms, such as from 1 to 10 carbon atoms and 1 to 10 heteroatoms selected from the group consisting of oxygen, nitrogen, and sulfur within the ring. Such heteroaryl groups can have a single ring (such as, pyridinyl, imidazolyl or furyl) or multiple condensed rings in a ring system (for example as in groups such as, indolizinyl, quinolinyl, benzofuran, benzimidazolyl or benzothienyl), wherein at least one ring within the ring system is aromatic. To satisfy valence requirements, any heteroatoms in such heteroaryl rings may or may not be bonded to H or a substituent group, e.g., an alkyl group or other substituent as described herein. In certain embodiments, the nitrogen and/or sulfur ring atom(s) of the heteroaryl group are optionally oxidized to provide for the N-oxide (N→O), sulfinyl, or sulfonyl moieties. This term includes, by way of example, pyridinyl, pyrrolyl, indolyl, thiophenyl, and furanyl. Unless otherwise constrained by the definition for the heteroaryl substituent, such heteroaryl groups can be optionally substituted with 1 to 5 substituents, or from 1 to 3 substituents, selected from acyloxy, hydroxy, thiol, acyl, alkyl, alkoxy, alkenyl, alkynyl, cycloalkyl, cycloalkenyl, substituted alkyl, substituted alkoxy, substituted alkenyl, substituted alkynyl, substituted cycloalkyl, substituted cycloalkenyl, amino, substituted amino, aminoacyl, acylamino, alkaryl, aryl, aryloxy, azido, carboxyl, carboxylalkyl, cyano, halogen, nitro, heteroaryl, heteroaryloxy, heterocyclyl, heterocyclooxy, aminoacyloxy, oxyacylamino, thioalkoxy, substituted thioalkoxy, thioaryloxy, thioheteroaryloxy, —SO-alkyl, —SO-substituted alkyl, —SO-aryl, —SO-heteroaryl, —SO$_2$-alkyl, —SO$_2$-substituted alkyl, —SO$_2$-aryl and —SO$_2$-heteroaryl, and trihalomethyl.

The term "heteroaralkyl" refers to the groups-alkylene-heteroaryl where alkylene and heteroaryl are defined herein. This term includes, by way of example, pyridylmethyl, pyridylethyl, indolylmethyl, and the like.

"Heteroaryloxy" refers to —O-heteroaryl.

"Heterocycle," "heterocyclic," "heterocycloalkyl," and "heterocyclyl" refer to a saturated or unsaturated group having a single ring or multiple condensed rings, including fused bridged and spiro ring systems, and having from 3 to 20 ring atoms, including 1 to 10 hetero atoms. These ring atoms are selected from nitrogen, sulfur, or oxygen, where, in fused ring systems, one or more of the rings can be cycloalkyl, aryl, or heteroaryl, provided that the point of attachment is through the non-aromatic ring. In certain embodiments, the nitrogen and/or sulfur atom(s) of the heterocyclic group are optionally oxidized to provide for the N-oxide, —S(O)—, or —SO$_2$— moieties. To satisfy valence requirements, any heteroatoms in such heterocyclic rings may or may not be bonded to one or more H or one or more substituent group(s), e.g., an alkyl group or other substituent as described herein.

Examples of heterocycles and heteroaryls include, but are not limited to, azetidine, pyrrole, imidazole, pyrazole, pyridine, pyrazine, pyrimidine, pyridazine, indolizine, isoindole, indole, dihydroindole, indazole, purine, quinolizine, isoquinoline, quinoline, phthalazine, naphthylpyridine, quinoxaline, quinazoline, cinnoline, pteridine, carbazole, carboline, phenanthridine, acridine, phenanthroline, isothiazole, phenazine, isoxazole, phenoxazine, phenothiazine, imidazolidine, imidazoline, piperidine, piperazine, indoline, phthalimide, 1,2,3,4-tetrahydroisoquinoline, 4,5,6,7-tetrahydrobenzo[b]thiophene, thiazole, thiazolidine, thiophene, benzo[b]thiophene, morpholinyl, thiomorpholinyl (also referred to as thiamorpholinyl), 1,1-dioxothiomorpholinyl, piperidinyl, pyrrolidine, tetrahydrofuranyl, and the like.

Unless otherwise constrained by the definition for the heterocyclic substituent, such heterocyclic groups can be optionally substituted with 1 to 5, or from 1 to 3 substituents, selected from alkoxy, substituted alkoxy, cycloalkyl, substituted cycloalkyl, cycloalkenyl, substituted cycloalkenyl, acyl, acylamino, acyloxy, amino, substituted amino, aminoacyl, aminoacyloxy, oxyaminoacyl, azido, cyano, halogen, hydroxyl, oxo, thioketo, carboxyl, carboxylalkyl, thioaryloxy, thioheteroaryloxy, thioheterocyclooxy, thiol, thioalkoxy, substituted thioalkoxy, aryl, aryloxy, heteroaryl, heteroaryloxy, heterocyclyl, heterocyclooxy, hydroxyamino, alkoxyamino, nitro, —SO-alkyl, —SO-substituted alkyl, —SO-aryl, —SO-heteroaryl, —SO$_2$-alkyl, —SO$_2$-substituted alkyl, —SO$_2$-aryl, —SO$_2$-heteroaryl, and fused heterocycle.

"Heterocyclyloxy" refers to the group —O-heterocyclyl.

The term "heterocyclylthio" refers to the group heterocyclic-S—.

The term "heterocyclene" refers to the diradical group formed from a heterocycle, as defined herein.

The term "hydroxyamino" refers to the group —NHOH.

"Nitro" refers to the group —NO$_2$.

"Oxo" refers to the atom (=O).

"Sulfonyl" refers to the group SO$_2$-alkyl, SO$_2$-substituted alkyl, SO$_2$-alkenyl, SO$_2$-substituted alkenyl, SO$_2$-cycloalkyl, SO$_2$-substituted cycloalkyl, SO$_2$-cycloalkenyl, SO$_2$-substituted cylcoalkenyl, SO$_2$-aryl, SO$_2$-substituted aryl, SO$_2$-heteroaryl, SO$_2$-substituted heteroaryl, SO$_2$-heterocyclic, and SO$_2$-substituted heterocyclic, wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein. Sulfonyl includes, by way of example, methyl-SO$_2$—, phenyl-SO$_2$—, and 4-methylphenyl-SO$_2$—.

"Sulfonyloxy" refers to the group —OSO$_2$-alkyl, OSO$_2$-substituted alkyl, OSO$_2$-alkenyl, OSO$_2$-substituted alkenyl, OSO$_2$-cycloalkyl, OSO$_2$-substituted cycloalkyl, OSO$_2$-cycloalkenyl, OSO$_2$-substituted cylcoalkenyl, OSO$_2$-aryl, OSO$_2$-substituted aryl, OSO$_2$-heteroaryl, OSO$_2$-substituted heteroaryl, OSO$_2$-heterocyclic, and OSO$_2$ substituted heterocyclic, wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

The term "aminocarbonyloxy" refers to the group —OC(O)NRR where each R is independently hydrogen, alkyl, substituted alkyl, aryl, heteroaryl, or heterocyclic wherein alkyl, substituted alkyl, aryl, heteroaryl and heterocyclic are as defined herein.

"Thiol" refers to the group —SH.

"Thioxo" or the term "thioketo" refers to the atom (=S).

"Alkylthio" or the term "thioalkoxy" refers to the group —S-alkyl, wherein alkyl is as defined herein. In certain embodiments, sulfur may be oxidized to —S(O)—. The sulfoxide may exist as one or more stereoisomers.

The term "substituted thioalkoxy" refers to the group —S-substituted alkyl.

The term "thioaryloxy" refers to the group aryl-S— wherein the aryl group is as defined herein including optionally substituted aryl groups also defined herein.

The term "thioheteroaryloxy" refers to the group heteroaryl-S— wherein the heteroaryl group is as defined herein including optionally substituted aryl groups as also defined herein.

The term "thioheterocyclooxy" refers to the group heterocyclyl-S— wherein the heterocyclyl group is as defined herein including optionally substituted heterocyclyl groups as also defined herein.

In addition to the disclosure herein, the term "substituted," when used to modify a specified group or radical, can also mean that one or more hydrogen atoms of the specified group or radical are each, independently of one another, replaced with the same or different substituent groups as defined below.

In addition to the groups disclosed with respect to the individual terms herein, substituent groups for substituting for one or more hydrogens (any two hydrogens on a single carbon can be replaced with =O, =$NR^{70}$, =N—$OR^{70}$, =$N_2$ or =S) on saturated carbon atoms in the specified group or radical are, unless otherwise specified, —$R^{60}$, halo, =O, —$OR^{70}$, —$SR^{70}$, —$NR^{80}R^{80}$, trihalomethyl, —CN, —OCN, —SCN, —NO, —$NO_2$, =$N_2$, —$N_3$, —$SO_2R^{70}$, —$SO_2O^-M^+$, —$SO_2OR^{70}$, —$OSO_2R^{70}$, —$OSO_2O^-M^+$, —$OSO_2OR^{70}$, —P(O)(O—$)_2(M^+)_2$, —P(O)($OR^{70}$)$O^-M^+$, —P(O)($OR^{70}$)$_2$, —C(O)$R^{70}$, —C(S)$R^{70}$, —C($NR^{70}$)$R^{70}$, —C(O)$O^-M^+$, —C(O)$OR^{70}$, —C(S)$OR^{70}$, —C(O)$NR^{80}R^{80}$, —C($NR^{70}$)$NR^{80}R^{80}$, —OC(O)$R^{70}$, —OC(S)$R^{70}$, —OC(O)$O^-M^+$, —OC(O)$OR^{70}$, —OC(S)$OR^{70}$, —$NR^{70}$C(O)$R^{70}$, —$NR^{70}$C(S)$R^{70}$, —$NR^{70}CO_2^-M^+$, —$NR^{70}CO_2R^{70}$, —$NR^{70}$C(S)$OR^{70}$, —$NR^{70}$C(O)$NR^{80}R^{80}$, —$NR^{70}$C($NR^{70}$)$R^{70}$ and —$NR^{70}$C($NR^{70}$)$NR^{80}R^{80}$, where $R^{60}$ is selected from the group consisting of optionally substituted alkyl, cycloalkyl, heteroalkyl, heterocycloalkylalkyl, cycloalkylalkyl, aryl, arylalkyl, heteroaryl and heteroarylalkyl, each $R^{70}$ is independently hydrogen or $R^{60}$; each $R^{80}$ is independently $R^{70}$ or alternatively, two $R^{80}$'s, taken together with the nitrogen atom to which they are bonded, form a 5-, 6- or 7-membered heterocycloalkyl which may optionally include from 1 to 4 of the same or different additional heteroatoms selected from the group consisting of O, N and S, of which N may have —H or $C_1$-$C_3$ alkyl substitution; and each $M^+$ is a counter ion with a net single positive charge. Each $M^+$ may independently be, for example, an alkali ion, such as $K^+$, $Na^+$, $Li^+$; an ammonium ion, such as $^+N(R^{60})_4$; or an alkaline earth ion, such as $[Ca^{2+}]_{0.5}$, $[Mg^{2+}]_{0.5}$, or $[Ba^{2+}]_{0.5}$ ("subscript 0.5 means that one of the counter ions for such divalent alkali earth ions can be an ionized form of a compound of the invention and the other a typical counter ion such as chloride, or two ionized compounds disclosed herein can serve as counter ions for such divalent alkali earth ions, or a doubly ionized compound of the invention can serve as the counter ion for such divalent alkali earth ions). As specific examples, —$NR^{80}R^{80}$ is meant to include —$NH_2$, —NH-alkyl, N-pyrrolidinyl, N-piperazinyl, 4N-methyl-piperazin-1-yl and N-morpholinyl.

In addition to the disclosure herein, substituent groups for hydrogens on unsaturated carbon atoms in "substituted" alkene, alkyne, aryl and heteroaryl groups are, unless otherwise specified, —$R^{60}$, halo, —$O^-M^+$, —$OR^{70}$, —$SR^{70}$, —$S^-M^+$, —$NR^{80}R^{80}$, trihalomethyl, —$CF_3$, —CN, —OCN, —SCN, —NO, —$NO_2$, —$N_3$, —$SO_2R^{70}$, —$SO_3^-M^+$, —$SO_3R^{70}$, —$OSO_2R^{70}$, —$OSO_3^-M^+$, —$OSO_3R^{70}$, —$PO_3^{-2}$ $(M^+)_2$, —P(O)($OR^{70}$)$O^-M^+$, —P(O)($OR^{70}$)$_2$, —C(O)$R^{70}$, —C(S)$R^{70}$, —C($NR^{70}$)$R^{70}$, —$CO_2^-M^+$, —$CO_2R^{70}$, —C(S)$OR^{70}$, —C(O)$NR^{80}$, —$OR^{80}$, —C($NR^{70}$)$NR^{80}R^{80}$, —OC(O)$R^{70}$, —OC(S)$R^{70}$, —$OCO_2^-M^+$, —$OCO_2R^{70}$, —OC(S)$OR^{70}$, —$NR^{70}$C(O)$R^{70}$, —$NR^{70}$, —OC(S)$R^{70}$, —$NR^{70}CO_2^-M^+$, —$NR^{70}CO_2R^{70}$, —$NR^{70}$C(S)$OR^{70}$, —$NR^{70}$C(O)$NR^{80}R^{80}$, —$NR^{70}$C($NR^{70}$)$R^{70}$ and —$NR^{70}$C($NR^{70}$)$NR^{80}R^{80}$, where $R^{60}$, $R^{70}$, $R^{80}$ and $M^+$ are as previously defined, provided that in case of substituted alkene or alkyne, the substituents are not —$O^-M^+$, —$OR^{70}$, —$SR^{70}$, or —$S^-M^+$.

In addition to the groups disclosed with respect to the individual terms herein, substituent groups for hydrogens on nitrogen atoms in "substituted" heteroalkyl and cycloheteroalkyl groups are, unless otherwise specified, —$R^{60}$, —$O^-M^+$, —$OR^{70}$, —$SR^{70}$, —$S^-M^+$, —$NR^{80}R^{80}$, trihalomethyl, —$CF_3$, —CN, —NO, —$NO_2$, —$S(O)_2R^{70}$, —$S(O)_2O^-M^+$, —$S(O)_2OR^{70}$, —OS(O)$_2R^{70}$, —OS(O)$_2O^-M^+$, —OS(O)$_2OR^{70}$, —P(O)($O^-)_2(M^+)_2$, —P(O)($OR^{70}$)$O^-M^+$, —P(O)($OR^{70}$)($OR^{70}$), —C(O)$R^{70}$, —C(S)$R^{70}$, —C($NR^{70}$)$R^{70}$, —C(O)$OR^{70}$, —C(S)$OR^{70}$, —C(O)$NR^{80}R^{80}$, —C($NR^{70}$)$NR^{80}$, —$OR^{80}$, —OC(O)$R^{70}$, —OC(S)$R^{70}$, —OC(O)$OR^{70}$, —OC(S)$OR^{70}$, —$NR^{70}$C(O)$R^{70}$, —$NR^{70}$C(S)$R^{70}$, —$NR^{70}$C(O)$OR^{70}$, —$NR^{70}$C(S)$OR^{70}$, —$NR^{70}$C(O)$NR^{80}R^{80}$, —$NR^{70}$C($NR^{70}$)$R^{70}$ and —$NR^{70}$C($NR^{70}$)$NR^{80}R^{80}$, where $R^{60}$, $R^{70}$, $R^{80}$ and $M^+$ are as previously defined.

In addition to the disclosure herein, in a certain embodiment, a group that is substituted has 1, 2, 3, or 4 substituents, 1, 2, or 3 substituents, 1 or 2 substituents, or 1 substituent.

It is understood that in all substituted groups defined above, polymers arrived at by defining substituents with further substituents to themselves (e.g., substituted aryl having a substituted aryl group as a substituent which is itself substituted with a substituted aryl group, which is further substituted by a substituted aryl group, etc.) are not intended for inclusion herein. In such cases, the maximum number of such substitutions is three. For example, serial substitutions of substituted aryl groups specifically contemplated herein are limited to substituted aryl-(substituted aryl)-substituted aryl.

Unless indicated otherwise, the nomenclature of substituents that are not explicitly defined herein are arrived at by naming the terminal portion of the functionality followed by the adjacent functionality toward the point of attachment. For example, the substituent "arylalkyloxycarbonyl" refers to the group (aryl)-(alkyl)-O—C(O)—.

As to any of the groups disclosed herein which contain one or more substituents, it is understood, of course, that such groups do not contain any substitution or substitution patterns which are sterically impractical and/or synthetically non-feasible. In addition, the subject compounds include all stereochemical isomers arising from the substitution of these compounds.

The term "pharmaceutically acceptable salt" means a salt which is acceptable for administration to a patient, such as a mammal (salts with counterions having acceptable mammalian safety for a given dosage regime). Such salts can be derived from pharmaceutically acceptable inorganic or organic bases and from pharmaceutically acceptable inorganic or organic acids. "Pharmaceutically acceptable salt" refers to pharmaceutically acceptable salts of a compound, which salts are derived from a variety of organic and inorganic counter ions well known in the art and include, by way of example only, sodium, potassium, calcium, magnesium, ammonium, tetraalkylammonium, and the like; and when the molecule contains a basic functionality, salts of organic or inorganic acids, such as hydrochloride, hydrobromide, formate, tartrate, besylate, mesylate, acetate, maleate, oxalate, and the like.

The term "salt thereof" means a compound formed when a proton of an acid is replaced by a cation, such as a metal cation or an organic cation and the like. Where applicable, the salt is a pharmaceutically acceptable salt, although this is not required for salts of intermediate compounds that are not intended for administration to a patient. By way of example, salts of the present compounds include those wherein the compound is protonated by an inorganic or organic acid to form a cation, with the conjugate base of the inorganic or organic acid as the anionic component of the salt.

"Solvate" refers to a complex formed by combination of solvent molecules with molecules or ions of the solute. The solvent can be an organic compound, an inorganic compound, or a mixture of both. Some examples of solvents include, but are not limited to, methanol, N,N-dimethylformamide, tetrahydrofuran, dimethylsulfoxide, and water. When the solvent is water, the solvate formed is a hydrate.

"Stereoisomer" and "stereoisomers" refer to compounds that have same atomic connectivity but different atomic arrangement in space. Stereoisomers include cis-trans isomers, E and Z isomers, enantiomers, and diastereomers.

"Tautomer" refers to alternate forms of a molecule that differ only in electronic bonding of atoms and/or in the position of a proton, such as enol-keto and imine-enamine tautomers, or the tautomeric forms of heteroaryl groups containing a —N=C(H)—NH— ring atom arrangement, such as pyrazoles, imidazoles, benzimidazoles, triazoles, and tetrazoles. A person of ordinary skill in the art would recognize that other tautomeric ring atom arrangements are possible.

It will be appreciated that the term "or a salt or solvate or stereoisomer thereof" is intended to include all permutations of salts, solvates and stereoisomers, such as a solvate of a pharmaceutically acceptable salt of a stereoisomer of subject compound.

"Pharmaceutically effective amount" and "therapeutically effective amount" refer to an amount of a compound sufficient to treat a specified disorder or disease or one or more of its symptoms and/or to prevent the occurrence of the disease or disorder. In reference to tumorigenic proliferative disorders, a pharmaceutically or therapeutically effective amount comprises an amount sufficient to, among other things, cause the tumor to shrink or decrease the growth rate of the tumor.

"Patient" refers to human and non-human subjects, especially mammalian subjects.

The term "treating" or "treatment" as used herein means the treating or treatment of a disease or medical condition in a patient, such as a mammal (particularly a human) that includes: (a) preventing the disease or medical condition from occurring, such as, prophylactic treatment of a subject; (b) ameliorating the disease or medical condition, such as, eliminating or causing regression of the disease or medical condition in a patient; (c) suppressing the disease or medical condition, for example by, slowing or arresting the development of the disease or medical condition in a patient; or (d) alleviating a symptom of the disease or medical condition in a patient.

The terms "polypeptide," "peptide," and "protein" are used interchangeably herein to refer to a polymeric form of amino acids of any length. Unless specifically indicated otherwise, "polypeptide," "peptide," and "protein" can include genetically coded and non-coded amino acids, chemically or biochemically modified or derivatized amino acids, and polypeptides having modified peptide backbones. The term includes fusion proteins, including, but not limited to, fusion proteins with a heterologous amino acid sequence, fusions with heterologous and homologous leader sequences, proteins which contain at least one N-terminal methionine residue (e.g., to facilitate production in a recombinant bacterial host cell); immunologically tagged proteins; and the like.

"Native amino acid sequence" or "parent amino acid sequence" are used interchangeably herein to refer to the amino acid sequence of a polypeptide prior to modification to include a modified amino acid residue.

The terms "amino acid analog," "unnatural amino acid," and the like may be used interchangeably, and include amino acid-like compounds that are similar in structure and/or overall shape to one or more amino acids commonly found in naturally occurring proteins (e.g., Ala or A, Cys or C, Asp or D, Glu or E, Phe or F, Gly or G, His or H, Ile or I, Lys or K, Leu or L, Met or M, Asn or N, Pro or P, Gln or Q, Arg or R, Ser or S, Thr or T, Val or V, Trp or W, Tyr or Y). Amino acid analogs also include natural amino acids with modified side chains or backbones. Amino acid analogs also include amino acid analogs with the same stereochemistry as in the naturally occurring D-form, as well as the L-form of amino acid analogs. In some instances, the amino acid analogs share backbone structures, and/or the side chain structures of one or more natural amino acids, with difference(s) being one or more modified groups in the molecule. Such modification may include, but is not limited to, substitution of an atom (such as N) for a related atom (such as S), addition of a group (such as methyl, or hydroxyl, etc.) or an atom (such as Cl or Br, etc.), deletion of a group, substitution of a covalent bond (single bond for double bond, etc.), or combinations thereof. For example, amino acid analogs may include α-hydroxy acids, and α-amino acids, and the like.

The terms "amino acid side chain" or "side chain of an amino acid" and the like may be used to refer to the substituent attached to the α-carbon of an amino acid residue, including natural amino acids, unnatural amino acids, and amino acid analogs. An amino acid side chain can also include an amino acid side chain as described in the context of the modified amino acids and/or conjugates described herein.

The term "carbohydrate" and the like may be used to refer to monomers units and/or polymers of monosaccharides, disaccharides, oligosaccharides, and polysaccharides. The term sugar may be used to refer to the smaller carbohydrates, such as monosaccharides, disaccharides. The term "carbohydrate derivative" includes compounds where one or more functional groups of a carbohydrate of interest are substituted (replaced by any convenient substituent), modified (converted to another group using any convenient chemistry) or absent (e.g., eliminated or replaced by H). A variety of carbohydrates and carbohydrate derivatives are available and may be adapted for use in the subject compounds and conjugates.

The term "antibody" is used in the broadest sense and includes monoclonal antibodies (including full length monoclonal antibodies), polyclonal antibodies, and multispecific antibodies (e.g., bispecific antibodies), humanized antibodies, single-chain antibodies, chimeric antibodies, antibody fragments (e.g., Fab fragments), and the like. An antibody is capable of binding a target antigen. (Janeway, C., Travers, P., Walport, M., Shlomchik (2001) Immuno Biology, 5th Ed., Garland Publishing, New York). A target antigen can have one or more binding sites, also called epitopes, recognized by complementarity determining regions (CDRs) formed by one or more variable regions of an antibody.

The term "natural antibody" refers to an antibody in which the heavy and light chains of the antibody have been made and paired by the immune system of a multi-cellular organism. Spleen, lymph nodes, bone marrow and serum are examples of tissues that produce natural antibodies. For example, the antibodies produced by the antibody producing cells isolated from a first animal immunized with an antigen are natural antibodies.

The term "humanized antibody" or "humanized immunoglobulin" refers to a non-human (e.g., mouse or rabbit) antibody containing one or more amino acids (in a framework region, a constant region or a CDR, for example) that have been substituted with a correspondingly positioned amino acid from a human antibody. In general, humanized antibodies produce a reduced immune response in a human host, as compared to a non-humanized version of the same antibody. Antibodies can be humanized using a variety of techniques known in the art including, for example, CDR-grafting (EP 239,400; PCT publication WO 91/09967; U.S. Pat. Nos. 5,225,539; 5,530,101; and 5,585,089), veneering or resurfacing (EP 592,106; EP 519,596; Padlan, Molecular Immunology 28(4/5):489-498 (1991); Studnicka et al., Protein Engineering 7(6):805-814 (1994); Roguska. et al., PNAS 91:969-973 (1994)), and chain shuffling (U.S. Pat. No. 5,565,332). In certain embodiments, framework substitutions are identified by modeling of the interactions of the CDR and framework residues to identify framework residues important for antigen binding and sequence comparison to identify unusual framework residues at particular positions (see, e.g., U.S. Pat. No. 5,585,089; Riechmann et al., Nature 332:323 (1988)). Additional methods for humanizing antibodies contemplated for use in the present invention are described in U.S. Pat. Nos. 5,750,078; 5,502,167; 5,705,154; 5,770,403; 5,698,417; 5,693,493; 5,558,864; 4,935,496; and 4,816,567, and PCT publications WO 98/45331 and WO 98/45332. In particular embodiments, a subject rabbit antibody may be humanized according to the methods set forth in US20040086979 and US20050033031. Accordingly, the antibodies described above may be humanized using methods that are well known in the art.

The term "chimeric antibodies" refer to antibodies whose light and heavy chain genes have been constructed, typically by genetic engineering, from antibody variable and constant region genes belonging to different species. For example, the variable segments of the genes from a mouse monoclonal antibody may be joined to human constant segments, such as gamma 1 and gamma 3. An example of a therapeutic chimeric antibody is a hybrid protein composed of the variable or antigen-binding domain from a mouse antibody and the constant or effector domain from a human antibody, although domains from other mammalian species may be used.

An immunoglobulin polypeptide immunoglobulin light or heavy chain variable region is composed of a framework region (FR) interrupted by three hypervariable regions, also called "complementarity determining regions" or "CDRs". The extent of the framework region and CDRs have been defined (see, "Sequences of Proteins of Immunological Interest," E. Kabat et al., U.S. Department of Health and Human Services, 1991). The framework region of an antibody, that is the combined framework regions of the constituent light and heavy chains, serves to position and align the CDRs. The CDRs are primarily responsible for binding to an epitope of an antigen.

Throughout the present disclosure, the numbering of the residues in an immunoglobulin heavy chain and in an immunoglobulin light chain is that as in Kabat et al., Sequences of Proteins of Immunological Interest, 5th Ed. Public Health Service, National Institutes of Health, Bethesda, Md. (1991), expressly incorporated herein by reference.

A "parent Ig polypeptide" is a polypeptide comprising an amino acid sequence which lacks an aldehyde-tagged constant region as described herein. The parent polypeptide may comprise a native sequence constant region, or may comprise a constant region with pre-existing amino acid sequence modifications (such as additions, deletions and/or substitutions).

In the context of an Ig polypeptide, the term "constant region" is well understood in the art, and refers to a C-terminal region of an Ig heavy chain, or an Ig light chain. An Ig heavy chain constant region includes CH1, CH2, and CH3 domains (and CH4 domains, where the heavy chain is a or an F heavy chain). In a native Ig heavy chain, the CH1, CH2, CH3 (and, if present, CH4) domains begin immediately after (C-terminal to) the heavy chain variable (VH) region, and are each from about 100 amino acids to about 130 amino acids in length. In a native Ig light chain, the constant region begins begin immediately after (C-terminal to) the light chain variable (VL) region, and is about 100 amino acids to 120 amino acids in length.

As used herein, the term "CDR" or "complementarity determining region" is intended to mean the non-contiguous antigen combining sites found within the variable region of both heavy and light chain polypeptides. CDRs have been described by Kabat et al., J. Biol. Chem. 252:6609-6616 (1977); Kabat et al., U.S. Dept. of Health and Human Services, "Sequences of proteins of immunological interest" (1991); by Chothia et al., J. Mol. Biol. 196:901-917 (1987); and MacCallum et al., J. Mol. Biol. 262:732-745 (1996), where the definitions include overlapping or subsets of amino acid residues when compared against each other. Nevertheless, application of either definition to refer to a CDR of an antibody or grafted antibodies or variants thereof is intended to be within the scope of the term as defined and used herein. The amino acid residues which encompass the CDRs as defined by each of the above cited references are set forth below in Table 1 as a comparison.

TABLE 1

CDR Definitions

|  | Kabat[1] | Chothia[2] | MacCallum[3] |
| --- | --- | --- | --- |
| $V_H$ CDR1 | 31-35 | 26-32 | 30-35 |
| $V_H$ CDR2 | 50-65 | 53-55 | 47-58 |
| $V_H$ CDR3 | 95-102 | 96-101 | 93-101 |
| $V_L$ CDR1 | 24-34 | 26-32 | 30-36 |
| $V_L$ CDR2 | 50-56 | 50-52 | 46-55 |
| $V_L$ CDR3 | 89-97 | 91-96 | 89-96 |

[1]Residue numbering follows the nomenclature of Kabat et al., supra
[2]Residue numbering follows the nomenclature of Chothia et al., supra
[3]Residue numbering follows the nomenclature of MacCallum et al., supra By "genetically-encodable" as used in reference to an amino acid sequence of polypeptide, peptide or protein means that the amino acid sequence is composed of amino acid residues that are capable of production by transcription and translation of a nucleic acid encoding the amino acid sequence, where transcription and/or translation may occur in a cell or in a cell-free in vitro transcription/translation system.

The term "control sequences" refers to DNA sequences that facilitate expression of an operably linked coding sequence in a particular expression system, e.g. mammalian cell, bacterial cell, cell-free synthesis, etc. The control sequences that are suitable for prokaryote systems, for example, include a promoter, optionally an operator sequence, and a ribosome binding site. Eukaryotic cell systems may utilize promoters, polyadenylation signals, and enhancers.

A nucleic acid is "operably linked" when it is placed into a functional relationship with another nucleic acid sequence. For example, DNA for a presequence or secretory leader is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate the initiation of translation. Generally, "operably linked" means that the DNA sequences being linked are contiguous, and, in the case of a secretory leader, contiguous and in reading frame. Linking is accomplished by ligation or through amplification reactions. Synthetic oligonucleotide adaptors or linkers may be used for linking sequences in accordance with conventional practice.

The term "expression cassette" as used herein refers to a segment of nucleic acid, usually DNA, that can be inserted into a nucleic acid (e.g., by use of restriction sites compatible with ligation into a construct of interest or by homologous recombination into a construct of interest or into a host cell genome). In general, the nucleic acid segment comprises a polynucleotide that encodes a polypeptide of interest, and the cassette and restriction sites are designed to facilitate insertion of the cassette in the proper reading frame for transcription and translation. Expression cassettes can also comprise elements that facilitate expression of a polynucleotide encoding a polypeptide of interest in a host cell. These elements may include, but are not limited to: a promoter, a minimal promoter, an enhancer, a response element, a terminator sequence, a polyadenylation sequence, and the like.

As used herein the term "isolated" is meant to describe a compound of interest that is in an environment different from that in which the compound naturally occurs. "Isolated" is meant to include compounds that are within samples that are substantially enriched for the compound of interest and/or in which the compound of interest is partially or substantially purified.

As used herein, the term "substantially purified" refers to a compound that is removed from its natural environment and is at least 60% free, at least 75% free, at least 80% free, at least 85% free, at least 90% free, at least 95% free, at least 98% free, or more than 98% free, from other components with which it is naturally associated.

The term "physiological conditions" is meant to encompass those conditions compatible with living cells, e.g., predominantly aqueous conditions of a temperature, pH, salinity, etc. that are compatible with living cells.

By "reactive partner" is meant a molecule or molecular moiety that specifically reacts with another reactive partner to produce a reaction product. Exemplary reactive partners include a cysteine or serine of a sulfatase motif and Formylglycine Generating Enzyme (FGE), which react to form a reaction product of a converted aldehyde tag containing a formylglycine (FGly) in lieu of cysteine or serine in the motif. Other exemplary reactive partners include an aldehyde of an fGly residue of a converted aldehyde tag (e.g., a reactive aldehyde group) and an "aldehyde-reactive reactive partner", which comprises an aldehyde-reactive group and a moiety of interest, and which reacts to form a reaction product of a modified aldehyde tagged polypeptide having the moiety of interest conjugated to the modified polypeptide through a modified fGly residue.

"N-terminus" refers to the terminal amino acid residue of a polypeptide having a free amine group, which amine group in non-N-terminus amino acid residues normally forms part of the covalent backbone of the polypeptide.

"C-terminus" refers to the terminal amino acid residue of a polypeptide having a free carboxyl group, which carboxyl group in non-C-terminus amino acid residues normally forms part of the covalent backbone of the polypeptide.

By "internal site" as used in referenced to a polypeptide or an amino acid sequence of a polypeptide means a region of the polypeptide that is not at the N-terminus or at the C-terminus.

Before the present invention is further described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination. All combinations of the embodiments pertaining to the invention are specifically embraced by the present invention and are disclosed herein just as if each and every combination was individually and explicitly disclosed, to the extent that such combinations embrace subject matter that are, for example, compounds that are stable compounds (i.e., compounds that can be made, isolated, characterized, and tested for biological activity). In addition, all sub-combinations of the various embodiments and elements thereof (e.g., elements of the chemical groups listed in the embodiments describing such variables) are also specifically embraced by the present invention and are disclosed herein just as if each and every such sub-combination was individually and explicitly disclosed herein.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms "a," "an," and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

DETAILED DESCRIPTION

The present disclosure provides anti-CD22 antibody-maytansine conjugate structures. The disclosure also encompasses methods of production of such conjugates, as well as methods of using the same. Embodiments of each are described in more detail in the sections below.

Antibody-Drug Conjugates

The present disclosure provides conjugates, e.g., antibody-drug conjugates. By "conjugate" is meant a first moiety (e.g., an antibody) is stably associated with a second moiety (e.g., a drug). For example, a maytansine conjugate includes a maytansine (e.g., a maytansine active agent moiety) stably associated with another moiety (e.g., the antibody). By "stably associated" is meant that a moiety is bound to another moiety or structure under standard conditions. In certain embodiments, the first and second moieties are bound to each other through one or more covalent bonds.

In certain embodiments, the conjugate is a polypeptide conjugate, which includes a polypeptide conjugated to a second moiety. In certain embodiments, the moiety conjugated to the polypeptide can be any of a variety of moieties of interest such as, but not limited to, a detectable label, a drug, a water-soluble polymer, or a moiety for immobilization of the polypeptide to a membrane or a surface. In certain embodiments, the conjugate is a maytansine conjugate, where a polypeptide is conjugated to a maytansine or a maytansine active agent moiety. "Maytansine", "maytansine moiety", "maytansine active agent moiety" and "maytansinoid" refer to a maytansine and analogs and derivatives thereof, and pharmaceutically active maytansine moieties and/or portions thereof. A maytansine conjugated to the polypeptide can be any of a variety of maytansinoid moieties such as, but not limited to, maytansine and analogs and derivatives thereof as described herein.

The moiety of interest can be conjugated to the polypeptide at any desired site of the polypeptide. Thus, the present disclosure provides, for example, a modified polypeptide having a moiety conjugated at a site at or near the C-terminus of the polypeptide. Other examples include a modified polypeptide having a moiety conjugated at a position at or near the N-terminus of the polypeptide. Examples also include a modified polypeptide having a moiety conjugated at a position between the C-terminus and the N-terminus of the polypeptide (e.g., at an internal site of the polypeptide). Combinations of the above are also possible where the modified polypeptide is conjugated to two or more moieties.

In certain embodiments, a conjugate of the present disclosure includes a maytansine conjugated to an amino acid reside of a polypeptide at the α-carbon of an amino acid residue. Stated another way, a maytansine conjugate includes a polypeptide where the side chain of one or more amino acid residues in the polypeptide have been modified to be attached to a maytansine (e.g., attached to a maytansine through a linker as described herein). For example, a maytansine conjugate includes a polypeptide where the α-carbon of one or more amino acid residues in the polypeptide has been modified to be attached to a maytansine (e.g., attached to a maytansine through a linker as described herein).

Embodiments of the present disclosure include conjugates where a polypeptide is conjugated to one or more moieties, such as 2 moieties, 3 moieties, 4 moieties, 5 moieties, 6 moieties, 7 moieties, 8 moieties, 9 moieties, or 10 or more moieties. The moieties may be conjugated to the polypeptide at one or more sites in the polypeptide. For example, one or more moieties may be conjugated to a single amino acid residue of the polypeptide. In some cases, one moiety is conjugated to an amino acid residue of the polypeptide. In other embodiments, two moieties may be conjugated to the same amino acid residue of the polypeptide. In other embodiments, a first moiety is conjugated to a first amino acid residue of the polypeptide and a second moiety is conjugated to a second amino acid residue of the polypeptide. Combinations of the above are also possible, for example where a polypeptide is conjugated to a first moiety at a first amino acid residue and conjugated to two other moieties at a second amino acid residue. Other combinations are also possible, such as, but not limited to, a polypeptide conjugated to first and second moieties at a first amino acid residue and conjugated to third and fourth moieties at a second amino acid residue, etc.

The one or more amino acid residues of the polypeptide that are conjugated to the one or more moieties may be naturally occurring amino acids, unnatural amino acids, or combinations thereof. For instance, the conjugate may include a moiety conjugated to a naturally occurring amino acid residue of the polypeptide. In other instances, the conjugate may include a moiety conjugated to an unnatural amino acid residue of the polypeptide. One or more moieties may be conjugated to the polypeptide at a single natural or unnatural amino acid residue as described above. One or more natural or unnatural amino acid residues in the polypeptide may be conjugated to the moiety or moieties as described herein. For example, two (or more) amino acid residues (e.g., natural or unnatural amino acid residues) in the polypeptide may each be conjugated to one or two moieties, such that multiple sites in the polypeptide are modified.

As described herein, a polypeptide may be conjugated to one or more moieties. In certain embodiments, the moiety of interest is a chemical entity, such as a drug or a detectable label. For example, a drug (e.g., maytansine) may be conjugated to the polypeptide, or in other embodiments, a detectable label may be conjugated to the polypeptide. Thus, for instance, embodiments of the present disclosure include, but are not limited to, the following: a conjugate of a polypeptide and a drug; a conjugate of a polypeptide and a detectable label; a conjugate of two or more drugs and a polypeptide; a conjugate of two or more detectable labels and a polypeptide; and the like.

In certain embodiments, the polypeptide and the moiety of interest are conjugated through a coupling moiety. For example, the polypeptide and the moiety of interest may each be bound (e.g., covalently bonded) to the coupling moiety, thus indirectly binding the polypeptide and the moiety of interest (e.g., a drug, such as maytansine) together through the coupling moiety. In some cases, the coupling moiety includes a hydrazinyl-indolyl or a hydrazinyl-pyrrolo-pyridinyl compound, or a derivative of a hydrazinyl-indolyl or a hydrazinyl-pyrrolo-pyridinyl compound. For instance, a general scheme for coupling a moiety of interest (e.g., a maytansine) to a polypeptide through a hydrazinyl-indolyl or a hydrazinyl-pyrrolo-pyridinyl coupling moiety is shown in the general reaction scheme below. Hydrazinyl-indolyl and hydrazinyl-pyrrolo-pyridinyl coupling moiety are also referred to herein as a hydrazino-iso-Pictet-Spengler (HIPS) coupling moiety and an aza-hydrazino-iso-Pictet-Spengler (azaHIPS) coupling moiety, respectively.

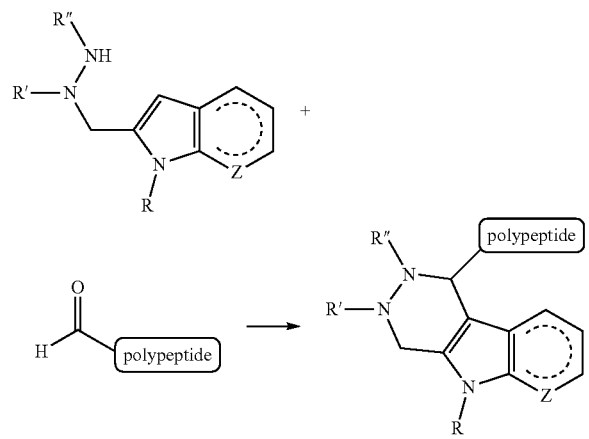

In the reaction scheme above, R is the moiety of interest (e.g., maytansine) that is conjugated to the polypeptide. As shown in the reaction scheme above, a polypeptide that includes a 2-formylglycine residue (fGly) is reacted with a drug (e.g., maytansine) that has been modified to include a coupling moiety (e.g., a hydrazinyl-indolyl or a hydrazinyl-pyrrolo-pyridinyl coupling moiety) to produce a polypeptide conjugate attached to the coupling moiety, thus attaching the maytansine to the polypeptide through the coupling moiety.

As described herein, the moiety can be any of a variety of moieties such as, but not limited to, chemical entity, such as a detectable label, or a drug (e.g., a maytansinoid). R' and R" may each independently be any desired substituent, such as, but not limited to, hydrogen, alkyl, substituted alkyl, alkenyl, substituted alkenyl, alkynyl, substituted alkynyl, alkoxy, substituted alkoxy, amino, substituted amino, carboxyl, carboxyl ester, acyl, acyloxy, acyl amino, amino acyl, alkylamide, substituted alkylamide, sulfonyl, thioalkoxy, substituted thioalkoxy, aryl, substituted aryl, heteroaryl, substituted heteroaryl, cycloalkyl, substituted cycloalkyl, heterocyclyl, and substituted heterocyclyl. Z may be $CR^{11}$, $NR^{12}$, N, O or S, where $R^{11}$ and $R^{12}$ are each independently selected from any of the substituents described for R' and R" above.

Other hydrazinyl-indolyl or hydrazinyl-pyrrolo-pyridinyl coupling moieties are also possible, as shown in the conjugates and compounds described herein. For example, the hydrazinyl-indolyl or hydrazinyl-pyrrolo-pyridinyl coupling moieties may be modified to be attached (e.g., covalently attached) to a linker. As such, embodiments of the present disclosure include a hydrazinyl-indolyl or hydrazinyl-pyrrolo-pyridinyl coupling moiety attached to a drug (e.g., maytansine) through a linker. Various embodiments of the linker that may couple the hydrazinyl-indolyl or hydrazinyl-pyrrolo-pyridinyl coupling moiety to the drug (e.g., maytansine) are described in detail herein.

In certain embodiments, the polypeptide may be conjugated to a moiety of interest, where the polypeptide is modified before conjugation to the moiety of interest. Modification of the polypeptide may produce a modified polypeptide that contains one or more reactive groups suitable for conjugation to the moiety of interest. In some cases, the polypeptide may be modified at one or more amino acid residues to provide one or more reactive groups suitable for conjugation to the moiety of interest (e.g., a moiety that includes a coupling moiety, such as a hydrazinyl-indolyl or a hydrazinyl-pyrrolo-pyridinyl coupling moiety as described above). For example, the polypeptide may be modified to include a reactive aldehyde group (e.g., a reactive aldehyde). A reactive aldehyde may be included in an "aldehyde tag" or "ald-tag", which as used herein refers to an amino acid sequence derived from a sulfatase motif (e.g., L(C/S)TPSR (SEQ ID NO: 37)) that has been converted by action of a formylglycine generating enzyme (FGE) to contain a 2-formylglycine residue (referred to herein as "FGly"). The FGly residue generated by an FGE may also be referred to as a "formylglycine". Stated differently, the term "aldehyde tag" is used herein to refer to an amino acid sequence that includes a "converted" sulfatase motif (i.e., a sulfatase motif in which a cysteine or serine residue has been converted to FGly by action of an FGE, e.g., L(FGly)TPSR (SEQ ID NO: 11)). A converted sulfatase motif may be derived from an amino acid sequence that includes an "unconverted" sulfatase motif (i.e., a sulfatase motif in which the cysteine or serine residue has not been converted to FGly by an FGE, but is capable of being converted, e.g., an unconverted sulfatase motif with the sequence: L(C/S)TPSR (SEQ ID NO: 37)). By "conversion" as used in the context of action of a formylglycine generating enzyme (FGE) on a sulfatase motif refers to biochemical modification of a cysteine or serine residue in a sulfatase motif to a formylglycine (FGly) residue (e.g., Cys to FGly, or Ser to FGly). Additional aspects of aldehyde tags and uses thereof in site-specific protein modification are described in U.S. Pat. Nos. 7,985,783 and 8,729,232, the disclosures of each of which are incorporated herein by reference.

In some cases, the modified polypeptide containing the FGly residue may be conjugated to the moiety of interest by reaction of the FGly with a compound (e.g., a compound containing a hydrazinyl-indolyl or a hydrazinyl-pyrrolo-pyridinyl coupling moiety, as described above). For example, an FGly-containing polypeptide may be contacted with a reactive partner-containing drug under conditions suitable to provide for conjugation of the drug to the polypeptide. In some instances, the reactive partner-containing drug may include a hydrazinyl-indolyl or a hydrazinyl-pyrrolo-pyridinyl coupling moiety as described above. For example, a maytansine may be modified to include a hydrazinyl-indolyl or a hydrazinyl-pyrrolo-pyridinyl coupling moiety. In some cases, the maytansine is attached to a hydrazinyl-indolyl or a hydrazinyl-pyrrolo-pyridinyl, such as covalently attached to a a hydrazinyl-indolyl or a hydrazinyl-pyrrolo-pyridinyl through a linker, as described in detail herein.

In certain embodiments, a conjugate of the present disclosure includes a polypeptide (e.g., an antibody, such as an anti-CD22 antibody) having at least one modified amino acid residue. The modified amino acid residue of the polypeptide may be coupled to a drug (e.g., maytansine) containing a hydrazinyl-indolyl or a hydrazinyl-pyrrolo-pyridinyl coupling moiety as described above. In certain embodiments, the modified amino acid residue of the polypeptide (e.g., anti-CD22 antibody) may be derived from a cysteine or serine residue that has been converted to an FGly residue as described above. In certain embodiments, the FGly residue is conjugated to a drug containing a hydrazinyl-indolyl or a hydrazinyl-pyrrolo-pyridinyl coupling moiety as described above to provide a conjugate of the present disclosure where the drug is conjugated to the polypeptide through the hydrazinyl-indolyl or hydrazinyl-pyrrolo-pyridinyl coupling moiety. As used herein, the term FGly' refers to the modified amino acid residue of the polypeptide (e.g., anti-CD22 antibody) that is coupled to the moiety of interest (e.g., a drug, such as a maytansinoid).

In certain embodiments, the conjugate includes at least one modified amino acid residue of the formula (I) described herein. For instance, the conjugate may include at least one modified amino acid residue with a side chain of the formula (I):

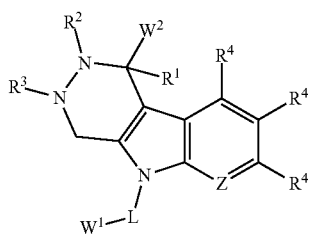

(I)

wherein

Z is $CR^4$ or N;

$R^1$ is selected from hydrogen, alkyl, substituted alkyl, alkenyl, substituted alkenyl, alkynyl, substituted alkynyl, aryl, substituted aryl, heteroaryl, substituted heteroaryl, cycloalkyl, substituted cycloalkyl, heterocyclyl, and substituted heterocyclyl;

$R^2$ and $R^3$ are each independently selected from hydrogen, alkyl, substituted alkyl, alkenyl, substituted alkenyl, alkynyl, substituted alkynyl, alkoxy, substituted alkoxy, amino, substituted amino, carboxyl, carboxyl ester, acyl, acyloxy, acyl amino, amino acyl, alkylamide, substituted alkylamide, sulfonyl, thioalkoxy, substituted thioalkoxy, aryl, substituted aryl, heteroaryl, substituted heteroaryl, cycloalkyl, substituted cycloalkyl, heterocyclyl, and substituted heterocyclyl, or $R^2$ and $R^3$ are optionally cyclically linked to form a 5 or 6-membered heterocyclyl;

each $R^4$ is independently selected from hydrogen, halogen, alkyl, substituted alkyl, alkenyl, substituted alkenyl, alkynyl, substituted alkynyl, alkoxy, substituted alkoxy, amino, substituted amino, carboxyl, carboxyl ester, acyl, acyloxy, acyl amino, amino acyl, alkylamide, substituted alkylamide, sulfonyl, thioalkoxy, substituted thioalkoxy, aryl, substituted aryl, heteroaryl, substituted heteroaryl, cycloalkyl, substituted cycloalkyl, heterocyclyl, and substituted heterocyclyl;

L is a linker comprising $-(T^1-V^1)_a-(T^2-V^2)_b-(T^3-V^3)_c-(T^4-V^4)_d-$, wherein a, b, c and d are each independently 0 or 1, where the sum of a, b, c and d is 1 to 4;

$T^1$, $T^2$, $T^3$ and $T^4$ are each independently selected from $(C_1-C_{12})$alkyl, substituted $(C_1-C_{12})$alkyl, $(EDA)_w$, $(PEG)_n$, $(AA)_p$, $-(CR^{13}OH)_h-$, piperidin-4-amino (4AP), an acetal group, a hydrazine, a disulfide, and an ester, wherein EDA is an ethylene diamine moiety, PEG is a polyethylene glycol or a modified polyethylene glycol, and AA is an amino acid residue, wherein w is an integer from 1 to 20, n is an integer from 1 to 30, p is an integer from 1 to 20, and h is an integer from 1 to 12;

$V^1$, $V^2$, $V^3$ and $V^4$ are each independently selected from the group consisting of a covalent bond, —CO—, —$NR^{15}$—, —$NR^{15}CH_2)_q$—, —$NR^{15}(C_6H_4)$—, —$CONR^{15}$—, —$NR^{15}CO$—, —C(O)O—, —OC(O)—, —O—, —S—, —S(O)—, —$SO_2$—, —$SO_2NR^{15}$—, —$NR^{15}SO_2$— and —P(O)OH—, wherein q is an integer from 1 to 6;

each $R^{13}$ is independently selected from hydrogen, an alkyl, a substituted alkyl, an aryl, and a substituted aryl;

each $R^{15}$ is independently selected from hydrogen, alkyl, substituted alkyl, alkenyl, substituted alkenyl, alkynyl, substituted alkynyl, carboxyl, carboxyl ester, acyl, aryl, substituted aryl, heteroaryl, substituted heteroaryl, cycloalkyl, substituted cycloalkyl, heterocyclyl, and substituted heterocyclyl;

$W^1$ is a maytansinoid; and $W^2$ is an anti-CD22 antibody.

In certain embodiments, Z is $CR^4$ or N. In certain embodiments, Z is $CR^4$. In certain embodiments, Z is N.

In certain embodiments, $R^1$ is selected from hydrogen, alkyl, substituted alkyl, alkenyl, substituted alkenyl, alkynyl, substituted alkynyl, aryl, substituted aryl, heteroaryl, substituted heteroaryl, cycloalkyl, substituted cycloalkyl, heterocyclyl, and substituted heterocyclyl. In certain embodiments, $R^1$ is hydrogen. In certain embodiments, $R^1$ is alkyl or substituted alkyl, such as $C_{1-6}$ alkyl or $C_{1-6}$ substituted alkyl, or $C_{1-4}$ alkyl or $C_{1-4}$ substituted alkyl, or $C_{1-3}$ alkyl or $C_{1-3}$ substituted alkyl. In certain embodiments, $R^1$ is alkenyl or substituted alkenyl, such as $C_{2-6}$ alkenyl or $C_{2-6}$ substituted alkenyl, or $C_{2-4}$ alkenyl or $C_2$-4 substituted alkenyl, or $C_{2-3}$ alkenyl or $C_{2-3}$ substituted alkenyl. In certain embodiments, $R^1$ is alkynyl or substituted alkynyl, such as $C_{2-6}$ alkenyl or $C_{2-6}$ substituted alkenyl, or $C_{2-4}$ alkenyl or $C_{2-4}$ substituted alkenyl, or $C_{2-3}$ alkenyl or $C_{2-3}$ substituted alkenyl. In certain embodiments, $R^1$ is aryl or substituted aryl, such as $C_{5-8}$ aryl or $C_{5-8}$ substituted aryl, such as a $C_5$ aryl or $C_5$ substituted aryl, or a $C_6$ aryl or $C_6$ substituted aryl. In certain embodiments, $R^1$ is heteroaryl or substituted heteroaryl, such as $C_{5-8}$ heteroaryl or $C_{5-8}$ substituted heteroaryl, such as a $C_5$ heteroaryl or $C_5$ substituted heteroaryl, or a $C_6$ heteroaryl or $C_6$ substituted heteroaryl. In certain embodiments, $R^1$ is cycloalkyl or substituted cycloalkyl, such as $C_{3-8}$ cycloalkyl or $C_{3-8}$ substituted cycloalkyl, such as a $C_{3-6}$ cycloalkyl or $C_{3-6}$ substituted cycloalkyl, or a $C_{3-5}$ cycloalkyl or $C_{3-5}$ substituted cycloalkyl. In certain embodiments, $R^1$ is heterocyclyl or substituted heterocyclyl, such as $C_{3-8}$ heterocyclyl or $C_{3-8}$ substituted heterocyclyl, such as a $C_{3-6}$ heterocyclyl or $C_{3-6}$ substituted heterocyclyl, or a $C_{3-5}$ heterocyclyl or $C_{3-5}$ substituted heterocyclyl.

In certain embodiments, $R^2$ and $R^3$ are each independently selected from hydrogen, alkyl, substituted alkyl, alkenyl, substituted alkenyl, alkynyl, substituted alkynyl, alkoxy, substituted alkoxy, amino, substituted amino, carboxyl, carboxyl ester, acyl, acyloxy, acyl amino, amino acyl, alkylamide, substituted alkylamide, sulfonyl, thioalkoxy, substituted thioalkoxy, aryl, substituted aryl, heteroaryl, substituted heteroaryl, cycloalkyl, substituted cycloalkyl, heterocyclyl, and substituted heterocyclyl, or $R^2$ and $R^3$ are optionally cyclically linked to form a 5 or 6-membered heterocyclyl.

In certain embodiments, $R^2$ is selected from hydrogen, alkyl, substituted alkyl, alkenyl, substituted alkenyl, alkynyl, substituted alkynyl, alkoxy, substituted alkoxy, amino, substituted amino, carboxyl, carboxyl ester, acyl, acyloxy, acyl amino, amino acyl, alkylamide, substituted alkylamide, sulfonyl, thioalkoxy, substituted thioalkoxy, aryl, substituted aryl, heteroaryl, substituted heteroaryl, cycloalkyl, substituted cycloalkyl, heterocyclyl, and substituted heterocyclyl. In certain embodiments, $R^2$ is hydrogen. In certain embodiments, $R^2$ is alkyl or substituted alkyl, such as $C_{1-6}$ alkyl or $C_{1-6}$ substituted alkyl, or $C_{1-4}$ alkyl or $C_{1-4}$ substituted alkyl, or $C_{1-3}$ alkyl or $C_{1-3}$ substituted alkyl. In certain embodiments, $R^2$ is alkenyl or substituted alkenyl, such as $C_{2-6}$ alkenyl or $C_{2-6}$ substituted alkenyl, or $C_{2-4}$ alkenyl or $C_{2-4}$ substituted alkenyl, or $C_{2-3}$ alkenyl or $C_{2-3}$ substituted alkenyl. In certain embodiments, $R^2$ is alkynyl or substituted alkynyl. In certain embodiments, $R^2$ is alkoxy or substituted alkoxy. In certain embodiments, $R^2$ is amino or substituted amino. In certain embodiments, $R^2$ is carboxyl or carboxyl ester. In certain embodiments, $R^2$ is acyl or acyloxy. In certain embodiments, $R^2$ is acyl amino or amino acyl. In certain embodiments, $R^2$ is alkylamide or substituted alkylamide. In certain embodiments, $R^2$ is sulfonyl. In certain embodiments, $R^2$ is thioalkoxy or substituted thioalkoxy. In certain embodiments, $R^2$ is aryl or substituted aryl, such as $C_{5-8}$ aryl or $C_{5-8}$ substituted aryl, such as a $C_5$ aryl or $C_5$ substituted aryl, or a $C_6$ aryl or $C_6$ substituted aryl. In certain embodiments, $R^2$ is heteroaryl or substituted heteroaryl, such as $C_{5-8}$ heteroaryl or $C_{5-8}$ substituted heteroaryl, such as a $C_5$ heteroaryl or $C_5$ substituted heteroaryl, or a $C_6$ heteroaryl or $C_6$ substituted heteroaryl. In certain embodiments, $R^2$ is cycloalkyl or substituted cycloalkyl, such as $C_{3-8}$ cycloalkyl or $C_{3-8}$ substituted cycloalkyl, such as a $C_{3-6}$ cycloalkyl or $C_{3-6}$ substituted cycloalkyl, or a $C_{3-5}$ cycloalkyl or $C_{3-5}$ substituted cycloalkyl. In certain embodiments, $R^2$ is heterocyclyl or substituted heterocyclyl, such as a $C_{3-6}$ heterocyclyl or $C_{3-6}$ substituted heterocyclyl, or a $C_{3-5}$ heterocyclyl or $C_{3-5}$ substituted heterocyclyl.

In certain embodiments, $R^3$ is selected from hydrogen, alkyl, substituted alkyl, alkenyl, substituted alkenyl, alkynyl, substituted alkynyl, alkoxy, substituted alkoxy, amino, substituted amino, carboxyl, carboxyl ester, acyl, acyloxy, acyl amino, amino acyl, alkylamide, substituted alkylamide, sulfonyl, thioalkoxy, substituted thioalkoxy, aryl, substituted aryl, heteroaryl, substituted heteroaryl, cycloalkyl, substituted cycloalkyl, heterocyclyl, and substituted heterocyclyl. In certain embodiments, $R^3$ is hydrogen. In certain embodiments, $R^3$ is alkyl or substituted alkyl, such as $C_{1-6}$ alkyl or $C_{1-6}$ substituted alkyl, or $C_{1-4}$ alkyl or $C_{1-4}$ substituted alkyl, or $C_{1-3}$ alkyl or $C_{1-3}$ substituted alkyl. In certain embodiments, $R^3$ is alkenyl or substituted alkenyl, such as $C_{2-6}$ alkenyl or $C_{2-6}$ substituted alkenyl, or $C_{2-4}$ alkenyl or $C_{2-4}$ substituted alkenyl, or $C_{2-3}$ alkenyl or $C_{2-3}$ substituted alkenyl. In certain embodiments, $R^3$ is alkynyl or substituted alkynyl. In certain embodiments, $R^3$ is alkoxy or substituted alkoxy. In certain embodiments, $R^3$ is amino or substituted amino. In certain embodiments, $R^3$ is carboxyl or carboxyl ester. In certain embodiments, $R^3$ is acyl or acyloxy. In certain embodiments, $R^3$ is acyl amino or amino acyl. In certain embodiments, $R^3$ is alkylamide or substituted alkylamide. In certain embodiments, $R^3$ is sulfonyl. In certain embodiments, $R^3$ is thioalkoxy or substituted thioalkoxy. In certain embodiments, $R^3$ is aryl or substituted aryl, such as $C_{5-8}$ aryl or $C_{5-8}$ substituted aryl, such as a $C_5$ aryl or $C_5$ substituted aryl, or a $C_6$ aryl or $C_6$ substituted aryl. In certain embodiments, $R^3$ is heteroaryl or substituted heteroaryl, such as $C_{5-8}$ heteroaryl or $C_{5-8}$ substituted heteroaryl, such as a $C_5$ heteroaryl or $C_5$ substituted heteroaryl, or a $C_6$ heteroaryl or $C_6$ substituted heteroaryl. In certain embodiments, $R^3$ is cycloalkyl or substituted cycloalkyl, such as $C_{3-8}$ cycloalkyl or $C_{3-8}$ substituted cycloalkyl, such as a $C_{3-6}$ cycloalkyl or $C_{3-6}$ substituted cycloalkyl, or a $C_{3-5}$ cycloalkyl or $C_{3-5}$ substituted cycloalkyl. In certain embodiments, $R^3$ is heterocyclyl or substituted heterocyclyl, such as $C_{3-8}$ heterocyclyl or $C_{3-8}$ substituted heterocyclyl, such as a $C_{3-6}$ heterocyclyl or $C_{3-6}$ substituted heterocyclyl, or a $C_{3-5}$ heterocyclyl or $C_{3-5}$ substituted heterocyclyl.

In certain embodiments, $R^2$ and $R^3$ are optionally cyclically linked to form a 5 or 6-membered heterocyclyl. In certain embodiments, $R^2$ and $R^3$ are cyclically linked to form a 5 or 6-membered heterocyclyl. In certain embodiments, $R^2$ and $R^3$ are cyclically linked to form a 5-membered heterocyclyl. In certain embodiments, $R^2$ and $R^3$ are cyclically linked to form a 6-membered heterocyclyl.

In certain embodiments, each $R^4$ is independently selected from hydrogen, halogen, alkyl, substituted alkyl, alkenyl, substituted alkenyl, alkynyl, substituted alkynyl, alkoxy, substituted alkoxy, amino, substituted amino, carboxyl, carboxyl ester, acyl, acyloxy, acyl amino, amino acyl, alkylamide, substituted alkylamide, sulfonyl, thioalkoxy, substituted thioalkoxy, aryl, substituted aryl, heteroaryl, substituted heteroaryl, cycloalkyl, substituted cycloalkyl, heterocyclyl, and substituted heterocyclyl.

The various possibilities for each $R^4$ are described in more detail as follows. In certain embodiments, $R^4$ is hydrogen. In certain embodiments, each $R^4$ is hydrogen. In certain embodiments, $R^4$ is halogen, such as F, Cl, Br or I. In certain embodiments, $R^4$ is F. In certain embodiments, $R^4$ is Cl. In certain embodiments, $R^4$ is Br. In certain embodiments, $R^4$ is I. In certain embodiments, $R^4$ is alkyl or substituted alkyl, such as $C_{1-6}$ alkyl or $C_{1-6}$ substituted alkyl, or $C_{1-4}$ alkyl or $C_{1-4}$ substituted alkyl, or $C_{1-3}$ alkyl or $C_{1-3}$ substituted alkyl. In certain embodiments, $R^4$ is alkenyl or substituted alkenyl, such as $C_{2-6}$ alkenyl or $C_{2-6}$ substituted alkenyl, or $C_{2-4}$ alkenyl or $C_{2-4}$ substituted alkenyl, or $C_{2-3}$ alkenyl or $C_{2-3}$ substituted alkenyl. In certain embodiments, $R^4$ is alkynyl or substituted alkynyl. In certain embodiments, $R^4$ is alkoxy or substituted alkoxy. In certain embodiments, $R^4$ is amino or substituted amino. In certain embodiments, $R^4$ is carboxyl or carboxyl ester. In certain embodiments, $R^4$ is acyl or acyloxy. In certain embodiments, $R^4$ is acyl amino or amino acyl. In certain embodiments, $R^4$ is alkylamide or substituted alkylamide. In certain embodiments, $R^4$ is sulfonyl. In certain embodiments, $R^4$ is thioalkoxy or substituted thioalkoxy. In certain embodiments, $R^4$ is aryl or substituted aryl, such as $C_{5-8}$ aryl or $C_{5-8}$ substituted aryl, such as a $C_5$ aryl or $C_5$ substituted aryl, or a $C_6$ aryl or $C_6$ substituted aryl (e.g., phenyl or substituted phenyl). In certain embodiments, $R^4$ is heteroaryl or substituted heteroaryl, such as $C_{5-8}$ heteroaryl or $C_{5-8}$ substituted heteroaryl, such as a $C_5$ heteroaryl or $C_5$ substituted heteroaryl, or a $C_6$ heteroaryl or $C_6$ substituted heteroaryl. In certain embodiments, $R^4$ is cycloalkyl or substituted cycloalkyl, such as $C_{3-8}$ cycloalkyl or $C_{3-8}$ substituted cycloalkyl, such as a $C_{3-6}$ cycloalkyl or $C_{3-6}$ substituted cycloalkyl, or a $C_{3-5}$ cycloalkyl or $C_{3-5}$ substituted cycloalkyl. In certain embodiments, $R^4$ is heterocyclyl or substituted heterocyclyl, such as $C_{3-8}$ heterocyclyl or $C_{3-8}$ substituted heterocyclyl, such as a $C_{3-6}$ heterocyclyl or $C_{3-6}$ substituted heterocyclyl, or a $C_{3-5}$ heterocyclyl or $C_{3-5}$ substituted heterocyclyl.

In certain embodiments, $W^1$ is a maytansinoid. Further description of the maytansinoid is found in the disclosure herein.

In certain embodiments, $W^2$ is an anti-CD22 antibody. Further description of the anti-CD22 antibody is found in the disclosure herein.

In certain embodiments, the compounds of formula (I) include a linker, L. The linker may be utilized to bind a coupling moiety to one or more moieties of interest and/or one or more polypeptides. In some embodiments, the linker binds a coupling moiety to either a polypeptide or a chemical entity. The linker may be bound (e.g., covalently bonded) to the coupling moiety (e.g., as described herein) at any convenient position. For example, the linker may attach a hydrazinyl-indolyl or a hydrazinyl-pyrrolo-pyridinyl coupling moiety to a drug (e.g., a maytansine). The hydrazinyl-indolyl or hydrazinyl-pyrrolo-pyridinyl coupling moiety may be used to conjugate the linker (and thus the drug, e.g., maytansine) to a polypeptide, such as an anti-CD22 antibody.

In certain embodiments, L attaches the coupling moiety to $W^1$, and thus the coupling moiety is indirectly bonded to $W^1$ through the linker L. As described above, $W^1$ is a maytansinoid, and thus L attaches the coupling moiety to a maytansinoid, e.g., the coupling moiety is indirectly bonded to the maytansinoid through the linker, L.

Any convenient linkers may be utilized in the subject conjugates and compounds. In certain embodiments, L includes a group selected from alkyl, substituted alkyl, alkenyl, substituted alkenyl, alkynyl, substituted alkynyl, alkoxy, substituted alkoxy, amino, substituted amino, carboxyl, carboxyl ester, acyl amino, alkylamide, substituted alkylamide, aryl, substituted aryl, heteroaryl, substituted heteroaryl, cycloalkyl, substituted cycloalkyl, heterocyclyl, and substituted heterocyclyl. In certain embodiments, L includes an alkyl or substituted alkyl group. In certain embodiments, L includes an alkenyl or substituted alkenyl group. In certain embodiments, L includes an alkynyl or substituted alkynyl group. In certain embodiments, L includes an alkoxy or substituted alkoxy group. In certain embodiments, L includes an amino or substituted amino group. In certain embodiments, L includes a carboxyl or carboxyl ester group. In certain embodiments, L includes an acyl amino group. In certain embodiments, L includes an alkylamide or substituted alkylamide group. In certain embodiments, L includes an aryl or substituted aryl group. In certain embodiments, L includes a heteroaryl or substituted heteroaryl group. In certain embodiments, L includes a cycloalkyl or substituted cycloalkyl group. In certain embodiments, L includes a heterocyclyl or substituted heterocyclyl group.

In certain embodiments, L includes a polymer. For example, the polymer may include a polyalkylene glycol and derivatives thereof, including polyethylene glycol, methoxypolyethylene glycol, polyethylene glycol homopolymers, polypropylene glycol homopolymers, copolymers of ethylene glycol with propylene glycol (e.g., where the homopolymers and copolymers are unsubstituted or substituted at one end with an alkyl group), polyvinyl alcohol, polyvinyl ethyl ethers, polyvinylpyrrolidone, combinations thereof, and the like. In certain embodiments, the polymer is a polyalkylene glycol. In certain embodiments, the polymer is a polyethylene glycol. Other linkers are also possible, as shown in the conjugates and compounds described in more detail below.

In some embodiments, L is a linker described by the formula $-(L^1)_a-(L^2)_b-(L^3)_c-(L^4)_d-$, wherein $L^1$, $L^2$, $L^3$ and $L^4$ are each independently a linker unit, and a, b, c and d are each independently 0 or 1, wherein the sum of a, b, c and d is 1 to 4.

In certain embodiments, the sum of a, b, c and d is 1. In certain embodiments, the sum of a, b, c and d is 2. In certain embodiments, the sum of a, b, c and d is 3. In certain embodiments, the sum of a, b, c and d is 4. In certain embodiments, a, b, c and d are each 1. In certain embodiments, a, b and c are each 1 and d is 0. In certain embodiments, a and b are each 1 and c and d are each 0. In certain embodiments, a is 1 and b, c and d are each 0.

In certain embodiments, $L^1$ is attached to the hydrazinyl-indolyl or the hydrazinyl-pyrrolo-pyridinyl coupling moiety (e.g., as shown in formula (I) above). In certain embodiments, $L^2$, if present, is attached to $W^1$. In certain embodiments, $L^3$, if present, is attached to $W^1$. In certain embodiments, $L^4$, if present, is attached to $W^1$.

Any convenient linker units may be utilized in the subject linkers. Linker units of interest include, but are not limited to, units of polymers such as polyethylene glycols, polyethylenes and polyacrylates, amino acid residue(s), carbohydrate-based polymers or carbohydrate residues and derivatives thereof, polynucleotides, alkyl groups, aryl groups, heterocyclic groups, combinations thereof, and substituted versions thereof. In some embodiments, each of $L^1$, $L^2$, $L^3$ and $L^4$ (if present) comprise one or more groups independently selected from a polyethylene glycol, a modified polyethylene glycol, an amino acid residue, an alkyl group, a substituted alkyl, an aryl group, a substituted aryl group, and a diamine (e.g., a linking group that includes an alkylene diamine).

In some embodiments, $L^1$ (if present) comprises a polyethylene glycol, a modified polyethylene glycol, an amino acid residue, an alkyl group, a substituted alkyl, an aryl group, a substituted aryl group, or a diamine. In some embodiments, $L^1$ comprises a polyethylene glycol. In some embodiments, $L^1$ comprises a modified polyethylene glycol. In some embodiments, Li comprises an amino acid residue. In some embodiments, $L^1$ comprises an alkyl group or a substituted alkyl. In some embodiments, $L^1$ comprises an aryl group or a substituted aryl group. In some embodiments, $L^1$ comprises a diamine (e.g., a linking group comprising an alkylene diamine).

In some embodiments, $L^2$ (if present) comprises a polyethylene glycol, a modified polyethylene glycol, an amino acid residue, an alkyl group, a substituted alkyl, an aryl group, a substituted aryl group, or a diamine. In some embodiments, $L^2$ comprises a polyethylene glycol. In some embodiments, $L^2$ comprises a modified polyethylene glycol. In some embodiments, $L^2$ comprises an amino acid residue. In some embodiments, $L^2$ comprises an alkyl group or a substituted alkyl. In some embodiments, $L^2$ comprises an aryl group or a substituted aryl group. In some embodiments, $L^2$ comprises a diamine (e.g., a linking group comprising an alkylene diamine).

In some embodiments, $L^3$ (if present) comprises a polyethylene glycol, a modified polyethylene glycol, an amino acid residue, an alkyl group, a substituted alkyl, an aryl group, a substituted aryl group, or a diamine. In some embodiments, $L^3$ comprises a polyethylene glycol. In some embodiments, $L^3$ comprises a modified polyethylene glycol. In some embodiments, $L^3$ comprises an amino acid residue. In some embodiments, $L^3$ comprises an alkyl group or a substituted alkyl. In some embodiments, $L^3$ comprises an aryl group or a substituted aryl group. In some embodiments, $L^3$ comprises a diamine (e.g., a linking group comprising an alkylene diamine).

In some embodiments, $L^4$ (if present) comprises a polyethylene glycol, a modified polyethylene glycol, an amino acid residue, an alkyl group, a substituted alkyl, an aryl group, a substituted aryl group, or a diamine. In some embodiments, $L^4$ comprises a polyethylene glycol. In some embodiments, $L^4$ comprises a modified polyethylene glycol. In some embodiments, $L^4$ comprises an amino acid residue. In some embodiments, $L^4$ comprises an alkyl group or a substituted alkyl. In some embodiments, $L^4$ comprises an aryl group or a substituted aryl group. In some embodiments, $L^4$ comprises a diamine (e.g., a linking group comprising an alkylene diamine).

In some embodiments, L is a linker comprising $-(L^1)_a-(L^2)_b-(L^3)_c-(L^4)_d-$, where:

$-(L^1)_a-$ is $-(T^1-V^1)_a-$;

$-(L^2)_b-$ is $-(T^2-V^2)_b-$;

$-(L^3)_c-$ is $-(T^3-V^3)_c-$; and $-(L^4)_d-$ is $-(T^4-V^4)_d-$, wherein $T^1$, $T^2$, $T^3$ and $T^4$, if present, are tether groups; $V^1$, $V^2$, $V^3$ and $V^4$, if present, are covalent bonds or linking functional groups; and a, b, c and d are each independently 0 or 1, wherein the sum of a, b, c and d is 1 to 4.

As described above, in certain embodiments, $L^1$ is attached to the hydrazinyl-indolyl or the hydrazinyl-pyrrolo-pyridinyl coupling moiety (e.g., as shown in formula (I) above). As such, in certain embodiments, $T^1$ is attached to the hydrazinyl-indolyl or the hydrazinyl-pyrrolo-pyridinyl coupling moiety (e.g., as shown in formula (I) above). In certain embodiments, $V^1$ is attached to $W^1$ (the maytansinoid). In certain embodiments, $L^2$, if present, is attached to $W^1$. As such, in certain embodiments, $T^2$, if present, is attached to $W^1$, or $V^2$, if present, is attached to $W^1$. In certain embodiments, $L^3$, if present, is attached to $W^1$. As such, in certain embodiments, $T^3$, if present, is attached to $W^1$, or $V^3$, if present, is attached to $W^1$. In certain embodiments, $L^4$, if present, is attached to $W^1$. As such, in certain embodiments, $T^4$, if present, is attached to $W^1$, or $V^4$, if present, is attached to $W^1$.

Regarding the tether groups, $T^1$, $T^2$, $T^3$ and $T^4$, any convenient tether groups may be utilized in the subject linkers. In some embodiments, $T^1$, $T^2$, $T^3$ and $T^4$ each comprise one or more groups independently selected from a $(C_1-C_{12})$alkyl, a substituted $(C_1-C_{12})$alkyl, an $(EDA)_w$, $(PEG)_n$, $(AA)_p$, $-(CR^{13}OH)_h-$, piperidin-4-amino (4AP), an acetal group, a disulfide, a hydrazine, and an ester, where w is an integer from 1 to 20, n is an integer from 1 to 30, p is an integer from 1 to 20, and h is an integer from 1 to 12.

In certain embodiments, when the sum of a, b, c and d is 2 and one of $T^1-V^1$, $T^2-V^2$, $T^3-V^3$, or $T^4-V^4$ is $(PEG)_n-CO$, then n is not 6. For example, in some instances, the linker may have the following structure:

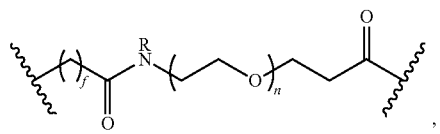

where n is not 6.

In certain embodiments, when the sum of a, b, c and d is 2 and one of $T^1-V^1$, $T^2-V^2$, $T^3-V^3$, or $T^4-V^4$ is $(C_1-C_{12})$alkyl-$NR^{15}$, then $(C_1-C_{12})$alkyl is not a $C_5$-alkyl. For example, in some instances, the linker may have the following structure:

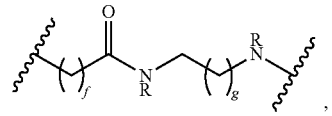

where g is not 4.

In certain embodiments, the tether group (e.g., $T^1$, $T^2$, $T^3$ and/or $T^4$) includes a $(C_1-C_{12})$alkyl or a substituted $(C_1-C_{12})$alkyl. In certain embodiments, $(C_1-C_{12})$alkyl is a straight chain or branched alkyl group that includes from 1 to 12 carbon atoms, such as 1 to 10 carbon atoms, or 1 to 8 carbon atoms, or 1 to 6 carbon atoms, or 1 to 5 carbon atoms, or 1 to 4 carbon atoms, or 1 to 3 carbon atoms. In some instances, $(C_1-C_{12})$alkyl may be an alkyl or substituted alkyl, such as $C_1-C_{12}$ alkyl, or $C_1-C_{10}$ alkyl, or $C_1-C_6$ alkyl, or $C_1-C_3$ alkyl. In some instances, $(C_1-C_{12})$alkyl is a $C_2$-alkyl. For example, $(C_1-C_{12})$alkyl may be an alkylene or substituted alkylene, such as $C_1-C_{12}$ alkylene, or $C_1-C_{10}$ alkylene, or $C_1-C_6$ alkylene, or $C_1-C_3$ alkylene. In some instances, $(C_1-C_{12})$alkyl is a $C_2$-alkylene.

In certain embodiments, substituted $(C_1-C_{12})$alkyl is a straight chain or branched substituted alkyl group that includes from 1 to 12 carbon atoms, such as 1 to 10 carbon atoms, or 1 to 8 carbon atoms, or 1 to 6 carbon atoms, or 1 to 5 carbon atoms, or 1 to 4 carbon atoms, or 1 to 3 carbon atoms. In some instances, substituted $(C_1-C_{12})$alkyl may be a substituted alkyl, such as substituted $C_1-C_{12}$ alkyl, or substituted $C_1-C_{10}$ alkyl, or substituted $C_1-C_6$ alkyl, or substituted $C_1-C_3$ alkyl. In some instances, substituted $(C_1-C_{12})$alkyl is a substituted $C_2$-alkyl. For example, substituted $(C_1-C_{12})$alkyl may be a substituted alkylene, such as substituted $C_1-C_{12}$ alkylene, or substituted $C_1-C_{10}$ alkylene, or substituted $C_1-C_6$ alkylene, or substituted $C_1-C_3$ alkylene. In some instances, substituted $(C_1-C_{12})$alkyl is a substituted $C_2$-alkylene.

In certain embodiments, the tether group (e.g., $T^1$, $T^2$, $T^3$ and/or $T^4$) includes an ethylene diamine (EDA) moiety, e.g., an EDA containing tether. In certain embodiments, $(EDA)_w$ includes one or more EDA moieties, such as where w is an integer from 1 to 50, such as from 1 to 40, from 1 to 30, from 1 to 20, from 1 to 12 or from 1 to 6, such as 1, 2, 3, 4, 5 or 6). The linked ethylene diamine (EDA) moieties may optionally be substituted at one or more convenient positions with any convenient substituents, e.g., with an alkyl, a substituted alkyl, an acyl, a substituted acyl, an aryl or a substituted aryl. In certain embodiments, the EDA moiety is described by the structure:

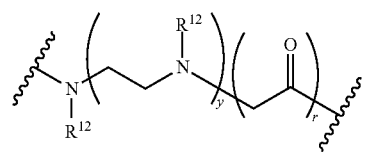

where y is an integer from 1 to 6, r is 0 or 1, and each $R^{12}$ is independently selected from hydrogen, alkyl, substituted alkyl, alkenyl, substituted alkenyl, alkynyl, substituted alkynyl, alkoxy, substituted alkoxy, amino, substituted amino, carboxyl, carboxyl ester, acyl, acyloxy, acyl amino, amino acyl, alkylamide, substituted alkylamide, sulfonyl, thioalkoxy, substituted thioalkoxy, aryl, substituted aryl, heteroaryl, substituted heteroaryl, cycloalkyl, substituted cycloalkyl, heterocyclyl, and substituted heterocyclyl. In certain embodiments, y is 1, 2, 3, 4, 5 or 6. In certain embodiments, y is 1 and r is 0. In certain embodiments, y is 1 and r is 1. In certain embodiments, y is 2 and r is 0. In certain embodiments, y is 2 and r is 1. In certain embodiments, each $R^{12}$ is independently selected from hydrogen, an alkyl, a substituted alkyl, an aryl and a substituted aryl. In certain embodiments, any two adjacent $R^{12}$ groups of the EDA may be cyclically linked, e.g., to form a piperazinyl ring. In certain embodiments, y is 1 and the two adjacent $R^{12}$ groups are an alkyl group, cyclically linked to form a piperazinyl ring. In certain embodiments, y is 1 and the adjacent $R^{12}$ groups are selected from hydrogen, an alkyl (e.g., methyl) and a substituted alkyl (e.g., lower alkyl-OH, such as ethyl-OH or propyl-OH).

In certain embodiments, the tether group includes a 4-amino-piperidine (4AP) moiety (also referred to herein as piperidin-4-amino, P4A). The 4AP moiety may optionally be substituted at one or more convenient positions with any convenient substituents, e.g., with an alkyl, a substituted alkyl, a polyethylene glycol moiety, an acyl, a substituted acyl, an aryl or a substituted aryl. In certain embodiments, the 4AP moiety is described by the structure:

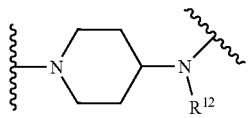

where $R^{12}$ is selected from hydrogen, alkyl, substituted alkyl, a polyethylene glycol moiety (e.g., a polyethylene glycol or a modified polyethylene glycol), alkenyl, substituted alkenyl, alkynyl, substituted alkynyl, alkoxy, substituted alkoxy, amino, substituted amino, carboxyl, carboxyl ester, acyl, acyloxy, acyl amino, amino acyl, alkylamide, substituted alkylamide, sulfonyl, thioalkoxy, substituted thioalkoxy, aryl, substituted aryl, heteroaryl, substituted heteroaryl, cycloalkyl, substituted cycloalkyl, heterocyclyl, and substituted heterocyclyl. In certain embodiments, $R^{12}$ is a polyethylene glycol moiety. In certain embodiments, $R^{12}$ is a carboxy modified polyethylene glycol.

In certain embodiments, $R^{12}$ includes a polyethylene glycol moiety described by the formula: $(PEG)_k$, which may be represented by the structure:

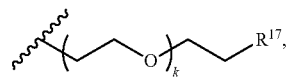

where k is an integer from 1 to 20, such as from 1 to 18, or from 1 to 16, or from 1 to 14, or from 1 to 12, or from 1 to 10, or from 1 to 8, or from 1 to 6, or from 1 to 4, or 1 or 2, such as 1, 2, 3, 4, 5, 6, 7, 8, 9, 10, 11, 12, 13, 14, 15, 16, 17, 18, 19 or 20. In some instances, k is 2. In certain embodiments, $R^{17}$ is selected from OH, COOH, or COOR, where R is selected from alkyl, substituted alkyl, alkenyl, substituted alkenyl, alkynyl, substituted alkynyl, aryl, substituted aryl, heteroaryl, substituted heteroaryl, cycloalkyl, substituted cycloalkyl, heterocyclyl, and substituted heterocyclyl. In certain embodiments, $R^{17}$ is COOH.

In certain embodiments, a tether group (e.g., $T^1$, $T^2$, $T^3$ and/or $T^4$) includes $(PEG)_n$, where $(PEG)_n$ is a polyethylene glycol or a modified polyethylene glycol linking unit. In certain embodiments, $(PEG)_n$ is described by the structure:

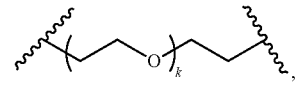

where n is an integer from 1 to 50, such as from 1 to 40, from 1 to 30, from 1 to 20, from 1 to 12 or from 1 to 6, such as 1, 2, 3, 4, 5, 6, 7, 8, 9, 10, 11, 12, 13, 14, 15, 16, 17, 18, 19 or 20. In some instances, n is 2. In some instances, n is 3. In some instances, n is 6. In some instances, n is 12.

In certain embodiments, a tether group (e.g., $T^1$, $T^2$, $T^3$ and/or $T^4$) includes $(AA)_p$, where AA is an amino acid residue. Any convenient amino acids may be utilized. Amino acids of interest include but are not limited to, L- and D-amino acids, naturally occurring amino acids such as any of the 20 primary alpha-amino acids and beta-alanine, non-naturally occurring amino acids (e.g., amino acid analogs), such as a non-naturally occurring alpha-amino acid or a non-naturally occurring beta-amino acid, etc. In certain embodiments, p is an integer from 1 to 50, such as from 1 to 40, from 1 to 30, from 1 to 20, from 1 to 12 or from 1 to 6, such as 1, 2, 3, 4, 5, 6, 7, 8, 9, 10, 11, 12, 13, 14, 15, 16, 17, 18, 19 or 20. In certain embodiments, p is 1. In certain embodiments, p is 2.

In certain embodiments, a tether group (e.g., $T^1$, $T^2$, $T^3$ and/or $T^4$) includes a moiety described by the formula $-(CR^{13}OH)_h-$, where h is 0 or n is an integer from 1 to 50, such as from 1 to 40, from 1 to 30, from 1 to 20, from 1 to 12 or from 1 to 6, such as 1, 2, 3, 4, 5, 6, 7, 8, 9, 10, 11 or 12. In certain embodiments, h is 1. In certain embodiments, h is 2. In certain embodiments, $R^{13}$ is selected from hydrogen, alkyl, substituted alkyl, alkenyl, substituted alkenyl, alkynyl, substituted alkynyl, alkoxy, substituted alkoxy, amino, substituted amino, carboxyl, carboxyl ester, acyl, acyloxy, acyl amino, amino acyl, alkylamide, substituted alkylamide, sulfonyl, thioalkoxy, substituted thioalkoxy, aryl, substituted aryl, heteroaryl, substituted heteroaryl, cycloalkyl, substituted cycloalkyl, heterocyclyl, and substituted heterocyclyl. In certain embodiments, $R^{13}$ is hydrogen. In certain embodiments, $R^{13}$ is alkyl or substituted alkyl, such as $C_{1-6}$ alkyl or $C_{1-6}$ substituted alkyl, or $C_{1-4}$ alkyl or $C_{1-4}$ substituted alkyl, or $C_{1-3}$ alkyl or $C_{1-3}$ substituted alkyl. In certain embodiments, $R^{13}$ is alkenyl or substituted alkenyl, such as $C_{2-6}$ alkenyl or $C_{2-6}$ substituted alkenyl, or $C_{2-4}$ alkenyl or $C_{2-4}$ substituted alkenyl, or $C_{2-3}$ alkenyl or $C_{2-3}$ substituted alkenyl. In certain embodiments, $R^{13}$ is alkynyl or substituted alkynyl. In certain embodiments, $R^{13}$ is alkoxy or substituted alkoxy. In certain embodiments, $R^{13}$ is amino or substituted amino. In certain embodiments, $R^{13}$ is carboxyl or carboxyl ester. In certain embodiments, $R^{13}$ is acyl or acyloxy. In certain embodiments, $R^{13}$ is acyl amino or amino acyl. In certain embodiments, $R^{13}$ is alkylamide or substituted alkylamide. In certain embodiments, $R^{13}$ is sulfonyl. In certain embodiments, $R^{13}$ is thioalkoxy or substituted thioalkoxy. In certain embodiments, $R^{13}$ is aryl or substituted aryl, such as $C_{5-8}$ aryl or $C_{5-8}$ substituted aryl, such as a $C_5$ aryl or $C_5$ substituted aryl, or a $C_6$ aryl or $C_6$ substituted aryl. In certain embodiments, $R^{13}$ is heteroaryl or substituted heteroaryl, such as $C_{5-8}$ heteroaryl or $C_{5-8}$ substituted heteroaryl, such as a $C_5$ heteroaryl or $C_5$ substituted heteroaryl, or a $C_6$ heteroaryl or $C_6$ substituted heteroaryl. In certain embodiments, $R^{13}$ is cycloalkyl or substituted cycloalkyl, such as $C_{3-8}$ cycloalkyl or $C_{3-8}$ substituted cycloalkyl, such as a $C_{3-6}$ cycloalkyl or $C_{3-6}$ substituted cycloalkyl, or a $C_{3-5}$ cycloalkyl or $C_{3-5}$ substituted cycloalkyl. In certain embodiments, $R^{13}$ is heterocyclyl or substituted heterocyclyl, such as $C_{3-8}$ heterocyclyl or $C_{3-8}$ substituted heterocyclyl, such as a $C_{3-6}$ heterocyclyl or $C_{3-6}$ substituted heterocyclyl, or a $C_{3-5}$ heterocyclyl or $C_{3-5}$ substituted heterocyclyl.

In certain embodiments, $R^{13}$ is selected from hydrogen, an alkyl, a substituted alkyl, an aryl, and a substituted aryl. In these embodiments, alkyl, substituted alkyl, aryl, and substituted aryl are as described above for $R^{13}$.

Regarding the linking functional groups, $V^1$, $V^2$, $V^3$ and $V^4$, any convenient linking functional groups may be utilized in the subject linkers. Linking functional groups of interest include, but are not limited to, amino, carbonyl, amido, oxycarbonyl, carboxy, sulfonyl, sulfoxide, sulfonylamino, aminosulfonyl, thio, oxy, phospho, phosphoramidate, thiophosphoraidate, and the like. In some embodiments, $V^1$, $V^2$, $V^3$ and $V^4$ are each independently selected from a covalent bond, —CO—, —NR$^{15}$—, —NR$^{15}$(CH$_2$)$_q$—, —NR$^{15}$(C$_6$H$_4$)—, —CONR$^{15}$—, —NR$^{15}$CO—, —C(O)O—, —OC(O)—, —O—, —S—, —S(O)—, —SO$_2$—, —SO$_2$NR$^{15}$—, —NR$^{15}$SO$_2$— and —P(O)OH—, where q is an integer from 1 to 6. In certain embodiments, q is an integer from 1 to 6 (e.g., 1, 2, 3, 4, 5 or 6). In certain embodiments, q is 1. In certain embodiments, q is 2.

In some embodiments, each $R^{15}$ is independently selected from hydrogen, alkyl, substituted alkyl, alkenyl, substituted alkenyl, alkynyl, substituted alkynyl, alkoxy, substituted alkoxy, amino, substituted amino, carboxyl, carboxyl ester, acyl, acyloxy, acyl amino, amino acyl, alkylamide, substituted alkylamide, sulfonyl, thioalkoxy, substituted thioalkoxy, aryl, substituted aryl, heteroaryl, substituted heteroaryl, cycloalkyl, substituted cycloalkyl, heterocyclyl, and substituted heterocyclyl.

The various possibilities for each $R^{15}$ are described in more detail as follows. In certain embodiments, $R^{15}$ is hydrogen. In certain embodiments, each $R^{15}$ is hydrogen. In certain embodiments, $R^{15}$ is alkyl or substituted alkyl, such as $C_{1-6}$ alkyl or $C_{1-6}$ substituted alkyl, or $C_{1-4}$ alkyl or $C_{1-4}$ substituted alkyl, or $C_{1-3}$ alkyl or $C_{1-3}$ substituted alkyl. In certain embodiments, $R^{15}$ is alkenyl or substituted alkenyl, such as $C_{2-6}$ alkenyl or $C_{2-6}$ substituted alkenyl, or $C_{2-4}$ alkenyl or $C_{2-4}$ substituted alkenyl, or $C_{2-3}$ alkenyl or $C_{2-3}$ substituted alkenyl. In certain embodiments, $R^{15}$ is alkynyl or substituted alkynyl. In certain embodiments, $R^{15}$ is alkoxy or substituted alkoxy. In certain embodiments, $R^{15}$ is amino or substituted amino. In certain embodiments, $R^{15}$ is carboxyl or carboxyl ester. In certain embodiments, $R^{15}$ is acyl or acyloxy. In certain embodiments, $R^{15}$ is acyl amino or amino acyl. In certain embodiments, $R^{15}$ is alkylamide or substituted alkylamide. In certain embodiments, $R^{15}$ is sulfonyl. In certain embodiments, $R^{15}$ is thioalkoxy or substituted thioalkoxy. In certain embodiments, $R^{15}$ is aryl or substituted aryl, such as $C_{5-8}$ aryl or $C_{5-8}$ substituted aryl, such as a $C_5$ aryl or $C_5$ substituted aryl, or a $C_6$ aryl or $C_6$ substituted aryl. In certain embodiments, $R^{15}$ is heteroaryl or substituted heteroaryl, such as $C_{5-8}$ heteroaryl or $C_{5-8}$ substituted heteroaryl, such as a $C_5$ heteroaryl or $C_5$ substituted heteroaryl, or a $C_6$ heteroaryl or $C_6$ substituted heteroaryl. In certain embodiments, $R^{15}$ is cycloalkyl or substituted cycloalkyl, such as $C_{3-8}$ cycloalkyl or $C_{3-8}$ substituted cycloalkyl, such as a $C_{3-6}$ cycloalkyl or $C_{3-6}$ substituted cycloalkyl, or a $C_{3-5}$ cycloalkyl or $C_{3-5}$ substituted cycloalkyl. In certain embodiments, $R^{15}$ is heterocyclyl or substituted heterocyclyl, such as $C_{3-8}$ heterocyclyl or $C_{3-8}$ substituted heterocyclyl, such as a $C_{3-6}$ heterocyclyl or $C_{3-6}$ substituted heterocyclyl, or a $C_{3-5}$ heterocyclyl or $C_{3-5}$ substituted heterocyclyl.

In certain embodiments, each $R^{15}$ is independently selected from hydrogen, alkyl, substituted alkyl, alkenyl, substituted alkenyl, alkynyl, substituted alkynyl, carboxyl, carboxyl ester, acyl, aryl, substituted aryl, heteroaryl, substituted heteroaryl, cycloalkyl, substituted cycloalkyl, heterocyclyl, and substituted heterocyclyl. In these embodiments, the hydrogen, alkyl, substituted alkyl, alkenyl, substituted alkenyl, alkynyl, substituted alkynyl, carboxyl, carboxyl ester, acyl, aryl, substituted aryl, heteroaryl, substituted heteroaryl, cycloalkyl, substituted cycloalkyl, heterocyclyl, and substituted heterocyclyl substituents are as described above for $R^{15}$.

In certain embodiments, the tether group includes an acetal group, a disulfide, a hydrazine, or an ester. In some embodiments, the tether group includes an acetal group. In some embodiments, the tether group includes a disulfide. In some embodiments, the tether group includes a hydrazine. In some embodiments, the tether group includes an ester.

As described above, in some embodiments, L is a linker comprising -(T$^1$-V$^1$)$_a$-(T$^2$-V$^2$)$_b$-(T$^3$-V$^3$)$_c$-(T$^4$-V$^4$)$_d$—, where a, b, c and d are each independently 0 or 1, where the sum of a, b, c and d is 1 to 4.

In some embodiments, in the subject linker:

$T^1$ is selected from a (C$_1$-C$_{12}$)alkyl and a substituted (C$_1$-C$_{12}$)alkyl;

$T^2$, $T^3$ and $T^4$ are each independently selected from (C$_1$-C$_{12}$)alkyl, substituted (C$_1$-C$_{12}$)alkyl, (EDA)$_w$, (PEG)$_n$, (AA)$_p$, —(CR$^{13}$OH)$_h$—, 4-amino-piperidine (4AP), an acetal group, a disulfide, a hydrazine, and an ester; and $V^1$, $V^2$, $V^3$ and $V^4$ are each independently selected from a covalent bond, —CO—, —NR$^{15}$— —NR$^{15}$(CH$_2$)$_q$—, —NR$^{15}$(C$_6$H$_4$)—, —CONR$^{15}$—, —NR$^{15}$CO—, —C(O)O—, —OC(O)—, —O—, —S—, —S(O)—, —SO$_2$—, —SO$_2$NR$^{15}$—, —NR$^{15}$SO$_2$— and —P(O)OH—, wherein q is an integer from 1 to 6;

wherein:

(PEG)$_n$ is

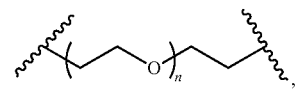

where n is an integer from 1 to 30;

EDA is an ethylene diamine moiety having the following structure:

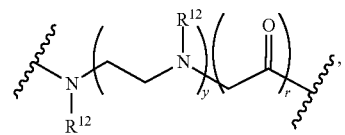

where y is an integer from 1 to 6 and r is 0 or 1;

4-amino-piperidine (4AP) is

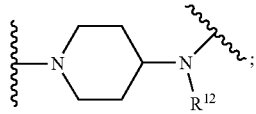

AA is an amino acid residue, where p is an integer from 1 to 20; and each $R^{15}$ and $R^{12}$ is independently selected from hydrogen, an alkyl, a substituted alkyl, an aryl and a substituted aryl, wherein any two adjacent $R^{12}$ groups may be cyclically linked to form a piperazinyl ring; and $R^{13}$ is selected from hydrogen, an alkyl, a substituted alkyl, an aryl, and a substituted aryl.

In certain embodiments, $T^1$, $T^2$, $T^3$ and $T^4$ and $V^1$, $V^2$, $V^3$ and $V^4$ are selected from the following table, e.g., one row of the following table:

| $T^1$ | $V^1$ | $T^2$ | $V^2$ | $T^3$ | $V^3$ | $T^4$ | $V^4$ |
|---|---|---|---|---|---|---|---|
| $(C_1-C_{12})$alkyl | —$CONR^{15}$— | $(PEG)_n$ | —CO— | — | — | — | — |
| $(C_1-C_{12})$alkyl | —CO— | $(AA)_p$ | —$NR^{15}$— | $(PEG)_n$ | —CO— | — | — |
| $(C_1-C_{12})$alkyl | —CO— | $(AA)_p$ | — | — | — | — | — |
| $(C_1-C_{12})$alkyl | —$CONR^{15}$— | $(PEG)_n$ | —$NR^{15}$— | — | — | — | — |
| $(C_1-C_{12})$alkyl | —CO— | $(AA)_p$ | —$NR^{15}$— | $(PEG)_n$ | —$NR^{15}$— | — | — |
| $(C_1-C_{12})$alkyl | —CO— | $(EDA)_w$ | —CO— | — | — | — | — |
| $(C_1-C_{12})$alkyl | —$CONR^{15}$— | $(C_1-C_{12})$alkyl | —$NR^{15}$— | — | — | — | — |
| $(C_1-C_{12})$alkyl | —$CONR^{15}$— | $(PEG)_n$ | —CO— | $(EDA)_w$ | — | — | — |
| $(C_1-C_{12})$alkyl | —CO— | $(EDA)_w$ | — | — | — | — | — |
| $(C_1-C_{12})$alkyl | —CO— | $(EDA)_w$ | —CO— | $(CR^{13}OH)_h$ | —$CONR^{15}$— | $(C_1-C_{12})$alkyl | —CO— |
| $(C_1-C_{12})$alkyl | —CO— | $(AA)_p$ | —$NR^{15}$— | $(C_1-C_{12})$alkyl | —CO— | — | — |
| $(C_1-C_{12})$alkyl | —$CONR^{15}$— | $(PEG)_n$ | —CO— | $(AA)_p$ | — | — | — |
| $(C_1-C_{12})$alkyl | —CO— | $(EDA)_w$ | —CO— | $(CR^{13}OH)_h$ | —CO— | $(AA)_p$ | — |
| $(C_1-C_{12})$alkyl | —CO— | $(AA)_p$ | —$NR^{15}$— | $(C_1-C_{12})$alkyl | —CO— | $(AA)_p$ | — |
| $(C_1-C_{12})$alkyl | —CO— | $(AA)_p$ | —$NR^{15}$— | $(PEG)_n$ | —CO— | $(AA)_p$ | — |
| $(C_1-C_{12})$alkyl | —CO— | $(AA)_p$ | —$NR^{15}$— | $(PEG)_n$ | —$SO_2$— | $(AA)_p$ | — |
| $(C_1-C_{12})$alkyl | —CO— | $(EDA)_w$ | —CO— | $(CR^{13}OH)_h$ | —$CONR^{15}$— | $(PEG)_n$ | —CO— |
| $(C_1-C_{12})$alkyl | —CO— | $(CR^{13}OH)_h$ | —CO— | — | — | — | — |
| $(C_1-C_{12})$alkyl | —$CONR^{15}$— | substituted $(C_1-C_{12})$alkyl | —$NR^{15}$— | $(PEG)_n$ | —CO— | — | — |
| $(C_1-C_{12})$alkyl | —$SO_2$— | $(C_1-C_{12})$alkyl | —CO— | — | — | — | — |
| $(C_1-C_{12})$alkyl | —$CONR^{15}$— | $(C_1-C_{12})$alkyl | — | $(CR^{13}OH)_h$ | —$CONR^{15}$— | — | — |
| $(C_1-C_{12})$alkyl | —CO— | $(AA)_p$ | —$NR^{15}$— | $(PEG)_n$ | —CO— | $(AA)_p$ | —$NR^{15}$— |
| $(C_1-C_{12})$alkyl | —CO— | $(AA)_p$ | —$NR^{15}$— | $(PEG)_n$ | —P(O)OH— | $(AA)_p$ | — |
| $(C_1-C_{12})$alkyl | —CO— | $(EDA)_w$ | — | $(AA)_p$ | — | — | — |
| $(C_1-C_{12})$alkyl | —$CONR^{15}$— | $(C_1-C_{12})$alkyl | —$NR^{15}$— | — | —CO— | — | — |
| $(C_1-C_{12})$alkyl | —$CONR^{15}$— | $(C_1-C_{12})$alkyl | —$NR^{15}$— | — | —CO— | $(C_1-C_{12})$alkyl | —$NR^{15}$— |
| $(C_1-C_{12})$alkyl | —CO— | 4AP | —CO— | $(C_1-C_{12})$alkyl | —CO— | $(AA)_p$ | — |
| $(C_1-C_{12})$alkyl | —CO— | 4AP | —CO— | $(C_1-C_{12})$alkyl | —CO— | — | — |

In certain embodiments, L is a linker comprising -$(L^1)_a$-$(L^2)_b$-$(L^3)_c$-$(L^4)_d$-, where -$(L^1)_a$- is -$(T^1-V^1)_a$-; -$(L^2)_b$- is -$(T^2-V^2)_b$-; -$(L^3)_c$- is -$(T^3-V^3)_c$-; and -$(L^4)_d$- is -$(T^4-V^4)_d$-.

In certain embodiments, $T^1$ is $(C_1-C_{12})$alkyl, $V^1$ is —CO—, $T^2$ is $(AA)_p$, $V^2$ is —$NR^{15}$—, $T^3$ is $(PEG)_n$, $V^3$ is —CO—, $T^4$ is absent and $V^4$ is absent.

In certain embodiments, $T^1$ is $(C_1-C_{12})$alkyl, $V^1$ is —CO—, $T^2$ is $(EDA)_w$, $V^2$ is —CO—, $T^3$ is $(CR^{13}OH)_h$, $V^3$ is —$CONR^{15}$—, $T^4$ is $(C_1-C_{12})$alkyl and $V^4$ is —CO—.

In certain embodiments, $T^1$ is $(C_1-C_{12})$alkyl, $V^1$ is —CO—, $T^2$ is $(AA)_p$, $V^2$ is —$NR^{15}$—, $T^3$ is $(C_1-C_{12})$alkyl, $V^3$ is —CO—, $T^4$ is absent and $V^4$ is absent.

In certain embodiments, $T^1$ is $(C_1-C_{12})$alkyl, $V^1$ is —$CONR^{15}$—, $T^2$ is $(PEG)_n$, $V^2$ is —CO—, $T^3$ is absent, $V^3$ is absent, $T^4$ is absent and $V^4$ is absent.

In certain embodiments, $T^1$ is $(C_1-C_{12})$alkyl, $V^1$ is —CO—, $T^2$ is $(AA)_p$, $V^2$ is absent, $T^3$ is absent, $V^3$ is absent, $T^4$ is absent and $V^4$ is absent.

In certain embodiments, $T^1$ is $(C_1-C_{12})$alkyl, $V^1$ is —$CONR^{15}$—, $T^2$ is $(PEG)_n$, $V^2$ is —$NR^{15}$—, $T^3$ is absent, $V^3$ is absent, $T^4$ is absent and $V^4$ is absent.

In certain embodiments, $T^1$ is $(C_1-C_{12})$alkyl, $V^1$ is —CO—, $T^2$ is $(AA)_p$, $V^2$ is —$NR^{15}$—, $T^3$ is $(PEG)_n$, $V^3$ is —$NR^{15}$—, $T^4$ is absent and $V^4$ is absent.

In certain embodiments, $T^1$ is $(C_1-C_{12})$alkyl, $V^1$ is —CO—, $T^2$ is $(EDA)_w$, $V^2$ is —CO—, $T^3$ is absent, $V^3$ is absent, $T^4$ is absent and $V^4$ is absent.

In certain embodiments, $T^1$ is $(C_1-C_{12})$alkyl, $V^1$ is —$CONR^{15}$—, $T^2$ is $(C_1-C_{12})$alkyl, $V^2$ is —$NR^{15}$—, $T^3$ is absent, $V^3$ is absent, $T^4$ is absent and $V^4$ is absent.

In certain embodiments, $T^1$ is $(C_1-C_{12})$alkyl, $V^1$ is —$CONR^{15}$—, $T^2$ is $(PEG)_n$, $V^2$ is —CO—, $T^3$ is $(EDA)_w$, $V^3$ is absent, $T^4$ is absent and $V^4$ is absent.

In certain embodiments, $T^1$ is $(C_1-C_{12})$alkyl, $V^1$ is —CO—, $T^2$ is $(EDA)_w$, $V^2$ is absent, $T^3$ is absent, $V^3$ is absent, $T^4$ is absent and $V^4$ is absent.

In certain embodiments, $T^1$ is $(C_1-C_{12})$alkyl, $V^1$ is —$CONR^{15}$—, $T^2$ is $(PEG)_n$, $V^2$ is —CO—, $T^3$ is $(AA)_p$, $V^3$ is absent, $T^4$ is absent and $V^4$ is absent.

In certain embodiments, $T^1$ is $(C_1-C_{12})$alkyl, $V^1$ is —CO—, $T^2$ is $(EDA)_w$, $V^2$ is —CO—, $T^3$ is $(CR^{13}OH)_h$, $V^3$ is —CO—, $T^4$ is $(AA)_p$ and $V^4$ is absent.

In certain embodiments, $T^1$ is $(C_1-C_{12})$alkyl, $V^1$ is —CO—, $T^2$ is $(AA)_p$, $V^2$ is —$NR^{15}$—, $T^3$ is $(C_1-C_{12})$alkyl, $V^3$ is —CO—, $T^4$ is $(AA)_p$ and $V^4$ is absent.

In certain embodiments, $T^1$ is $(C_1-C_{12})$alkyl, $V^1$ is —CO—, $T^2$ is $(AA)_p$, $V^2$ is —$NR^{15}$—, $T^3$ is $(PEG)_n$, $V^3$ is —CO—, $T^4$ is $(AA)_p$ and $V^4$ is absent.

In certain embodiments, $T^1$ is $(C_1-C_{12})$alkyl, $V^1$ is —CO—, $T^2$ is $(AA)_p$, $V^2$ is —$NR^{15}$—, $T^3$ is $(PEG)_n$, $V^3$ is —$SO_2$—, $T^4$ is $(AA)_p$ and $V^4$ is absent.

In certain embodiments, $T^1$ is $(C_1-C_{12})$alkyl, $V^1$ is —CO—, $T^2$ is $(EDA)_w$, $V^2$ is —CO-$T^3$ is $(CR^{13}OH)_h$, $V^3$ is —$CONR^{15}$—, $T^4$ is $(PEG)_n$ and $V^4$ is —CO—.

In certain embodiments, $T^1$ is $(C_1\text{-}C_{12})$alkyl, $V^1$ is —CO—, $T^2$ is $(CR^{13}OH)_h$, $V^2$ is —CO—, $T^3$ is absent, $V^3$ is absent, $T^4$ is absent and $V^4$ is absent.

In certain embodiments, $T^1$ is $(C_1\text{-}C_{12})$alkyl, $V^1$ is —CONR$^{15}$—, $T^2$ is substituted $(C_1\text{-}C_{12})$alkyl, $V^2$ is —NR$^{15}$—, $T^3$ is (PEG)$_n$, $V^3$ is —CO—, $T^4$ is absent and $V^4$ is absent.

In certain embodiments, $T^1$ is $(C_1\text{-}C_{12})$alkyl, $V^1$ is —SO$_2$—, $T^2$ is $(C_1\text{-}C_{12})$alkyl, $V^2$ is —CO—, $T^3$ is absent, $V^3$ is absent, $T^4$ is absent and $V^4$ is absent.

In certain embodiments, $T^1$ is $(C_1\text{-}C_{12})$alkyl, $V^1$ is —CONR$^{15}$—, $T^2$ is $(C_1\text{-}C_{12})$alkyl, $V^2$ is absent, $T^3$ is $(CR^{13}OH)_h$, $V^3$ is —CONR$^{15}$—, $T^4$ is absent and $V^4$ is absent.

In certain embodiments, $T^1$ is $(C_1\text{-}C_{12})$alkyl, $V^1$ is —CO—, $T^2$ is (AA)$_p$, $V^2$ is —NR$^{15}$–, $T^3$ is (PEG)$_n$, $V^3$ is —CO—, $T^4$ is (AA)$_p$ and $V^4$ is —NR$^{15}$—.

In certain embodiments, $T^1$ is $(C_1\text{-}C_{12})$alkyl, $V^1$ is —CO—, $T^2$ is (AA)$_p$, $V^2$ is —NR$^{15}$–, $T^3$ is (PEG)$_n$, $V^3$ is —P(O)OH—, $T^4$ is (AA)$_p$ and $V^4$ is absent.

In certain embodiments, $T^1$ is $(C_1\text{-}C_{12})$alkyl, $V^1$ is —CO—, $T^2$ is (EDA)$_w$, $V^2$ is absent, $T^3$ is (AA)$_p$, $V^3$ is absent, $T^4$ is absent and $V^4$ is absent.

In certain embodiments, $T^1$ is $(C_1\text{-}C_{12})$alkyl, $V^1$ is —CO—, $T^2$ is (EDA)$_w$, $V^2$ is —CO—, $T^3$ is $(CR^{13}OH)_h$, $V^3$ is —CONR$^{15}$—, $T^4$ is $(C_1\text{-}C_{12})$alkyl and $V^4$ is —CO(AA)$_p$-.

In certain embodiments, $T^1$ is $(C_1\text{-}C_{12})$alkyl, $V^1$ is —CONR$^{15}$—, $T^2$ is $(C_1\text{-}C_{12})$alkyl, $V^2$ is —NR$^{15}$—, $T^3$ is absent, $V^3$ is —CO—, $T^4$ is absent and $V^4$ is absent.

In certain embodiments, $T^1$ is $(C_1\text{-}C_{12})$alkyl, $V^1$ is —CONR$^{15}$—, $T^2$ is $(C_1\text{-}C_{12})$alkyl, $V^2$ is —NR$^{15}$—, $T^3$ is absent, $V^3$ is —CO—, $T^4$ is $(C_1\text{-}C_{12})$alkyl and $V^4$ is —NR$^{15}$—.

In certain embodiments, $T^1$ is $(C_1\text{-}C_{12})$alkyl, $V^1$ is —CO—, $T^2$ is (EDA)$_w$, $V^2$ is —CO—, $T^3$ is $(CR^{13}OH)_h$, $V^3$ is —CONR$^{15}$—, $T^4$ is (PEG)$_n$ and $V^4$ is —CO(AA)$_p$-.

In certain embodiments, $T^1$ is $(C_1\text{-}C_{12})$alkyl, $V^1$ is —CO—, $T^2$ is 4AP, $V^2$ is —CO—, $T^3$ is $(C_1\text{-}C_{12})$alkyl, $V^3$ is —CO—, $T^4$ is (AA)$_p$ and $V^4$ is absent.

In certain embodiments, $T^1$ is $(C_1\text{-}C_{12})$alkyl, $V^1$ is —CO—, $T^2$ is 4AP, $V^2$ is —CO—, $T^3$ is $(C_1\text{-}C_{12})$alkyl, $V^3$ is —CO—, $T^4$ is absent and $V^4$ is absent.

In certain embodiments, the linker is described by one of the following structures:

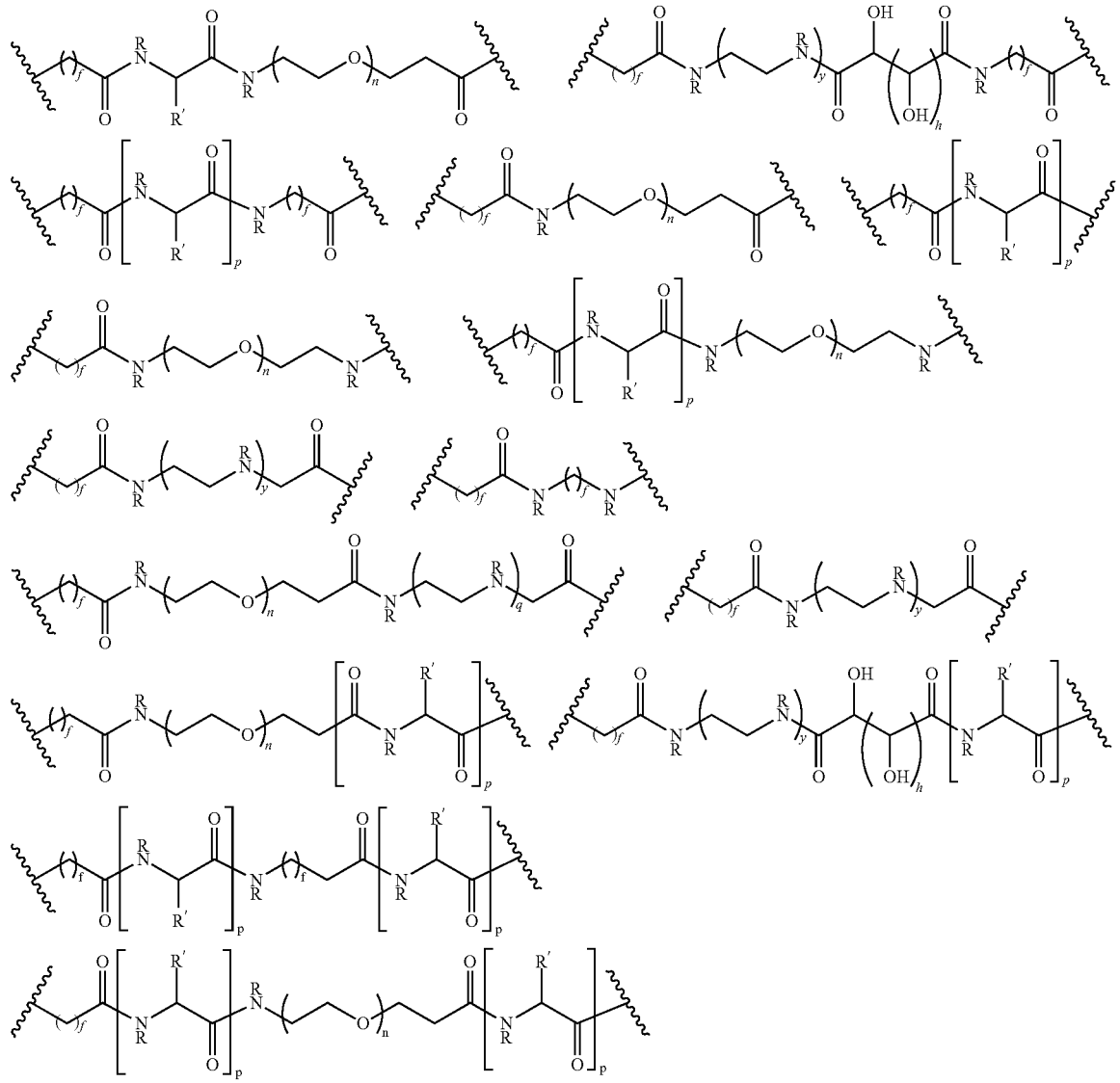

-continued
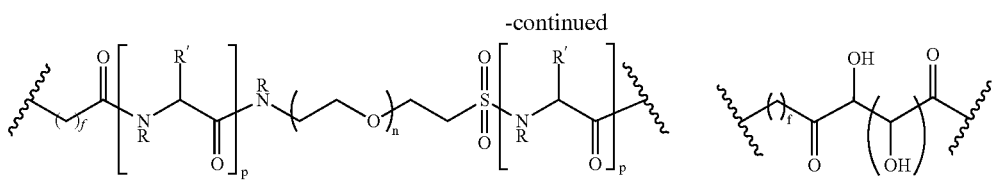
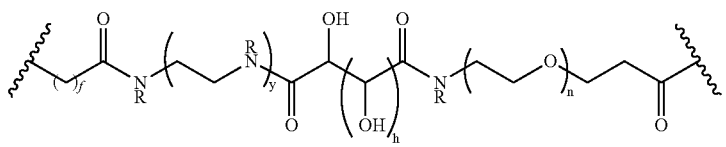
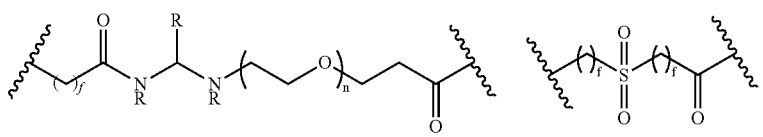
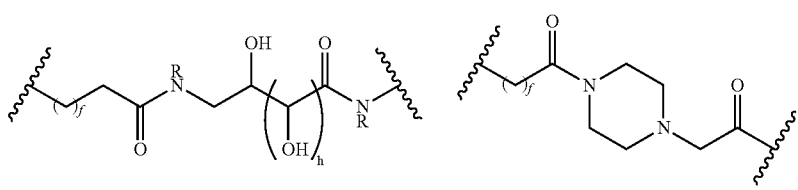
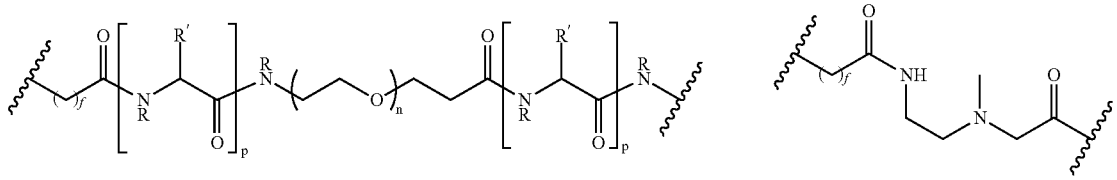
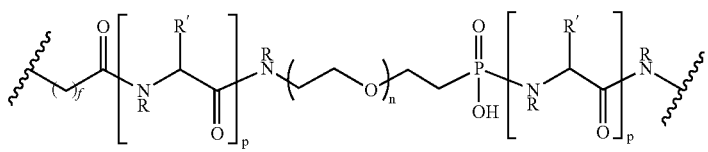
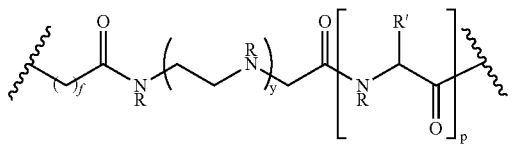
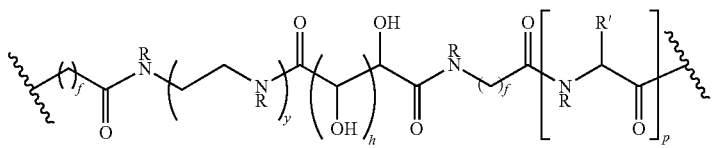
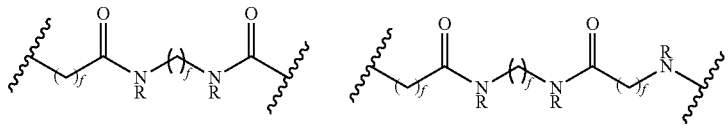
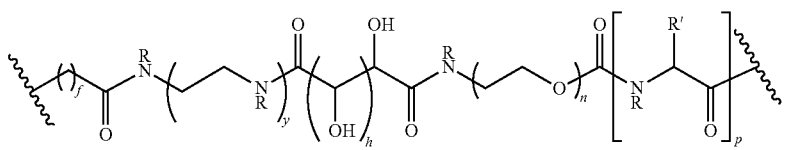

-continued

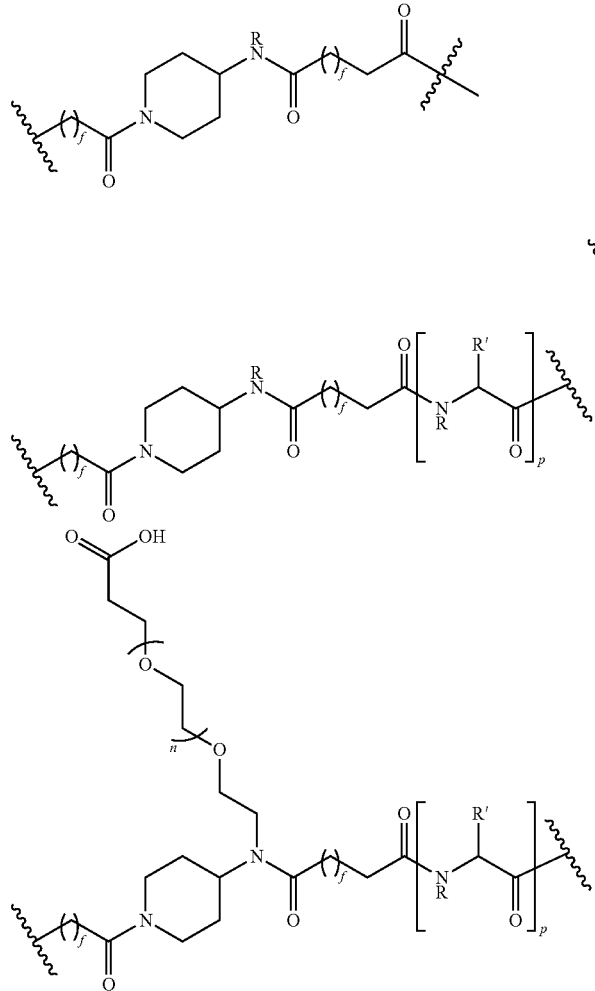
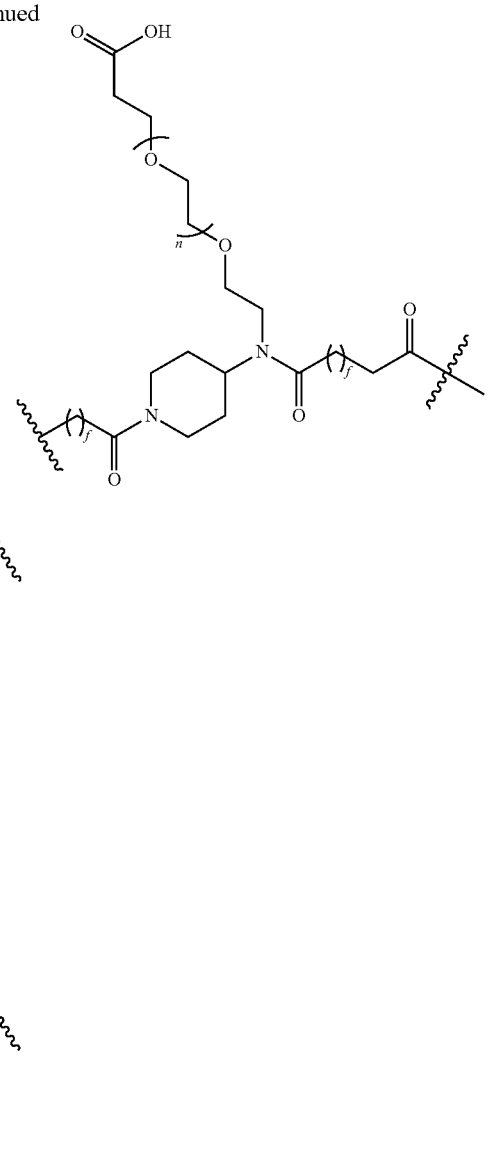

In certain embodiments of the linker structures depicted above, each f is independently 0 or an integer from 1 to 12; each y is independently 0 or an integer from 1 to 20; each n is independently 0 or an integer from 1 to 30; each p is independently 0 or an integer from 1 to 20; each h is independently 0 or an integer from 1 to 12; each R is independently hydrogen, alkyl, substituted alkyl, alkenyl, substituted alkenyl, alkynyl, substituted alkynyl, alkoxy, substituted alkoxy, amino, substituted amino, carboxyl, carboxyl ester, acyl, acyloxy, acyl amino, amino acyl, alkylamide, substituted alkylamide, sulfonyl, thioalkoxy, substituted thioalkoxy, aryl, substituted aryl, heteroaryl, substituted heteroaryl, cycloalkyl, substituted cycloalkyl, heterocyclyl, and substituted heterocyclyl; and each R' is independently H, a sidechain of an amino acid, alkyl, substituted alkyl, alkenyl, substituted alkenyl, alkynyl, substituted alkynyl, alkoxy, substituted alkoxy, amino, substituted amino, carboxyl, carboxyl ester, acyl, acyloxy, acyl amino, amino acyl, alkylamide, substituted alkylamide, sulfonyl, thioalkoxy, substituted thioalkoxy, aryl, substituted aryl, heteroaryl, substituted heteroaryl, cycloalkyl, substituted cycloalkyl, heterocyclyl, and substituted heterocyclyl. In certain embodiments of the linker structures depicted above, each f is independently 0, 1, 2, 3, 4, 5 or 6; each y is independently 0, 1, 2, 3, 4, 5 or 6; each n is independently 0, 1, 2, 3, 4, 5 or 6; each p is independently 0, 1, 2, 3, 4, 5 or 6; and each h is independently 0, 1, 2, 3, 4, 5 or 6. In certain embodiments of the linker structures depicted above, each R is independently H, methyl or —(CH$_2$)$_m$—OH where m is 1, 2, 3 or 4 (e.g., 2).

In certain embodiments of the linker, L, $T^1$ is (C$_1$-C$_{12}$)alkyl, V$^1$ is —CO—, T$^2$ is 4AP, V$^2$ is —CO—, T$^3$ is (C$_1$-C$_{12}$)alkyl, V$^3$ is —CO—, T$^4$ is absent and V$^4$ is absent. In certain embodiments, T$^1$ is ethylene, V$^1$ is —CO—, T$^2$ is 4AP, V$^2$ is —CO—, T$^3$ is ethylene, V$^3$ is —CO—, T$^4$ is absent and V$^4$ is absent. In certain embodiments, T$^1$ is ethylene, V$^1$ is —CO—, T$^2$ is 4AP, V$^2$ is —CO—, T$^3$ is ethylene, V$^3$ is —CO—, T$^4$ is absent and V$^4$ is absent, where T$^2$ (e.g., 4AP) has the following structure:

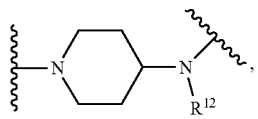

wherein
$R^{12}$ is a polyethylene glycol moiety (e.g., a polyethylene glycol or a modified polyethylene glycol).

In certain embodiments, the linker, L, includes the following structure:

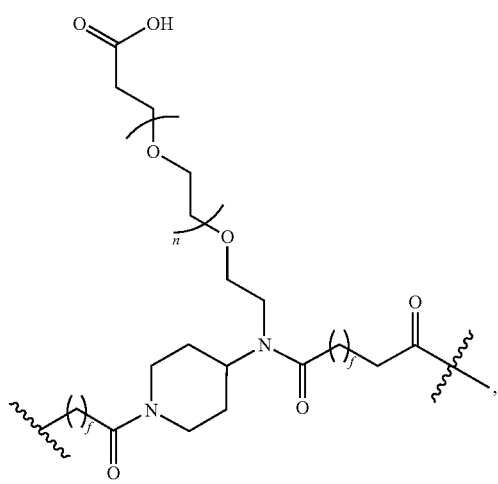

wherein
each f is independently an integer from 1 to 12; and
n is an integer from 1 to 30.

In certain embodiments, f is 1. In certain embodiments, f is 2. In certain embodiments, one f is 2 and one f is 1.

In certain embodiments, n is 1.

In certain embodiments, the left-hand side of the above linker structure is attached to the hydrazinyl-indolyl or the hydrazinyl-pyrrolo-pyridinyl coupling moiety, and the right-hand side of the above linker structure is attached to a maytansine.

Any of the chemical entities, linkers and coupling moieties set forth in the structures above may be adapted for use in the subject compounds and conjugates.

Additional disclosure related to hydrazinyl-indolyl and hydrazinyl-pyrrolo-pyridinyl compounds and methods for producing a conjugate is found in U.S. Application Publication No. 2014/0141025, filed Mar. 11, 2013, and U.S. Application Publication No. 2015/0157736, filed Nov. 26, 2014, the disclosures of each of which are incorporated herein by reference.

Anti-CD22 Antibodies

As noted above, a subject conjugate can comprise, as substituent $W^2$ an anti-CD22 antibody, where the anti-CD22 antibody has been modified to include a 2-formylglycine (FGly) residue. As used herein, amino acids may be referred to by their standard name, their standard three letter abbreviation and/or their standard one letter abbreviation, such as: Alanine or Ala or A; Cysteine or Cys or C; Aspartic acid or Asp or D; Glutamic acid or Glu or E; Phenylalanine or Phe or F; Glycine or Gly or G; Histidine or His or H; Isoleucine or Ile or I; Lysine or Lys or K; Leucine or Leu or L; Methionine or Met or M; Asparagine or Asn or N; Proline or Pro or P; Glutamine or Gln or Q; Arginine or Arg or R; Serine or Ser or S; Threonine or Thr or T; Valine or Val or V; Tryptophan or Trp or W; and Tyrosine or Tyr or Y.

In some cases, a suitable anti-CD22 antibody specifically binds a CD22 polypeptide, where the epitope comprises amino acid residues within a CD22 antigen (e.g., within amino acids 1 to 846 (SEQ ID NO: 23), within amino acids 1-759 (SEQ ID NO: 21), within amino acids 1-751 (SEQ ID NO: 24), or within amino acids 1-670 (SEQ ID NO: 22), of a CD22 amino acid sequence depicted in FIG. 8A-8C).

The CD22 epitope can be formed by a polypeptide having at least about 75%, at least about 80%, at least about 85%, at least about 90%, at least about 95%, at least about 98%, at least about 99%, or 100%, amino acid sequence identity to a contiguous stretch of from about 500 amino acids to about 670 amino acids of the human CD22 isoform 4 amino acid sequence (SEQ ID NO: 22) depicted in FIG. 8A-8C. The CD22 epitope can be formed by a polypeptide having at least about 75%, at least about 80%, at least about 85%, at least about 90%, at least about 95%, at least about 98%, at least about 99%, or 100%, amino acid sequence identity to a contiguous stretch of from about 500 amino acids to about 751 amino acids of the human CD22 isoform 3 amino acid sequence (SEQ ID NO: 24) depicted in FIG. 8A-8C. The CD22 epitope can be formed by a polypeptide having at least about 75%, at least about 80%, at least about 85%, at least about 90%, at least about 95%, at least about 98%, at least about 99%, or 100%, amino acid sequence identity to a contiguous stretch of from about 500 amino acids to about 759 amino acids of the human CD22 isoform 2 amino acid sequence (SEQ ID NO: 21) depicted in FIG. 8A-8C. The CD22 epitope can be formed by a polypeptide having at least about 75%, at least about 80%, at least about 85%, at least about 90%, at least about 95%, at least about 98%, at least about 99%, or 100%, amino acid sequence identity to a contiguous stretch of from about 500 amino acids to about 846 amino acids of the human CD22 isoform 1 amino acid sequence (SEQ ID NO: 23) depicted in FIG. 8A-8C.

A "CD22 antigen" or "CD22 polypeptide" can comprises an amino acid sequence having at least about 75%, at least about 80%, at least about 90%, at least about 95%, at least about 98%, at least about 99%, or 100%, amino acid sequence identity to a contiguous stretch of from about 500 amino acids (aa) to about 846 aa (SEQ ID NO: 23) (isoform 1), to about 759 aa (SEQ ID NO: 21) (isoform 2), to about 751 aa (SEQ ID NO: 24) (isoform 3), or to about 670 aa (SEQ ID NO: 22) (isoform 4) of a CD22 isoform 1, 2, 3, or 4 amino acid sequence depicted in FIG. 8A-8C.

In some cases, a suitable anti-CD22 antibody exhibits high affinity binding to CD22. For example, in some cases, a suitable anti-CD22 antibody binds to CD22 with an affinity of at least about $10^{-7}$ M, at least about $10^{-8}$ M, at least about $10^{-9}$ M, at least about $10^{-10}$ M, at least about $10^{-11}$ M, or at least about $10^{-12}$ M, or greater than $10^{-12}$ M. In some cases, a suitable anti-CD22 antibody binds to an epitope present on CD22 with an affinity of from about $10^{-7}$ M to about $10^{-8}$ M, from about $10^{-8}$ M to about $10^{-9}$ M, from about $10^{-9}$ M to about $10^{-10}$ M, from about $10^{-10}$ M to about $10^{-11}$ M, or from about $10^{-11}$ M to about $10^{-12}$ M, or greater than $10^{-12}$ M.

In some cases, a suitable anti-CD22 antibody competes for binding to an epitope within CD22 with a second anti-CD22 antibody and/or binds to the same epitope within CD22, as a second anti-CD22 antibody. In some cases, an anti-CD22 antibody that competes for binding to an epitope within CD22 with a second anti-CD22 antibody also binds to the epitope as the second anti-CD22 antibody. In some cases, an anti-CD22 antibody that competes for binding to an epitope within CD22 with a second anti-CD22 antibody binds to an epitope that is overlapping with the epitope bound by the second anti-CD22 antibody. In some cases, the anti-CD22 antibody is humanized.

In some cases, a suitable anti-CD22 antibody can induce apoptosis in a cell that expresses CD22 on its cell surface.

An anti-CD22 antibody suitable for use in a subject conjugate will in some cases inhibit the proliferation of human tumor cells that overexpress CD22, where the inhibition occurs in vitro, in vivo, or both in vitro and in vivo. For example, in some cases, an anti-CD22 antibody suitable for use in a subject conjugate inhibits proliferation of human tumor cells that overexpress CD22 by at least about 15%, at least about 20%, at least about 25%, at least about 30%, at least about 40%, at least about 50%, at least about 60%, at least about 70%, at least about 80%, or more than 80%, e.g., by at least about 85%, at least about 90%, at least about 95%, at least about 98%, at least about 99%, or 100%.

In some cases, a suitable anti-CD22 antibody competes for binding to a CD22 epitope (e.g., an epitope comprising amino acid residues within a CD22 antigen (e.g., within amino acids 1 to 846 (SEQ ID NO: 23), within amino acids 1-759 (SEQ ID NO: 21), within amino acids 1-751 (SEQ ID NO: 24), or within amino acids 1-670 (SEQ ID NO: 22), of a CD22 amino acid sequence depicted in FIG. 8A-8C) with an antibody comprising a heavy chain complementarity determining region (CDR) selected from IYDMS (VH CDR1; SEQ ID NO:39), YISSGGGTTYYPDTVKG (VH CDR2; SEQ ID NO:40), and HSGYGSSYGVLFAY (VH CDR3; SEQ ID NO:41). In some cases, the anti-CD22 antibody is humanized. In some cases, a suitable anti-CD22 antibody competes for binding to a CD22 epitope (e.g., an epitope comprising amino acid residues within a CD22 antigen (e.g., within amino acids 1 to 846 (SEQ ID NO: 23), within amino acids 1-759 (SEQ ID NO: 21), within amino acids 1-751 (SEQ ID NO: 24), or within amino acids 1-670 (SEQ ID NO: 22), of a CD22 amino acid sequence depicted in FIG. 8A-8C) with an antibody comprising a light-chain CDR selected from RASQDISNYLN (VL CDR1; SEQ ID NO:42), YTSILHS (VL CDR2; SEQ ID NO:43), and QQGNTLPWT (VL CDR3; SEQ ID NO:44). In some cases, the anti-CD22 antibody is humanized.

In some cases, a suitable anti-CD22 antibody competes for binding to a CD22 epitope (e.g., an epitope comprising amino acid residues within a CD22 antigen (e.g., within amino acids 1 to 846 (SEQ ID NO: 23), within amino acids 1-759 (SEQ ID NO: 21), within amino acids 1-751 (SEQ ID NO: 24), or within amino acids 1-670 (SEQ ID NO: 22), of a CD22 amino acid sequence depicted in FIG. 8A-8C) with an antibody comprising VH CDRs IYDMS (VH CDR1; SEQ ID NO:39), YISSGGGTTYYPDTVKG (VH CDR2; SEQ ID NO:40), and HSGYGSSYGVLFAY (VH CDR3; SEQ ID NO:41). In some cases, the anti-CD22 antibody is humanized. In some cases, a suitable anti-CD22 antibody competes for binding to a CD22 epitope (e.g., an epitope comprising amino acid residues within a CD22 antigen (e.g., an epitope within amino acids 1 to 846 (SEQ ID NO: 23), within amino acids 1-759 (SEQ ID NO: 21), within amino acids 1-751 (SEQ ID NO: 24), or within amino acids 1-670 (SEQ ID NO: 22), of a CD22 amino acid sequence depicted in FIG. 8A-8C) with an antibody comprising VL CDRs RASQDISNYLN (VL CDR1; SEQ ID NO:42), YTSILHS (VL CDR2; SEQ ID NO:43), and QQGNTLPWT (VL CDR3; SEQ ID NO:44). In some cases, the anti-CD22 antibody is humanized.

In some cases, a suitable anti-CD22 antibody competes for binding to a CD22 epitope (e.g., an epitope comprising amino acid residues within a CD22 antigen (e.g., within amino acids 1 to 846 (SEQ ID NO: 23), within amino acids 1-759 (SEQ ID NO: 21), within amino acids 1-751 (SEQ ID NO: 24), or within amino acids 1-670 (SEQ ID NO: 22), of a CD22 amino acid sequence depicted in FIG. 8A-8C) with an antibody that comprises VH CDRs IYDMS (VH CDR1; SEQ ID NO:39), YISSGGGT-TYYPDTVKG (VH CDR2; SEQ ID NO:40), and HSGYGSSYGVLFAY (VH CDR3; SEQ ID NO:41) and VL CDRs RASQDISNYLN (VL CDR1; SEQ ID NO:42), YTSILHS (VL CDR2; SEQ ID NO:43), and QQGNTLPWT (VL CDR3; SEQ ID NO:44). In some cases, the anti-CD22 antibody is humanized.

In some cases, a suitable anti-CD22 antibody comprises VH CDRs IYDMS (VH CDR1; SEQ ID NO:39), YISSGGGTTYYPDTVKG (VH CDR2; SEQ ID NO:40), and HSGYGSSYGVLFAY (VH CDR3; SEQ ID NO:41). In some cases, the anti-CD22 antibody is humanized. In some cases, a suitable anti-CD22 antibody comprises VL CDRs RASQDISNYLN (VL CDR1; SEQ ID NO:42), YTSILHS (VL CDR2; SEQ ID NO:43), and QQGNTLPWT (VL CDR3; SEQ ID NO:44). In some cases, the anti-CD22 antibody is humanized. In some cases, a suitable anti-CD22 antibody comprises VH CDRs IYDMS (VH CDR1; SEQ ID NO:39), YISSGGGTTYYPDTVKG (VH CDR2; SEQ ID NO:40), and HSGYGSSYGVLFAY (VH CDR3; SEQ ID NO:41) and VL CDRs RASQDISNYLN (VL CDR1; SEQ ID NO:42), YTSILHS (VL CDR2; SEQ ID NO:43), and QQGNTLPWT (VL CDR3; SEQ ID NO:44). In some cases, the anti-CD22 antibody is humanized.

In some cases, a suitable anti-CD22 antibody comprises VH CDRs present in an anti-CD22 VH region comprising the following amino acid sequence: EVQLVESGG-GLVKPGGSLRLSCAASGFAFSIYDMSWVRQAPGK-GLEWVAYISSGGGTT YYPDTVKGRFTISRDNAKNS-LYLQMSSLRAEDTAMYYCARHSGYGSSYGVLFAYW GQ GTLVTVSS (SEQ ID NO:4). In some cases, the anti-CD22 antibody is humanized.

In some cases, a suitable anti-CD22 antibody comprises VL CDRs present in an anti-CD22 VL region comprising the following amino acid sequence: DIQMTQSPSSL-SASVGDRVTITCRASQDISNYLNWYQQKPG-KAVKLLIYYTSILHSGVPS RFSGSGSGTDY-TLTISSLQQEDFATYFCQQGNTLPWTFGGGTKVEIKR (SEQ ID NO:7). In some cases, the anti-CD22 antibody is humanized.

In some cases, a suitable anti-CD22 antibody comprises VH CDRs present in EVQLVESGGGLVKPGGSLRLS-CAASGFAFSIYDMSWVRQAPGKGLEWVAYIS-SGGGTT YYPDTVKGRFTISRDNAKNSLYLQMSSL-RAEDTAMYYCARHSGYGSSYGVLFAYWGQ GTLVTVSS (SEQ ID NO:4) and VL CDRs present in DIQMTQSPSSLSASVGDRVTITCRASQDIS-NYLNWYQQKPGKAVKLLIYYTSILHSGVPS RFSGSGSGTDYTLTISSLQQEDFATYFCQQGNTLP-WTFGGGTKVEIKR (SEQ ID NO:7). In some cases, the anti-CD22 antibody is humanized.

In some cases, a suitable anti-CD22 antibody comprises: a) a heavy chain comprising a VH region having the amino acid sequence EVQLVESGGGLVKPGGSLX$^1$LSCA-ASGFAFSIYDMSWVRQAPGKGLEWVAYISSGGGTT YYPDTVKGRFTISRDNAKNX$^2$LYLQMX$^3$SLRAED-TAMYYCARHSGYGSSYGVLFAYWG QGTLVTVSS (SEQ ID NO:1), where X$^1$ is K (Lys) or R (Arg); X$^2$ is S (Ser) or T (Thr); and X$^3$ is N (Asn) or S (Ser); and b) an immunoglobulin light chain.

A light chain can have any suitable VL amino acid sequence, so long as the resulting antibody binds specifically to CD22.

Exemplary VL amino acid sequences include:

(SEQ ID NO: 7; VK1)
DIQMTQSPSSLSASVGDRVTITCRASQDISNYLNWYQQKPGKAVKLLIYY

TSILHSGVPSRFSGSGSGTDYTLTISSLQQEDFATYFCQQGNTLPWTFGG

GTKVEIKR;

(SEQ ID NO: 8; VK2)
DIQMTQSPSSLSASVGDRVTITCRASQDISNYLNWYQQKPGKAVKLLIYY

TSILHSGVPSRFSGSGSGTDYTLTISSLQPEDFATYFCQQGNTLPWTFGG

GTKVEIKR;
and (SEQ ID NO: 9; VK4)
DIQMTQSPSSVSASVGDRVTITCRASQDISNYLNWYQQKPGKAPKLLIYY

TSILHSGVPSRFSGSGSGTDYTLTISSLQPEDFATYFCQQGNTLPWTFGG

GTKVEIKR.

Thus, e.g., a suitable anti-CD22 antibody can comprise: a) a heavy chain comprising a VH region having the amino acid sequence set forth in SEQ ID NO:1); and a light chain comprising the VL region of VK1. In other cases, a suitable anti-CD22 antibody can comprise: a) a heavy chain comprising a VH region having the amino acid sequence set forth in SEQ ID NO:1); and a light chain comprising the VL region of VK2. In still other cases, a subject anti-CD22 antibody can comprise: a) a heavy chain comprising a VH region having the amino acid sequence set forth in SEQ ID NO:1); and a light chain comprising the VL region of VK4.

In some instances, a suitable anti-CD22 antibody comprises: a) an immunoglobulin light chain comprising the amino acid sequence DIQMTQSPSSX$^1$SASVGDR-VTITCRASQDISNYLNWYQQKPGKAX$^2$KLLIYYTSI-LHSGVP SRFSGSGSGTDYTLTISSLQX$^3$EDFATYFC-QQGNTLPWTFGGGTKVEIK (SEQ ID NO:2), where X$^1$ is L (Leu) or V (Val); X$^2$ is V (Val) or P (Pro); and X$^3$ is Q (Gln) or P (Pro); and b) an immunoglobulin heavy chain. The heavy chain can comprise an amino acid sequence selected from:

(SEQ ID NO: 3; VH3)
EVQLVESGGGLVKPGGSLKLSCAASGFAFSIYDMSWVRQAPGKGLEWVAY

ISSGGGTTYYPDTVKGRFTISRDNAKNTLYLQMSSLRAEDTAMYYCARHS

GYGSSYGVLFAYWGQGTLVTVSS;

(SEQ ID NO: 4; VH4)
EVQLVESGGGLVKPGGSLRLSCAASGFAFSIYDMSWVRQAPGKGLEWVAY

ISSGGGTTYYPDTVKGRFTISRDNAKNSLYLQMSSLRAEDTAMYYCARHS

GYGSSYGVLFAYWGQGTLVTVSS;

(SEQ ID NO: 5; VH5)
EVQLVESGGGLVKPGGSLKLSCAASGFAFSIYDMSWVRQAPGKGLEWVAY

ISSGGGTTYYPDTVKGRFTISRDNAKNSLYLQMNSLRAEDTAMYYCARHS

GYGSSYGVLFAYWGQGTLVTVSS;
and (SEQ ID NO: 6; VH6)
EVQLVESGGGLVKPGGSLKLSCAASGFAFSIYDMSWVRQAPGKGLEWVAY

ISSGGGTTYYPDTVKGRFTISRDNAKNSLYLQMSSLRAEDTAMYYCARHS

GYGSSYGVLFAYWGQGTLVTVSS.

In some cases, a suitable anti-CD22 antibody comprises a VH region comprising the following amino acid sequence:

(SEQ ID NO: 4)
EVQLVESGGGLVKPGGSLRLSCAASGFAFSIYDMSWVRQAPGKGLEWVAY

ISSGGGTTYYPDTVKGRFTISRDNAKNSLYLQMSSLRAEDTAMYYCARHS

GYGSSYGVLFAYWGQGTLVTVSS.

In some cases, a suitable anti-CD22 antibody comprises a VH region comprising the following amino acid sequence:

(SEQ ID NO: 4)
EVQLVESGGGLVKPGGSLRLSCAASGFAFSIYDMSWVRQAPGKGLEWVA

YISSGGGTTYYPDTVKGRFTISRDNAKNSLYLQMSSLRAEDTAMYYCAR

HSGYGSSYGVLFAYWGQGTLVTVSS and VL region comprising the following amino acid sequences.

(SEQ ID NO: 7)
DIQMTQSPSSLSASVGDRVTITCRASQDISNYLNWYQQKPGKAVKLLIYY

TSILHSGVPSRFSGSGSGTDYTLTISSLQQEDFATYFCQQGNTLPWTFGG

GTKVEIKR.

Modified Constant Region Sequences

As noted above, the amino acid sequence of an anti-CD22 antibody is modified to include a sulfatase motif that contains a serine or cysteine residue that is capable of being converted (oxidized) to a 2-formylglycine (FG1y) residue by action of a formylglycine generating enzyme (FGE) either in vivo (e.g., at the time of translation of an ald tag-containing protein in a cell) or in vitro (e.g., by contacting an ald tag-containing protein with an FGE in a cell-free system). Such sulfatase motifs may also be referred to herein as an FGE-modification site.

Sulfatase Motifs

A minimal sulfatase motif of an aldehyde tag is usually 5 or 6 amino acid residues in length, usually no more than 6 amino acid residues in length. Sulfatase motifs provided in an Ig polypeptide are at least 5 or 6 amino acid residues, and can be, for example, from 5 to 16, 6-16, 5-15, 6-15, 5-14, 6-14, 5-13, 6-13, 5-12, 6-12, 5-11, 6-11, 5-10, 6-10, 5-9, 6-9, 5-8, or 6-8 amino acid residues in length, so as to define a sulfatase motif of less than 16, 15, 14, 13, 12, 11, 10, 9, 8 or 7 amino acid residues in length.

In certain embodiments, polypeptides of interest include those where one or more amino acid residues, such as 2 or more, or 3 or more, or 4 or more, or 5 or more, or 6 or more, or 7 or more, or 8 or more, or 9 or more, or 10 or more, or 11 or more, or 12 or more, or 13 or more, or 14 or more, or 15 or more, or 16 or more, or 17 or more, or 18 or more, or 19 or more, or 20 or more amino acid residues have been inserted, deleted, substituted (replaced) relative to the native amino acid sequence to provide for a sequence of a sulfatase motif in the polypeptide. In certain embodiments, the polypeptide includes a modification (insertion, addition, deletion, and/or substitution/replacement) of less than 20, 19, 18, 17, 16, 15, 14, 13, 12, 11, 10, 9, 8, 7, 6, 5, 4, 3 or 2 amino acid residues of the amino acid sequence relative to the native amino acid sequence of the polypeptide. Where an amino acid sequence native to the polypeptide (e.g., anti-CD22 antibody) contains one or more residues of the desired sulfatase motif, the total number of modifications of residues can be reduced, e.g., by site-specification modification (insertion, addition, deletion, substitution/replacement) of amino acid residues flanking the native amino acid residues to provide a sequence of the desired sulfatase motif. In certain embodiments, the extent of modification of the native amino acid sequence of the target anti-CD22 polypeptide is minimized, so as to minimize the number of amino acid residues that are inserted, deleted, substituted (replaced), or added (e.g., to the N- or C-terminus). Minimizing the extent of amino acid sequence modification of the target anti-CD22 polypeptide may minimize the impact such modifications may have upon anti-CD22 function and/or structure.

It should be noted that while aldehyde tags of particular interest are those comprising at least a minimal sulfatase motif (also referred to a "consensus sulfatase motif"), it will be readily appreciated that longer aldehyde tags are both contemplated and encompassed by the present disclosure and can find use in the compositions and methods of the present disclosure. Aldehyde tags can thus comprise a minimal sulfatase motif of 5 or 6 residues, or can be longer and comprise a minimal sulfatase motif which can be flanked at the N- and/or C-terminal sides of the motif by additional amino acid residues. Aldehyde tags of, for example, 5 or 6 amino acid residues are contemplated, as well as longer amino acid sequences of more than 5, 6, 7, 8, 9, 10, 11, 12, 13, 14, 15, 16, 17, 18, 19, 20 or more amino acid residues.

An aldehyde tag can be present at or near the C-terminus of an Ig heavy chain; e.g., an aldehyde tag can be present within 1, 2, 3, 4, 5, 6, 7, 8, 9, or 10 amino acids of the C-terminus of a native, wild-type Ig heavy chain. An aldehyde tag can be present within a CH1 domain of an Ig heavy chain. An aldehyde tag can be present within a CH2 domain of an Ig heavy chain. An aldehyde tag can be present within a CH3 domain of an Ig heavy chain. An aldehyde tag can be present in an Ig light chain constant region, e.g., in a kappa light chain constant region or a lambda light chain constant region.

In certain embodiments, the sulfatase motif used may be described by the formula:

$$X^1Z^{10}X^2Z^{20}X^3Z^{30} \text{(SEQ ID NO:45)} \qquad \text{(I')}$$

where $Z^{10}$ is cysteine or serine (which can also be represented by (C/S));

$Z^{20}$ is either a proline or alanine residue (which can also be represented by (P/A));

$Z^{30}$ is a basic amino acid (e.g., arginine (R), and may be lysine (K) or histidine (H), e.g., lysine), or an aliphatic amino acid (alanine (A), glycine (G), leucine (L), valine (V), isoleucine (I), or proline (P), e.g., A, G, L, V, or I;

$X^1$ is present or absent and, when present, can be any amino acid, e.g., an aliphatic amino acid, a sulfur-containing amino acid, or a polar, uncharged amino acid, (i.e., other than an aromatic amino acid or a charged amino acid), e.g., L, M, V, S or T, e.g., L, M, S or V, with the proviso that when the sulfatase motif is at the N-terminus of the target polypeptide, $X^1$ is present; and $X^2$ and $X^3$ independently can be any amino acid, though usually an aliphatic amino acid, a polar, uncharged amino acid, or a sulfur containing amino acid (i.e., other than an aromatic amino acid or a charged amino acid), e.g., S, T, A, V, G or C, e.g., S, T, A, V or G.

The amino acid sequence of an anti-CD22 heavy and/or light chain can be modified to provide a sequence of at least 5 amino acids of the formula $X^1Z^{10}X^2Z^{20}X^3Z^{30}$ (SEQ ID NO: 45), where $Z^{10}$ is cysteine or serine;

$Z^{20}$ is a proline or alanine residue;

$Z^{30}$ is an aliphatic amino acid or a basic amino acid;

$X^1$ is present or absent and, when present, is any amino acid, with the proviso that when the heterologous sulfatase motif is at an N-terminus of the polypeptide, $X^1$ is present;

$X^2$ and $X^3$ are each independently any amino acid, where the sequence is within or adjacent a solvent-accessible loop region of the Ig constant region, and wherein the sequence is not at the C-terminus of the Ig heavy chain.

The sulfatase motif is generally selected so as to be capable of conversion by a selected FGE, e.g., an FGE present in a host cell in which the aldehyde tagged polypeptide is expressed or an FGE which is to be contacted with the aldehyde tagged polypeptide in a cell-free in vitro method.

For example, where the FGE is a eukaryotic FGE (e.g., a mammalian FGE, including a human FGE), the sulfatase motif can be of the formula:

$$X^1CX^2PX^3Z^{30} \text{(SEQ ID NO:46)} \qquad \text{(I'')}$$

where $X^1$ may be present or absent and, when present, can be any amino acid, e.g., an aliphatic amino acid, a sulfur-containing amino acid, or a polar, uncharged amino acid, (i.e., other than an aromatic amino acid or a charged amino acid), e.g., L, M, S or V, with the proviso that when the sulfatase motif is at the N-terminus of the target polypeptide, $X^1$ is present;

$X^2$ and $X^3$ independently can be any amino acid, e.g., an aliphatic amino acid, a sulfur-containing amino acid, or a polar, uncharged amino acid, (i.e., other than an aromatic amino acid or a charged amino acid), e.g., S, T, A, V, G, or C, e.g., S, T, A, V or G; and $Z^{30}$ is a basic amino acid (e.g., arginine (R), and may be lysine (K) or histidine (H), e.g., lysine), or an aliphatic amino acid (alanine (A), glycine (G), leucine (L), valine (V), isoleucine (I), or proline (P), e.g., A, G, L, V, or I.

Specific examples of sulfatase motifs include LCTPSR (SEQ ID NO:47), MCTPSR (SEQ ID NO:48), VCTPSR (SEQ ID NO:49), LCSPSR (SEQ ID NO:50), LCAPSR (SEQ ID NO:51), LCVPSR (SEQ ID NO:52), LCGPSR (SEQ ID NO:53), ICTPAR (SEQ ID NO:54), LCTPSK (SEQ ID NO:55), MCTPSK (SEQ ID NO:56), VCTPSK (SEQ ID NO:57), LCSPSK (SEQ ID NO:58), LCAPSK (SEQ ID NO:59), LCVPSK (SEQ ID NO:60), LCGPSK (SEQ ID NO:61), LCTPSA (SEQ ID NO:62), ICTPAA (SEQ ID NO:63), MCTPSA (SEQ ID NO:64), VCTPSA (SEQ ID NO:65), LCSPSA (SEQ ID NO:66), LCAPSA (SEQ ID NO:67), LCVPSA (SEQ ID NO:68), and LCGPSA (SEQ ID NO:69).

FG1y-Containing Sequences

Upon action of FGE on the modified anti-CD22 heavy and/or light chain, the serine or the cysteine in the sulfatase motif is modified to FG1y. Thus, the FG1y-containing sulfatase motif can be of the formula:

$$X^1(FG1y)X^2Z^{20}X^3Z^{30} \text{(SEQ ID NO:70)} \qquad \text{(I''')}$$

where

FG1y is the formylglycine residue;

$Z^{20}$ is either a proline or alanine residue (which can also be represented by (P/A));

$Z^{30}$ is a basic amino acid (e.g., arginine (R), and may be lysine (K) or histidine (H), usually lysine), or an aliphatic amino acid (alanine (A), glycine (G), leucine (L), valine (V), isoleucine (I), or proline (P), e.g., A, G, L, V, or I;

$X^1$ may be present or absent and, when present, can be any amino acid, e.g., an aliphatic amino acid, a sulfur-containing amino acid, or a polar, uncharged amino acid, (i.e., other than an aromatic amino acid or a charged amino acid), e.g., L, M, V, S or T, e.g., L, M or V, with the proviso that when the sulfatase motif is at the N-terminus of the target polypeptide, $X^1$ is present; and $X^2$ and $X^3$ independently can be any amino acid, e.g., an aliphatic amino acid, a sulfur-containing amino acid, or a polar, uncharged amino acid, (i.e., other than an aromatic amino acid or a charged amino acid), e.g., S, T, A, V, G or C, e.g., S, T, A, V or G.

As described above, the modified polypeptide containing the FGly residue may be conjugated to a drug (e.g., a maytansinoid) by reaction of the FGly with the drug (e.g., a drug containing a hydrazinyl-indolyl or a hydrazinyl-pyrrolo-pyridinyl coupling moiety, as described above) to produce an FGly'-containing sulfatase motif. As used herein, the term FGly' refers to the modified amino acid residue of the sulfatase motif that is coupled to the drug, such as a maytansinoid (e.g., the modified amino acid residue of formula (I)). Thus, the FGly'-containing sulfatase motif can be of the formula:

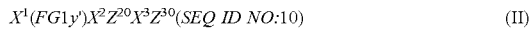

where

FGly' is the modified amino acid residue of formula (I);
$Z^{20}$ is either a proline or alanine residue (which can also be represented by (P/A));
$Z^{30}$ is a basic amino acid (e.g., arginine (R), and may be lysine (K) or histidine (H), usually lysine), or an aliphatic amino acid (alanine (A), glycine (G), leucine (L), valine (V), isoleucine (I), or proline (P), e.g., A, G, L, V, or I;
$X^1$ may be present or absent and, when present, can be any amino acid, e.g., an aliphatic amino acid, a sulfur-containing amino acid, or a polar, uncharged amino acid, (i.e., other than an aromatic amino acid or a charged amino acid), e.g., L, M, V, S or T, e.g., L, M or V, with the proviso that when the sulfatase motif is at the N-terminus of the target polypeptide, $X^1$ is present; and
$X^2$ and $X^3$ independently can be any amino acid, e.g., an aliphatic amino acid, a sulfur-containing amino acid, or a polar, uncharged amino acid, (i.e., other than an aromatic amino acid or a charged amino acid), e.g., S, T, A, V, G or C, e.g., S, T, A, V or G.

In certain embodiments, the modified amino acid residue of formula (I) is positioned at a C-terminus of a heavy chain constant region of the anti-CD22 antibody. In some instances, the heavy chain constant region comprises a sequence of the formula (II):

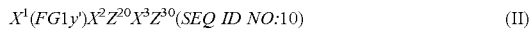

wherein
FGly' is the modified amino acid residue of formula (I);
$Z^{20}$ is either a proline or alanine residue (which can also be represented by (P/A));
$Z^{30}$ is a basic amino acid (e.g., arginine (R), and may be lysine (K) or histidine (H), usually lysine), or an aliphatic amino acid (alanine (A), glycine (G), leucine (L), valine (V), isoleucine (I), or proline (P), e.g., A, G, L, V, or I;
$X^1$ may be present or absent and, when present, can be any amino acid, e.g., an aliphatic amino acid, a sulfur-containing amino acid, or a polar, uncharged amino acid, (i.e., other than an aromatic amino acid or a charged amino acid), e.g., L, M, V, S or T, e.g., L, M or V, with the proviso that when the sulfatase motif is at the N-terminus of the target polypeptide, $X^1$ is present;
$X^2$ and $X^3$ independently can be any amino acid, e.g., an aliphatic amino acid, a sulfur-containing amino acid, or a polar, uncharged amino acid, (i.e., other than an aromatic amino acid or a charged amino acid), e.g., S, T, A, V, G or C, e.g., S, T, A, V or G; and wherein the sequence is C-terminal to the amino acid sequence QKSLSLSPGK (SEQ ID NO: 71), and where the sequence may include 1, 2, 3, 4, 5, or from 5 to 10, amino acids not present in a native, wild-type heavy Ig chain constant region.

In certain embodiments, the heavy chain constant region comprises the sequence SLSLSPGSL(FGly')TPSRGS (SEQ ID NO: 72) at the C-terminus of the Ig heavy chain, e.g., in place of a native SLSLSPGK (SEQ ID NO:73) sequence.

In certain embodiments, the modified amino acid residue of formula (I) is positioned in a light chain constant region of the anti-CD22 antibody. In certain embodiments, the light chain constant region comprises a sequence of the formula (II):

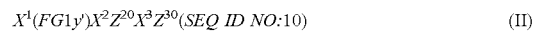

wherein
FGly' is the modified amino acid residue of formula (I);
$Z^{20}$ is either a proline or alanine residue (which can also be represented by (P/A));
$Z^{30}$ is a basic amino acid (e.g., arginine (R), and may be lysine (K) or histidine (H), usually lysine), or an aliphatic amino acid (alanine (A), glycine (G), leucine (L), valine (V), isoleucine (I), or proline (P), e.g., A, G, L, V, or I;
$X^1$ may be present or absent and, when present, can be any amino acid, e.g., an aliphatic amino acid, a sulfur-containing amino acid, or a polar, uncharged amino acid, (i.e., other than an aromatic amino acid or a charged amino acid), e.g., L, M, V, S or T, e.g., L, M or V, with the proviso that when the sulfatase motif is at the N-terminus of the target polypeptide, $X^1$ is present;
$X^2$ and $X^3$ independently can be any amino acid, e.g., an aliphatic amino acid, a sulfur-containing amino acid, or a polar, uncharged amino acid, (i.e., other than an aromatic amino acid or a charged amino acid), e.g., S, T, A, V, G or C, e.g., S, T, A, V or G; and
wherein the sequence is C-terminal to the amino acid sequence KVDNAL (SEQ ID NO:14) and/or is N-terminal to the amino acid sequence QSGNSQ (SEQ ID NO:15).

In certain embodiments, the light chain constant region comprises the sequence KVDNAL(FGly')TPSRQSGNSQ (SEQ ID NO:16).

In certain embodiments, the modified amino acid residue of formula (I) is positioned in a heavy chain CH1 region of the anti-CD22 antibody. In certain embodiments, the heavy chain CH1 region comprises a sequence of the formula (II):

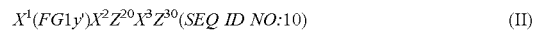

wherein
FG1y' is the modified amino acid residue of formula (I);
$Z^{21}$ is either a proline or alanine residue (which can also be represented by (P/A));
$Z^{30}$ is a basic amino acid (e.g., arginine (R), and may be lysine (K) or histidine (H), usually lysine), or an aliphatic amino acid (alanine (A), glycine (G), leucine (L), valine (V), isoleucine (I), or proline (P), e.g., A, G, L, V, or I;
$X^1$ may be present or absent and, when present, can be any amino acid, e.g., an aliphatic amino acid, a sulfur-containing amino acid, or a polar, uncharged amino acid, (i.e., other than an aromatic amino acid or a charged amino acid), e.g., L, M, V, S or T, e.g., L, M or V, with the proviso that when the sulfatase motif is at the N-terminus of the target polypeptide, $X^1$ is present;
$X^2$ and $X^3$ independently can be any amino acid, e.g., an aliphatic amino acid, a sulfur-containing amino acid, or a polar, uncharged amino acid, (i.e., other than an aromatic amino acid or a charged amino acid), e.g., S, T, A, V, G or C, e.g., S, T, A, V or G; and
wherein the sequence is C-terminal to the amino acid sequence SWNSGA (SEQ ID NO:17) and/or is N-terminal to the amino acid sequence GVHTFP (SEQ ID NO:18).

In certain embodiments, the heavy chain CH1 region comprises the sequence SWNSGAL(FG1y')TPSRGVHTFP (SEQ ID NO:19).

Site of Modification

As noted above, the amino acid sequence of an anti-CD22 antibody is modified to include a sulfatase motif that contains a serine or cysteine residue that is capable of being converted (oxidized) to an FG1y residue by action of an FGE either in vivo (e.g., at the time of translation of an ald tag-containing protein in a cell) or in vitro (e.g., by contacting an ald tag-containing protein with an FGE in a cell-free system). The anti-CD22 polypeptides used to generate a conjugate of the present disclosure include at least an Ig constant region, e.g., an Ig heavy chain constant region (e.g., at least a CH1 domain; at least a CH1 and a CH2 domain; a CH1, a CH2, and a CH3 domain; or a CH1, a CH2, a CH3, and a CH4 domain), or an Ig light chain constant region. Such Ig polypeptides are referred to herein as "target Ig polypeptides" or "target anti-CD22 antibodies" or "target anti-CD22 Ig polypeptides."

The site in an anti-CD22 antibody into which a sulfatase motif is introduced can be any convenient site. As noted above, in some instances, the extent of modification of the native amino acid sequence of the target anti-CD22 polypeptide is minimized, so as to minimize the number of amino acid residues that are inserted, deleted, substituted (replaced), and/or added (e.g., to the N- or C-terminus). Minimizing the extent of amino acid sequence modification of the target anti-CD22 polypeptide may minimize the impact such modifications may have upon anti-CD22 function and/or structure.

An anti-CD22 antibody heavy chain constant region can include Ig constant regions of any heavy chain isotype, non-naturally occurring Ig heavy chain constant regions (including consensus Ig heavy chain constant regions). An Ig constant region can be modified to include an aldehyde tag, where the aldehyde tag is present in or adjacent a solvent-accessible loop region of the Ig constant region. An Ig constant region can be modified by insertion and/or substitution of 1, 2, 3, 4, 5, 6, 7, 8, 9, 10, 11, 12, 13, 14, 15, or 16 amino acids, or more than 16 amino acids, to provide an amino acid sequence of a sulfatase motif as described above.

In some cases, an aldehyde-tagged anti-CD22 antibody comprises an aldehyde-tagged Ig heavy chain constant region (e.g., at least a CH1 domain; at least a CH1 and a $CH_2$ domain; a CH1, a CH2, and a CH3 domain; or a CH1, a CH2, a CH3, and a CH4 domain). The aldehyde-tagged Ig heavy chain constant region can include heavy chain constant region sequences of an IgA, IgM, IgD, IgE, IgG1, IgG2, IgG3, or IgG4 isotype heavy chain or any allotypic variant of same, e.g., human heavy chain constant region sequences or mouse heavy chain constant region sequences, a hybrid heavy chain constant region, a synthetic heavy chain constant region, or a consensus heavy chain constant region sequence, etc., modified to include at least one sulfatase motif that can be modified by an FGE to generate an FG1y-modified Ig polypeptide. Allotypic variants of Ig heavy chains are known in the art. See, e.g., Jefferis and Lefranc (2009) MAbs 1:4.

In some cases, an aldehyde-tagged anti-CD22 antibody comprises an aldehyde-tagged Ig light chain constant region. The aldehyde-tagged Ig light chain constant region can include constant region sequences of a kappa light chain, a lambda light chain, e.g., human kappa or lambda light chain constant regions, a hybrid light chain constant region, a synthetic light chain constant region, or a consensus light chain constant region sequence, etc., modified to include at least one sulfatase motif that can be modified by an FGE to generate an FG1y-modified anti-CD22 antibody polypeptide. Exemplary constant regions include human gamma 1 and gamma 3 regions. With the exception of the sulfatase motif, a modified constant region may have a wild-type amino acid sequence, or it may have an amino acid sequence that is at least 70% identical (e.g., at least 80%, at least 90% or at least 95% identical) to a wild type amino acid sequence.

In some embodiments the sulfatase motif is at a position other than, or in addition to, the C-terminus of the Ig polypeptide heavy chain. As noted above, an isolated aldehyde-tagged anti-CD22 polypeptide can comprise a heavy chain constant region modified to include a sulfatase motif as described above, where the sulfatase motif is in or adjacent a surface-accessible loop region of the anti-CD22 polypeptide heavy chain constant region.

In some instances, a target anti-CD22 immunoglobulin is modified to include a sulfatase motif as described above, where the modification includes one or more amino acid residue insertions, deletions, and/or substitutions. In certain embodiments, the sulfatase motif is within, or adjacent to, a region of an IgG1 heavy chain constant region corresponding to one or more of: 1) amino acids 122-127; 2) amino acids 137-143; 3) amino acids 155-158; 4) amino acids 163-170; 5) amino acids 163-183; 6) amino acids 179-183; 7) amino acids 190-192; 8) amino acids 200-202; 9) amino acids 199-202; 10) amino acids 208-212; 11) amino acids 220-241; 12) amino acids 247-251; 13) amino acids 257-261; 14) amino acid 269-277; 15) amino acids 271-277; 16) amino acids 284-285; 17) amino acids 284-292; 18) amino acids 289-291; 19) amino acids 299-303; 20) amino acids 309-313; 21) amino acids 320-322; 22) amino acids 329-335; 23) amino acids 341-349; 24) amino acids 342-348; 25) amino acids 356-365; 26) amino acids 377-381; 27) amino acids 388-394; 28) amino acids 398-407; 29) amino acids 433-451; and 30) amino acids 446-451; wherein the amino acid numbering is based on the amino acid numbering of human IgG1 as depicted in FIG. 9B.

In some instances, a target anti-CD22 immunoglobulin is modified to include a sulfatase motif as described above, where the modification includes one or more amino acid residue insertions, deletions, and/or substitutions. In certain embodiments, the sulfatase motif is within, or adjacent to, a region of an IgG1 heavy chain constant region corresponding to one or more of: 1) amino acids 1-6; 2) amino acids 16-22; 3) amino acids 34-47; 4) amino acids 42-49; 5) amino acids 42-62; 6) amino acids 34-37; 7) amino acids 69-71; 8) amino acids 79-81; 9) amino acids 78-81; 10) amino acids 87-91; 11) amino acids 100-121; 12) amino acids 127-131; 13) amino acids 137-141; 14) amino acid 149-157; 15) amino acids 151-157; 16) amino acids 164-165; 17) amino acids 164-172; 18) amino acids 169-171; 19) amino acids 179-183; 20) amino acids 189-193; 21) amino acids 200-202; 22) amino acids 209-215; 23) amino acids 221-229; 24) amino acids 22-228; 25) amino acids 236-245; 26) amino acids 217-261; 27) amino acids 268-274; 28) amino acids 278-287; 29) amino acids 313-331; and 30) amino acids 324-331; wherein the amino acid numbering is based on the amino acid numbering of human IgG1 as set out in SEQ ID NO:27 (human IgG1 constant region; sequence depicted in FIG. 9B.

Exemplary surface-accessible loop regions of an IgG1 heavy chain include: 1) ASTKGP (SEQ ID NO:74); 2) KSTSGGT (SEQ ID NO:75); 3) PEPV (SEQ ID NO:76); 4) NSGALTSG (SEQ ID NO:77); 5) NSGALTSGVHTFPAVLQSSGL (SEQ ID NO:78); 6) QSSGL (SEQ ID NO:79); 7) VTV; 8) QTY; 9) TQTY (SEQ ID NO:80); 10) HKPSN (SEQ ID NO:81); 11) EPKSCDKTHTCPPCPAPELLGG (SEQ ID NO: 82); 12) FPPKP (SEQ ID NO:83); 13) ISRTP (SEQ ID NO:84); 14) DVSHEDPEV (SEQ ID NO:85); 15) SHEDPEV (SEQ ID NO:86); 16) DG; 17) DGVEVHNAK (SEQ ID NO:87); 18) HNA; 19) QYNST (SEQ ID NO:88); 20) VLTVL (SEQ ID NO:89); 21) GKE; 22) NKALPAP (SEQ ID NO:90); 23) SKAKGQPRE (SEQ ID NO:91); 24) KAKGQPR (SEQ ID NO:92); 25) PPSRKELTKN (SEQ ID NO:93); 26) YPSDI (SEQ ID NO:94); 27) NGQPENN (SEQ ID NO:95); 28) TPPVLDSDGS (SEQ ID NO:96); 29) HEALHNHYTQKSLSLSPGK (SEQ ID NO:97); and 30) SLSPGK (SEQ ID NO:98), as shown in FIGS. 9A and 9B.

In some instances, a target immunoglobulin is modified to include a sulfatase motif as described above, where the modification includes one or more amino acid residue insertions, deletions, and/or substitutions. In certain embodiments, the sulfatase motif is within, or adjacent to, a region of an IgG2 heavy chain constant region corresponding to one or more of: 1) amino acids 1-6; 2) amino acids 13-24; 3) amino acids 33-37; 4) amino acids 43-54; 5) amino acids 58-63; 6) amino acids 69-71; 7) amino acids 78-80; 8) 87-89; 9) amino acids 95-96; 10) 114-118; 11) 122-126; 12) 134-136; 13) 144-152; 14) 159-167; 15) 175-176; 16) 184-188; 17) 195-197; 18) 204-210; 19) 216-224; 20) 231-233; 21) 237-241; 22) 252-256; 23) 263-269; 24) 273-282; 25) amino acids 299-302; where the amino acid numbering is based on the numbering of the amino acid sequence set forth in SEQ ID NO:28 (human IgG2; also depicted in FIG. 9B).

Exemplary surface-accessible loop regions of an IgG2 heavy chain include 1) ASTKGP (SEQ ID NO:74); 2) PCSRSTSESTAA (SEQ ID NO:99); 3) FPEPV (SEQ ID NO:100); 4) SGALTSGVHTFP (SEQ ID NO:101); 5) QSSGLY (SEQ ID NO:102); 6) VTV; 7) TQT; 8) HKP; 9) DK; 10) VAGPS (SEQ ID NO: 103); 11) FPPKP (SEQ ID NO:83); 12) RTP; 13) DVSHEDPEV (SEQ ID NO:85); 14) DGVEVHNAK (SEQ ID NO:87); 15) FN; 16) VLTVV (SEQ ID NO:104); 17) GKE; 18) NKGLPAP (SEQ ID NO:105); 19) SKTKGQPRE (SEQ ID NO:106); 20) PPS; 21) MTKNQ (SEQ ID NO:107); 22) YPSDI (SEQ ID NO:94); 23) NGQPENN (SEQ ID NO:95); 24) TPPMLDSDGS (SEQ ID NO:108); 25) GNVF (SEQ ID NO:109); and 26) HEALHNHYTQKSLSLSPGK (SEQ ID NO:97), as shown in FIG. 9B.

In some instances, a target immunoglobulin is modified to include a sulfatase motif as described above, where the modification includes one or more amino acid residue insertions, deletions, and/or substitutions. In certain embodiments, the sulfatase motif is within, or adjacent to, a region of an IgG3 heavy chain constant region corresponding to one or more of: 1) amino acids 1-6; 2) amino acids 13-22; 3) amino acids 33-37; 4) amino acids 43-61; 5) amino acid 71; 6) amino acids 78-80; 7) 87-91; 8) amino acids 97-106; 9) 111-115; 10) 147-167; 11) 173-177; 16) 185-187; 13) 195-203; 14) 210-218; 15) 226-227; 16) 238-239; 17) 246-248; 18) 255-261; 19) 267-275; 20) 282-291; 21) amino acids 303-307; 22) amino acids 313-320; 23) amino acids 324-333; 24) amino acids 350-352; 25) amino acids 359-365; and 26) amino acids 372-377; where the amino acid numbering is based on the numbering of the amino acid sequence set forth in SEQ ID NO:29 (human IgG3; also depicted in FIG. 9B).

Exemplary surface-accessible loop regions of an IgG3 heavy chain include 1) ASTKGP (SEQ ID NO:74); 2) PCSRSTSGGT (SEQ ID NO:110); 3) FPEPV (SEQ ID NO:100); 4) SGALTSGVHTFPAVLQSSG (SEQ ID NO:111); 5) V; 6) TQT; 7) HKPSN (SEQ ID NO:81); 8) RVELKTPLGD (SEQ ID NO:112); 9) CPRCPKP (SEQ ID NO:113); 10) PKSCDTPPPCPRCPAPELLGG (SEQ ID NO:114); 11) FPPKP (SEQ ID NO:83); 12) RTP; 13) DVSHEDPEV (SEQ ID NO:85); 14) DGVEVHNAK (SEQ ID NO:87); 15) YN; 16) VL; 17) GKE; 18) NKALPAP (SEQ ID NO:90); 19) SKTKGQPRE (SEQ ID NO: 106); 20) PPSREEMTKN (SEQ ID NO: 115); 21) YPSDI (SEQ ID NO:94); 22) SSGQPENN (SEQ ID NO:116); 23) TPPMLDSDGS (SEQ ID NO: 108); 24) GNI; 25) HEALHNR (SEQ ID NO:117); and 26) SLSPGK (SEQ ID NO:98), as shown in FIG. 9B.

In some instances, a target immunoglobulin is modified to include a sulfatase motif as described above, where the modification includes one or more amino acid residue insertions, deletions, and/or substitutions. In certain embodiments, the sulfatase motif is within, or adjacent to, a region of an IgG4 heavy chain constant region corresponding to one or more of: 1) amino acids 1-5; 2) amino acids 12-23; 3) amino acids 32-36; 4) amino acids 42-53; 5) amino acids 57-62; 6) amino acids 68-70; 7) amino acids 77-79; 8) amino acids 86-88; 9) amino acids 94-95; 10) amino acids 101-102; 11) amino acids 108-118; 12) amino acids 122-126; 13) amino acids 134-136; 14) amino acids 144-152; 15) amino acids 159-167; 16) amino acids 175-176; 17) amino acids 185-186; 18) amino acids 196-198; 19) amino acids 205-211; 20) amino acids 217-226; 21) amino acids 232-241; 22) amino acids 253-257; 23) amino acids 264-265; 24) 269-270; 25) amino acids 274-283; 26) amino acids 300-303; 27) amino acids 399-417; where the amino acid numbering is based on the numbering of the amino acid sequence set forth in SEQ ID NO:30 (human IgG4; also depicted in FIG. 9B).

Exemplary surface-accessible loop regions of an IgG4 heavy chain include 1) STKGP (SEQ ID NO:118); 2) PCSRSTSESTAA (SEQ ID NO:99); 3) FPEPV (SEQ ID NO:100); 4) SGALTSGVHTFP (SEQ ID NO:101); 5) QSSGLY (SEQ ID NO:102); 6) VTV; 7) TKT; 8) HKP; 9) DK; 10) YG; 11) CPAPEFLGGPS (SEQ ID NO:119); 12) FPPKP (SEQ ID NO:83); 13) RTP; 14) DVSQEDPEV (SEQ ID NO:120); 15) DGVEVHNAK (SEQ ID NO:87); 16) FN; 17) VL; 18) GKE; 19) NKGLPSS (SEQ ID NO:121); 20) SKAKGQPREP (SEQ ID NO:122); 21) PPSQEEMTKN (SEQ ID NO:123); 22) YPSDI (SEQ ID NO:94); 23) NG;

24) NN; 25) TPPVLDSDGS (SEQ ID NO:96); 26) GNVF (SEQ ID NO:109); and 27) HEALHNHYTQKSLSLSLGK (SEQ ID NO:124), as shown in FIG. 9B.

In some instances, a target immunoglobulin is modified to include a sulfatase motif as described above, where the modification includes one or more amino acid residue insertions, deletions, and/or substitutions. In certain embodiments, the sulfatase motif is within, or adjacent to, a region of an IgA heavy chain constant region corresponding to one or more of: 1) amino acids 1-13; 2) amino acids 17-21; 3) amino acids 28-32; 4) amino acids 44-54; 5) amino acids 60-66; 6) amino acids 73-76; 7) amino acids 80-82; 8) amino acids 90-91; 9) amino acids 123-125; 10) amino acids 130-133; 11) amino acids 138-142; 12) amino acids 151-158; 13) amino acids 165-174; 14) amino acids 181-184; 15) amino acids 192-195; 16) amino acid 199; 17) amino acids 209-210; 18) amino acids 222-245; 19) amino acids 252-256; 20) amino acids 266-276; 21) amino acids 293-294; 22) amino acids 301-304; 23) amino acids 317-320; 24) amino acids 329-353; where the amino acid numbering is based on the numbering of the amino acid sequence set forth in SEQ ID NO:31 (human IgA; also depicted in FIG. 9B).

Exemplary surface-accessible loop regions of an IgA heavy chain include 1) ASPTSPKVFPLSL (SEQ ID NO:125); 2) QPDGN (SEQ ID NO:126); 3) VQGFFPQEPL (SEQ ID NO:127); 4) SGQGVTARNFP (SEQ ID NO:128); 5) SGDLYTT (SEQ ID NO:129); 6) PATQ (SEQ ID NO:130); 7) GKS; 8) YT; 9) CHP; 10) HRPA (SEQ ID NO:131); 11) LLGSE (SEQ ID NO:132); 12) GLRDASGV (SEQ ID NO:133); 13) SSGKSAVQGP (SEQ ID NO:134); 14) GCYS (SEQ ID NO:135); 15) CAEP (SEQ ID NO:136); 16) PE; 17) SGNTFRPEVHLLPPPSEELALNEL (SEQ ID NO:137); 18) ARGFS (SEQ ID NO:138); 19) QGSQELPREKY (SEQ ID NO:139); 20) AV; 21) AAED (SEQ ID NO:140); 22) HEAL (SEQ ID NO:141); and 23) IDRLAGKPTHVNVSVVMAEVDGTCY (SEQ ID NO:142), as shown in FIG. 9B.

A sulfatase motif can be provided within or adjacent one or more of these amino acid sequences of such modification sites of an Ig heavy chain. For example, an Ig heavy chain polypeptide can be modified (e.g., where the modification includes one or more amino acid residue insertions, deletions, and/or substitutions) at one or more of these amino acid sequences to provide a sulfatase motif adjacent and N-terminal and/or adjacent and C-terminal to these modification sites. Alternatively or in addition, an Ig heavy chain polypeptide can be modified (e.g., where the modification includes one or more amino acid residue insertions, deletions, and/or substitutions) at one or more of these amino acid sequences to provide a sulfatase motif between any two residues of the Ig heavy chain modifications sites. In some embodiments, an Ig heavy chain polypeptide may be modified to include two motifs, which may be adjacent to one another, or which may be separated by one, two, three, four or more (e.g., from about 1 to about 25, from about 25 to about 50, or from about 50 to about 100, or more, amino acids. Alternatively or in addition, where a native amino acid sequence provides for one or more amino acid residues of a sulfatase motif sequence, selected amino acid residues of the modification sites of an Ig heavy chain polypeptide amino acid sequence can be modified (e.g., where the modification includes one or more amino acid residue insertions, deletions, and/or substitutions) so as to provide a sulfatase motif at the modification site.

The amino acid sequence of a surface-accessible loop region can thus be modified to provide a sulfatase motif, where the modifications can include insertions, deletions, and/or substitutions. For example, where the modification is in a CH1 domain, the surface-accessible loop region can have the amino acid sequence NSGALTSG (SEQ ID NO:77), and the aldehyde-tagged sequence can be, e.g., NSGALCTPSRG (SEQ ID NO:143), e.g., where the "TS" residues of the NSGALTSG (SEQ ID NO:77) sequence are replaced with "CTPSR," (SEQ ID NO:144) such that the sulfatase motif has the sequence LCTPSR(SEQ ID NO:47). As another example, where the modification is in a CH2 domain, the surface-accessible loop region can have the amino acid sequence NKALPAP (SEQ ID NO:90), and the aldehyde-tagged sequence can be, e.g., NLCTPSRAP (SEQ ID NO:145), e.g., where the "KAL" residues of the NKALPAP (SEQ ID NO:90) sequence are replaced with "LCTPSR," (SEQ ID NO:47) such that the sulfatase motif has the sequence LCTPSR (SEQ ID NO:47). As another example, where the modification is in a CH2/CH3 domain, the surface-accessible loop region can have the amino acid sequence KAKGQPR (SEQ ID NO:92), and the aldehyde-tagged sequence can be, e.g., KAKGLCTPSR (SEQ ID NO:146), e.g., where the "GQP" residues of the KAKGQPR (SEQ ID NO:92) sequence are replaced with "LCTPS," (SEQ ID NO:147) such that the sulfatase motif has the sequence LCTPSR (SEQ ID NO:47).

As noted above, an isolated aldehyde-tagged anti-CD22 Ig polypeptide can comprise a light chain constant region modified to include a sulfatase motif as described above, where the sulfatase motif is in or adjacent a surface-accessible loop region of the Ig polypeptide light chain constant region. Illustrative examples of surface-accessible loop regions of a light chain constant region are presented in FIGS. 9A and 9C.

In some instances, a target immunoglobulin is modified to include a sulfatase motif as described above, where the modification includes one or more amino acid residue insertions, deletions, and/or substitutions. In certain embodiments, the sulfatase motif is within, or adjacent to, a region of an Ig light chain constant region corresponding to one or more of: 1) amino acids 130-135; 2) amino acids 141-143; 3) amino acid 150; 4) amino acids 162-166; 5) amino acids 163-166; 6) amino acids 173-180; 7) amino acids 186-194; 8) amino acids 211-212; 9) amino acids 220-225; 10) amino acids 233-236; wherein the amino acid numbering is based on the amino acid numbering of human kappa light chain as depicted in FIG. 9C. In some instances, a target immunoglobulin is modified to include a sulfatase motif as described above, where the modification includes one or more amino acid residue insertions, deletions, and/or substitutions. In certain embodiments, the sulfatase motif is within, or adjacent to, a region of an Ig light chain constant region corresponding to one or more of: 1) amino acids 1-6; 2) amino acids 12-14; 3) amino acid 21; 4) amino acids 33-37; 5) amino acids 34-37; 6) amino acids 44-51; 7) amino acids 57-65; 8) amino acids 83-83; 9) amino acids 91-96; 10) amino acids 104-107; where the amino acid numbering is based on SEQ ID NOs:32 and 33 (human kappa light chain; amino acid sequence depicted in FIG. 9C).

Exemplary surface-accessible loop regions of an Ig light chain (e.g., a human kappa light chain) include: 1) RTVAAP (SEQ ID NO:148); 2) PPS; 3) Gly (see, e.g., Gly at position 150 of the human kappa light chain sequence depicted in FIG. 9C); 4) YPREA (SEQ ID NO:149); 5) PREA (SEQ ID NO:150); 6) DNALQSGN (SEQ ID NO:151); 7) TEQDSKDST (SEQ ID NO:152); 8) HK; 9) HQGLSS (SEQ ID NO:153); and 10) RGEC (SEQ ID NO:154), as shown in FIGS. 9A and 9C.

Exemplary surface-accessible loop regions of an Ig lambda light chain include QPKAAP (SEQ ID NO:155), PPS, NK, DFYPGAV (SEQ ID NO:156), DSSPVKAG (SEQ ID NO:157), TTP, SN, HKS, EG, and APTECS (SEQ ID NO:158), as shown in FIG. 9C.

In some instances, a target immunoglobulin is modified to include a sulfatase motif as described above, where the modification includes one or more amino acid residue insertions, deletions, and/or substitutions. In certain embodiments, the sulfatase motif is within, or adjacent to, a region of a rat Ig light chain constant region corresponding to one or more of: 1) amino acids 1-6; 2) amino acids 12-14; 3) amino acids 121-22; 4) amino acids 31-37; 5) amino acids 44-51; 6) amino acids 55-57; 7) amino acids 61-62; 8) amino acids 81-83; 9) amino acids 91-92; 10) amino acids 102-105; wherein the amino acid numbering is based on the amino acid numbering of rat light chain as set forth in SEQ ID NO:35 (sequence depicted in FIG. 9C).

In some cases, a sulfatase motif is introduced into the CH1 region of an anti-CD22 heavy chain constant region. In some cases, a sulfatase motif is introduced at or near (e.g., within 1 to 10 amino acids of) the C-terminus of an anti-CD22 heavy chain. In some cases, a sulfatase motif is introduced in the light-chain constant region.

In some cases, a sulfatase motif is introduced into the CH1 region of an anti-CD22 heavy chain constant region, e.g., within amino acids 121-219 of the IgG1 heavy chain amino acid sequence depicted in FIG. 9A. For example, in some cases, a sulfatase motif is introduced into the amino acid sequence: ASTKGPSVFPLAPSSKSTSGGTAAL-GCLVKDYFPEPVTVSWNSGALTSGVHTFPAVLQSSGLYS-LSSVVTVPSSSLGTQTYICNVNHKPSNTKVDKKVE (SEQ ID NO:159). For example, in some of these embodiments, the amino acid sequence GALTSGVH (SEQ ID NO:160) is modified to GALCTPSRGVH (SEQ ID NO:161), where the sulfatase motif is LCTPSR (SEQ ID NO:47).

In some cases, a sulfatase motif is introduced at or near the C-terminus of an anti-CD22 heavy chain, e.g., the sulfatase motifs introduced within 1 amino acid, 2 amino acids (aa), 3 aa, 4 aa, 5 aa, 6 aa, 7 aa, 8 aa, 9 aa, or 10 aa the C-terminus of an anti-CD22 heavy chain. As one non-limiting example, the C-terminal lysine reside of an anti-CD22 heavy chain can be replaced with the amino acid sequence SLCTPSRGS (SEQ ID NO:162).

In some cases, a sulfatase motif is introduced into the constant region of a light chain of an anti-CD22 antibody. As one non-limiting example, in some cases, a sulfatase motif is introduced into the constant region of a light chain of an anti-CD22 antibody, where the sulfatase motif is C-terminal to KVDNAL (SEQ ID NO:14), and/or is N-terminal to QSGNSQ (SEQ ID NO:15). For example, in some cases, the sulfatase motif is LCTPSR (SEQ ID NO:47), and the anti-CD22 light chain comprises the amino acid sequence KVDNALLCTPSRQSGNSQ (SEQ ID NO:163).

Exemplary Anti-CD22 Antibodies

In some cases, a suitable anti-CD22 antibody competes for binding to a CD22 epitope (e.g., an epitope within amino acids 1 to 846 (SEQ ID NO: 23), within amino acids 1-759 (SEQ ID NO: 21), within amino acids 1-751 (SEQ ID NO: 24), or within amino acids 1-670 (SEQ ID NO: 22), of a CD22 amino acid sequence depicted in FIG. 8A-8C) with an antibody comprising a heavy chain VH CDR selected from IYDMS (VH CDR1; SEQ ID NO:39), YISSGGGT-TYYPDTVKG (VH CDR2; SEQ ID NO:40), and HSGYGSSYGVLFAY (VH CDR3; SEQ ID NO:41). In some cases, the anti-CD22 antibody is humanized. In some instances, the anti-CD22 antibody is modified to include a sulfatase motif as described above, where the modification includes one or more amino acid residue insertions, deletions, and/or substitutions. In certain embodiments, the sulfatase motif is within, or adjacent to, a region of an IgG1 heavy chain constant region corresponding to one or more of: 1) amino acids 1-6; 2) amino acids 16-22; 3) amino acids 34-47; 4) amino acids 42-49; 5) amino acids 42-62; 6) amino acids 34-37; 7) amino acids 69-71; 8) amino acids 79-81; 9) amino acids 78-81; 10) amino acids 87-91; 11) amino acids 100-121; 12) amino acids 127-131; 13) amino acids 137-141; 14) amino acid 149-157; 15) amino acids 151-157; 16) amino acids 164-165; 17) amino acids 164-172; 18) amino acids 169-171; 19) amino acids 179-183; 20) amino acids 189-193; 21) amino acids 200-202; 22) amino acids 209-215; 23) amino acids 221-229; 24) amino acids 22-228; 25) amino acids 236-245; 26) amino acids 217-261; 27) amino acids 268-274; 28) amino acids 278-287; 29) amino acids 313-331; and 30) amino acids 324-331; wherein the amino acid numbering is based on the amino acid numbering of human IgG1 as set out in SEQ ID NO:27 (human IgG1 constant region depicted in FIG. 9B). In some instances, the anti-CD22 antibody is modified to include a sulfatase motif as described above, where the modification includes one or more amino acid residue insertions, deletions, and/or substitutions; e.g., where the sulfatase motif is within, or adjacent to, a region of an Ig kappa constant region corresponding to one or more of: 1) amino acids 1-6; 2) amino acids 12-14; 3) amino acid 21; 4) amino acids 33-37; 5) amino acids 34-37; 6) amino acids 44-51; 7) amino acids 57-65; 8) amino acids 83-83; 9) amino acids 91-96; 10) amino acids 104-107; where the amino acid numbering is based on SEQ ID NOs:32 and 33 (human kappa light chain; amino acid sequence depicted in FIG. 9C).

In some cases, a suitable anti-CD22 antibody competes for binding to a CD22 epitope (e.g., an epitope within amino acids 1 to 846 (SEQ ID NO: 23), within amino acids 1-759 (SEQ ID NO: 21), within amino acids 1-751 (SEQ ID NO: 24), or within amino acids 1-670 (SEQ ID NO: 22), of a CD22 amino acid sequence depicted in FIG. 8A-8C) with an antibody comprising a light-chain CDR selected from RASQDISNYLN (VL CDR1; SEQ ID NO:42), YTSILHS (VL CDR2; SEQ ID NO:43), and QQGNTLPWT (VL CDR3; SEQ ID NO:44). In some cases, the anti-CD22 antibody is humanized. In some instances, the anti-CD22 antibody is modified to include a sulfatase motif as described above, where the modification includes one or more amino acid residue insertions, deletions, and/or substitutions. In certain embodiments, the sulfatase motif is within, or adjacent to, a region of an IgG1 heavy chain constant region corresponding to one or more of: 1) amino acids 122-127; 2) amino acids 137-143; 3) amino acids 155-158; 4) amino acids 163-170; 5) amino acids 163-183; 6) amino acids 179-183; 7) amino acids 190-192; 8) amino acids 200-202; 9) amino acids 199-202; 10) amino acids 208-212; 11) amino acids 220-241; 12) amino acids 247-251; 13) amino acids 257-261; 14) amino acid 269-277; 15) amino acids 271-277; 16) amino acids 284-285; 17) amino acids 284-292; 18) amino acids 289-291; 19) amino acids 299-303; 20) amino acids 309-313; 21) amino acids 320-322; 22) amino acids 329-335; 23) amino acids 341-349; 24) amino acids 342-348; 25) amino acids 356-365; 26) amino acids 377-381; 27) amino acids 388-394; 28) amino acids 398-407; 29) amino acids 433-451; and 30) amino acids 446-451; wherein the amino acid numbering is based on the amino acid numbering of human IgG1 as depicted in FIG.

9B. In some instances, the anti-CD22 antibody is modified to include a sulfatase motif as described above, where the modification includes one or more amino acid residue insertions, deletions, and/or substitutions; e.g., where the sulfatase motif is within, or adjacent to, a region of an Ig kappa constant region corresponding to one or more of: 1) amino acids 1-6; 2) amino acids 12-14; 3) amino acid 21; 4) amino acids 33-37; 5) amino acids 34-37; 6) amino acids 44-51; 7) amino acids 57-65; 8) amino acids 83-83; 9) amino acids 91-96; 10) amino acids 104-107; where the amino acid numbering is based on SEQ ID NOs:32 and 33 (human kappa light chain; amino acid sequence depicted in FIG. 9C).

In some cases, a suitable anti-CD22 antibody competes for binding to a CD22 epitope (e.g., an epitope within amino acids 1 to 846 (SEQ ID NO: 23), within amino acids 1-759 (SEQ ID NO: 21), within amino acids 1-751 (SEQ ID NO: 24), or within amino acids 1-670 (SEQ ID NO: 22), of a CD22 amino acid sequence depicted in FIG. 8A-8C) with an antibody comprising VH CDRs IYDMS (VH CDR1; SEQ ID NO:39), YISSGGGTTYYPDTVKG (VH CDR2; SEQ ID NO:40), and HSGYGSSYGVLFAY (VH CDR3; SEQ ID NO:41). In some cases, the anti-CD22 antibody is humanized. In some instances, the anti-CD22 antibody is modified to include a sulfatase motif as described above, where the modification includes one or more amino acid residue insertions, deletions, and/or substitutions. In certain embodiments, the sulfatase motif is within, or adjacent to, a region of an IgG1 heavy chain constant region corresponding to one or more of: 1) amino acids 1-6; 2) amino acids 16-22; 3) amino acids 34-47; 4) amino acids 42-49; 5) amino acids 42-62; 6) amino acids 34-37; 7) amino acids 69-71; 8) amino acids 79-81; 9) amino acids 78-81; 10) amino acids 87-91; 11) amino acids 100-121; 12) amino acids 127-131; 13) amino acids 137-141; 14) amino acid 149-157; 15) amino acids 151-157; 16) amino acids 164-165; 17) amino acids 164-172; 18) amino acids 169-171; 19) amino acids 179-183; 20) amino acids 189-193; 21) amino acids 200-202; 22) amino acids 209-215; 23) amino acids 221-229; 24) amino acids 22-228; 25) amino acids 236-245; 26) amino acids 217-261; 27) amino acids 268-274; 28) amino acids 278-287; 29) amino acids 313-331; and 30) amino acids 324-331; wherein the amino acid numbering is based on the amino acid numbering of human IgG1 as set out in SEQ ID NO:27 (human IgG1 constant region depicted in FIG. 9B). In some instances, the anti-CD22 antibody is modified to include a sulfatase motif as described above, where the modification includes one or more amino acid residue insertions, deletions, and/or substitutions; e.g., where the sulfatase motif is within, or adjacent to, a region of an Ig kappa constant region corresponding to one or more of: 1) amino acids 1-6; 2) amino acids 12-14; 3) amino acid 21; 4) amino acids 33-37; 5) amino acids 34-37; 6) amino acids 44-51; 7) amino acids 57-65; 8) amino acids 83-83; 9) amino acids 91-96; 10) amino acids 104-107; where the amino acid numbering is based on SEQ ID NOs:32 and 33 (human kappa light chain; amino acid sequence depicted in FIG. 9C).

In some cases, a suitable anti-CD22 antibody competes for binding to a CD22 epitope (e.g., an epitope within amino acids 1 to 846 (SEQ ID NO: 23), within amino acids 1-759 (SEQ ID NO: 21), within amino acids 1-751 (SEQ ID NO: 24), or within amino acids 1-670 (SEQ ID NO: 22), of a CD22 amino acid sequence depicted in FIG. 8A-8C) with an antibody comprising VL CDRs RASQDISNYLN (VL CDR1; SEQ ID NO:42), YTSILHS (VL CDR2; SEQ ID NO:43), and QQGNTLPWT (VL CDR3; SEQ ID NO:44).

In some cases, the anti-CD22 antibody is humanized. In some instances, the anti-CD22 antibody is modified to include a sulfatase motif as described above, where the modification includes one or more amino acid residue insertions, deletions, and/or substitutions. In certain embodiments, the sulfatase motif is within, or adjacent to, a region of an IgG1 heavy chain constant region corresponding to one or more of: 1) amino acids 1-6; 2) amino acids 16-22; 3) amino acids 34-47; 4) amino acids 42-49; 5) amino acids 42-62; 6) amino acids 34-37; 7) amino acids 69-71; 8) amino acids 79-81; 9) amino acids 78-81; 10) amino acids 87-91; 11) amino acids 100-121; 12) amino acids 127-131; 13) amino acids 137-141; 14) amino acid 149-157; 15) amino acids 151-157; 16) amino acids 164-165; 17) amino acids 164-172; 18) amino acids 169-171; 19) amino acids 179-183; 20) amino acids 189-193; 21) amino acids 200-202; 22) amino acids 209-215; 23) amino acids 221-229; 24) amino acids 22-228; 25) amino acids 236-245; 26) amino acids 217-261; 27) amino acids 268-274; 28) amino acids 278-287; 29) amino acids 313-331; and 30) amino acids 324-331; wherein the amino acid numbering is based on the amino acid numbering of human IgG1 as set out in SEQ ID NO:27 (human IgG1 constant region depicted in FIG. 9B). In some instances, the anti-CD22 antibody is modified to include a sulfatase motif as described above, where the modification includes one or more amino acid residue insertions, deletions, and/or substitutions; e.g., where the sulfatase motif is within, or adjacent to, a region of an Ig kappa constant region corresponding to one or more of: 1) amino acids 1-6; 2) amino acids 12-14; 3) amino acid 21; 4) amino acids 33-37; 5) amino acids 34-37; 6) amino acids 44-51; 7) amino acids 57-65; 8) amino acids 83-83; 9) amino acids 91-96; 10) amino acids 104-107; where the amino acid numbering is based on SEQ ID NOs:32 and 33 (human kappa light chain; amino acid sequence depicted in FIG. 9C).

In some cases, a suitable anti-CD22 antibody competes for binding to a CD22 epitope (e.g., an epitope within amino acids 1 to 846 (SEQ ID NO: 23), within amino acids 1-759 (SEQ ID NO: 21), within amino acids 1-751 (SEQ ID NO: 24), or within amino acids 1-670 (SEQ ID NO: 22), of a CD22 amino acid sequence depicted in FIG. 8A-8C) with an antibody that comprises VH CDRs IYDMS (VH CDR1; SEQ ID NO:39), YISSGGGTTYYPDTVKG (VH CDR2; SEQ ID NO:40), and HSGYGSSYGVLFAY (VH CDR3; SEQ ID NO:41) and VL CDRs RASQDISNYLN (VL CDR1; SEQ ID NO:42), YTSILHS (VL CDR2; SEQ ID NO:43), and QQGNTLPWT (VL CDR3; SEQ ID NO:44). In some cases, the anti-CD22 antibody is humanized. In some instances, the anti-CD22 antibody is modified to include a sulfatase motif as described above, where the modification includes one or more amino acid residue insertions, deletions, and/or substitutions. In certain embodiments, the sulfatase motif is within, or adjacent to, a region of an IgG1 heavy chain constant region corresponding to one or more of: 1) amino acids 1-6; 2) amino acids 16-22; 3) amino acids 34-47; 4) amino acids 42-49; 5) amino acids 42-62; 6) amino acids 34-37; 7) amino acids 69-71; 8) amino acids 79-81; 9) amino acids 78-81; 10) amino acids 87-91; 11) amino acids 100-121; 12) amino acids 127-131; 13) amino acids 137-141; 14) amino acid 149-157; 15) amino acids 151-157; 16) amino acids 164-165; 17) amino acids 164-172; 18) amino acids 169-171; 19) amino acids 179-183; 20) amino acids 189-193; 21) amino acids 200-202; 22) amino acids 209-215; 23) amino acids 221-229; 24) amino acids 22-228; 25) amino acids 236-245; 26) amino acids 217-261; 27) amino acids 268-274; 28) amino acids 278-

287; 29) amino acids 313-331; and 30) amino acids 324-331; wherein the amino acid numbering is based on the amino acid numbering of human IgG1 as set out in SEQ ID NO:27 (human IgG1 constant region depicted in FIG. 9B). In some instances, the anti-CD22 antibody is modified to include a sulfatase motif as described above, where the modification includes one or more amino acid residue insertions, deletions, and/or substitutions; e.g., where the sulfatase motif is within, or adjacent to, a region of an Ig kappa constant region corresponding to one or more of: 1) amino acids 1-6; 2) amino acids 12-14; 3) amino acid 21; 4) amino acids 33-37; 5) amino acids 34-37; 6) amino acids 44-51; 7) amino acids 57-65; 8) amino acids 83-83; 9) amino acids 91-96; 10) amino acids 104-107; where the amino acid numbering is based on SEQ ID NOs:32 and 33 (human kappa light chain; amino acid sequence depicted in FIG. 9C).

In some cases, a suitable anti-CD22 antibody comprises VH CDRs IYDMS (VH CDR1; SEQ ID NO:39), YIS-SGGGTTYYPDTVKG (VH CDR2; SEQ ID NO:40), and HSGYGSSYGVLFAY (VH CDR3; SEQ ID NO:41). In some cases, the anti-CD22 antibody is humanized. In some instances, the anti-CD22 antibody is modified to include a sulfatase motif as described above, where the modification includes one or more amino acid residue insertions, deletions, and/or substitutions. In certain embodiments, the sulfatase motif is within, or adjacent to, a region of an IgG1 heavy chain constant region corresponding to one or more of: 1) amino acids 1-6; 2) amino acids 16-22; 3) amino acids 34-47; 4) amino acids 42-49; 5) amino acids 42-62; 6) amino acids 34-37; 7) amino acids 69-71; 8) amino acids 79-81; 9) amino acids 78-81; 10) amino acids 87-91; 11) amino acids 100-121; 12) amino acids 127-131; 13) amino acids 137-141; 14) amino acid 149-157; 15) amino acids 151-157; 16) amino acids 164-165; 17) amino acids 164-172; 18) amino acids 169-171; 19) amino acids 179-183; 20) amino acids 189-193; 21) amino acids 200-202; 22) amino acids 209-215; 23) amino acids 221-229; 24) amino acids 22-228; 25) amino acids 236-245; 26) amino acids 217-261; 27) amino acids 268-274; 28) amino acids 278-287; 29) amino acids 313-331; and 30) amino acids 324-331; wherein the amino acid numbering is based on the amino acid numbering of human IgG1 as set out in SEQ ID NO:27 (human IgG1 constant region depicted in FIG. 9B). In some cases, the anti-CD22 antibody is modified to include a sulfatase motif as described above, where the modification includes one or more amino acid residue insertions, deletions, and/or substitutions; e.g., where the sulfatase motif is within, or adjacent to, a region of an Ig kappa constant region corresponding to one or more of: 1) amino acids 1-6; 2) amino acids 12-14; 3) amino acid 21; 4) amino acids 33-37; 5) amino acids 34-37; 6) amino acids 44-51; 7) amino acids 57-65; 8) amino acids 83-83; 9) amino acids 91-96; 10) amino acids 104-107; where the amino acid numbering is based on SEQ ID NOs:32 and 33 (human kappa light chain; amino acid sequence depicted in FIG. 9C).

In some cases, a suitable anti-CD22 antibody comprises VL CDRs RASQDISNYLN (VL CDR1; SEQ ID NO:42), YTSILHS (VL CDR2; SEQ ID NO:43), and QQGNTLPWT (VL CDR3; SEQ ID NO:44). In some cases, the anti-CD22 antibody is humanized. In some instances, the anti-CD22 antibody is modified to include a sulfatase motif as described above, where the modification includes one or more amino acid residue insertions, deletions, and/or substitutions. In certain embodiments, the sulfatase motif is within, or adjacent to, a region of an IgG1 heavy chain constant region corresponding to one or more of: 1) amino acids 1-6; 2) amino acids 16-22; 3) amino acids 34-47; 4) amino acids 42-49; 5) amino acids 42-62; 6) amino acids 34-37; 7) amino acids 69-71; 8) amino acids 79-81; 9) amino acids 78-81; 10) amino acids 87-91; 11) amino acids 100-121; 12) amino acids 127-131; 13) amino acids 137-141; 14) amino acid 149-157; 15) amino acids 151-157; 16) amino acids 164-165; 17) amino acids 164-172; 18) amino acids 169-171; 19) amino acids 179-183; 20) amino acids 189-193; 21) amino acids 200-202; 22) amino acids 209-215; 23) amino acids 221-229; 24) amino acids 22-228; 25) amino acids 236-245; 26) amino acids 217-261; 27) amino acids 268-274; 28) amino acids 278-287; 29) amino acids 313-331; and 30) amino acids 324-331; wherein the amino acid numbering is based on the amino acid numbering of human IgG1 as set out in SEQ ID NO:27 (human IgG1 constant region depicted in FIG. 9B). In some instances, the anti-CD22 antibody is modified to include a sulfatase motif as described above, where the modification includes one or more amino acid residue insertions, deletions, and/or substitutions; e.g., where the sulfatase motif is within, or adjacent to, a region of an Ig kappa constant region corresponding to one or more of: 1) amino acids 1-6; 2) amino acids 12-14; 3) amino acid 21; 4) amino acids 33-37; 5) amino acids 34-37; 6) amino acids 44-51; 7) amino acids 57-65; 8) amino acids 83-83; 9) amino acids 91-96; 10) amino acids 104-107; where the amino acid numbering is based on SEQ ID NOs:32 and 33 (human kappa light chain; amino acid sequence depicted in FIG. 9C).

In some cases, a suitable anti-CD22 antibody comprises VH CDRs IYDMS (VH CDR1; SEQ ID NO:39), YIS-SGGGTTYYPDTVKG (VH CDR2; SEQ ID NO:40), and HSGYGSSYGVLFAY (VH CDR3; SEQ ID NO:41) and VL CDRs RASQDISNYLN (VL CDR1; SEQ ID NO:42), YTSILHS (VL CDR2; SEQ ID NO:43), and QQGNTLPWT (VL CDR3; SEQ ID NO:44). In some cases, the anti-CD22 antibody is humanized. In some instances, the anti-CD22 antibody is modified to include a sulfatase motif as described above, where the modification includes one or more amino acid residue insertions, deletions, and/or substitutions. In certain embodiments, the sulfatase motif is within, or adjacent to, a region of an IgG1 heavy chain constant region corresponding to one or more of: 1) amino acids 1-6; 2) amino acids 16-22; 3) amino acids 34-47; 4) amino acids 42-49; 5) amino acids 42-62; 6) amino acids 34-37; 7) amino acids 69-71; 8) amino acids 79-81; 9) amino acids 78-81; 10) amino acids 87-91; 11) amino acids 100-121; 12) amino acids 127-131; 13) amino acids 137-141; 14) amino acid 149-157; 15) amino acids 151-157; 16) amino acids 164-165; 17) amino acids 164-172; 18) amino acids 169-171; 19) amino acids 179-183; 20) amino acids 189-193; 21) amino acids 200-202; 22) amino acids 209-215; 23) amino acids 221-229; 24) amino acids 22-228; 25) amino acids 236-245; 26) amino acids 217-261; 27) amino acids 268-274; 28) amino acids 278-287; 29) amino acids 313-331; and 30) amino acids 324-331; wherein the amino acid numbering is based on the amino acid numbering of human IgG1 as set out in SEQ ID NO:27 (human IgG1 constant region depicted in FIG. 9B). In some instances, the anti-CD22 antibody is modified to include a sulfatase motif as described above, where the modification includes one or more amino acid residue insertions, deletions, and/or substitutions; e.g., where the sulfatase motif is within, or adjacent to, a region of an Ig kappa constant region corresponding to one or more of: 1) amino acids 1-6; 2) amino acids 12-14; 3) amino acid 21; 4) amino acids 33-37; 5) amino acids 34-37; 6) amino acids 44-51; 7) amino acids 57-65; 8) amino acids 83-83; 9) amino acids 91-96; 10)

amino acids 104-107; where the amino acid numbering is based on SEQ ID NOs:32 and 33 (human kappa light chain; amino acid sequence depicted in FIG. 9C).

In some cases, a suitable anti-CD22 antibody comprises VH CDRs present in an anti-CD22 VH region comprising the following amino acid sequence: EVQLVESGG-GLVKPGGSLRLSCAASGFAFSIYDMSWVRQAPGK-GLEWVAYISSGGGTT YYPDTVKGRFTISRDNAKNS-LYLQMSSLRAEDTAMYYCARHSGYGSSYGVLFAY-WGQ GTLVTVSS (SEQ ID NO:4). In some cases, the anti-CD22 antibody is humanized. In some instances, the anti-CD22 antibody is modified to include a sulfatase motif as described above, where the modification includes one or more amino acid residue insertions, deletions, and/or substitutions. In certain embodiments, the sulfatase motif is within, or adjacent to, a region of an IgG1 heavy chain constant region corresponding to one or more of: 1) amino acids 1-6; 2) amino acids 16-22; 3) amino acids 34-47; 4) amino acids 42-49; 5) amino acids 42-62; 6) amino acids 34-37; 7) amino acids 69-71; 8) amino acids 79-81; 9) amino acids 78-81; 10) amino acids 87-91; 11) amino acids 100-121; 12) amino acids 127-131; 13) amino acids 137-141; 14) amino acid 149-157; 15) amino acids 151-157; 16) amino acids 164-165; 17) amino acids 164-172; 18) amino acids 169-171; 19) amino acids 179-183; 20) amino acids 189-193; 21) amino acids 200-202; 22) amino acids 209-215; 23) amino acids 221-229; 24) amino acids 22-228; 25) amino acids 236-245; 26) amino acids 217-261; 27) amino acids 268-274; 28) amino acids 278-287; 29) amino acids 313-331; and 30) amino acids 324-331; wherein the amino acid numbering is based on the amino acid numbering of human IgG1 as set out in SEQ ID NO:27 (human IgG1 constant region depicted in FIG. 9B). In some instances, the anti-CD22 antibody is modified to include a sulfatase motif as described above, where the modification includes one or more amino acid residue insertions, deletions, and/or substitutions; e.g., where the sulfatase motif is within, or adjacent to, a region of an Ig kappa constant region corresponding to one or more of: 1) amino acids 1-6; 2) amino acids 12-14; 3) amino acid 21; 4) amino acids 33-37; 5) amino acids 34-37; 6) amino acids 44-51; 7) amino acids 57-65; 8) amino acids 83-83; 9) amino acids 91-96; 10) amino acids 104-107; where the amino acid numbering is based on SEQ ID NOs:32 and 33 (human kappa light chain; amino acid sequence depicted in FIG. 9C).

In some cases, a suitable anti-CD22 antibody comprises VL CDRs present in an anti-CD22 VL region comprising the following amino acid sequence: DIQMTQSPSSL-SASVGDRVTITCRASQDISNYLNWYQQKPGKA-VKLLIYYTSILHSGVPS RFSGSGSGTDYTLTISS-LQQEDFATYFCQQGNTLPWTFGGGTKVEIKR (SEQ ID NO:7). In some cases, the anti-CD22 antibody is humanized. In some instances, the anti-CD22 antibody is modified to include a sulfatase motif as described above, where the modification includes one or more amino acid residue insertions, deletions, and/or substitutions. In certain embodiments, the sulfatase motif is within, or adjacent to, a region of an IgG1 heavy chain constant region corresponding to one or more of: 1) amino acids 1-6; 2) amino acids 16-22; 3) amino acids 34-47; 4) amino acids 42-49; 5) amino acids 42-62; 6) amino acids 34-37; 7) amino acids 69-71; 8) amino acids 79-81; 9) amino acids 78-81; 10) amino acids 87-91; 11) amino acids 100-121; 12) amino acids 127-131; 13) amino acids 137-141; 14) amino acid 149-157; 15) amino acids 151-157; 16) amino acids 164-165; 17) amino acids 164-172; 18) amino acids 169-171; 19) amino acids 179-183; 20) amino acids 189-193; 21) amino acids 200-202; 22) amino acids 209-215; 23) amino acids 221-229; 24) amino acids 22-228; 25) amino acids 236-245; 26) amino acids 217-261; 27) amino acids 268-274; 28) amino acids 278-287; 29) amino acids 313-331; and 30) amino acids 324-331; wherein the amino acid numbering is based on the amino acid numbering of human IgG1 as set out in SEQ ID NO:27 (human IgG1 constant region depicted in FIG. 9B). In some instances, the anti-CD22 antibody is modified to include a sulfatase motif as described above, where the modification includes one or more amino acid residue insertions, deletions, and/or substitutions; e.g., where the sulfatase motif is within, or adjacent to, a region of an Ig kappa constant region corresponding to one or more of: 1) amino acids 1-6; 2) amino acids 12-14; 3) amino acid 21; 4) amino acids 33-37; 5) amino acids 34-37; 6) amino acids 44-51; 7) amino acids 57-65; 8) amino acids 83-83; 9) amino acids 91-96; 10) amino acids 104-107; where the amino acid numbering is based on SEQ ID NOs:32 and 33 (human kappa light chain; amino acid sequence depicted in FIG. 9C).

In some cases, a suitable anti-CD22 antibody comprises VH CDRs present in EVQLVESGGGLVKPGGSLRLS-CAASGFAFSIYDMSWVRQAPGKGLEWVAYIS-SGGGTT YYPDTVKGRFTISRDNAKNSLYLQMSSL-RAEDTAMYYCARHSGYGSSYGVLFAYWGQ GTLVTVSS (SEQ ID NO:4) and VL CDRs present in DIQMTQSPSSLSASVGDRVTITCRASQDIS-NYLNWYQQKPGKAVKLLIYYTSILHSGVPS RFSGSGSGTDYTLTISSLQQEDFATYFCQQGNTLPWT-FGGGTKVEIKR (SEQ ID NO:7). In some cases, the anti-CD22 antibody is humanized. In some instances, the anti-CD22 antibody is modified to include a sulfatase motif as described above, where the modification includes one or more amino acid residue insertions, deletions, and/or substitutions. In certain embodiments, the sulfatase motif is within, or adjacent to, a region of an IgG1 heavy chain constant region corresponding to one or more of: 1) amino acids 1-6; 2) amino acids 16-22; 3) amino acids 34-47; 4) amino acids 42-49; 5) amino acids 42-62; 6) amino acids 34-37; 7) amino acids 69-71; 8) amino acids 79-81; 9) amino acids 78-81; 10) amino acids 87-91; 11) amino acids 100-121; 12) amino acids 127-131; 13) amino acids 137-141; 14) amino acid 149-157; 15) amino acids 151-157; 16) amino acids 164-165; 17) amino acids 164-172; 18) amino acids 169-171; 19) amino acids 179-183; 20) amino acids 189-193; 21) amino acids 200-202; 22) amino acids 209-215; 23) amino acids 221-229; 24) amino acids 22-228; 25) amino acids 236-245; 26) amino acids 217-261; 27) amino acids 268-274; 28) amino acids 278-287; 29) amino acids 313-331; and 30) amino acids 324-331; wherein the amino acid numbering is based on the amino acid numbering of human IgG1 as set out in SEQ ID NO:27 (human IgG1 constant region depicted in FIG. 9B). In some instances, the anti-CD22 antibody is modified to include a sulfatase motif as described above, where the modification includes one or more amino acid residue insertions, deletions, and/or substitutions; e.g., where the sulfatase motif is within, or adjacent to, a region of an Ig kappa constant region corresponding to one or more of: 1) amino acids 1-6; 2) amino acids 12-14; 3) amino acid 21; 4) amino acids 33-37; 5) amino acids 34-37; 6) amino acids 44-51; 7) amino acids 57-65; 8) amino acids 83-83; 9) amino acids 91-96; 10) amino acids 104-107; where the amino acid numbering is based on SEQ ID NOs:32 and 33 (human kappa light chain; amino acid sequence depicted in FIG. 9C).

In some cases, a suitable anti-CD22 antibody comprises the VH amino acid sequence EVQLVESGG- GLVKPGGSLRLSCAASGFAFSIYDMSWVRQAPGK-
GLEWVAYISSGGGTT YYPDTVKGRFTISRDNAKNS-
LYLQMSSLRAEDTAMYYCARHSGYGSSYGVLFAY-
WGQ GTLVTVSS (SEQ ID NO:4). In some cases, a
suitable anti-CD22 antibody comprises the VL amino acid
sequence DIQMTQSPSSLSASVGDRVTITCRASQDIS-
NYLNWYQQKPGKAVKLLIYYTSILHSGVPS
RFSGSGSGTDYTLTISSLQQEDFATYFCQQGNTLP-
WTFGGGTKVEIKR (SEQ ID NO:7). In some cases, a
suitable anti-CD22 antibody comprises the VH amino acid
sequence EVQLVESGGGLVKPGGSLRLSCAASGFA-
FSIYDMSWVRQAPGKGLEWVAYISSGGGTT
YYPDTVKGRFTISRDNAKNSLYLQMSSLRAED-
TAMYYCARHSGYGSSYGVLFAYWGQ GTLVTVSS
(SEQ ID NO:4); and the VL amino acid sequence
DIQMTQSPSSLSASVGDRVTITCRASQDISNYLNW-
YQQKPGKAVKLLIYYTSILHSGVPS RFSGSGSGT-
DYTLTISSLQQEDFATYFCQQGNTLPWTFGGGTK-
VEIKR (SEQ ID NO:7). In some instances, the anti-CD22
antibody is modified to include a sulfatase motif as
described above, where the modification includes one or
more amino acid residue insertions, deletions, and/or substitutions. In certain embodiments, the sulfatase motif is
within, or adjacent to, a region of an IgG1 heavy chain
constant region corresponding to one or more of: 1) amino
acids 1-6; 2) amino acids 16-22; 3) amino acids 34-47; 4)
amino acids 42-49; 5) amino acids 42-62; 6) amino acids
34-37; 7) amino acids 69-71; 8) amino acids 79-81; 9) amino
acids 78-81; 10) amino acids 87-91; 11) amino acids 100-
121; 12) amino acids 127-131; 13) amino acids 137-141; 14)
amino acid 149-157; 15) amino acids 151-157; 16) amino
acids 164-165; 17) amino acids 164-172; 18) amino acids
169-171; 19) amino acids 179-183; 20) amino acids 189-
193; 21) amino acids 200-202; 22) amino acids 209-215; 23)
amino acids 221-229; 24) amino acids 22-228; 25) amino
acids 236-245; 26) amino acids 217-261; 27) amino acids
268-274; 28) amino acids 278-287; 29) amino acids 313-
331; and 30) amino acids 324-331; wherein the amino acid
numbering is based on the amino acid numbering of human
IgG1 as set out in SEQ ID NO:27 (human IgG1 constant
region depicted in FIG. 9B).

Drugs for Conjugation to a Polypeptide

The present disclosure provides drug-polypeptide conjugates. Examples of drugs include small molecule drugs, such as a cancer chemotherapeutic agent. For example, where the polypeptide is an antibody (or fragment thereof) that has specificity for a tumor cell, the antibody can be modified as described herein to include a modified amino acid, which can be subsequently conjugated to a cancer chemotherapeutic agent, such as a microtubule affecting agents. In certain embodiments, the drug is a microtubule affecting agent that has antiproliferative activity, such as a maytansinoid. In certain embodiments, the drug is a maytansinoid, which as the following structure:

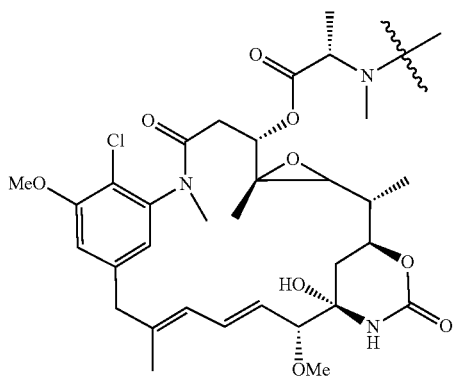

where ⁓ indicates the point of attachment between the maytansinoid and the linker, L, in formula (I). By "point of attachment" is meant that the ⁓ symbol indicates the bond between the N of the maytansinoid and the linker, L, in formula (I). For example, in formula (I), $W^1$ is a maytansinoid, such as a maytansinoid of the structure above, where ⁓ indicates the point of attachment between the maytansinoid and the linker, L.

As described above, in certain embodiments, L is a linker described by the formula $-(L^1)_a-(L^2)_b-(L^3)_c-(L^4)_d-$, wherein $L^1$, $L^2$, $L^3$ and $L^4$ are each independently a linker unit. In certain embodiments, $L^1$ is attached to the coupling moiety, such as a hydrazinyl-indolyl or a hydrazinyl-pyrrolo-pyridinyl coupling moiety (e.g., as shown in formula (I) above). In certain embodiments, $L^2$, if present, is attached to $W^1$ (the maytansinoid). In certain embodiments, $L^3$, if present, is attached to $W^1$ (the maytansinoid). In certain embodiments, $L^4$, if present, is attached to $W^1$ (the maytansinoid).

As described above, in certain embodiments, the linker $-(L^1)_a-(L^2)_b-(L^3)_c-(L^4)_d-$ is described by the formula $-(T^1-V^1)_a-(T^2-V^2)_b-(T^3-V^3)_c-(T^4-V^4)_d-$, wherein a, b, c and d are each independently 0 or 1, where the sum of a, b, c and d is 1 to 4. In certain embodiments, as described above, $L^1$ is attached to the hydrazinyl-indolyl or the hydrazinyl-pyrrolo-pyridinyl coupling moiety (e.g., as shown in formula (I) above). As such, in certain embodiments, $T^1$ is attached to the hydrazinyl-indolyl or the hydrazinyl-pyrrolo-pyridinyl coupling moiety (e.g., as shown in formula (I) above). In certain embodiments, $V^1$ is attached to $W^1$ (the maytansinoid). In certain embodiments, as described above, $L^2$, if present, is attached to $W^1$ (the maytansinoid). As such, in certain embodiments, $T^2$, if present, is attached to $W^1$ (the maytansinoid), or $V^2$, if present, is attached to $W^1$ (the maytansinoid). In certain embodiments, as described above, $L^3$, if present, is attached to $W^1$ (the maytansinoid). As such, in certain embodiments, $T^3$, if present, is attached to $W^1$ (the maytansinoid), or $V^3$, if present, is attached to $W^1$ (the maytansinoid). In certain embodiments, as described above, $L^4$, if present, is attached to $W^1$ (the maytansinoid). As such, in certain embodiments, $T^4$, if present, is attached to $W^1$ (the maytansinoid), or $V^4$, if present, is attached to $W^1$ (the maytansinoid).

Embodiments of the present disclosure include conjugates where a polypeptide (e.g., anti-CD22 antibody) is conjugated to one or more drug moieties (e.g., maytansinoid), such as 2 drug moieties, 3 drug moieties, 4 drug moieties, 5 drug moieties, 6 drug moieties, 7 drug moieties, 8 drug moieties, 9 drug moieties, or 10 or more drug moieties. The drug moieties may be conjugated to the polypeptide at one or more sites in the polypeptide, as described herein. In certain embodiments, the conjugates have an average drug-to-antibody ratio (DAR) (molar ratio) in the range of from 0.1 to 10, or from 0.5 to 10, or from 1 to 10, such as from 1 to 9, or from 1 to 8, or from 1 to 7, or from 1 to 6, or from 1 to 5, or from 1 to 4, or from 1 to 3, or from 1 to 2. In certain embodiments, the conjugates have an average DAR from 1 to 2, such as 1, 1.1, 1.2, 1.3, 1.4, 1.5, 1.6, 1.7, 1.8, 1.9 or 2. In certain embodiments, the conjugates have an average DAR of 1.6 to 1.9. In certain embodiments, the conjugates have an average DAR of 1.7. By average is meant the arithmetic mean.

Formulations

The conjugates (including antibody conjugates) of the present disclosure can be formulated in a variety of different ways. In general, where the conjugate is a polypeptide-drug conjugate, the conjugate is formulated in a manner compatible with the drug conjugated to the polypeptide, the condition to be treated, and the route of administration to be used.

The conjugate (e.g., polypeptide-drug conjugate) can be provided in any suitable form, e.g., in the form of a pharmaceutically acceptable salt, and can be formulated for any suitable route of administration, e.g., oral, topical or parenteral administration. Where the conjugate is provided as a liquid injectable (such as in those embodiments where they are administered intravenously or directly into a tissue), the conjugate can be provided as a ready-to-use dosage form, or as a reconstitutable storage-stable powder or liquid composed of pharmaceutically acceptable carriers and excipients.

Methods for formulating conjugates can be adapted from those readily available. For example, conjugates can be provided in a pharmaceutical composition comprising a therapeutically effective amount of a conjugate and a pharmaceutically acceptable carrier (e.g., saline). The pharmaceutical composition may optionally include other additives (e.g., buffers, stabilizers, preservatives, and the like). In some embodiments, the formulations are suitable for administration to a mammal, such as those that are suitable for administration to a human.

Methods of Treatment

The polypeptide-drug conjugates of the present disclosure find use in treatment of a condition or disease in a subject that is amenable to treatment by administration of the parent drug (i.e., the drug prior to conjugation to the polypeptide). By "treatment" is meant that at least an amelioration of the symptoms associated with the condition afflicting the host is achieved, where amelioration is used in a broad sense to refer to at least a reduction in the magnitude of a parameter, e.g. symptom, associated with the condition being treated. As such, treatment also includes situations where the pathological condition, or at least symptoms associated therewith, are completely inhibited, e.g., prevented from happening, or stopped, e.g. terminated, such that the host no longer suffers from the condition, or at least the symptoms that characterize the condition. Thus treatment includes: (i) prevention, that is, reducing the risk of development of clinical symptoms, including causing the clinical symptoms not to develop, e.g., preventing disease progression to a harmful state; (ii) inhibition, that is, arresting the development or further development of clinical symptoms, e.g., mitigating or completely inhibiting an active disease; and/or (iii) relief, that is, causing the regression of clinical symptoms.

In the context of cancer, the term "treating" includes any or all of: reducing growth of a solid tumor, inhibiting replication of cancer cells, reducing overall tumor burden, and ameliorating one or more symptoms associated with a cancer.

The subject to be treated can be one that is in need of therapy, where the host to be treated is one amenable to treatment using the parent drug. Accordingly, a variety of subjects may be amenable to treatment using the polypeptide-drug conjugates disclosed herein. Generally, such subjects are "mammals", with humans being of interest. Other subjects can include domestic pets (e.g., dogs and cats), livestock (e.g., cows, pigs, goats, horses, and the like), rodents (e.g., mice, guinea pigs, and rats, e.g., as in animal models of disease), as well as non-human primates (e.g., chimpanzees, and monkeys).

The amount of polypeptide-drug conjugate administered can be initially determined based on guidance of a dose and/or dosage regimen of the parent drug. In general, the polypeptide-drug conjugates can provide for targeted delivery and/or enhanced serum half-life of the bound drug, thus providing for at least one of reduced dose or reduced administrations in a dosage regimen. Thus, the polypeptide-drug conjugates can provide for reduced dose and/or reduced administration in a dosage regimen relative to the parent drug prior to being conjugated in an polypeptide-drug conjugate of the present disclosure.

Furthermore, as noted above, because the polypeptide-drug conjugates can provide for controlled stoichiometry of drug delivery, dosages of polypeptide-drug conjugates can be calculated based on the number of drug molecules provided on a per polypeptide-drug conjugate basis.

In some embodiments, multiple doses of a polypeptide-drug conjugate are administered. The frequency of administration of a polypeptide-drug conjugate can vary depending on any of a variety of factors, e.g., severity of the symptoms, condition of the subject, etc. For example, in some embodiments, a polypeptide-drug conjugate is administered once per month, twice per month, three times per month, every other week, once per week (qwk), twice per week, three times per week, four times per week, five times per week, six times per week, every other day, daily (qd/od), twice a day (bds/bid), or three times a day (tds/tid), etc.

Methods of Treating Cancer

The present disclosure provides methods for delivering a cancer chemotherapeutic agent to an individual having a cancer. The methods are useful for treating a wide variety of cancers, including carcinomas, sarcomas, leukemias, and lymphomas.

Carcinomas that can be treated using a subject method include, but are not limited to, esophageal carcinoma, hepatocellular carcinoma, basal cell carcinoma (a form of skin cancer), squamous cell carcinoma (various tissues), bladder carcinoma, including transitional cell carcinoma (a malignant neoplasm of the bladder), bronchogenic carcinoma, colon carcinoma, colorectal carcinoma, gastric carcinoma, lung carcinoma, including small cell carcinoma and non-small cell carcinoma of the lung, adrenocortical carcinoma, thyroid carcinoma, pancreatic carcinoma, breast carcinoma, ovarian carcinoma, prostate carcinoma, adenocarcinoma, sweat gland carcinoma, sebaceous gland carcinoma, papillary carcinoma, papillary adenocarcinoma, cystadenocarcinoma, medullary carcinoma, renal cell carcinoma, ductal carcinoma in situ or bile duct carcinoma, choriocarcinoma, seminoma, embryonal carcinoma, Wilm's tumor, cervical carcinoma, uterine carcinoma, testicular carcinoma, osteogenic carcinoma, epithelial carcinoma, and nasopharyngeal carcinoma, etc.

Sarcomas that can be treated using a subject method include, but are not limited to, fibrosarcoma, myxosarcoma, liposarcoma, chondrosarcoma, chordoma, osteogenic sarcoma, osteosarcoma, angiosarcoma, endotheliosarcoma, lymphangiosarcoma, lymphangioendotheliosarcoma, synovioma, mesothelioma, Ewing's sarcoma, leiomyosarcoma, rhabdomyosarcoma, and other soft tissue sarcomas.

Other solid tumors that can be treated using a subject method include, but are not limited to, glioma, astrocytoma, medulloblastoma, craniopharyngioma, ependymoma, pinealoma, hemangioblastoma, acoustic neuroma, oligodendroglioma, menangioma, melanoma, neuroblastoma, and retinoblastoma.

Leukemias that can be treated using a subject method include, but are not limited to, a) chronic myeloproliferative syndromes (neoplastic disorders of multipotential hematopoietic stem cells); b) acute myelogenous leukemias (neoplastic transformation of a multipotential hematopoietic stem cell or a hematopoietic cell of restricted lineage potential; c) chronic lymphocytic leukemias (CLL; clonal proliferation of immunologically immature and functionally incompetent small lymphocytes), including B-cell CLL, T-cell CLL prolymphocytic leukemia, and hairy cell leukemia; and d) acute lymphoblastic leukemias (characterized by accumulation of lymphoblasts). Lymphomas that can be treated using a subject method include, but are not limited to, B-cell lymphomas (e.g., Burkitt's lymphoma); Hodgkin's lymphoma; non-Hodgkin's B cell lymphoma; and the like.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Celsius, and pressure is at or near atmospheric. By "average" is meant the arithmetic mean. Standard abbreviations may be used, e.g., bp, base pair(s); kb, kilobase(s); pl, picoliter(s); s or see, second(s); min, minute(s); h or hr, hour(s); aa, amino acid(s); kb, kilobase(s); bp, base pair(s); nt, nucleotide(s); i.m., intramuscular(ly); i.p., intraperitoneal(ly); s.c., subcutaneous(ly); and the like.

General Synthetic Procedures

Many general references providing commonly known chemical synthetic schemes and conditions useful for synthesizing the disclosed compounds are available (see, e.g., Smith and March, March's Advanced Organic Chemistry: Reactions, Mechanisms, and Structure, Fifth Edition, Wiley-Interscience, 2001; or Vogel, A Textbook of Practical Organic Chemistry, Including Qualitative Organic Analysis, Fourth Edition, New York: Longman, 1978).

Compounds as described herein can be purified by any purification protocol known in the art, including chromatography, such as HPLC, preparative thin layer chromatography, flash column chromatography and ion exchange chromatography. Any suitable stationary phase can be used, including normal and reversed phases as well as ionic resins. In certain embodiments, the disclosed compounds are purified via silica gel and/or alumina chromatography. See, e.g., Introduction to Modern Liquid Chromatography, 2nd Edition, ed. L. R. Snyder and J. J. Kirkland, John Wiley and Sons, 1979; and Thin Layer Chromatography, ed E. Stahl, Springer-Verlag, New York, 1969.

During any of the processes for preparation of the subject compounds, it may be necessary and/or desirable to protect sensitive or reactive groups on any of the molecules concerned. This may be achieved by means of conventional protecting groups as described in standard works, such as J. F. W. McOmie, "Protective Groups in Organic Chemistry", Plenum Press, London and New York 1973, in T. W. Greene and P. G. M. Wuts, "Protective Groups in Organic Synthesis", Third edition, Wiley, New York 1999, in "The Peptides"; Volume 3 (editors: E. Gross and J. Meienhofer), Academic Press, London and New York 1981, in "Methoden der organischen Chemie", Houben-Weyl, $4^{th}$ edition, Vol. 15/1, Georg Thieme Verlag, Stuttgart 1974, in H.-D. Jakubke and H. Jescheit, "Aminosauren, Peptide, Proteine", Verlag Chemie, Weinheim, Deerfield Beach, and Basel 1982, and/or in Jochen Lehmann, "Chemie der Kohlenhydrate: Monosaccharide and Derivate", Georg Thieme Verlag, Stuttgart 1974. The protecting groups may be removed at a convenient subsequent stage using methods known from the art.

The subject compounds can be synthesized via a variety of different synthetic routes using commercially available starting materials and/or starting materials prepared by conventional synthetic methods. A variety of examples of synthetic routes that can be used to synthesize the compounds disclosed herein are described in the schemes below.

Example 1

A linker containing a 4-amino-piperidine (4AP) group was synthesized according to Scheme 1, shown below.

Scheme 1

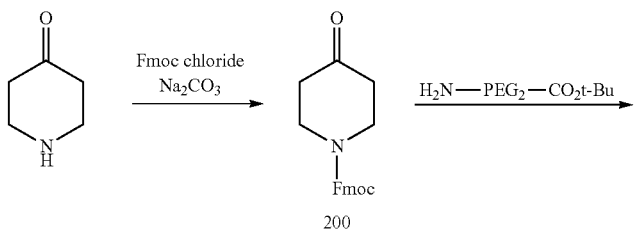

200

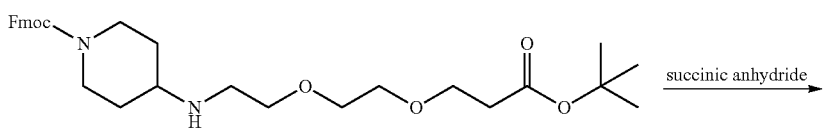

201

-continued
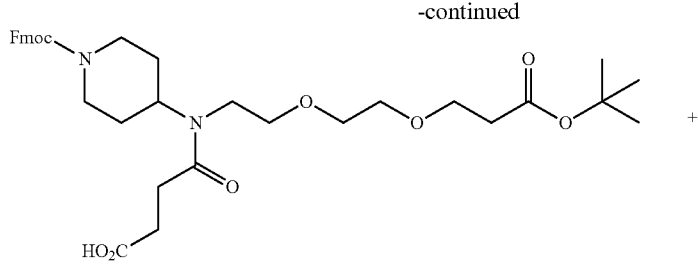
202
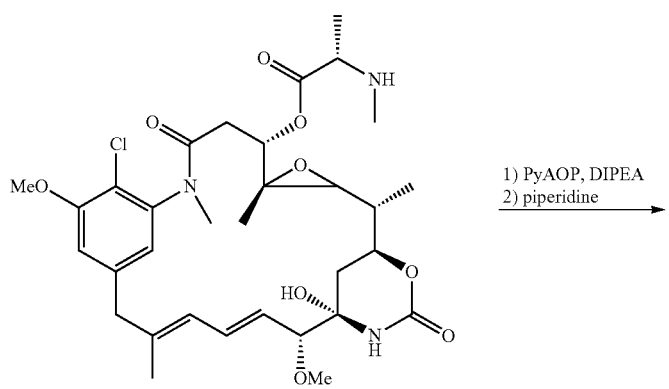
124
1) PyAOP, DIPEA
2) piperidine →
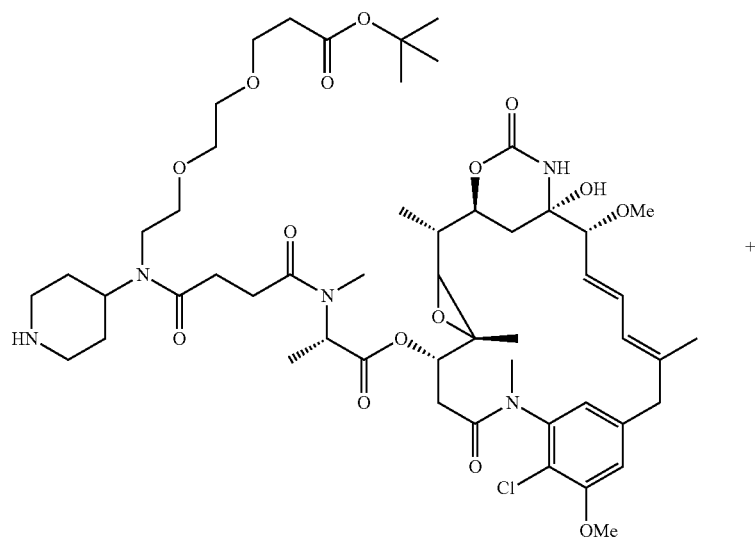
203
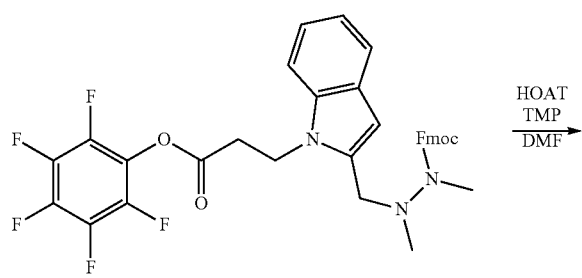
12
HOAT
TMP
DMF →

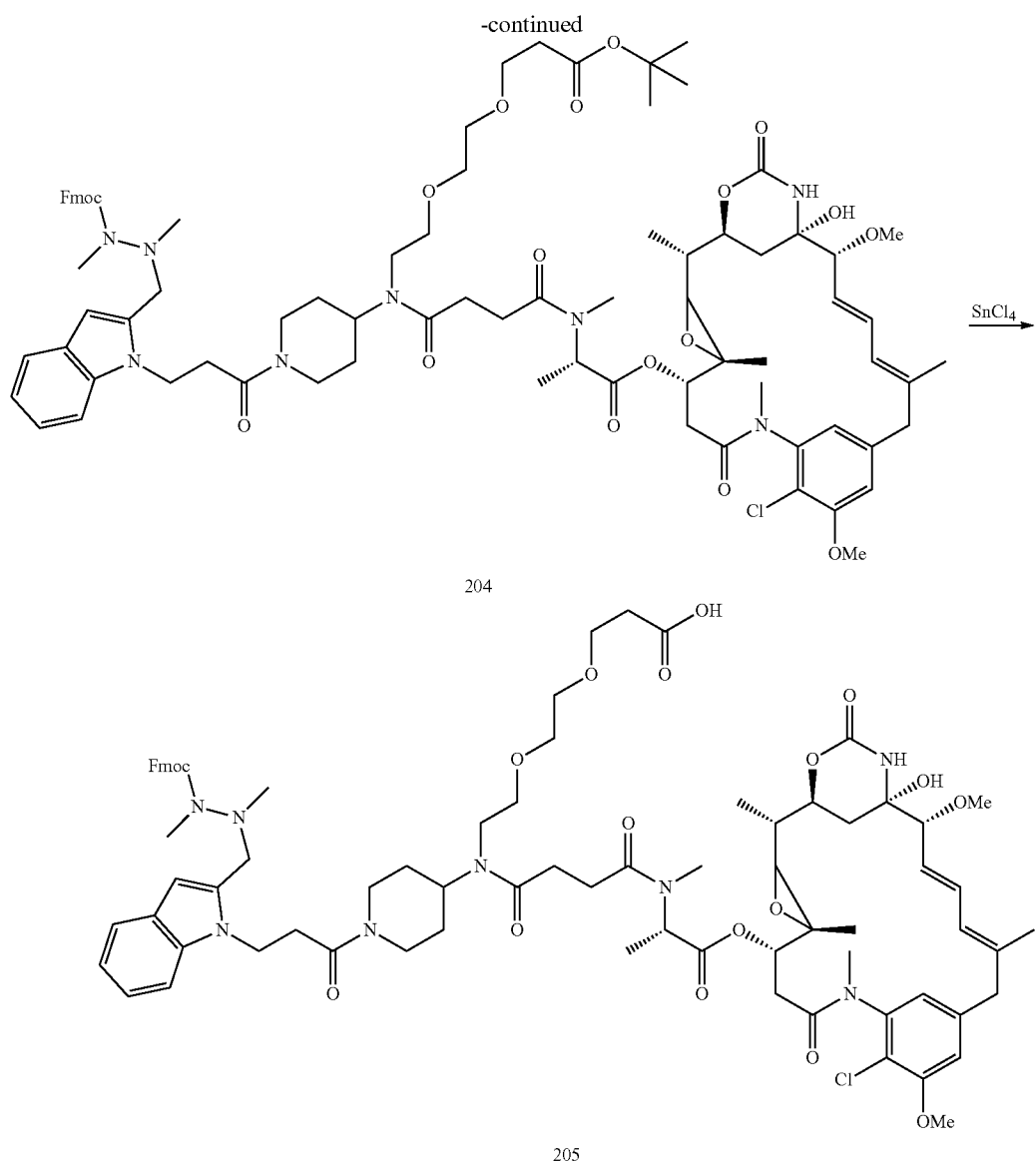

204

205

Synthesis of (9H-fluoren-9-yl)methyl 4-oxopiperidine-1-carboxylate (200)

To a 100 mL round-bottom flask containing a magnetic stir bar was added piperidin-4-one hydrochloride monohydrate (1.53 g, 10 mmol), Fmoc chloride (2.58 g, 10 mmol), sodium carbonate (3.18 g, 30 mmol), dioxane (20 mL), and water (2 mL). The reaction mixture was stirred at room temperature for 1 h. The mixture was diluted with EtOAc (100 mL) and extracted with water (1×100 mL). The organic layer was dried over $Na_2SO_4$, filtered, and concentrated under reduced pressure. The resulting material was dried in vacuo to yield compound 200 as a white solid (3.05 g, 9500 yield).

$^1$H NMR (CDCl$_3$) δ 7.78 (d, 2H, J=7.6), 7.59 (d, 2H, J=7.2), 7.43 (t, 2H, J=7.2), 7.37 (t, 2H, J=7.2), 4.60 (d, 2H, J=6.0), 4.28 (t, 2H, J=6.0), 3.72 (br, 2H), 3.63 (br, 2H), 2.39 (br, 2H), 2.28 (br, 2H).

MS (ESI) m/z: [M+H]$^+$ Calcd for $C_{20}H_{20}NO_3$ 322.4; Found 322.2.

Synthesis of (9H-fluoren-9-yl)methyl 4-((2-(2-(3-(tert-butoxy)-3-oxopropoxy)ethoxy)ethyl)amino)piperidine-1-carboxylate (201)

To a dried scintillation vial containing a magnetic stir bar was added piperidinone 200 (642 mg, 2.0 mmol), $H_2N$-$PEG_2$-$CO_2$t-Bu (560 mg, 2.4 mmol), 4 Å molecular sieves (activated powder, 500 mg), and 1,2-dichloroethane (5 mL). The mixture was stirred for 1 h at room temperature. To the reaction mixture was added sodium triacetoxyborohydride (845 mg, 4.0 mmol). The mixture was stirred for 5 days at room temperature. The resulting mixture was diluted with EtOAc. The organic layer was washed with saturated NaHCO$_3$ (1×50 mL), and brine (1×50 mL), dried over Na$_2$SO$_4$, filtered, and concentrated under reduced pressure to yield compound 201 as an oil, which was carried forward without further purification.

Synthesis of 13-(1-(((9H-fluoren-9-yl)methoxy)carbonyl)piperidin-4-yl)-2,2-dimethyl-4,14-dioxo-3,7,10-trioxa-13-azaheptadecan-17-oic acid (202)

To a dried scintillation vial containing a magnetic stir bar was added N-Fmoc-piperidine-4-amino-PEG$_2$-CO$_2$t-Bu (201) from the previous step, succinic anhydride (270 mg, 2.7 mmol), and dichloromethane (5 mL). The mixture was stirred for 18 hours at room temperature. The reaction mixture was partitioned between EtOAc and saturated NaHCO$_3$. The aqueous layer was extracted with EtOAc (3×). The aqueous layer was acidified with HCl (1 M) until the pH ~3. The aqueous layer was extracted (3×) with DCM. The combined organic layers were dried over Na$_2$SO$_4$, filtered, and concentrated under reduced pressure. The reaction mixture was purified by C18 flash chromatography (elute 10-100% MeCN/water with 0.1% acetic acid). Product-containing fractions were concentrated under reduced pressure and then azeotroped with toluene (3×50 mL) to remove residual acetic acid to afford 534 mg (42%, 2 steps) of compound 202 as a white solid.

$^1$H NMR (DMSO-d$_6$) δ 11.96 (br, 1H), 7.89 (d, 2H, J=7.2), 7.63 (d, 2H, J=7.2), 7.42 (t, 2H, J=7.2), 7.34 (t, 2H, J=7.2), 4.25-4.55 (m, 3H), 3.70-4.35 (m, 3H), 3.59 (t, 2H, J=6.0), 3.39 (m, 5H), 3.35 (m, 3H), 3.21 (br, 1H), 2.79 (br, 2H), 2.57 (m, 2H), 2.42 (q, 4H, J=6.0), 1.49 (br, 3H), 1.37 (s, 9H).

MS (ESI) m/z: [M+H]+Calcd for C$_{35}$H$_{47}$N$_2$O$_9$ 639.3; Found 639.2.

Synthesis of (2S)-1-(((1$^4$S, 1$^6$S, 3$^3$S, 2R, 4S, 10E, 12E, 14R)-8$^6$-chloro-1$^4$-hydroxy-8$^5$,14-dimethoxy-3$^3$,2,7,10-tetramethyl-1$^2$,6-dioxo-7-aza-1(6,4)-oxazinana-3(2,3)-oxirana-8(1,3)-benzenacyclotetradecaphane-10,12-dien-4-yl)oxy)-2,3-dimethyl-1,4,7-trioxo-8-(piperidin-4-yl)-11,14-dioxa-3,8-diazaheptadecan-17-oic acid (203)

To a solution of ester 202 (227 mg, 0.356 mmol), diisopropylethylamine (174 μL, 1.065 mmol), N-deacetyl maytansine 124 (231 mg, 0.355 mmol) in 2 mL of DMF was added PyAOP (185 mg, 0.355 mmol). The solution was stirred for 30 min. Piperidine (0.5 mL) was added to the reaction mixture and stirred for an additional 20 min. The crude reaction mixture was purified by C18 reverse phase chromatography using a gradient of 0-100% acetonitrile:water affording 203.2 mg (55%, 2 steps) of compound 203.

Synthesis of 17-(tert-butyl)1-((1$^4$S, 1$^6$S, 3$^3$S, 2R, 4S, 10E, 12E, 14R)-8$^6$-chloro-1$^4$-hydroxy-8$^5$,14-dimethoxy-3$^3$,2,7,10-tetramethyl-1$^2$,6-dioxo-7-aza-1(6,4)-oxazinana-3(2,3)-oxirana-8(1,3)-benzenacyclotetradecaphane-10,12-dien-4-yl) (2S)-8-(1-(3-(2-((2-(((9H-fluoren-9-yl)methoxy)carbonyl)-1,2-dimethylhydrazinyl)methyl)-1H-indol-1-yl)propanoyl)piperidin-4-yl)-2,3-dimethyl-4,7-dioxo-11,14-dioxa-3,8-diazaheptadecanedioate (204)

A solution of piperidine 203 (203.2 mg, 0.194 mmol), ester 12 (126.5 mg, 0.194 mmol), 2,4,6-trimethylpyridine (77 μL, 0.582 mmol), HOAT (26.4 mg, 0.194 mmol) in 1 mL DMF was stirred 30 min. The crude reaction was purified by C18 reverse phase chromatography using a gradient of 0-100% acetonitrile:water with 0.1% formic acid affording 280.5 mg (97% yield) of compound 204.

MS (ESI) m/z: [M+H]+ Calcd for C$_{81}$H$_{106}$ClN$_8$O$_{18}$ 1513.7; Found 1514.0.

Synthesis of (2S)-8-(1-(3-(2-((2-(((9H-fluoren-9-yl)methoxy)carbonyl)-1,2-dimethylhydrazinyl)methyl)-1H-indol-1-yl)propanoyl)piperidin-4-yl)-1-(((1$^4$S, 1$^6$S, 3$^3$S, 2R, 4S, 10E, 12E, 14R)-8$^6$-chloro-1$^4$-hydroxy-8$^5$,14-dimethoxy-3$^3$,2,7,10-tetramethyl-1$^2$,6-dioxo-7-aza-1(6,4)-oxazinana-3(2,3)-oxirana-8(1,3)-benzenacyclotetradecaphane-10,12-dien-4-yl)oxy)-2,3-dimethyl-1,4,7-trioxo-11,14-dioxa-3,8-diazaheptadecan-17-oic acid (205)

To a solution of compound 204 (108 mg, 0.0714 mmol) in 500 μL anhydrous DCM was added 357 μL of a 1M solution of SnCl4 in DCM. The heterogeneous mixture was stirred for 1 h and then purified by C18 reverse phase chromatography using a gradient of 0-100% acetonitrile:water with 0.1% formic acid affording 78.4 mg (75% yield) of compound 205.

MS (ESI) m/z: [M−H]− Calcd for C$_{77}$H$_{96}$ClN$_8$O is 1455.7; Found 1455.9.

Example 2

A linker containing a 4-amino-piperidine (4AP) group was synthesized according to Scheme 2, shown below.

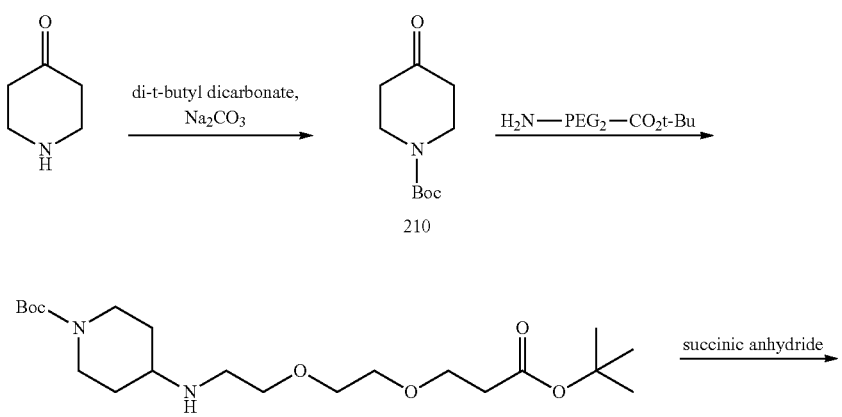

Scheme 2

-continued
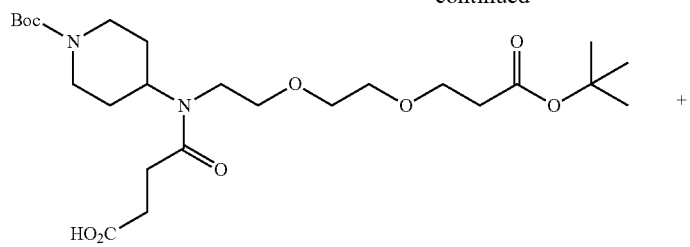
212
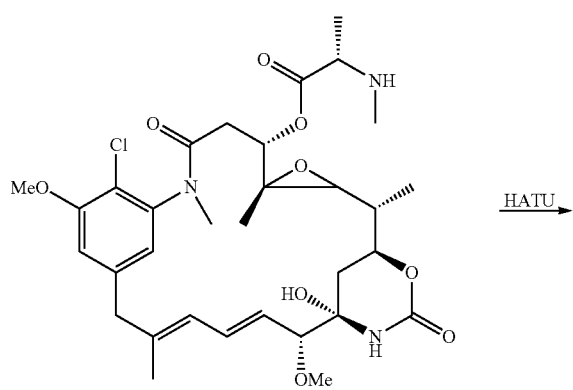
124
HATU→
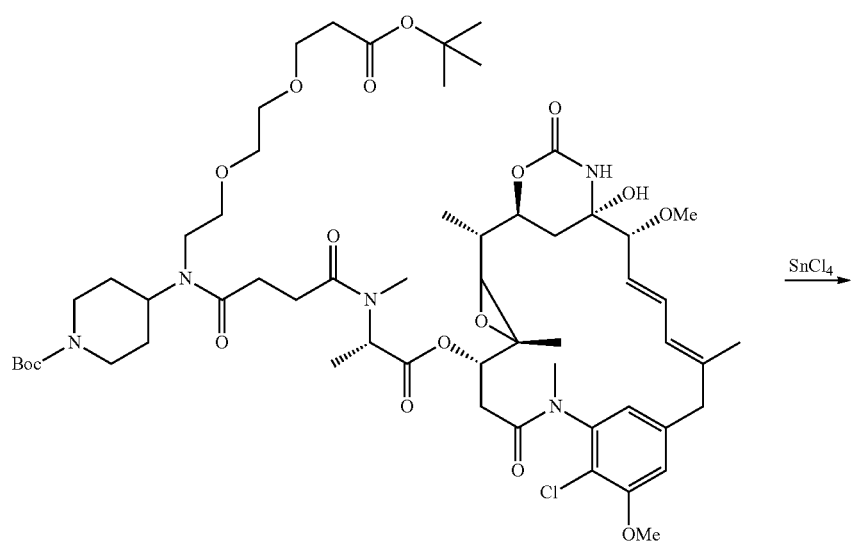
213
SnCl₄→

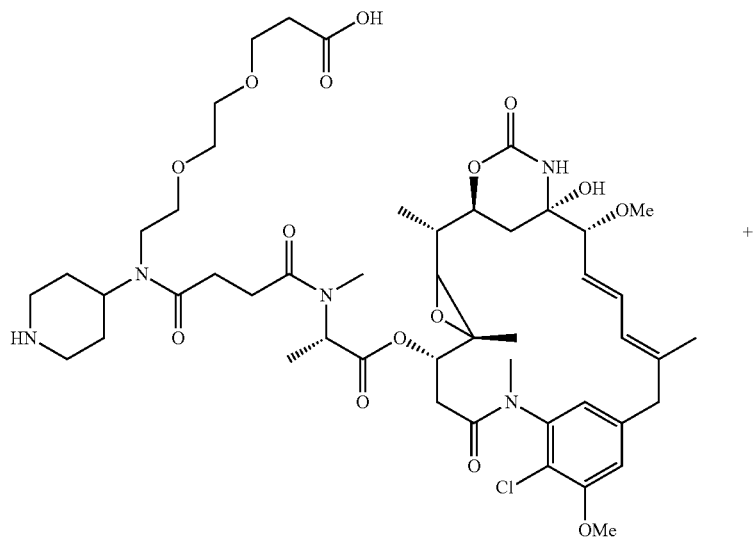
214
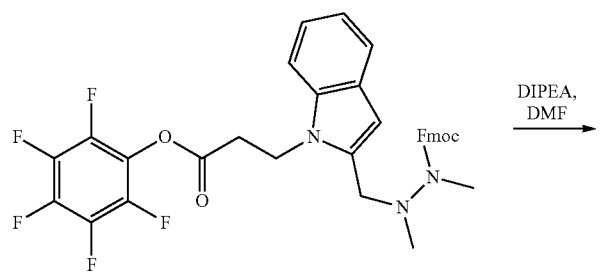
5
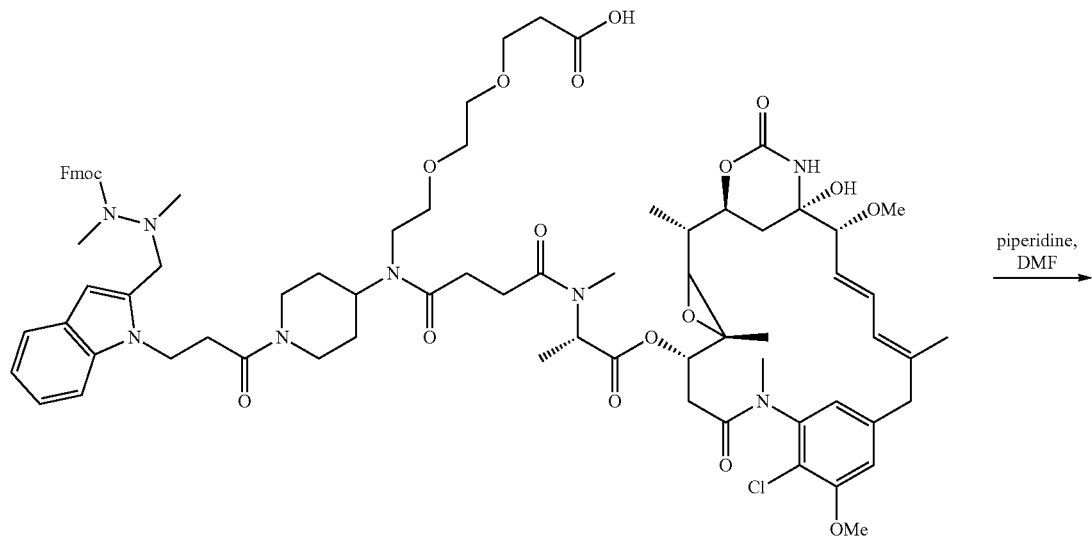
215

-continued

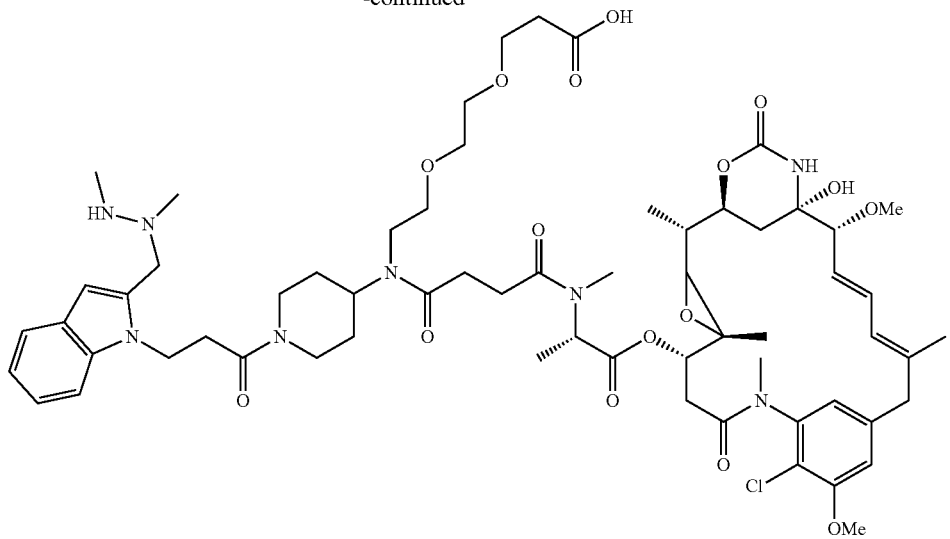

216

Synthesis of tert-butyl 4-oxopiperidine-1-carboxylate (210)

To a 100 mL round-bottom flask containing a magnetic stir bar was added piperidin-4-one hydrochloride monohydrate (1.53 g, 10 mmol), di-tert-butyl dicarbonate (2.39 g, 11 mmol), sodium carbonate (1.22 g, 11.5 mmol), dioxane (10 mL), and water (1 mL). The reaction mixture was stirred at room temperature for 1 h. The mixture was diluted with water (100 mL) and extracted with EtOAc (3×100 mL). The combined organic layers were washed with brine, dried over $Na_2SO_4$, filtered, and concentrated under reduced pressure. The resulting material was dried in vacuo to yield 1.74 g (87%) of compound 210 as a white solid.

$^1$H NMR ($CDCl_3$) δ 3.73 (t, 4H, J=6.0), 2.46 (t, 4H, J=6.0), 1.51 (s, 9H).

MS (ESI) m/z: [M+H]$^+$ Calcd for $C_{10}H_{18}NO_3$ 200.3; Found 200.2.

Synthesis of tert-butyl 4-((2-(2-(3-(tert-butoxy)-3-oxopropoxy)ethoxy)ethyl)amino)piperidine-1-carboxylate (211)

To a dried scintillation vial containing a magnetic stir bar was added tert-butyl 4-oxopiperidine-1-carboxylate (399 mg, 2 mmol), $H_2N$-$PEG_2$-COOt-Bu (550 mg, 2.4 mmol), 4 Å molecular sieves (activated powder, 200 mg), and 1,2-dichloroethane (5 mL). The mixture was stirred for 1 h at room temperature. To the reaction mixture was added sodium triacetoxyborohydride (845 mg, 4 mmol). The mixture was stirred for 3 days at room temperature. The resulting mixture was partitioned between EtOAc and saturated aqueous $NaHCO_3$. The organic layer was washed with brine, dried over $Na_2SO_4$, filtered, and concentrated under reduced pressure to afford 850 mg of compound 211 as a viscous oil.

MS (ESI) m/z: [M+H]$^+$ Calcd for $C_{21}H_{41}N_2O_6$ 417.3; Found 417.2.

Synthesis of 13-(1-(tert-butoxycarbonyl)piperidin-4-yl)-2,2-dimethyl-4,14-dioxo-3,7,10-trioxa-13-azaheptadecan-17-oic acid (212)

To a dried scintillation vial containing a magnetic stir bar was added tert-butyl 4-((2-(2-(3-(tert-butoxy)-3-oxo-propoxy)ethoxy)ethyl)amino)piperidine-1-carboxylate 211 (220 mg, 0.5 mmol), succinic anhydride (55 mg, 0.55 mmol), 4-(dimethylamino)pyridine (5 mg, 0.04 mmol), and dichloromethane (3 mL). The mixture was stirred for 24 h at room temperature. The reaction mixture was partially purified by flash chromatography (elute 50-100% EtOAc/hexanes) to yield 117 mg of compound 212 as a clear oil, which was carried forward without further characterization.

MS (ESI) m/z: [M+H]$^+$ Calcd for $C_{25}H_{45}N_2O_9$ 517.6; Found 517.5.

Synthesis of 17-(tert-butyl)1-((1$^4$S, 1$^6$S, 3$^3$S, 2R, 4S, 10E, 12E, 14R)-8$^6$-chloro-1$^4$-hydroxy-8$^5$,14-dimethoxy-3$^3$,2,7,10-tetramethyl-1$^2$,6-dioxo-7-aza-1 (6,4)-oxazinana-3(2,3)-oxirana-8(1,3)-benzenacyclo-tetradecaphane-10,12-dien-4-yl) (2S)-8-(1-(tert-butoxycarbonyl)piperidin-4-yl)-2,3-dimethyl-4,7-dioxo-11,14-dioxa-3,8-diazaheptadecanedioate (213)

To a dried scintillation vial containing a magnetic stir bar was added 13-(1-(tert-butoxycarbonyl)piperidin-4-yl)-2,2-dimethyl-4,14-dioxo-3,7,10-trioxa-13-azaheptadecan-17-oic acid 212 (55 mg, 0.1 mmol), N-deacyl maytansine 124 (65 mg, 0.1 mmol), HATU (43 mg, 0.11 mmol), DMF (1 mL), and dichloromethane (0.5 mL). The mixture was stirred for 8 h at room temperature. The reaction mixture was directly purified by C18 flash chromatography (elute 5-100% MeCN/water) to give 18 mg (16%) of compound 213 as a white film.

MS (ESI) m/z: [M+H]$^+$ Calcd for $C_{57}H_{87}ClN_5O_{17}$ 1148.6; Found 1148.7.

Synthesis of (2S)-1-(((1$^4$S, 1$^6$S, 3$^3$S, 2R, 4S, 10E, 12E, 14R)-8$^6$-chloro-1$^4$-hydroxy-8$^5$,14-dimethoxy-3$^3$,2,7,10-tetramethyl-1$^2$,6-dioxo-7-aza-1(6,4)-oxazinana-3(2,3)-oxirana-8(1,3)-benzenacyclotetrade-caphane-10,12-dien-4-yl)oxy)-2,3-dimethyl-1,4,7-trioxo-8-(piperidin-4-yl)-11,14-dioxa-3,8-diazaheptadecan-17-oic acid (214)

To a dried scintillation vial containing a magnetic stir bar was added maytansinoid 213 (31 mg, 0.027 mmol) and dichloromethane (1 mL). The solution was cooled to 0° C. and tin(IV) tetrachloride (1.0 M solution in dichloromethane, 0.3 mL, 0.3 mmol) was added. The reaction mixture was stirred for 1 h at 0° C. The reaction mixture was directly purified by C18 flash chromatography (elute 5-100% MeCN/water) to yield 16 mg (60%) of compound 214 as a white solid (16 mg, 60% yield).

MS (ESI) m/z: [M+H]$^+$ Calcd for $C_{48}H_{71}ClN_5O_{15}$ 992.5; Found 992.6.

Synthesis of (2S)-8-(1-(3-(2-((2-(((9H-fluoren-9-yl)methoxy)carbonyl)-1,2-dimethylhydrazinyl)methyl)-1H-indol-1-yl)propanoyl)piperidin-4-yl)-1-(((1$^4$S, 1$^6$S, 3$^3$S, 2R, 4S, 10E, 12E, 14R)-8$^6$-chloro-1$^4$-hydroxy-8$^5$,14-dimethoxy-3$^3$,2,7,10-tetramethyl-1$^2$, 6-dioxo-7-aza-1(6,4)-oxazinana-3(2,3)-oxirana-8(1,3)-benzenacyclotetradecaphane-10,12-dien-4-yl)oxy)-2,3-dimethyl-1,4,7-trioxo-11,14-dioxa-3,8-diazaheptadecan-17-oic acid (215)

To a dried scintillation vial containing a magnetic stir bar was added maytansinoid 214 (16 mg, 0.016 mmol), (9H-fluoren-9-yl)methyl 1,2-dimethyl-2-((1-(3-oxo-3-(perfluorophenoxy)propyl)-1H-indol-2-yl)methyl)hydrazine-1-carboxylate (5) (13 mg, 0.02 mmol), DIPEA (8 μL, 0.05 mmol), and DMF (1 mL). The solution was stirred for 18 h at room temperature. The reaction mixture was directly purified by C18 flash chromatography (elute 5-100% MeCN/water) to yield 18 mg (77%) of compound 215 as a white solid.

MS (ESI) m/z: [M+H]$^+$ Calcd for $C_{77}H_{98}ClN_5O_{18}$ 1457.7; Found 1457.9.

Synthesis of (2S)-1-(((1$^4$S, 1$^6$S, 3$^3$S, 2R, 4S, 10E, 12E, 14R)-8$^6$-chloro-1$^4$-hydroxy-8$^5$,14-dimethoxy-3$^3$,2,7,10-tetramethyl-1$^2$,6-dioxo-7-aza-1(6,4)-oxazinana-3(2,3)-oxirana-8(1,3)-benzenacyclotetradecaphane-10,12-dien-4-yl)oxy)-8-(1-(3-(2-((1,2-dimethylhydrazinyl)methyl)-1H-indol-1-yl)propanoyl)piperidin-4-yl)-2,3-dimethyl-1,4,7-trioxo-11,14-dioxa-3,8-diazaheptadecan-17-oic acid (216)

To a dried scintillation vial containing a magnetic stir bar was added maytansinoid 215 (18 mg, 0.012 mmol), piperidine (20 μL, 0.02 mmol), and DMF (1 mL). The solution was stirred for 20 minutes at room temperature. The reaction mixture was directly purified by C18 flash chromatography (elute 1-60% MeCN/water) to yield 15 mg (98%) of compound 216 (also referred to herein as HIPS-4AP-maytansine or HIPS-4-amino-piperidin-maytansine) as a white solid.

MS (ESI) m/z: [M+H]$^+$ Calcd for $C_{62}H_{88}ClN_5O_{16}$ 1235.6; Found 1236.0.

Example 3

Experimental Procedures

General

Experiments were performed to create site-specifically conjugated antibody-drug conjugates (ADCs). Site-specific ADC production included the incorporation of formylglycine (FGly), a non-natural amino acid, into the protein sequence. To install FGly (FIG. 1), a short consensus sequence, CXPXR (SEQ ID NO: 20), where X is serine, threonine, alanine, or glycine, was inserted at the desired location in the conserved regions of antibody heavy or light chains using standard molecular biology cloning techniques. This "tagged" construct was produced recombinantly in cells that coexpress the formylglycine-generating enzyme (FGE), which cotranslationally converted the cysteine within the tag into an FGly residue, generating an aldehyde functional group (also referred to herein as an aldehyde tag). The aldehyde functional group served as a chemical handle for bioorthogonal conjugation. A hydrazino-iso-Pictet-Spengler (HIPS) ligation was used to connect the payload (e.g., a drug, such as a cytotoxin (e.g., maytansine)) to FGly, resulting in the formation of a stable, covalent C—C bond between the cytotoxin payload and the antibody. This C—C bond was expected to be stable to physiologically-relevant conditions encountered by the ADC during circulation and FcRn recycling, e.g., proteases, low pH, and reducing reagents. Antibodies bearing the aldehyde tag may be produced at a variety of locations. Experiments were performed to test the effects of inserting the aldehyde tag at the heavy chain C-terminus (CT). Biophysical and functional characteriziaton was performed on the resulting ADCs made by conjugation to maytansine payloads via a HIPS linker.

Cloning, Expression, and Purification of Tagged Antibodies

The aldehyde tag sequence was inserted at the heavy chain C-terminus (CT) using standard molecular biology techniques. For small-scale production, CHO—S cells were transfected with human FGE expression constructs and pools of FGE-overexpressing cells were used for the transient production of antibodies. For larger-scale production, GPEx technology (Catalent, Inc., Somerset, NJ) was used to generate a clonal cell line overexpressing human FGE (GPEx). Then, the FGE clone was used to generate bulk stable pools of antibody-expressing cells. Antibodies were purified from the conditioned medium using a Protein A chromatography (MabSelect, GE Healthcare Life Sciences, Pittsburgh, PA). Purified antibodies were flash frozen and stored at −80° C. until further use.

Bioconjugation, Purification, and HPLC Analytics

C-terminally aldehyde-tagged αCD22 antibody (15 mg/mL) was conjugated to HIPS-4AP-maytansine (8 mol. equivalents drug:antibody) for 72 h at 37° C. in 50 mM sodium citrate, 50 mM NaCl pH 5.5 containing 0.85% DMA. Unconjugated antibody was removed using preparative-scale hydrophobic interaction chromatography (HIC; GE Healthcare 17-5195-01) with mobile phase A: 1.0 M ammonium sulfate, 25 mM sodium phosphate pH 7.0, and mobile phase B: 25% isopropanol, 18.75 mM sodium phosphate pH 7.0. An isocratic gradient of 33% B was used to elute unconjugated material, followed by a linear gradient of 41-95% B to elute mono- and diconjugated species. To determine the DAR of the final product, ADCs were examined by analytical HIC (Tosoh #14947, Grove City, OH) with mobile phase A: 1.5 M ammonium sulfate, 25 mM sodium phosphate pH 7.0, and mobile phase B: 25% isopropanol, 18.75 mM sodium phosphate pH 7.0. To determine aggregation, samples were analyzed using analytical size exclusion chromatography (SEC; Tosoh #08541) with a mobile phase of 300 mM NaCl, 25 mM sodium phosphate pH 6.8.

Results

αCD22 antibodies modified to contain the aldehyde tag at the heavy chain C-terminus (CT) were conjugated to a maytansine payload attached to a HIPS-4AP linker as described above. Upon completion of the conjugation reaction, the unconjugated antibody was removed by preparative HIC and remaining free drug was removed during buffer exchange by tangential flow filtration. The reactions were high yielding, with ≥84% conjugation efficiency and >70% total yield. The resulting ADCs had drug-to-antibody ratios (DARs) of 1.6-1.9 and were predominately monomeric.

FIGS. 2-5 show DARs from representative crude reactions and the purified ADCs as determined by HIC and reversed phase PLRP chromatography, and show the monomeric integrity as determined by SEC.

Figure 2:
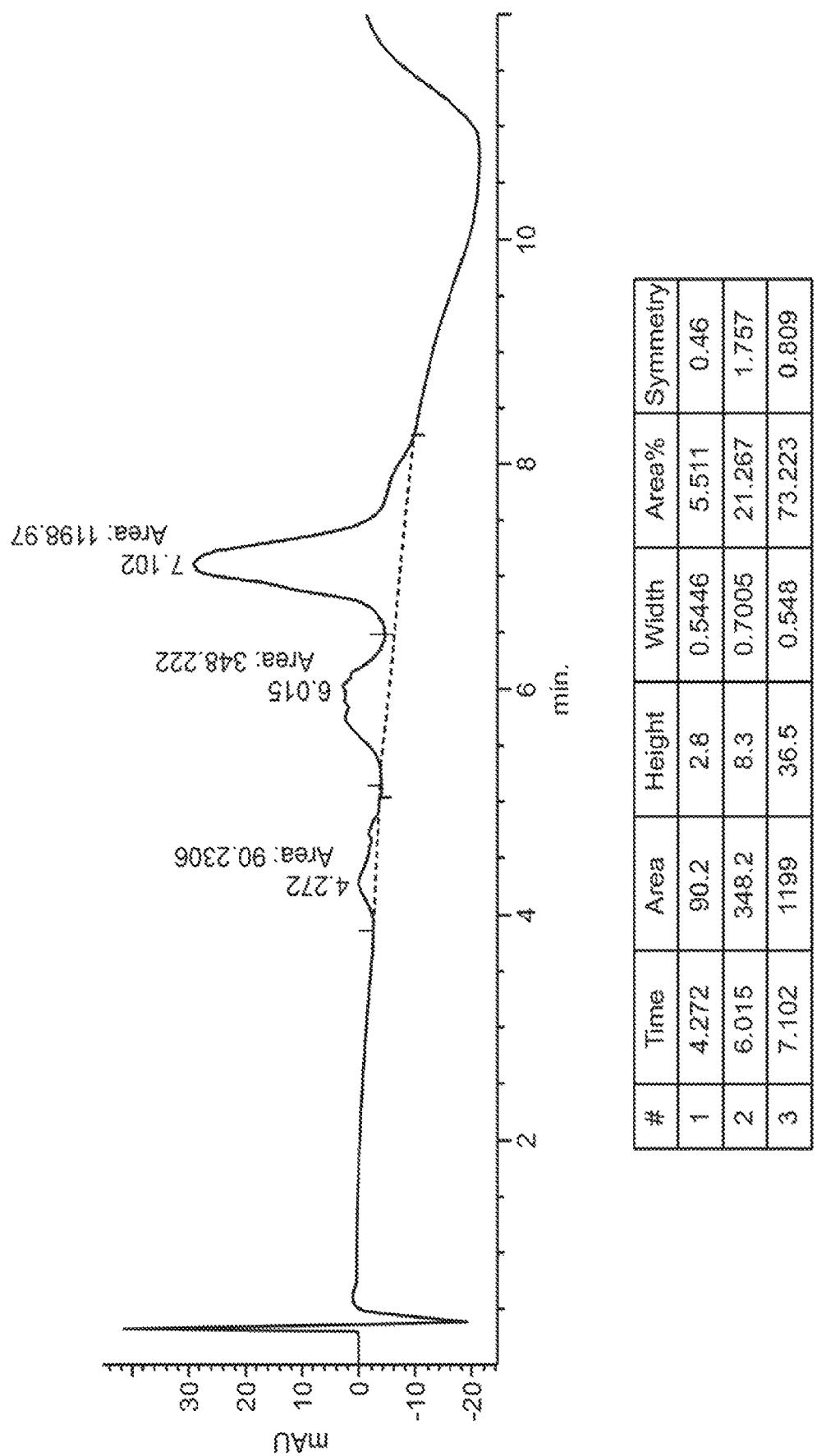
FIG. 2 shows a hydrophobic interaction column (HIC) trace of an aldehyde-tagged anti-CD22 antibody conjugated at the C-terminus (CT) to a maytansine payload attached to a HIPS-4AP linker, according to embodiments of the present disclosure.

FIG. 2 shows shows a hydrophobic interaction column (HIC) trace of an aldehyde-tagged anti-CD22 antibody conjugated at the C-terminus (CT) to a maytansine payload attached to a HIPS-4AP linker. FIG. 2 indicates that the crude DAR was 1.68 as determined by HIC.

Figure 3:
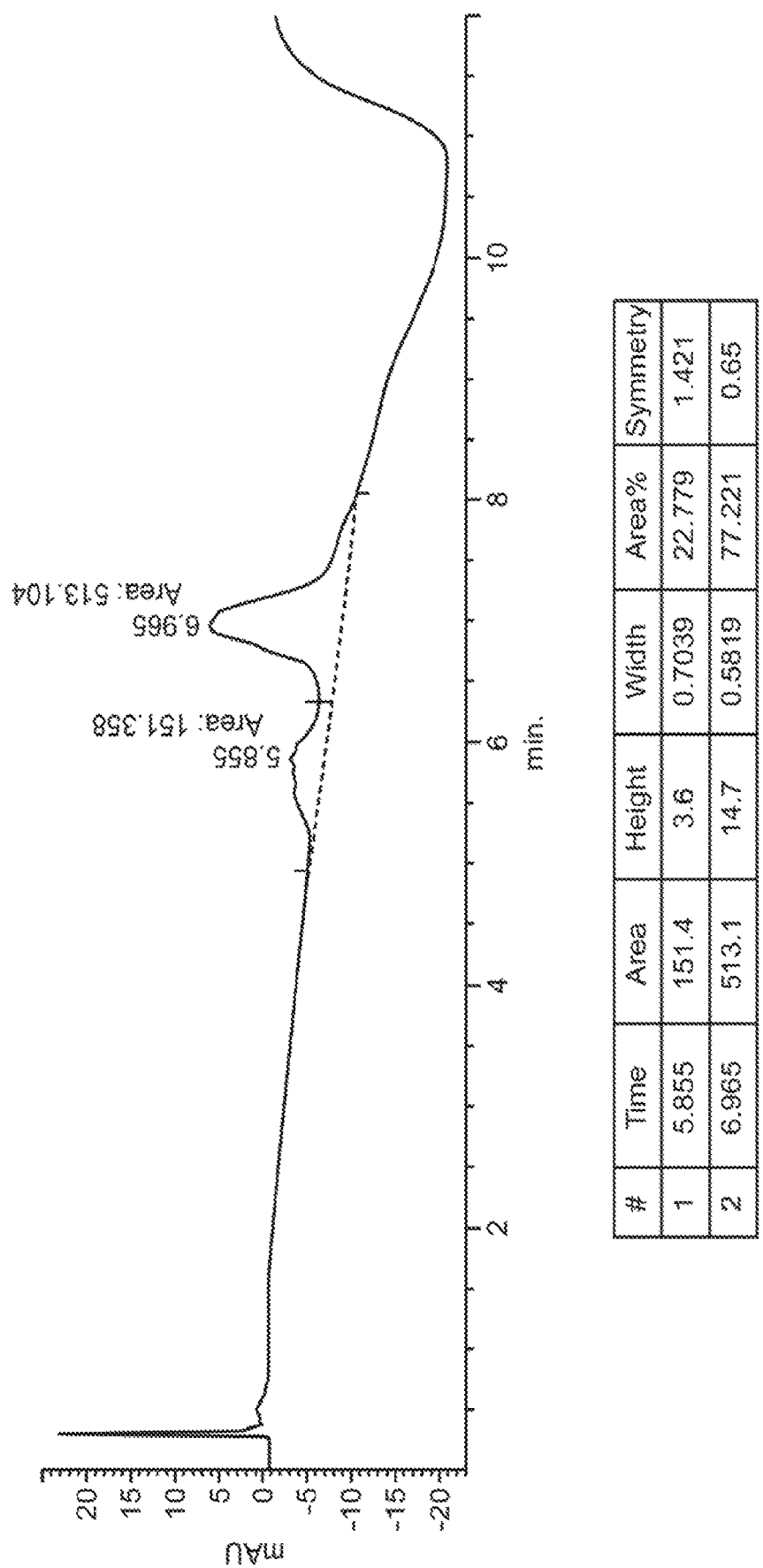
FIG. 3 shows a HIC trace of an aldehyde-tagged anti-CD22 antibody conjugated at the C-terminus (CT) to a maytansine payload attached to a HIPS-4AP linker, according to embodiments of the present disclosure.

FIG. 3 shows a HIC trace of an aldehyde-tagged anti-CD22 antibody conjugated at the C-terminus (CT) to a maytansine payload attached to a HIPS-4AP linker. FIG. 3 indicates that the final DAR was 1.77 as determined by HIC.

Figure 4:
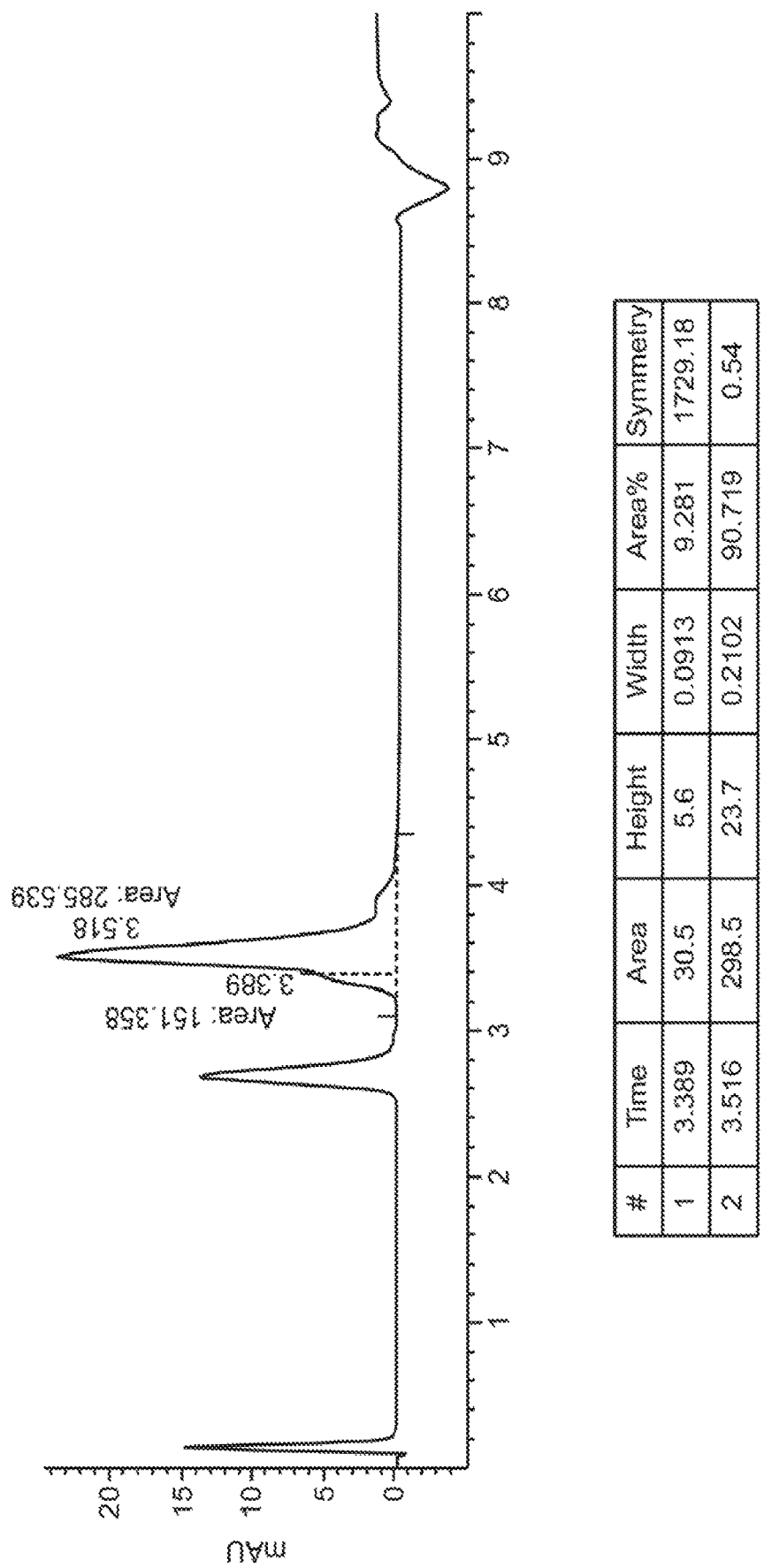
FIG. 4 shows a reversed phase chromatography (PLRP) trace of an aldehyde-tagged anti-CD22 antibody conjugated at the C-terminus (CT) to a maytansine payload attached to a HIPS-4AP linker, according to embodiments of the present disclosure.

FIG. 4 shows a reversed phase chromatography (PLRP) trace of an aldehyde-tagged anti-CD22 antibody conjugated at the C-terminus (CT) to a maytansine payload attached to a HIPS-4AP linker. FIG. 4 indicates that the final DAR was 1.81 as determined by PLRP.

Figure 5:
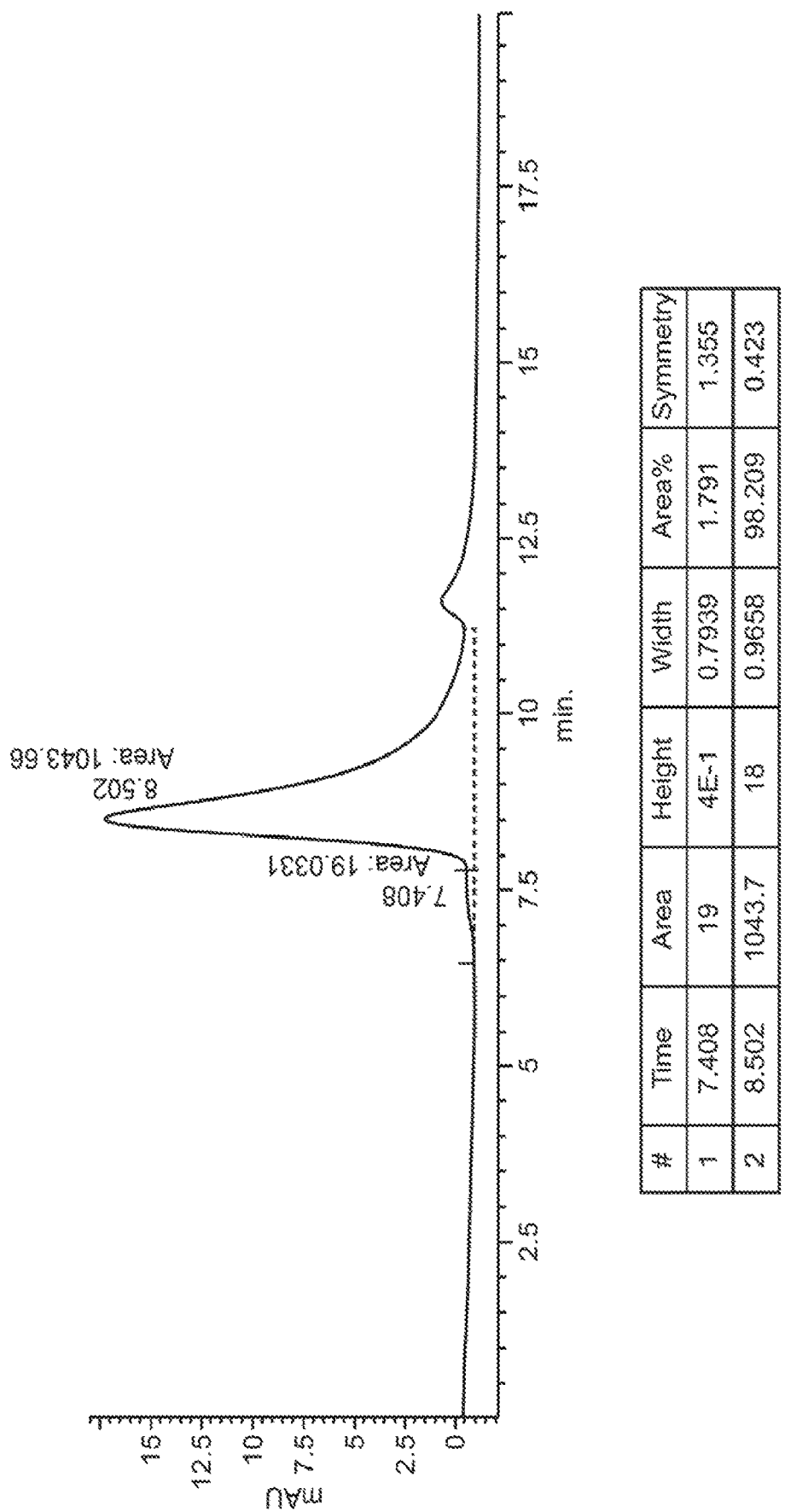
FIG. 5 shows a graph of analytical size exclusion chromatography (SEC) analysis of an aldehyde-tagged anti-CD22 antibody conjugated at the C-terminus (CT) to a maytansine payload attached to a HIPS-4AP linker, according to embodiments of the present disclosure.

FIG. 5 shows a graph of analytical size exclusion chromatography (SEC) analysis of an aldehyde-tagged anti-CD22 antibody conjugated at the C-terminus (CT) to a maytansine payload attached to a HIPS-4AP linker. As shown in FIG. 5, analytical SEC indicated 98.2% monomer for the final product.

In Vitro Cytotoxicity

The CD22-positive B-cell lymphoma cell lines, Ramos and WSU-DLCL2, were obtained from the ATCC and DSMZ cell banks, respectively. The cells were maintained in RPMI-1640 medium (Cellgro, Manassas, VA) supplemented with 10% fetal bovine serum (Invitrogen, Grand Island, NY) and Glutamax (Invitrogen). 24 h prior to plating, cells were passaged to ensure log-phase growth. On the day of plating, 5000 cells/well were seeded onto 96-well plates in 90 µL normal growth medium supplemented with 10 IU penicillin and 10 µg/mL streptomycin (Cellgro). Cells were treated at various concentrations with 10 µL of diluted analytes, and the plates were incubated at 37° C. in an atmosphere of 5% $CO_2$. After 5 d, 100 µL/well of Cell Titer-Glo reagent (Promega, Madison, WI) was added, and luminescence was measured using a Molecular Devices SpectraMax M5 plate reader. GraphPad Prism software was used for data analysis.

Results

αCD22 CT HIPS-4AP-maytansine exhibited very potent activity against WSU-DLCL2 and Ramos cells in vitro as compared to free maytansine (FIG. 6). The $IC_{50}$ concentrations were 0.018 and 0.086 nM for the ADC and the free drug, respectively, against WSU-DLCL2 cells, and were 0.007 and 0.040 nM for the ADC and the free drug, respectively, against Ramos cells.

Figure 6A:
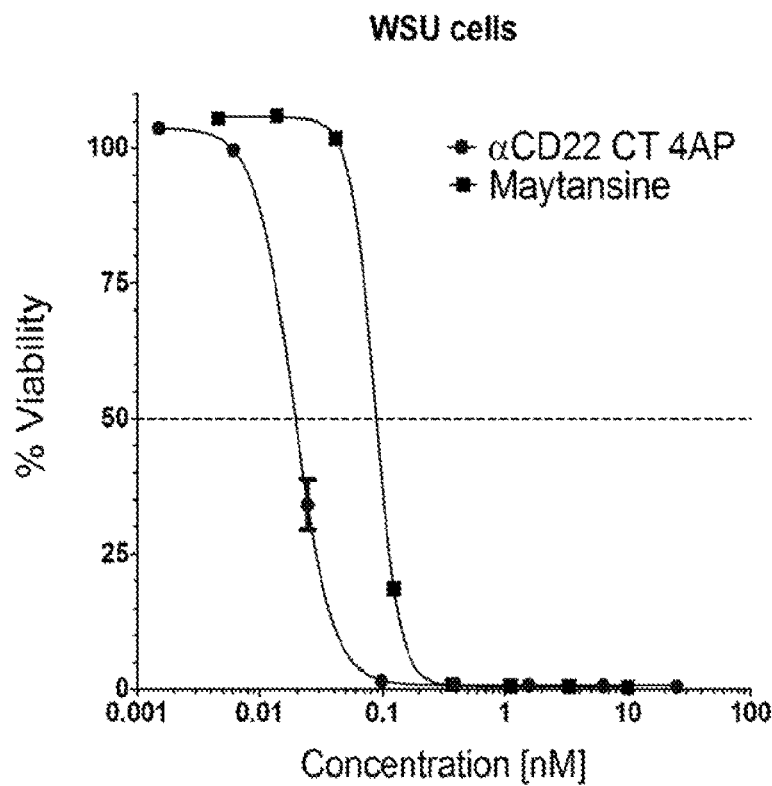
FIG. 6A shows a graph indicating the in vitro potency against WSU-DLCL2 cells (% viability vs. Log antibody-drug conjugate (ADC) concentration (nM)) for anti-CD22 ADCs conjugated at the C-terminus (CT) to a maytansine payload attached to a HIPS-4AP linker, according to embodiments of the present disclosure.
Figure 6B:
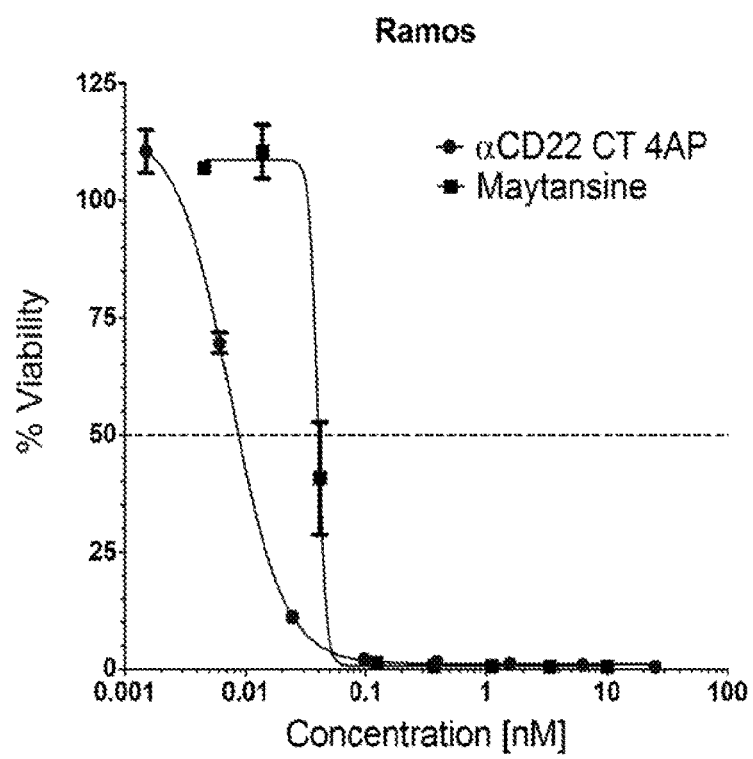
FIG. 6B shows a graph of in vitro potency against Ramos cells (% viability vs. Log antibody-drug conjugate (ADC) concentration (nM)) for anti-CD22 ADCs conjugated at the C-terminus (CT) to a maytansine payload attached to a HIPS-4AP linker, according to embodiments of the present disclosure.

FIG. 6A shows a graph of in vitro potency against WSU-DLCL2 cells (% viability vs. Log antibody-drug conjugate (ADC) concentration (nM)) for anti-CD22 ADCs conjugated at the C-terminus (CT) to a maytansine payload attached to a HIPS-4AP linker. FIG. 6B shows a graph of in vitro potency against Ramos cells (% viability vs. Log antibody-drug conjugate (ADC) concentration (nM)) for anti-CD22 ADCs conjugated at the C-terminus (CT) to a maytansine payload attached to a HIPS-4AP linker.

Xenograft Studies

Female ICR SCID mice (8/group) were inoculated subcutaneously with $5 \times 10^6$ WSU-DLCL2 cells. Treatment began when the tumors reached an average of 262 mm³, at which time the animals were dosed intravenously with vehicle alone or CT-tagged αCD22 HIPS-4AP-maytansine (10 mg/kg). Dosing proceeded every four days for a total of four doses (q4d×4). The animals were monitored twice weekly for body weight and tumor size. Animals were euthanized when tumors reached 2000 mm³.

Results

The median time to endpoint for animals in the vehicle control groups was 16 days; therefore, tumor growth inhibition (TGI %) was calculated at that day. TGI % was defined by the following formula:

$$TGI(\%) = (TV_{control\ group} - TV_{treated\ group})/TV_{control} \times 100$$

were TV is tumor volume.

Figure 7:
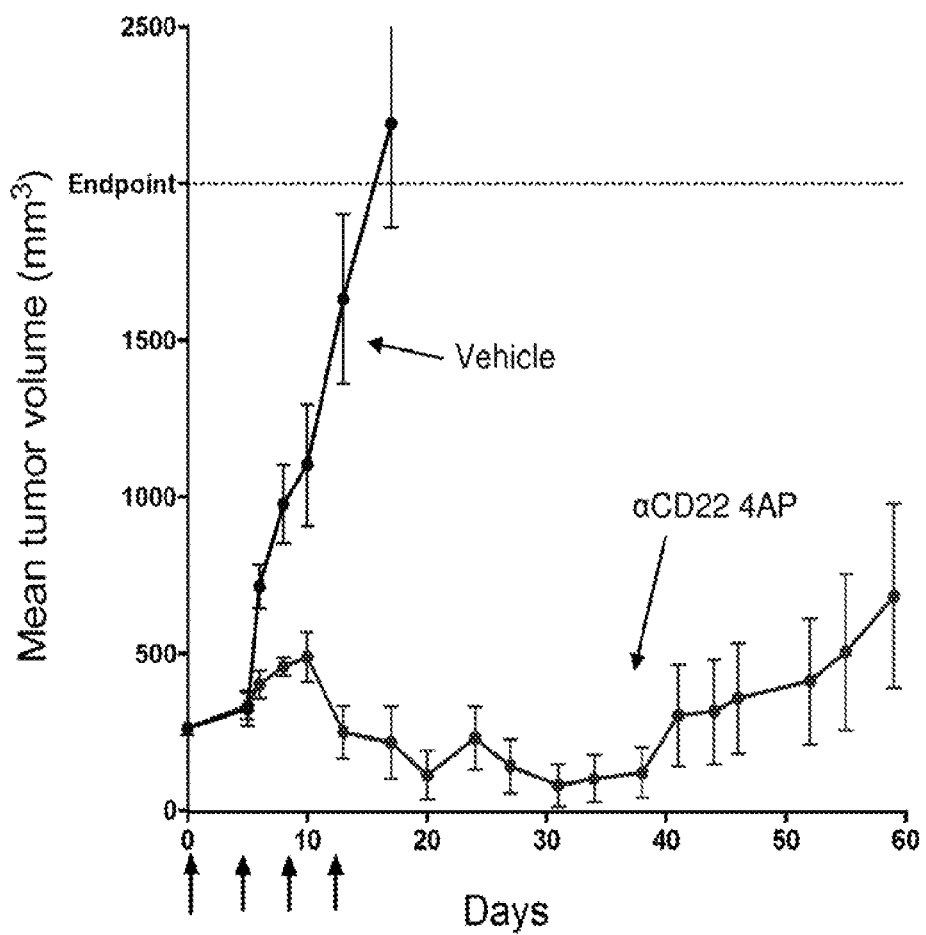
FIG. 7 shows a graph indicating the in vivo efficacy against a WSU-DLCL2 xenograft model (mean tumor volume ($mm^3$) vs. days) for anti-CD22 ADCs conjugated at the C-terminus (CT) to a maytansine payload attached to a HIPS-4AP linker, according to embodiments of the present disclosure.

The animals that were dosed with αCD22 HIPS-4AP-maytansine demonstrated 90% TGI at day 16, with 5 of the 8 tumors undergoing complete regression (FIG. 7). Three of these complete regressions were durable through the end of the study (day 58). FIG. 7 shows a graph indicating the in vivo efficacy against a WSU-DLCL2 xenograft model (mean tumor volume (mm³) vs. days) for anti-CD22 ADCs conjugated at the C-terminus (CT) to a maytansine payload attached to a HIPS-4AP linker. The vertical arrows in FIG. 7 indicate dosing, which occurred every four days for a total of four doses (q4d×4).

Example 4

Introduction

Hematologically-derived tumors make up ~10% of all newly-diagnosed cancer cases in the U.S. Of these, the non-Hodgkin lymphoma (NHL) designation describes a diverse group of cancers that collectively rank among the top 10 most commonly diagnosed cancers worldwide. Although long-term survival trends are improving, there remains a significant unmet clinical need for treatments to help patients with relapsed or refractory disease, one cause of which is drug efflux through upregulation of xenobiotic pumps, such as MDR1. A site-specifically-conjugated antibody-drug conjugate targeted against CD22 and bearing a noncleavable maytansine payload that was resistant to MDR1-mediated efflux was produced. The construct was efficacious against CD22+NHL xenografts and can be repeatedly dosed in cynomolgus monkeys at 60 mg/kg with no observed adverse effects. Together, the data indicated that this drug has the potential to be used effectively in patients with CD22+ tumors that have developed MDR1-related resistance to prior therapies. CD22 is a clinically-validated target for the treatment of NHL and ALL. An anti-CD22 antibody-drug conjugate (ADC) according to the present disclosure can be used for the treatment of relapsed/refractory NHL and ALL patients.

Material and Methods

An anti-CD22 antibody was conjugated site-specifically, using aldehyde tag technology, to a noncleavable maytansine payload. The ADC was characterized both biophysically and functionally in vitro. Then, in vivo efficacy was determined in mice using two xenograft models and toxicity studies were performed in both rat and cynomolgus monkeys. Pharmacodynamic studies were conducted in monkeys, and pharmaco- and toxicokinetic studies compared total ADC exposure in the efficacy and toxicity studies.

Results

The ADC was very potent in vivo, even against cell lines that had been constructed to overexpress the efflux pump, MDR1. The construct was efficacious at 10 mg/kg×4 doses against NHL xenograft tumor models, and in a cynomolgus toxicity study, the ADC was dosed twice at 60 mg/kg with no observed adverse effects. Exposure to total ADC at these doses (as assessed by $AUC_{0-inf}$) indicated that the exposure needed to achieve efficacy was below tolerable limits. Finally, an examination of the pharmacodynamic response in the treated monkeys demonstrated that the B-cell compartment was selectively depleted, indicating that the ADC eliminated targeted cells without notable off-target toxicity.

The results indicated that the ADC can be used effectively in patients with CD22+ tumors that have developed MDR1-related resistance to prior therapies.

Example 5

Introduction

Leukemias, lymphomas, and myelomas are highly prevalent in the population, accounting for ~10% of all newly diagnosed cancer cases in the U.S. during 2015. Of these cancers, B-cell derived malignancies make up a large and diverse group that includes non-Hodgkin lymphoma (NHL), chronic lymphocytic leukemia (CLL), and acute lymphoblastic leukemia (ALL). Similarly, as a category, NHL designates about 60 lymphoma subsets, of which about 85% are B-cell derived, including diffuse large B-cell lymphoma (DLBCL), follicular lymphoma (FL), and mantle cell lymphoma (MCL). Collectively, NHL diseases are among the most common cancer types observed, ranking as the $7^{th}$ most common cancer in the U.S., and the $10^{th}$ most common cancer diagnosed worldwide in 2012. While long-term trends show improvements in 5-year survival rates for most blood cancer diagnoses, there remains a significant unmet clinical need, with 16% of CLL, 30% of ALL, and 30% of NHL patients diagnosed from 2004 to 2010 failing to meet the 5-year survival endpoint.

CD22 is a B-cell lineage-restricted cell surface glycoprotein that is expressed on the majority of B-cell hematologic malignancies, but is not expressed on hematopoietic stem cells, memory B cells, or other normal non-hematopoietic tissues. Its expression pattern and rapid internalization kinetics make it a target for antibody-drug conjugate (ADC) therapies, and it has been validated as such in clinical trials against NHL and ALL.

In the experiments described herein, site-specific conjugation technology based upon the aldehyde tag and Hydrazino-iso-Pictet-Spengler (HIPS) chemistry was used to place a maytansine payload coupled through a noncleavable linker to the antibody heavy chain C-terminus. The genetically-encoded aldehyde tag incorporated the six amino acid sequence, LCTPSR (SEQ ID NO: 47). Cotranslationally, overexpressed formylglycine generating enzyme (FGE) converted the cysteine within the consensus sequence to a formylglycine residue, bearing an aldehyde functional group, which was reacted with a HIPS-linker-payload to generate an ADC. This approach afforded control over both payload placement and DAR, and yielded highly homogenous ADC preparations. Site-specifically conjugated ADCs displayed improved pharmacokinetics (PK) and efficacy relative to stochastic conjugates, likely due to the lack of under- and overconjugated species in the preparation, which can lead to ineffective or overly toxic molecules, respectively. Furthermore, the noncleavable linker-maytansine payload used on the anti-CD22 ADC was resistant to efflux by MDR1 and did not mediate off-target or bystander killing. Together, these features contributed to the efficacy and safety of the anti-CD22 ADC observed in preclinical studies.

Materials and Methods

General

All animal studies were conducted in accordance with Institutional Animal Care and Use Committee guidelines and were performed at Charles River Laboratories, Aragen Bioscience, or Covance Laboratories. The murine anti-maytansine antibody was made by ProMab and validated in-house. The rabbit anti-AF488 antibody was purchased from Life Technologies. The horseradish peroxidase (HRP)-conjugated secondary antibodies were from Jackson Immunoresearch. The antibodies used for pharmacodynamic studies were from BD Pharmingen. Cell lines were obtained from ATCC and DSMZ cell banks where they were authenticated by morphology, karyotyping, and PCR based approaches.

Cloning, Expression, and Purification of Tagged Antibodies

Antibodies were generated using standard cloning and purification techniques and GPEx® expression technology.

Bioconjugation, Purification, and HPLC Analytics

ADCs were made and characterized as described in Drake et al., *Bioconjugate Chem.*, 2014, 25, 1331-41.

Generation of MDR1+ Cell Lines

MDR1 (ABCB1) cDNA was obtained from Sino Biological and cloned into a pEF plasmid with a hygromycin selection marker. An AMAXA Nucleofector™ instrument was used to electroporate Ramos (ATCC CRL-1923) and WSU-DLCL2 (DSMZ ACC 575) cells according to the manufacturer's instructions. After selection with hygromycin (Invitrogen 10687010), the pools were enriched with paclitaxel treatment (25 nM for up to 10 days) to further select cells with functional MDR1. The resulting cells were maintained under hygromycin selection in RPMI (Gibco 21870-092) supplemented with 10% fetal bovine serum (FBS) and 1× GlutaMax (Gibco 35050-079).

In Vitro Cytotoxicity Assays

Cell lines were plated in 96-well plates (Costar 3610) at a density of $5 \times 10^4$ cells/well in 100 µL of growth media and allowed to rest for 5 h. Serial dilution of test samples was performed in RPMI at 6× the final concentration and 20 µL was added to the cells. After incubation at 37° C. with 5% $CO_2$ for 5 days, viability was measured using a Promega CellTiter 96® AQueous One Solution Cell Proliferation Assay (G3581) according to the manufacturer's instructions. $GI_{50}$ curves were calculated in GraphPad Prism using the ADC's drug-to-antibody ratio (DAR) value to normalize the dose to the payload concentration.

Xenograft Studies

Female CB17 ICR SCID mice were inoculated subcutaneously with either WSU-DLCL2 or Ramos cells in 50% Matrigel. Tumors were measured twice weekly and tumor volume was estimated according to the formula: tumor volume $$(mm^3) = \frac{w^2 \times l}{2}$$

where w=tumor width and l=tumor length. When tumors reached the desired mean volume, animals were randomized into groups of 8-12 mice and were dosed as described below. Animals were euthanized at the end of the study or when tumors reached 2000 mm$^3$.

Rat Toxicology Study and Toxicokinetic (TK) Analysis

Male Sprague-Dawley rats (8-9 wk old at study start) were given a single intravenous dose of 6, 20, 40, or 60 mg/kg of the anti-CD22 ADC (5 animals/group). Animals were observed for 12 days post-dose. Body weights were recorded on days 0, 1, 4, 8, and 11. Blood was collected from all animals at 8 h and at 5, 9, and 12 d and was used for toxicokinetic analyses (all time points) and for clinical chemistry and hematology analyses (days 5 and 12). Toxicokinetic analyses were performed by ELISA, using the same conditions and reagents as described for the pharmacokinetic analyses.

Non-Human Primate Toxicology and TK Studies

Cynomolgus monkeys (2/sex/group) were given two doses (every 21 days) of 10, 30, or 60 mg/kg of the anti-CD22 ADC followed by a 21 day observation period. Body weights were assessed prior to dosing on day 1, and on days 8, 15, 22 (predose), 29, 36, and 42. Blood was collected for toxicokinetic, clinical chemistry, and hematology analyses according to the schedules presented in Table 2. Toxicokinetic analyses were performed by ELISA, using the same conditions and reagents as described for the pharmacokinetic analyses, except that CD22-His protein was used as the capture reagent for the total antibody and total ADC measurements.

TABLE 2

Summary of pharmacokinetic findings in rats dosed at 3 mg/kg with anti-CD22 ADC

| Parameter, mean (SD) | Total Ab | Total ADC | Total Conjugate |
|---|---|---|---|
| $AUC_{0\text{-}inf}$ (day · µg/mL) | 304 (40) | 218 (18) | 261 (26) |
| Clearance (mL/day/kg) | 10.0 (1) | 13.8 (1) | 11.6 (1) |
| $C_{0.04d}$ | 73.2 (5) | 83.9 (16) | 76.8 (6) |
| $t_{1/2\ effective}$ (days)* | 9.48 (1) | 6.13 (0.6) | 7.22 (0.6) |
| $V_{SS}$ (mL/kg) | 41.1 (3) | 36.7 (7) | 39.2 (3) |

Total antibody measures conjugated and unconjugated Ab; Total ADC is a DAR-sensitive measurement; Total conjugate measures all analytes with DAR ≥ 1.
SD, standard deviation; $AUC_{0\text{-}inf}$, area under the concentration versus time curve from time 0 to infinity; $C_{0.04d}$, concentration observed at 1 h; $t_{1/2\ effective}$, Effective half-life; $V_{SS}$, volume of distribution at steady state.
*The uncertainty for half-life is given as standard error.

Non-Human Primate Pharmacodynamic Study

Whole blood samples from the cynomolgus monkeys enrolled in the anti-CD22 ADC toxicology study were analyzed by flow cytometry to assess CD3+, CD20+, and CD3−/CD20− leukocyte populations. Briefly, to a 100 µL aliquot of whole blood, either fluorescein and phycoerythrin-conjugated isotype control antibodies or fluorescein-conjugated anti-CD20 and phycoerythrin-conjugated anti-CD3 antibodies were added and incubated on ice for 30 min. Then, red blood cells were lysed with an ammonium chloride solution (Stem Cell Technologies), and cells were washed twice in phosphate buffered saline+1% FBS. Labeled cells were analyzed by flow cytometry on a FACSCanto™ instrument running FACSDiva™ software.

Pharmacokinetic (PK) Study Designs

For the mouse study, animals used in the Ramos xenograft experiment were sampled in groups of three at time points beginning at 1 h post-first dose and continuing across the observation period. For the rat study, male Sprague-Dawley rats (3 per group) were dosed intravenously with a single 3 mg/kg bolus of ADC. Plasma was collected at 1 h, 8 h and 24 h, and 2, 4, 6, 8, 10, 14, and 21 days post-dose. Plasma samples were stored at −80° C. until use.

PK and TK Sample Analysis

Figure 10:
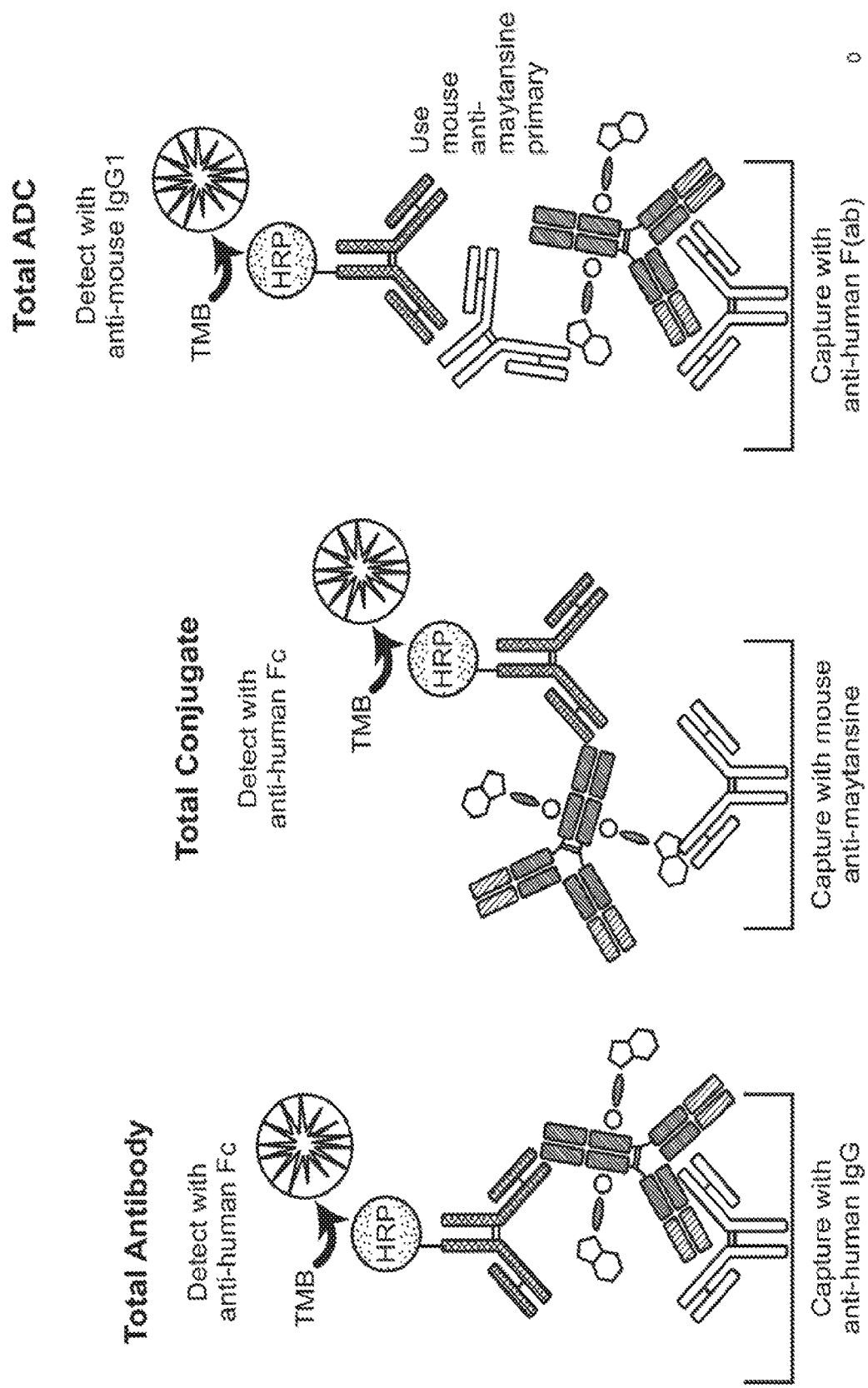
FIG. 10 shows illustrations of ELISA formats for detection of various analytes, according to embodiments of the present disclosure.

The concentrations of total antibody, total ADC (DAR-sensitive), and total conjugate (DAR 1) were quantified by ELISA as diagrammed in FIG. 10. For total antibody, conjugates were captured with an anti-human IgG-specific antibody and detected with an HRP-conjugated anti-human Fc-specific antibody. For total ADC, conjugates were captured with an anti-human Fab-specific antibody and detected with a mouse anti-maytansine primary antibody, followed by an HRP-conjugated anti-mouse IgG-subclass 1-specific secondary antibody. For total conjugate, conjugates were captured with an anti-maytansine antibody and detected with an HRP-conjugated anti-human Fc-specific antibody. Bound secondary antibody was detected using Ultra TMB One-Step ELISA substrate (Thermo Fisher). After quenching the reaction with sulfuric acid, signals were read by taking the absorbance at 450 nm on a Molecular Devices Spectra Max M5 plate reader equipped with SoftMax Pro software. Data were analyzed using GraphPad Prism and Microsoft Excel software.

Indirect ELISA CD22 Antigen Binding

Maxisorp 96-well plates (Nunc) were coated overnight at 4° C. with 1 µg/mL of human CD22-His (Sino Biological) in PBS. The plate was blocked with casein buffer (ThermoFisher), and then the anti-CD22 wild-type antibody and ADCs were plated in an 11-step series of 2-fold dilutions starting at 200 ng/mL. The plate was incubated, shaking, at room temperature for 2 h. After washing in phosphate-buffered saline (PBS) 0.1% Tween-20, bound analyte was detected with a donkey anti-human Fc-γ-specific horseradish peroxidase (RP)-conjugated secondary antibody. Signals were visualized with Ultra TMB (Pierce) and quenched with 2 N $H_2SO_4$. Absorbance at 450 nm was determined using a Molecular Devices SpectraMax M5 plate reader and the data were analyzed using GraphPad Prism.

Anti-CD22 ADC Mediated CD22 Internalization on CD22+ NHL Cell Lines

Ramos, Granta-519, and WSU-DLCL2 cells (1e6/test) were incubated either in labeling buffer alone [PBS+1% fetal bovine serum (FBS)], or in labeling buffer with the anti-CD22 ADC (1 µg/test). Samples were placed at 4 or 37° C. for 2 h. Then, cells were incubated on ice for 20 min with fluorescein-labeled anti-CD22. After washing 2× in labeling buffer, cells were analyzed by flow cytometry on a FACSCanto™ instrument running FACSDiva™ software. The difference in fluorescence between cells at 4 and 37° C.±ADC was interpreted as anti-CD22 ADC-mediated internalization.

Cynomolgus and Human Tissue Cross-Reactivity Studies

Tissue cross-reactivity studies were performed by Ensigna Biosystems Inc. (Richmond, CA) using biotinylated anti-CD22 ADC and a biotinylated HIPS-4AP-maytansine linker payload-conjugated isotype antibody as a control. Tissue microarrays containing skin, heart, lung, kidney, liver, pancreas, stomach, small intestine, large intestine, and spleen (a positive control) were used. Primary antibody was detected using streptavidin conjugated to horseradish peroxidase followed by visualization with DAB substrate.

Synthesis of HIPS-4AP-Maytansine Linker Payload

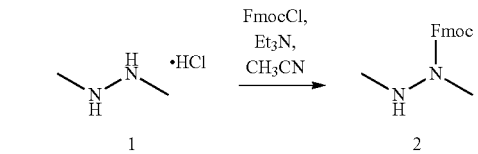

(9H-Fluoren-9-yl)methyl 1,2-dimethylhydrazine-1-carboxylate (2)

MeNHNIMe·2HCl (1) (5.0 g, 37.6 mmol) was dissolved in $CH_3CN$ (80 mL). $Et_3N$ (22 mL, 158 mmol) was added and the precipitate that formed was removed by filtration. To the remaining solution of MeNHNHMe, a solution of FmocCl (0.49 g, 18.9 mmol, 0.5 eq) was added dropwise over 2.5 h at −20° C. The reaction mixture was then diluted with EtOAc, washed with $H_2O$, brine, dried over $Na_2SO_4$, and concentrated in vacuo. The residue was purified by flash chromatography on silica (hexanes:EtOAc=3:2) to give 3.6 g (34%) of compound 2.

$^1H$ NMR (400 MHz, $CDCl_3$)δ7.75-7.37 (m, 8H), 4.48 (br s, 2H), 4.27 (t, J=6.0 Hz, 1H), 3.05 (s, 3H), 2.55 (br s, 3H).

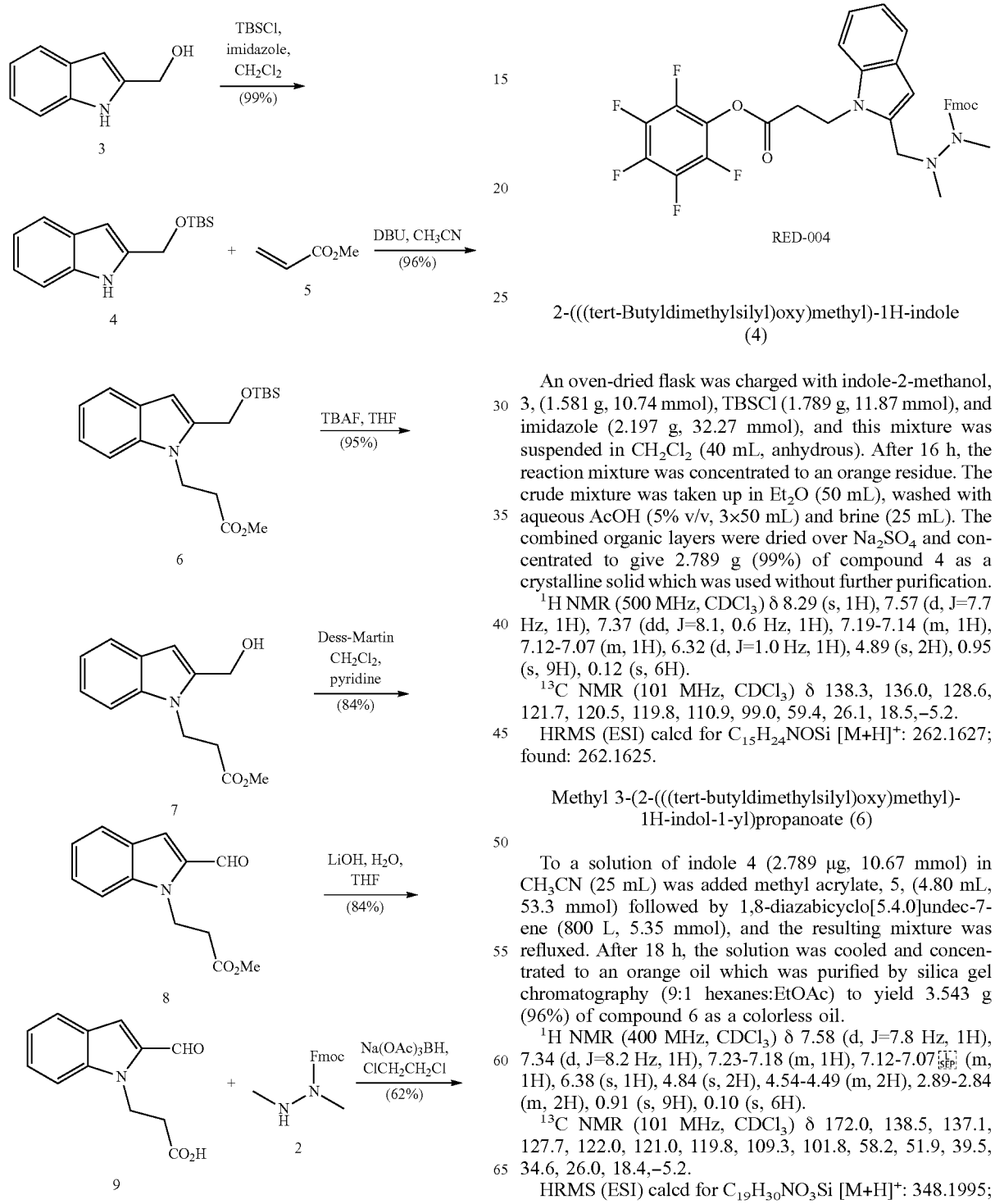

2-(((tert-Butyldimethylsilyl)oxy)methyl)-1H-indole (4)

An oven-dried flask was charged with indole-2-methanol, 3, (1.581 g, 10.74 mmol), TBSCl (1.789 g, 11.87 mmol), and imidazole (2.197 g, 32.27 mmol), and this mixture was suspended in $CH_2Cl_2$ (40 mL, anhydrous). After 16 h, the reaction mixture was concentrated to an orange residue. The crude mixture was taken up in $Et_2O$ (50 mL), washed with aqueous AcOH (5% v/v, 3×50 mL) and brine (25 mL). The combined organic layers were dried over $Na_2SO_4$ and concentrated to give 2.789 g (99%) of compound 4 as a crystalline solid which was used without further purification.

$^1H$ NMR (500 MHz, $CDCl_3$) δ 8.29 (s, 1H), 7.57 (d, J=7.7 Hz, 1H), 7.37 (dd, J=8.1, 0.6 Hz, 1H), 7.19-7.14 (m, 1H), 7.12-7.07 (m, 1H), 6.32 (d, J=1.0 Hz, 1H), 4.89 (s, 2H), 0.95 (s, 9H), 0.12 (s, 6H).

$^{13}C$ NMR (101 MHz, $CDCl_3$) δ 138.3, 136.0, 128.6, 121.7, 120.5, 119.8, 110.9, 99.0, 59.4, 26.1, 18.5,−5.2.

HRMS (ESI) calcd for $C_{15}H_{24}NOSi$ $[M+H]^+$: 262.1627; found: 262.1625.

Methyl 3-(2-(((tert-butyldimethylsilyl)oxy)methyl)-1H-indol-1-yl)propanoate (6)

To a solution of indole 4 (2.789 μg, 10.67 mmol) in $CH_3CN$ (25 mL) was added methyl acrylate, 5, (4.80 mL, 53.3 mmol) followed by 1,8-diazabicyclo[5.4.0]undec-7-ene (800 L, 5.35 mmol), and the resulting mixture was refluxed. After 18 h, the solution was cooled and concentrated to an orange oil which was purified by silica gel chromatography (9:1 hexanes:EtOAc) to yield 3.543 g (96%) of compound 6 as a colorless oil.

$^1H$ NMR (400 MHz, $CDCl_3$) δ 7.58 (d, J=7.8 Hz, 1H), 7.34 (d, J=8.2 Hz, 1H), 7.23-7.18 (m, 1H), 7.12-7.07 (m, 1H), 6.38 (s, 1H), 4.84 (s, 2H), 4.54-4.49 (m, 2H), 2.89-2.84 (m, 2H), 0.91 (s, 9H), 0.10 (s, 6H).

$^{13}C$ NMR (101 MHz, $CDCl_3$) δ 172.0, 138.5, 137.1, 127.7, 122.0, 121.0, 119.8, 109.3, 101.8, 58.2, 51.9, 39.5, 34.6, 26.0, 18.4,−5.2.

HRMS (ESI) calcd for $C_{19}H_{30}NO_3Si$ $[M+H]^+$: 348.1995; found: 348.1996.

Methyl 3-(2-(hydroxymethyl)-1H-indol-1-yl)propanoate (7)

To a solution of compound 6 (1.283 g, 3.692 mmol) in THF (20 mL) at 0° C. was added a 1.0 M solution of tetrabutylammonium fluoride in THF (3.90 mL, 3.90 mmol). After 15 minutes, the reaction mixture was diluted with Et$_2$O (20 mL) and washed with NaHCO$_3$ (sat. aq., 3×20 mL), and concentrated to a pale green oil. The oil was purified by silica gel chromatography (2:1 hexanes:EtOAc) to yield 822 mg (95%) of 7 as a white crystalline solid.

$^1$H NMR (500 MHz, CDCl$_3$) δ 7.60 (d, J=7.8 Hz, 1H), 7.34 (dd, J=8.2, 0.4 Hz, 1H), 7.27-7.23 (m, 1H), 7.16-7.11 (m, 1H), 6.44 (s, 1H), 4.77 (s, 2H), 4.49 (t, J=7.3 Hz, 2H), 3.66 (s, 3H), 2.87 (t, J=7.3 Hz, 2H), 2.64 (s, 1H).

$^{13}$C NMR (126 MHz, CDCl$_3$) δ 172.3, 138.5, 137.0, 127.6, 122.2, 121.1, 119.9, 109.3, 102.3, 57.1, 52.0, 39.1, 34.3.

HRMS (ESI) calcd for C$_{13}$H$_{15}$NNaO$_3$ [M+Na]$^+$: 256.0950; found: 256.0946.

Methyl 3-(2-formyl-1H-indol-1-yl)propanoate (8)

Dess-Martin periodinane (5.195 g, 12.25 mmol) was suspended in a mixture of CH$_2$Cl$_2$ (20 mL) and pyridine (2.70 mL, 33.5 mmol). After 5 min, the resulting white suspension was transferred to a solution of methyl 3-(2-(hydroxymethyl)-1H-indol-1-yl)propanoate (7; 2.611 g, 11.19 mmol) in CH$_2$Cl$_2$ (10 mL), resulting in a red-brown susupension. After 1 h, the reaction was quenched with sodium thiosulfate (10% aqueous solution, 5 mL) and NaHCO$_3$ (saturated aqueous solution, 5 mL). The aqueous layer was extracted with CH$_2$Cl$_2$ (3×20 mL); the combined extracts were dried over Na$_2$SO$_4$, filtered, and concentrated to a brown oil. Purification by silica gel chromatography (5-50% EtOAc in hexanes) yielded 2.165 g (84%) of compound 8 as a colorless oil.

$^1$H NMR (400 MHz, CDCl$_3$) δ 9.87 (s, 1H), 7.73 (dt, J=8.1, 1.0 Hz, 1H), 7.51 (dd, J=8.6, 0.9 Hz, 1H), 7.45-7.40 (m, 1H), 7.29 (d, J=0.9 Hz, 1H), 7.18 (ddd, J=8.0, 6.9, 1.0 Hz, 1H), 4.84 (t, J=7.2 Hz, 2H), 3.62 (s, 3H), 2.83 (t, J=7.2 Hz, 2H).

$^{13}$C NMR (101 MHz, CDCl$_3$) δ 182.52, 171.75, 140.12, 135.10, 127.20, 126.39, 123.46, 121.18, 118.55, 110.62, 51.83, 40.56, 34.97.

HRMS (ESI) calcd for C$_{13}$H$_{13}$NO$_3$Na [M+Na]$^+$: 254.0793; found: 254.0786.

3-(2-Formyl-1H-indol-1-yl)propanoic acid (9)

To a solution of indole 8 (2.369 g, 10.24 mmol) dissolved in dioxane (100 mL) was added LiOH (4 M aqueous solution, 7.68 mL, 30.73 mmol). A thick white precipitate gradually formed over the course of several hours. After 21 h, HCl (1 M aqueous solution, 30 mL) was added dropwise to give a solution with pH=4. The solution was concentrated and the resulting pale brown oil was dissolved in EtOAc (50 mL) and washed with water (2×50 mL) and brine (20 mL). The organic layer was dried over Na$_2$SO$_4$, filtered, and concentrated to an orange solid. Purification by silica gel chromatography (10-50% EtOAc in hexanes with 0.1% acetic acid) yielded 1.994 g (84%) of compound 9 as a pale yellow solid.

$^1$H NMR (400 MHz, CDCl$_3$) δ 9.89 (s, 1H), 7.76 (dt, J=8.1, 0.9 Hz, 1H), 7.53 (dd, J=8.6, 0.9 Hz, 1H), 7.48-7.43 (m, 1H), 7.33 (d, J=0.8 Hz, 1H), 7.21 (ddd, J=8.0, 6.9, 1.0 Hz, 1H), 4.85 (t, J=7.2 Hz, 2H), 2.91 (t, J=7.2 Hz, 2H).

$^{13}$C NMR (101 MHz, CDCl$_3$) δ 182.65, 176.96, 140.12, 135.02, 127.33, 126.42, 123.53, 121.27, 118.76, 110.55, 40.19, 34.82.

HRMS (ESI) calcd for C$_{12}$H$_{10}$NO$_3$ [M–H]$^-$: 216.0666; found: 216.0665.

3-(2-((2-(((9H-Fluoren-9-yl)methoxy)carbonyl)-1,2-dimethylhydrazinyl)methyl)-1H-indol-1-yl)propanoic acid (10)

To a solution of compound 9 (1.193 g, 5.492 mmol) and (9H-fluoren-9-yl)methyl 1,2-dimethylhydrazinecarboxylate, 2, (2.147 g, 7.604 mmol) in 1,2-dichloroethane (anhydrous, 25 mL) was added sodium triacetoxyborohydride (1.273 g, 6.006 mmol). The resulting yellow suspension was stirred for 2 h and then quenched with NaHCO$_3$ (saturated aqueous solution, 10 mL), followed by addition of HCl (1 M aqueous solution) to pH 4. The organic layer was separated, and the aqueous layer was extracted with CH$_2$Cl$_2$ (5×10 mL). The pooled organic extracts were dried over Na$_2$SO$_4$, filtered, and concentrated to an orange oil. Purification by C18 silica gel chromatography (20-90% CH$_3$CN in water) yielded 1.656 g (62%) of compound 10 as a waxy pink solid.

$^1$H NMR (400 MHz, CDCl$_3$) δ 7.76 (d, J=7.4 Hz, 2H), 7.70-7.47 (br m, 3H), 7.42-7.16 (br m, 6H), 7.12-7.05 (m, 1H), 6.37 (s, 0.6H), 6.05 (s, 0.4H), 4.75-4.30 (br m, 4H), 4.23 (m, 1H), 4.10 (br s, 1H), 3.55 (br d, 1H), 3.11-2.69 (m, 5H), 2.57 (br s, 2H), 2.09 (br s, 1H).

$^{13}$C NMR (101 MHz, CDCl$_3$) δ 174.90, 155.65, 143.81, 141.42, 136.98, 134.64, 127.75, 127.48, 127.12, 124.92, 122.00, 120.73, 120.01, 119.75, 109.19, 103.74, 67.33, 66.80, 51.39, 47.30, 39.58, 39.32, 35.23, 32.10.

HRMS (ESI) calcd for C$_{29}$H$_{30}$N$_3$O$_4$ [M+H]$^+$: 484.2236; found: 484.2222.

(9H-Fluoren-9-yl)methyl 1,2-dimethyl-2-((1-(3-oxo-3-(perfluorophenoxy)propyl)-1H-indol-2-yl)methyl)hydrazine-1-carboxylate (RED-004)

Compound 10 (5.006 g, 10.4 mmol), was added to a dried 100 mL 2-neck round bottom flask containing a dried stir bar. Anhydrous EtOAc, 40 mL, was added by syringe and the solution stirred at 20° C. for 5 min. giving a clear, pale, yellow-green solution. The solution was cooled to 0° C. in an ice water bath and pentafluorophenol (2098.8 mg, 11.4 mmol), in 3 mL of anhydrous EtOAc, was added dropwise. The solution was stirred at 0° C. for 5 min. DCC (2348.0 mg, 11.4 mmol), in 7 mL of anhydrous EtOAc, was added dropwise, slowly by syringe. The solution was stirred at 0° C. for 5 min, then removed from the bath and warmed to 20° C. The reaction was stirred for 2 h, cooled to 0° C., and filtered to give a clear, pale, yellow-green solution. The solution was diluted with 50 mL of EtOAc, and washed with 2×25 mL H$_2$O, 1×25 mL 5 M NaCl, and dried over Na$_2$SO$_4$. The solution was filtered, evaporated, and dried under high vacuum, giving 6552.5 mg (97%) of RED-004 as a greenish-white solid.

$^1$H NMR (400 MHz, CDCl$_3$) δ 780 (d, J=7.2 Hz, 2H), 7.58 (m, 3H), 7.45-7.22 (m, 6H), 7.14 (dd(appt. t), J=7.4 Hz, 1H), 6.42 & 6.10 (2 br s, 1H), 4.74 (dd(appt. t), J=5.4 Hz, 2H), 3.65-3.18 (br, 3H), 3.08 & 2.65 (2 br s, 3H), 2.88 (s, 3H).

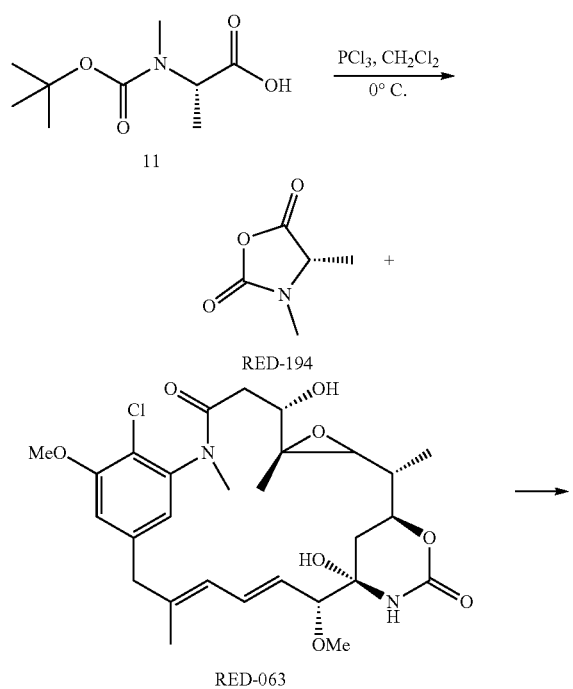

(S)-3,4-dimethyloxazolidine-2,5-dione (RED-194)

To a solution of N-Boc-Ala-OH (11) (0.005 mol) in methylene chloride (25 ml) at 0° C., was added under nitrogen 1.2 equivalent of phosphorous trichloride. The reaction mixture was stirred for 2 h at 0° C., the solvent was removed under reduced pressure and the residue was washed with carbon tetrachloride (3×20 ml) to afford RED-194.

($1^4$S, $1^6$S, $3^2$R, $3^3$R, 2R, 4S, 10E, 12E, 14R)-$8^6$-chloro-$1^4$-hydroxy-$8^5$,14-dimethoxy-$3^3$,2,7,10-tetramethyl-$1^2$,6-dioxo-7-aza-1(6,4)-oxazinana-3(2,3)-oxirana-8(1,3)-benzenacyclotetradecaphane-10,12-dien-4-yl methyl-L-alaninate (RED-062)

Maytansinol (RED-063) (4.53 g, 8 mmol) was dissolved in anhydrous DMF (11 mL) to give a clear, colorless solution that was transferred to a dried two neck round bottom flask under $N_2$. Anhydrous THF (44 mL) was added followed by DIPEA (8.4 mL, 48 mmol). A solution of RED-194 (5.4 g, 42 mmol) was added to give a clear, colorless solution. Dessicated, finely ground Zn(OTf)$_2$ (8.7 g, 24 mmol) was added to the stirring solution and the reaction mixture was stirred at 20° C. for 2 days. The reaction was quenched by adding to a solution of 70 mL of 1.2 M NaHCO$_3$ and 70 mL EtOAc. Upon stirring the resulting mixture produced a white precipitate that was removed by filtration. The filtrate was extracted with EtOAc (5×70 mL), dried (Na$_2$SO$_4$) and concentrated to give a reddish orange oil. This was dissolved in CH$_2$Cl$_2$ (15 mL) and purified using a Biotage system (adsorbed on 2×Biotage Ultra 10 g samplets, purification on 2× Biotage Ultra 100 g cartridge with 0-20% gradient of MeOH in CH$_2$Cl$_2$) to produce 4.38 g of the RED-062 as a pale peach solid (95% de, 93.7% desired diastereomer).

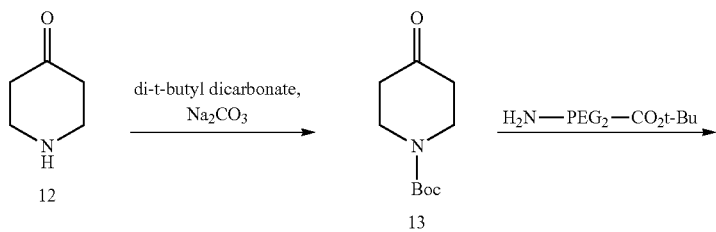

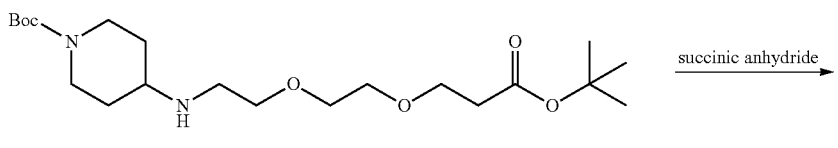

-continued
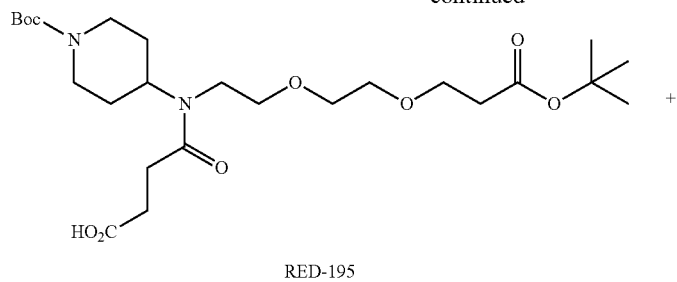
RED-195
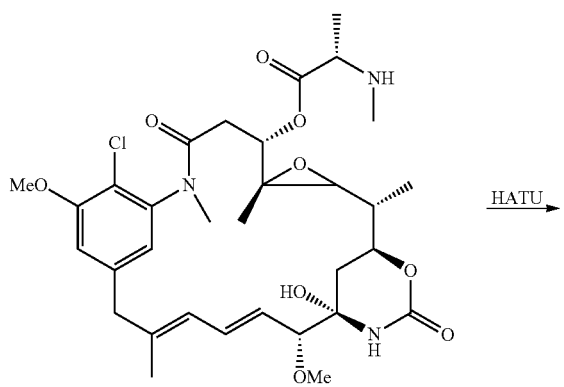
RED-062
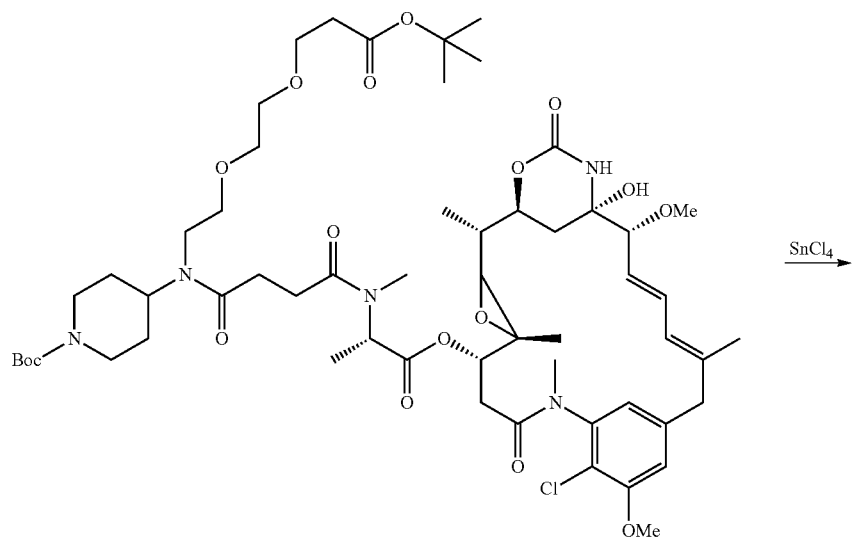
RED-196

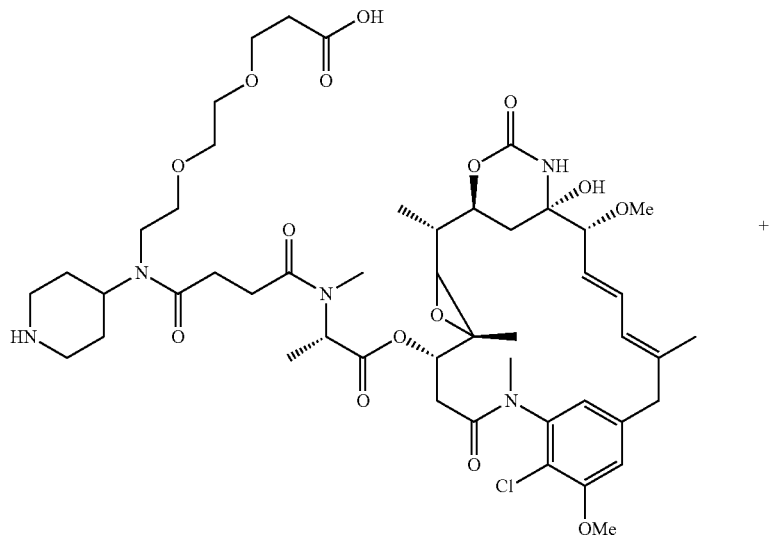
RED-197
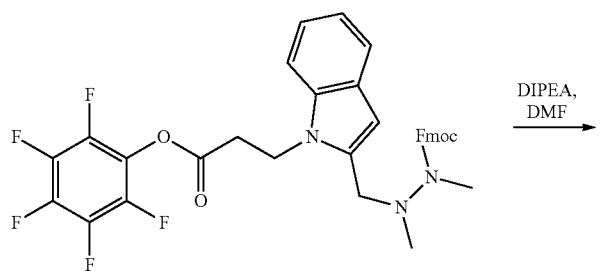
RED-004
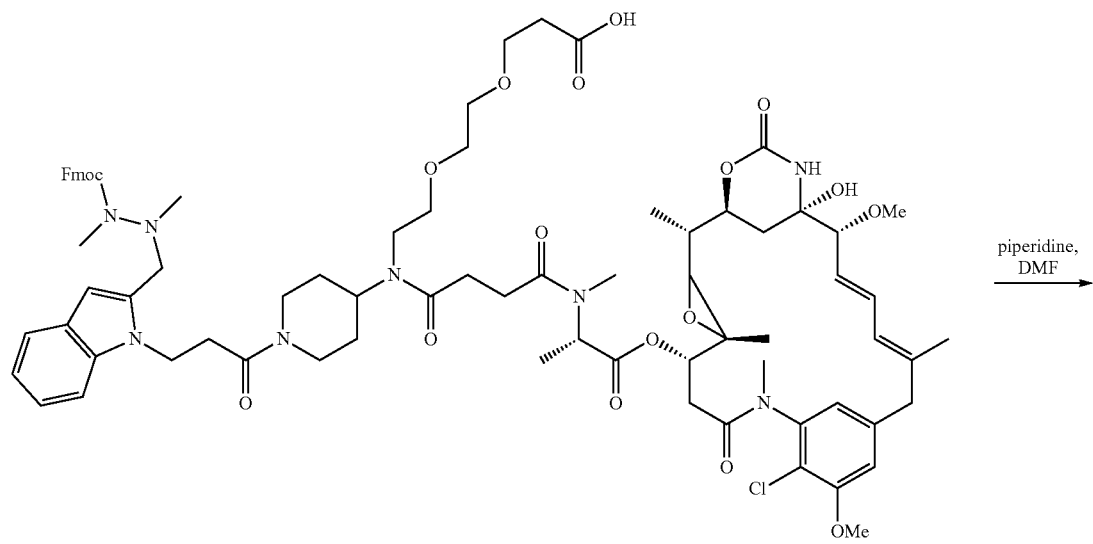
RED-198

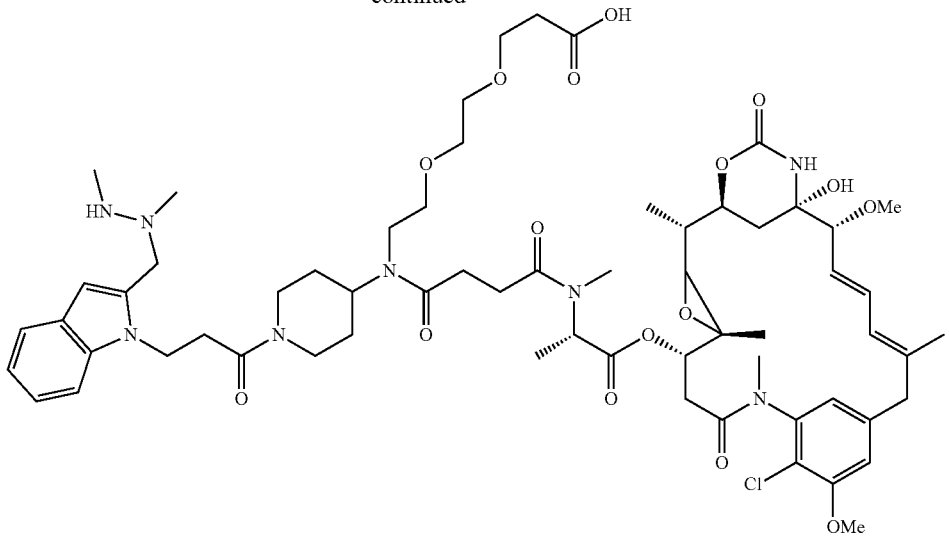

RED-106 tert-butyl 4-oxopiperidine-1-carboxylate (13)

To a 100 mL round-bottom flask containing a magnetic stir bar was added piperidin-4-one hydrochloride monohydrate (12) (1.53 g, 10 mmol), di-tert-butyl dicarbonate (2.39 g, 11 mmol), sodium carbonate (1.22 g, 11.5 mmol), dioxane (10 mL), and water (1 mL). The reaction mixture was stirred at room temperature for 1 h. The mixture was diluted with water (100 mL) and extracted with EtOAc (3×100 mL). The combined organic layers were washed with brine, dried over $Na_2SO_4$, filtered, and concentrated under reduced pressure. The resulting material was dried in vacuo to yield 1.74 g (87%) of compound 13 as a white solid.

$^1$H NMR ($CDCl_3$) δ 3.73 (t, 4H, J=6.0), 2.46 (t, 4H, J=6.0), 1.51 (s, 9H).

MS (ESI) m/z: [M+H]$^+$ Calcd for $C_{10}H_{18}NO_3$ 200.3; Found 200.2.

tert-butyl 4-((2-(2-(3-(tert-butoxy)-3-oxopropoxy)ethoxy)ethyl)amino)piperidine-1-carboxylate (14)

To a dried scintillation vial containing a magnetic stir bar was added compound 13 (399 mg, 2 mmol), $H_2N$-$PEG_2$-COOt-Bu (550 mg, 2.4 mmol), 4 Å molecular sieves (activated powder, 200 mg), and 1,2-dichloroethane (5 mL). The mixture was stirred for 1 h at room temperature. To the reaction mixture was added sodium triacetoxyborohydride (845 mg, 4 mmol). The mixture was stirred for 3 days at room temperature. The resulting mixture was partitioned between EtOAc and saturated aqueous $NaHCO_3$. The organic layer was washed with brine, dried over $Na_2SO_4$, filtered, and concentrated under reduced pressure to afford 850 mg of compound 14 as a viscous oil.

MS (ESI) m/z: [M+H]$^+$ Calcd for $C_{21}H_{41}N_2O_6$ 417.3; Found 417.2.

13-(1-(tert-butoxycarbonyl)piperidin-4-yl)-2,2-dimethyl-4,14-dioxo-3,7,10-trioxa-13-azaheptadecan-17-oic acid (RED-195)

To a dried scintillation vial containing a magnetic stir bar was added compound 14 (220 mg, 0.5 mmol), succinic anhydride (55 mg, 0.55 mmol), 4-(dimethylamino)pyridine (5 mg, 0.04 mmol), and dichloromethane (3 mL). The mixture was stirred for 24 h at room temperature. The reaction mixture was partially purified by flash chromatography (elute 50-100% EtOAc/hexanes) to yield 117 mg of compound RED-195 as a clear oil, which was carried forward without further characterization.

MS (ESI) m/z: [M+H]$^+$ Calcd for $C_{25}H_{45}N_2O_9$ 517.6; Found 517.5.

17-(tert-butyl) 1-((1$^4$S, 1$^6$S, 3$^3$S, 2R, 4S, 10E, 12E, 14R)-8$^6$-chloro-1$^4$-hydroxy-8$^5$,14-dimethoxy-33,2,7,10-tetramethyl-1$^2$,6-dioxo-7-aza-1(6,4)-oxazinana-3(2,3)-oxirana-8(1,3)-benzenacyclotetradecaphane-10,12-dien-4-yl) (2S)-8-(1-(tert-butoxycarbonyl)piperidin-4-yl)-2,3-dimethyl-4,7-dioxo-11,14-dioxa-3,8-diazaheptadecanedioate (RED-196)

To a dried scintillation vial containing a magnetic stir bar was added RED-195 (445 mg, 0.86 mmol), HATU (320 mg, 0.84 mmol), DIPEA (311 mg, 2.42 mmol), and dichloromethane (6 mL). The reaction mixture was stirred at room temperature for 5 minutes. The resulting solution was added to RED-062 (516 mg, 0.79 mmol) and the reaction mixture was stirred for an additional 30 minutes at room temperature. The reaction mixture was directly purified by flash chromatography (elute 3-10% MeOH/DCM) to give 820 mg (90%) of RED-196 as a light tan solid.

MS (ESI) m/z: [M+H]$^+$ Calcd for $C_{57}H_{87}ClN_5O_{17}$ 1148.6; Found 1148.8.

(2S)-1-(((1$^4$S, 1$^6$S, 3$^3$S, 2R, 4S, 10E, 12E, 14R)-8$^6$-chloro-1$^4$-hydroxy-8$^5$,14-dimethoxy-3$^3$,2,7,10-tetramethyl-1$^2$,6-dioxo-7-aza-1(6,4)-oxazinana-3(2,3)-oxirana-8(1,3)-benzenacyclotetradecaphane-10,12-dien-4-yl)oxy)-2,3-dimethyl-1,4,7-trioxo-8-(piperidin-4-yl)-11,14-dioxa-3,8-diazaheptadecan-17-oic acid (RED-197)

To a dried scintillation vial containing a magnetic stir bar was added RED-196 (31 mg, 0.027 mmol) and dichloromethane (1 mL). The solution was cooled to 0° C. and tin(IV) tetrachloride (1.0 M solution in dichloromethane, 0.3 mL, 0.3 mmol) was added. The reaction mixture was stirred for 1 h at 0° C. The reaction mixture was directly purified by C18 flash chromatography (elute 5-100% MeCN/water) to yield 16 mg (60%) of RED-197 as a white solid (16 mg, 60% yield).

MS (ESI) m/z: [M+H]$^+$ Calcd for $C_{48}H_{71}ClN_5O_{15}$ 992.5; Found 992.6.

(2S)-8-(1-(3-(2-((2-(((9H-fluoren-9-yl)methoxy) carbonyl)-1,2-dimethylhydrazinyl)methyl)-1H-indol-1-yl)propanoyl)piperidin-4-yl)-1-(((1$^4$S, 1$^6$S, 3$^3$S, 2R, 4S, 10E, 12E, 14R)-8$^6$-chloro-1$^4$-hydroxy-8$^5$, 14-dimethoxy-3$^3$,2,7,10-tetramethyl-1$^2$,6-dioxo-7-aza-1(6,4)-oxazinana-3(2,3)-oxirana-8(1,3)-benzenacyclotetradecaphane-10,12-dien-4-yl)oxy)-2,3-dimethyl-1,4,7-trioxo-11,14-dioxa-3,8-diazaheptadecan-17-oic acid (RED-198)

To a dried scintillation vial containing a magnetic stir bar was added RED-197 (16 mg, 0.016 mmol), (9H-fluoren-9-yl)methyl 1,2-dimethyl-2-((1-(3-oxo-3-(perfluorophenoxy) propyl)-1H-indol-2-yl)methyl)hydrazine-1-carboxylate (12) (13 mg, 0.02 mmol), DIPEA (8 µL, 0.05 mmol), and DMF (1 mL). The solution was stirred for 18 h at room temperature. The reaction mixture was directly purified by C18 flash chromatography (elute 5-100% MeCN/water) to yield 18 mg (77%) of RED-198 as a white solid.

MS (ESI) m/z: [M+H]$^+$ Calcd for $C_{77}H_{98}ClN_5O_{18}$ 1457.7; Found 1457.9.

(2S)-1-(((1$^4$S, 1$^6$S, 3$^3$S, 2R, 4S, 10E, 12E, 14R)-8$^6$-chloro-1$^4$-hydroxy-8$^5$,14-dimethoxy-3$^3$,2,7,10-tetramethyl-1$^2$,6-dioxo-7-aza-1(6,4)-oxazinana-3(2,3)-oxirana-8(1,3)-benzenacyclotetradecaphane-10,12-dien-4-yl)oxy)-8-(1-(3-(2-((1,2-dimethylhydrazinyl) methyl)-1H-indol-1-yl)propanoyl)piperidin-4-yl)-2, 3-dimethyl-1,4,7-trioxo-11,14-dioxa-3,8-diazaheptadecan-17-oic acid (RED-106)

To a dried scintillation vial containing a magnetic stir bar was added RED-197 (18 mg, 0.012 mmol), piperidine (20 µL, 0.02 mmol), and DMF (1 mL). The solution was stirred for 20 minutes at room temperature. The reaction mixture was directly purified by C18 flash chromatography (elute 1-60% MeCN/water) to yield 15 mg (98%) of compound RED-106 as a white solid.

MS (ESI) m/z: [M+H]$^+$ Calcd for $C_{62}H_{88}ClN_8O_{16}$ 1235.6; Found 1236.0.

Results and Discussion
Production and Initial Characterization of Anti-CD22 ADC

Figure 11:
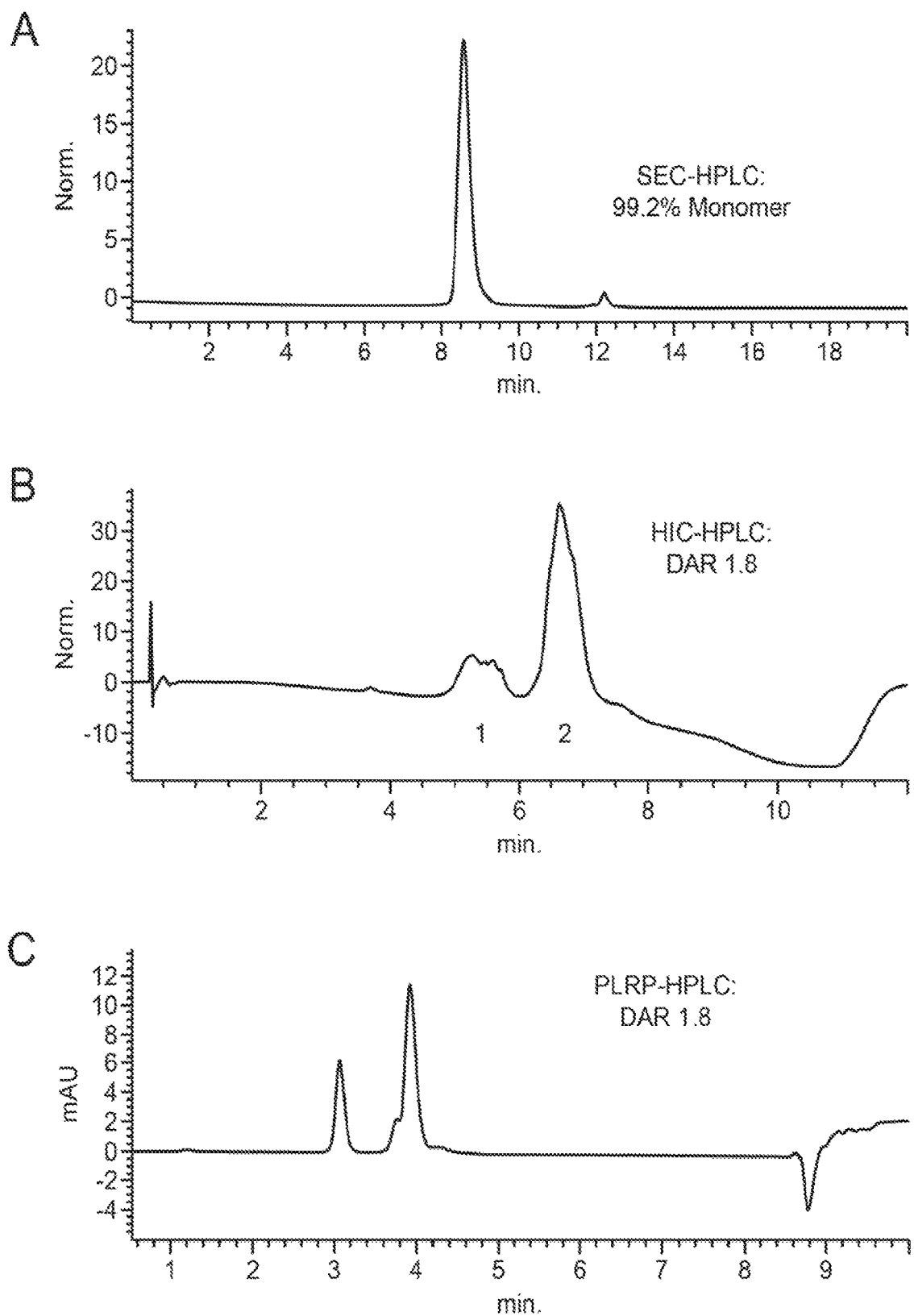
FIG. 11—an anti-CD22 ADC according to the present disclosure was highly monomeric, had a average DAR of 1.8, and included a single light and heavy chain species. The anti-CD22 ADC was analyzed by (FIG. 11, panel A) Size exclusion chromatography to assess percent monomer (99.2%), and by hydrophobic interaction (HIC.
Figure 12:
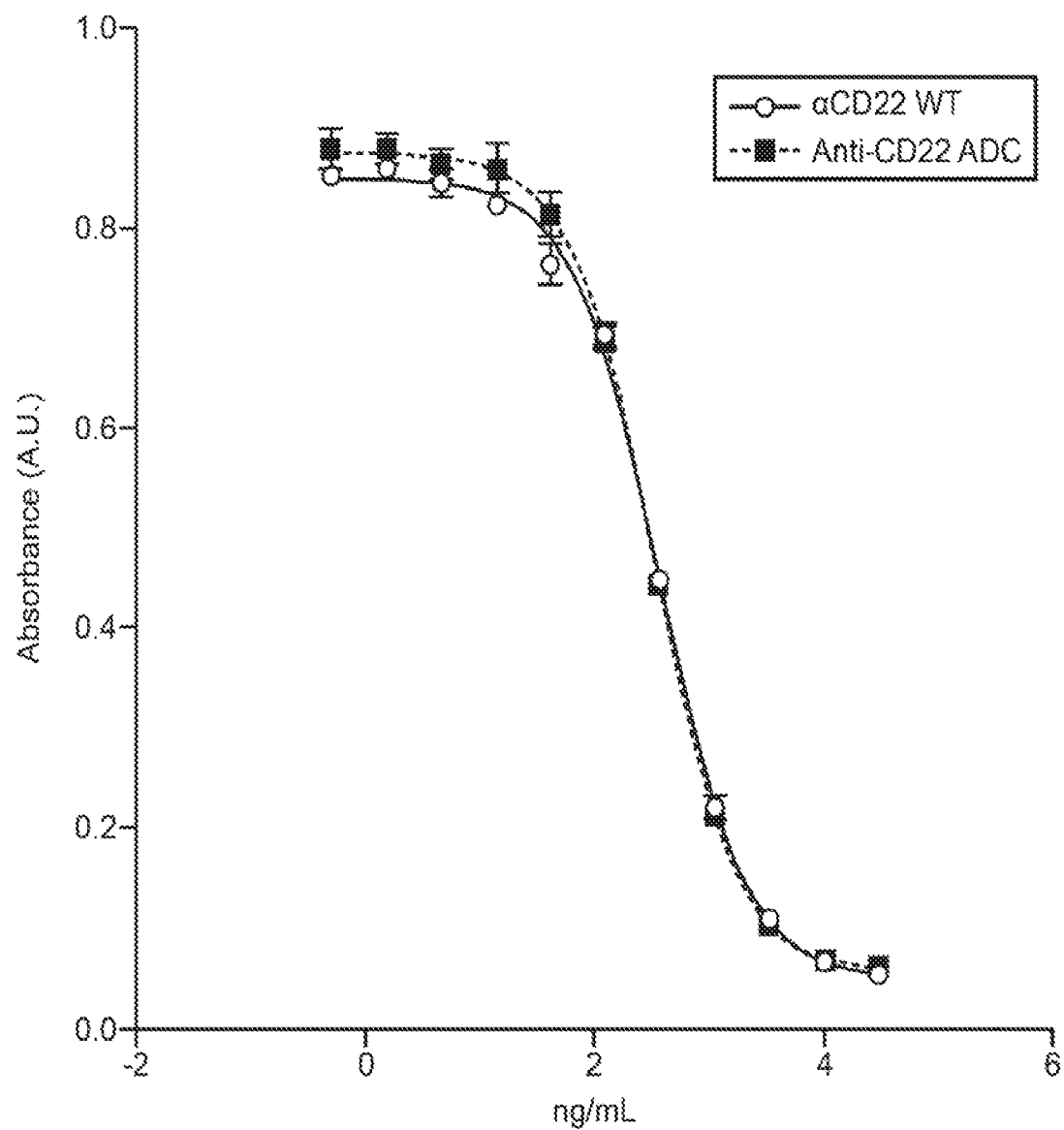
FIG. 12—an anti-CD22 ADC according to the present disclosure bound to human CD22 protein equally well as the wild-type anti-CD22 antibody. A competitive ELISA was used to compare the binding of the anti-CD22 ADC to the wild-type (WT) anti-CD22 antibody. The data are presented as the mean±S.D. (n=4).
Figure 13:
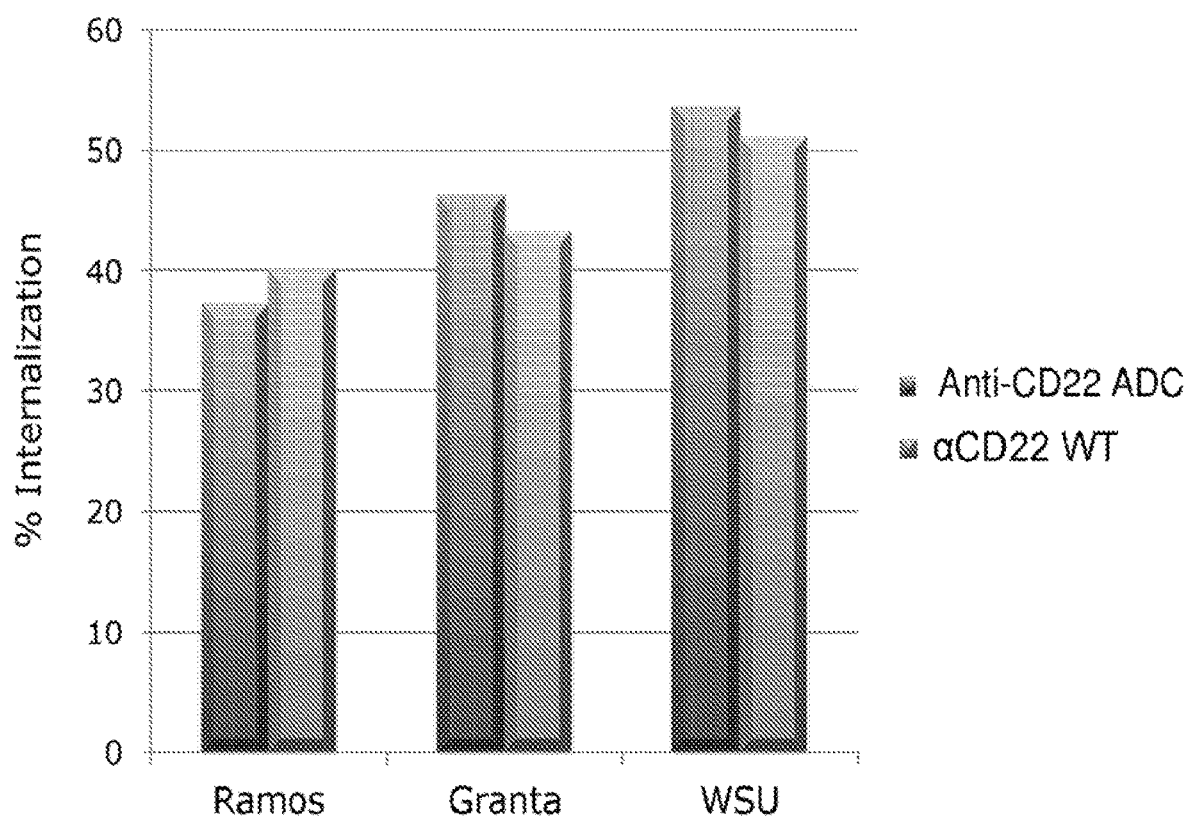
FIG. 13—an anti-CD22 ADC according to the present disclosure mediated the internalization of CD22 similarly to the wild-type anti-CD22 antibody. The NHL cell lines, Ramos, Granta-519, and WSU-DLCL2 were used to compare the internalization of cell surface CD22 as mediated by binding to either WT anti-CD22 or CAT-02-106.

The anti-CD22 antibody that was used (CAT-02) was a humanized variant of the RFB4 antibody. C-terminally tagged anti-CD22 antibody was made using a GPEx® clonal cell line with bioreactor titers of 1.6 g/L and 97% conversion of cysteine to formylglycine. The HIPS-4AP-maytansine linker payload was synthesized (described above) and conjugated to the aldehyde-tagged antibody. The resulting ADC was characterized (FIG. 11) by size exclusion chromatography to assess percent monomer (99.2%), and by hydrophobic interaction (HIC) and reversed-phase (PLRP) chromatography to assess the drug-to-antibody ratio (DAR), which was 1.8. The ADC was compared to the wild-type (untagged) anti-CD22 antibody in terms of affinity for human CD22 protein and internalization on CD22+ cells using an ELISA-based method (FIG. 12) and a flow cytometric-based method (FIG. 13), respectively. For both functional measures, the ADC performed equally well as the wild-type antibody, indicating that conjugation had no effect on these parameters.

Figure 14:
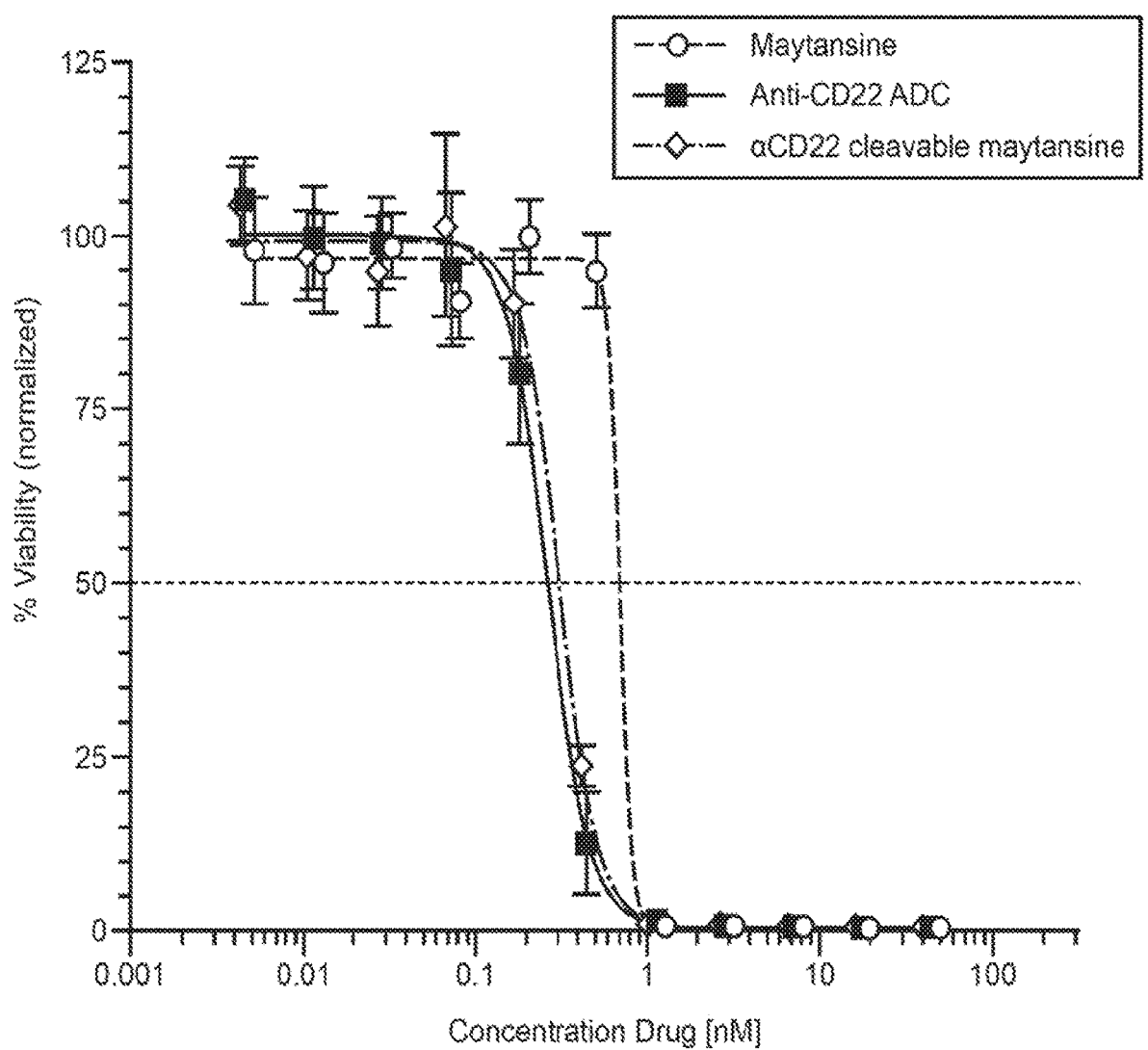
FIG. 14—an anti-CD22 ADC according to the present disclosure was equally potent against parental and MDR1-expressing NHL tumor cells in vitro. Ramos and WSU-DLCL2 parental (WT) cells (FIG. 14, panel A and panel C) and variants of those lines that were engineered to express MDR1 (MDR1+, FIG. 14, panel B and panel D) were used as targets for in vitro cytotoxicity studies of anti-CD22 ADC activity. Free maytansine and an αCD22 ADC made with the CAT-02 antibody but conjugated to maytansine using a valine-citrulline cleavable linker were used as controls. In an additional control experiment, the MDR1 inhibitor, cyclosporin, was added to WT or MDR1+WSU-DLCL2 cells (FIG. 14, panel E and panel F). The data are presented as the mean±S.D. (n=2).
Figure 14:
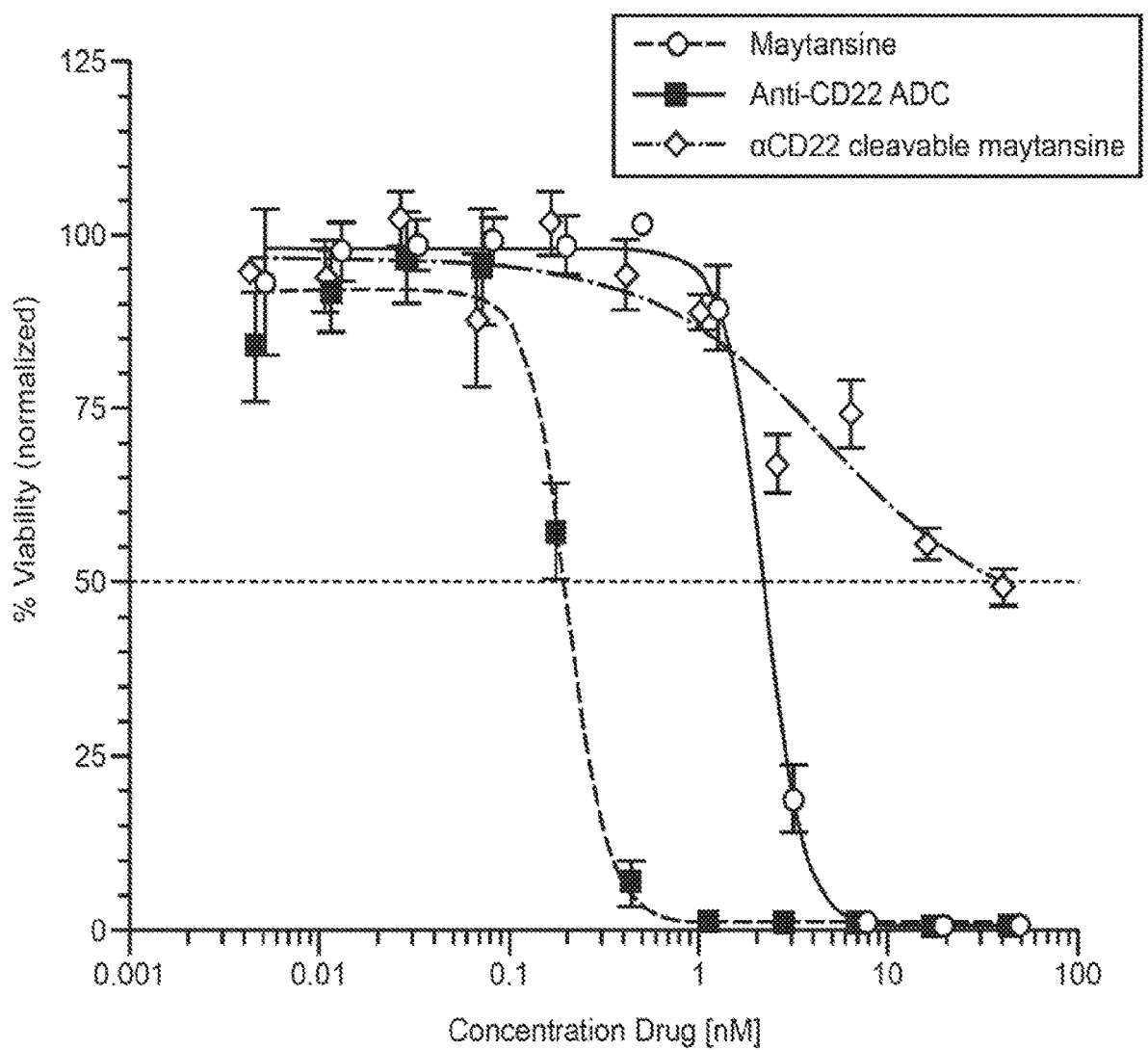
Figure 14:
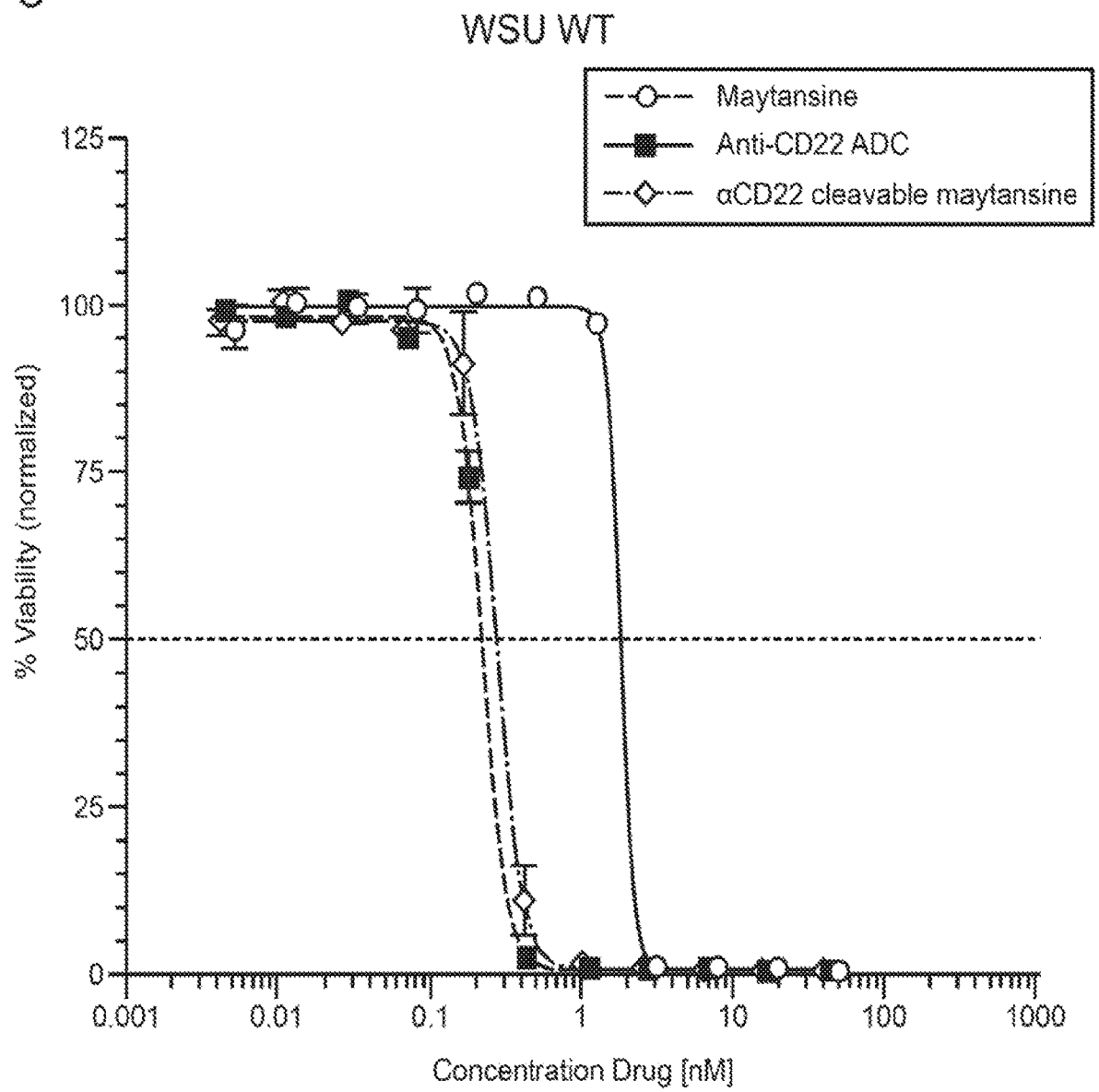
Figure 14:
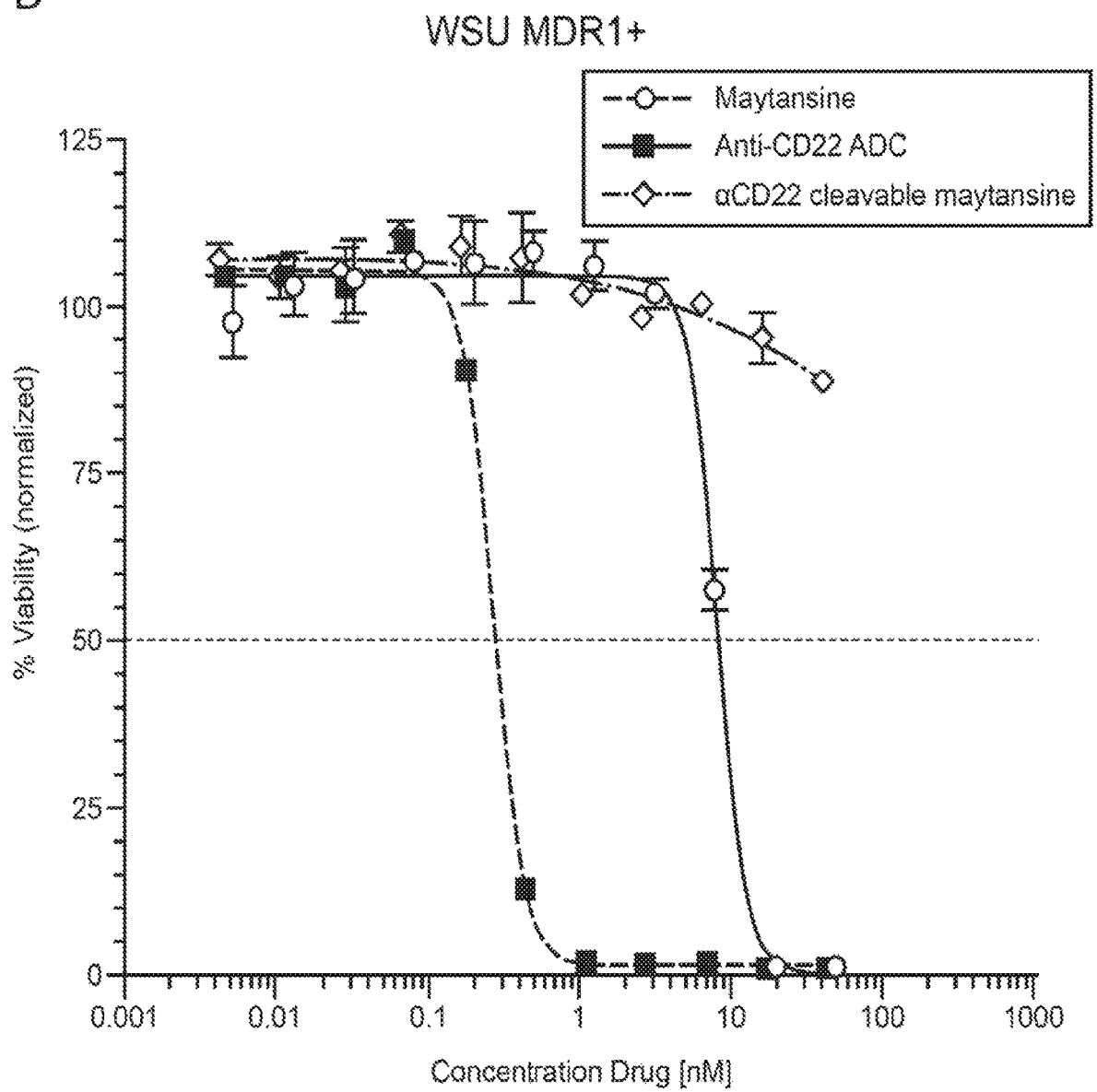
Figure 14:
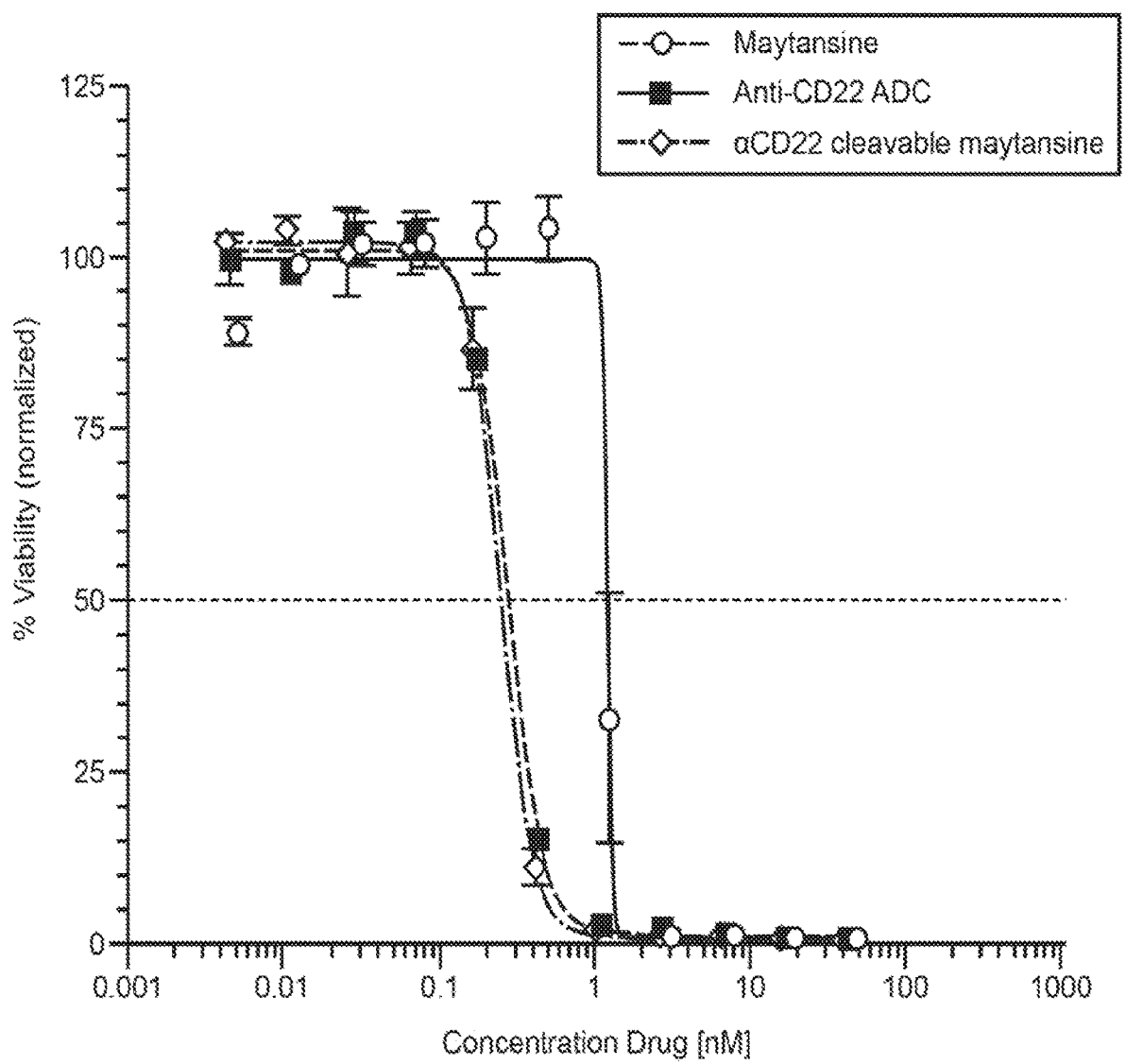
Figure 14:
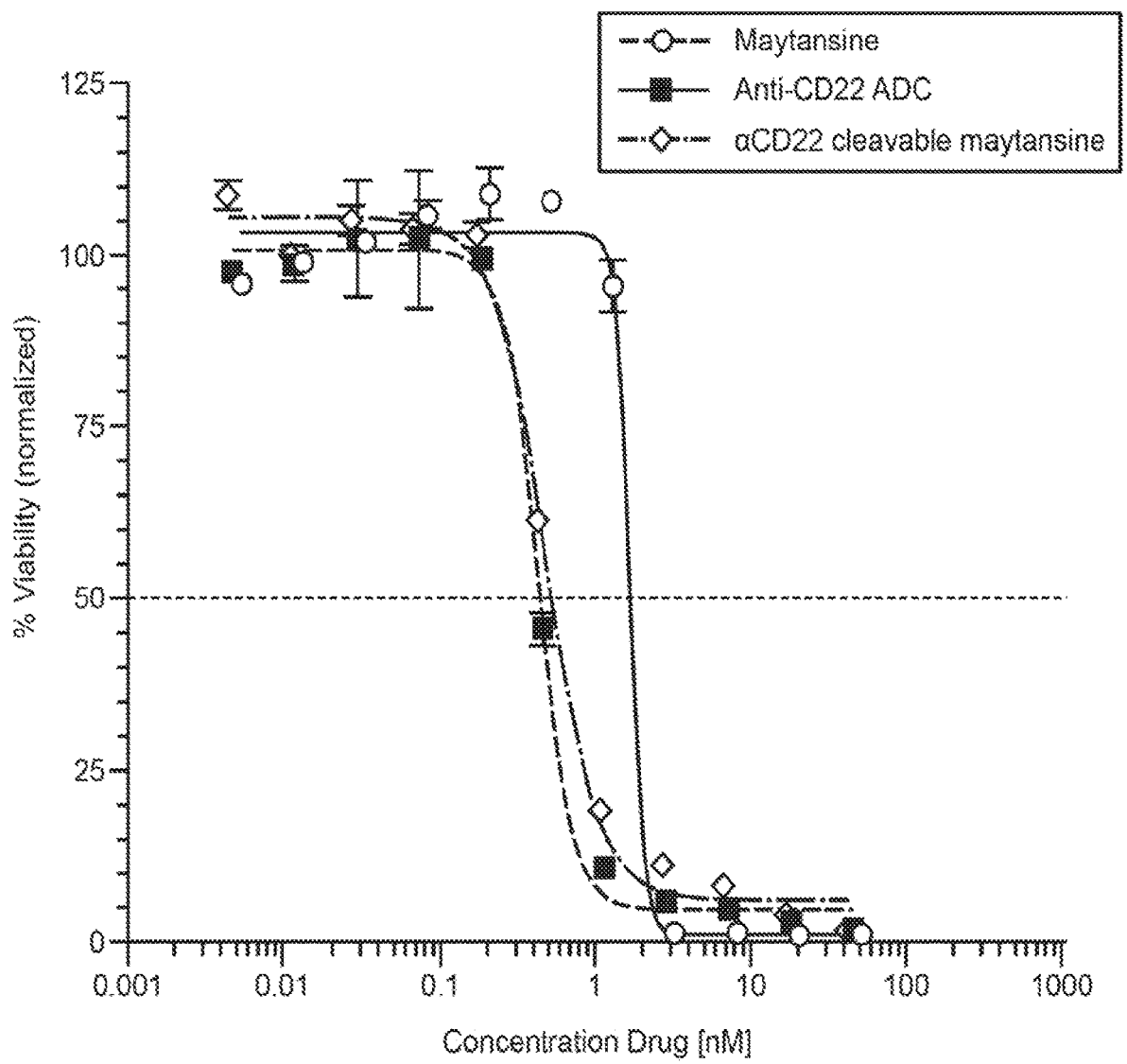
Figure 15:
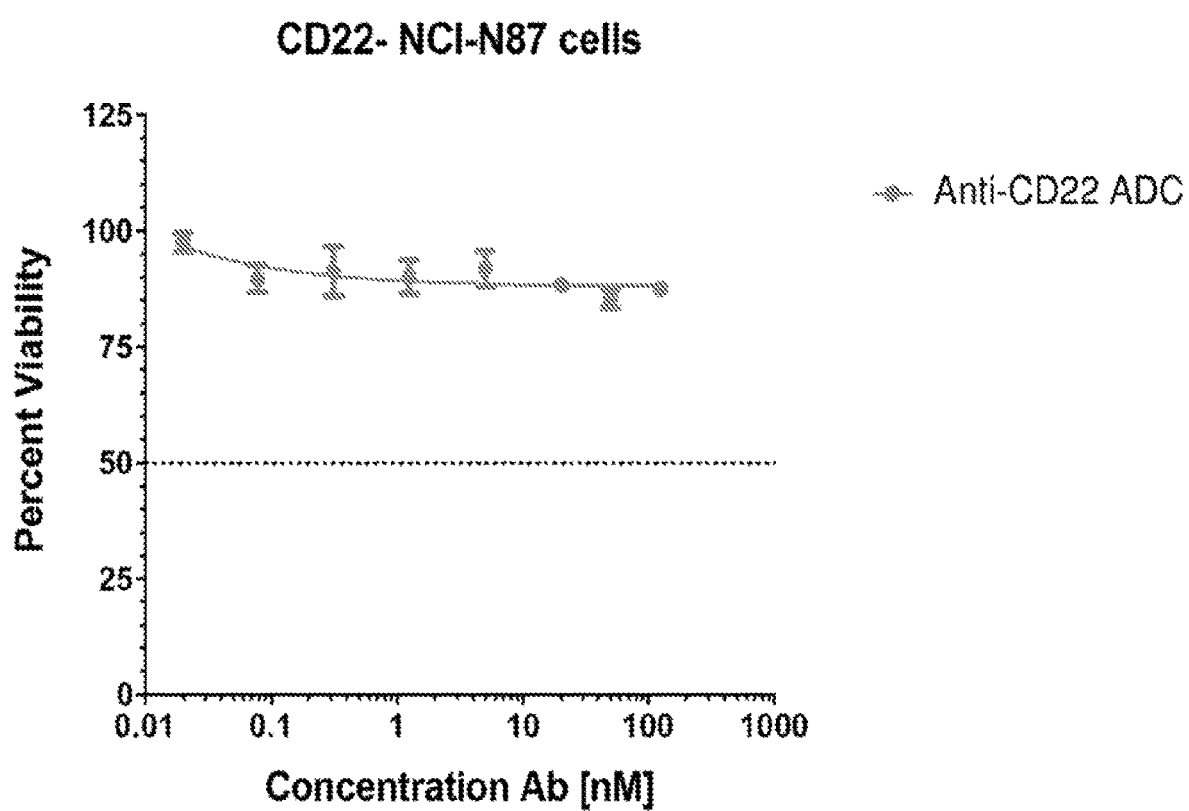
FIG. 15—an anti-CD22 ADC according to the present disclosure did not mediate off-target cytotoxicity. The gastric tumor cell line, NCI-N87, was incubated in vitro for 5 days in the presence of increasing concentrations of the anti-CD22 ADC. Then, cell viability was assessed using an MTS-based method. The data are presented as the mean±S.D. (n=2).
Figure 16:
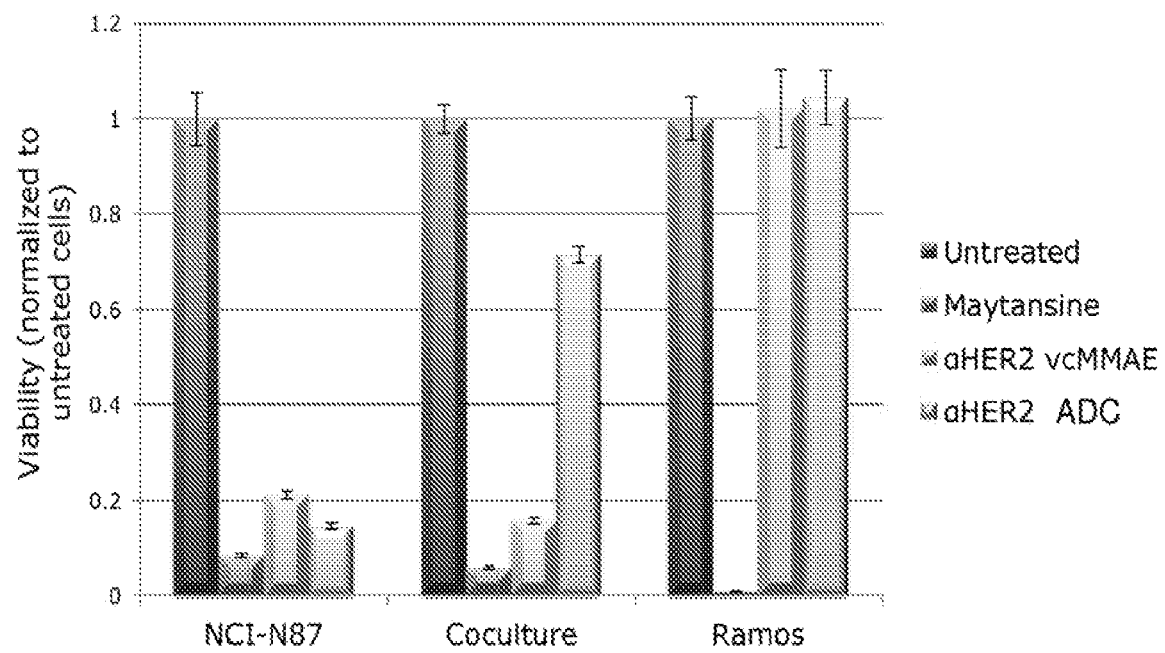
FIG. 16—The anti-CD22 ADC-related ADC, anti-HER2 conjugated to a HIPS-4AP-maytansine linker payload, did not induce bystander killing. In vitro cytotoxicity studies were conducted using HER2+ NCI-N87 cells, HER2-Ramos cells, or a coculture of both cells as targets. Free maytansine (2 nM) and anti-HER2 conjugated to MMAE via a cleavable valine-citrulline (vc) linker (2 nM payload), were used as positive controls for bystander killing. Anti-HER2 ADC was dosed at 2 nM payload. The data are presented as the mean±S.D. (n=2).

The Anti-CD22 ADC was not a Substrate for MDR1 and does not Promote Off-Target or Bystander Killing Potency of the anti-CD22 ADC was tested in vitro against the Ramos and WSU-DLCL2 HNL tumor cell lines. Activity was compared to that of free maytansine and a related ADC made with the CAT-02 anti-CD22 antibody conjugated to maytansine through a cleavable valine-citrulline dipeptide linker. Both ADCs showed subnanomolar activity against wild-type Ramos and WSU-DLCL2 cells (FIG. 14, panel A and panel C). In variants of those cells engineered to express the xenobiotic efflux pump, MDR1, only the anti-CD22 ADC of the present disclosure retained its original potency (FIG. 14, panel B and panel D). By contrast, free maytansine was ~10-fold less efficacious, and the ADC bearing cleavable maytansine was essentially devoid of activity. In a control experiment, cotreatment of WSU-DLCL2 cells with cyclosporin, an MDR1 inhibitor, had no effect on wild-type cells but restored the original potency of free maytansine and the cleavable ADC in MDR1+ cells (FIG. 14, panel E and panel F). Together, these results indicated that the active metabolite of the anti-CD22 ADC of the present disclosure was not a substrate for MDR1 efflux. In related in vitro cytotoxicity studies, the anti-CD22 ADC of the present disclosure had no effect on the antigen-negative cell line, NCI-N87 (FIG. 15), indicating that it had no off-target activity over a 5-day cell culture period. Furthermore, an anti-HER2-based ADC conjugated to the HIPS-4AP-maytansine linker payload did not mediate bystander killing of antigen-negative cells in coculture with antigen-positive cells (FIG. 16), implying that the active metabolite of the anti-CD22 ADC of the present disclosure, which would be the same as that of the anti-HER2 ADC conjugate, would also not mediate bystander killing.

The Anti-CD22 ADC was Efficacious Against NHL Xenograft Models

Figure 17:
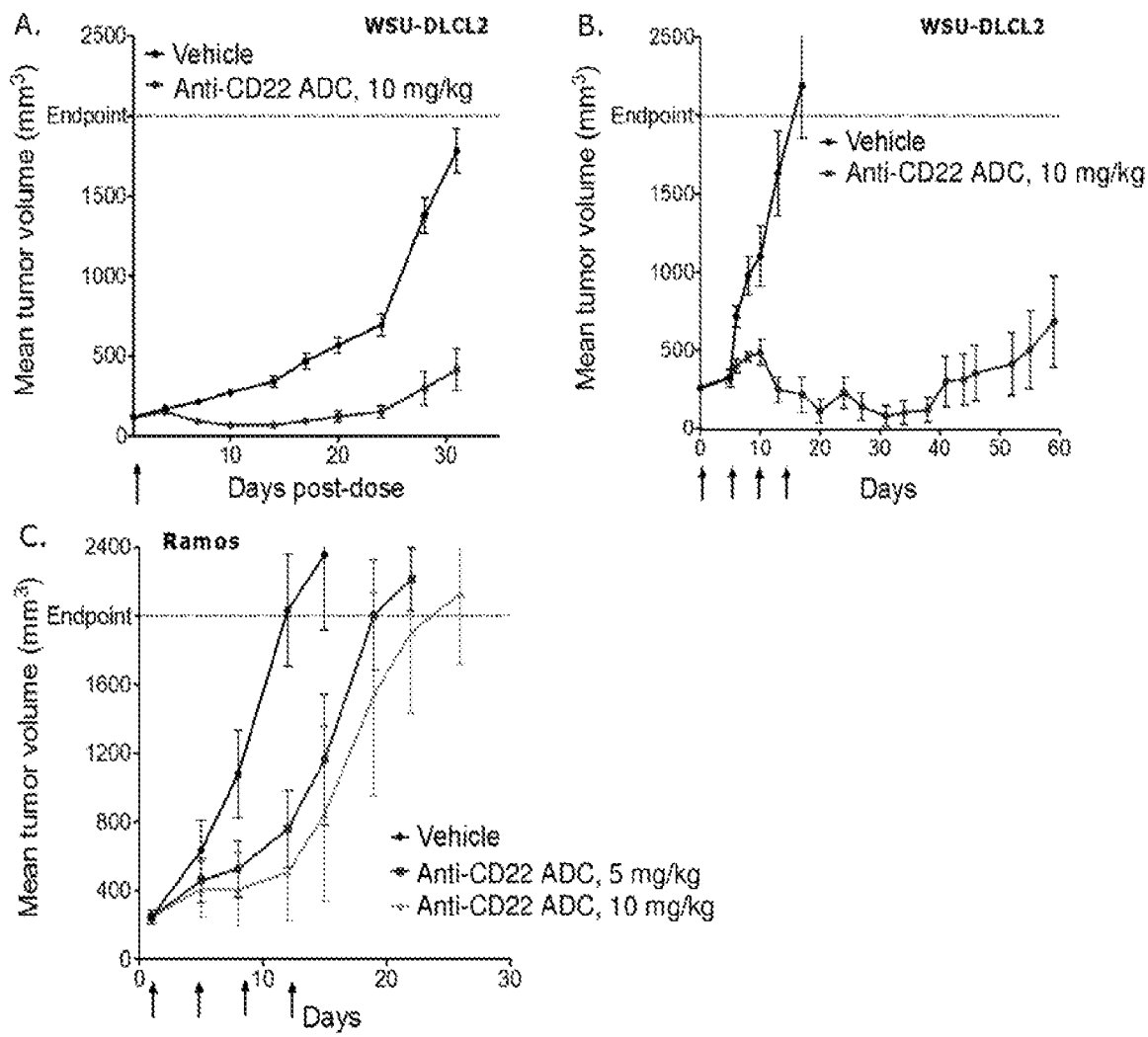
FIG. 17—an anti-CD22 ADC according to the present disclosure was efficacious in vivo against the NHL-derived WSU-DLCL2 and Ramos xenograft models. Female CB17 ICR SCID mice (8/group) bearing WSU-DLCL2 xenografts were treated with vehicle alone or with the anti-CD22 ADC as either a (FIG. 17, panel A) single 10 mg/kg dose or (FIG. 17, panel B) as multiple 10 mg/kg doses delivered every four days for a total of four doses (q4d×4). Treatment was initiated when tumors reached an average size of 118 or 262 $mm^3$ for the single or multidose studies, respectively.
Figure 18:
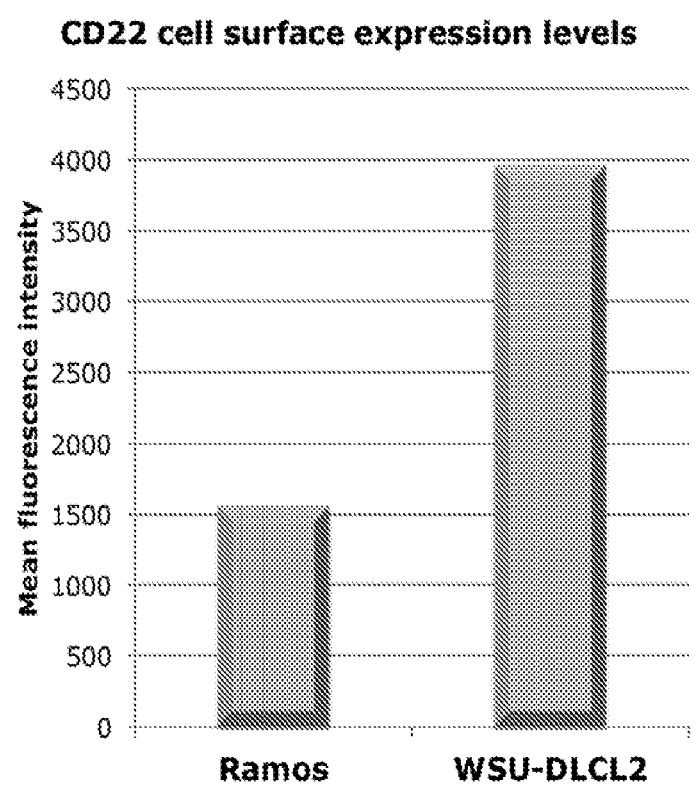
FIG. 18—Ramos and WSU-DLCL2 cells expressed different levels of cell surface CD22. Ramos and WSU-DLCL2 cells were incubated with a fluorescein-labeled anti-CD22 antibody and then analyzed by flow cytometry. The mean fluorescence intensity of the FL1 channel (detecting fluorescein) for each cell type is shown in the graph.
Figure 19:
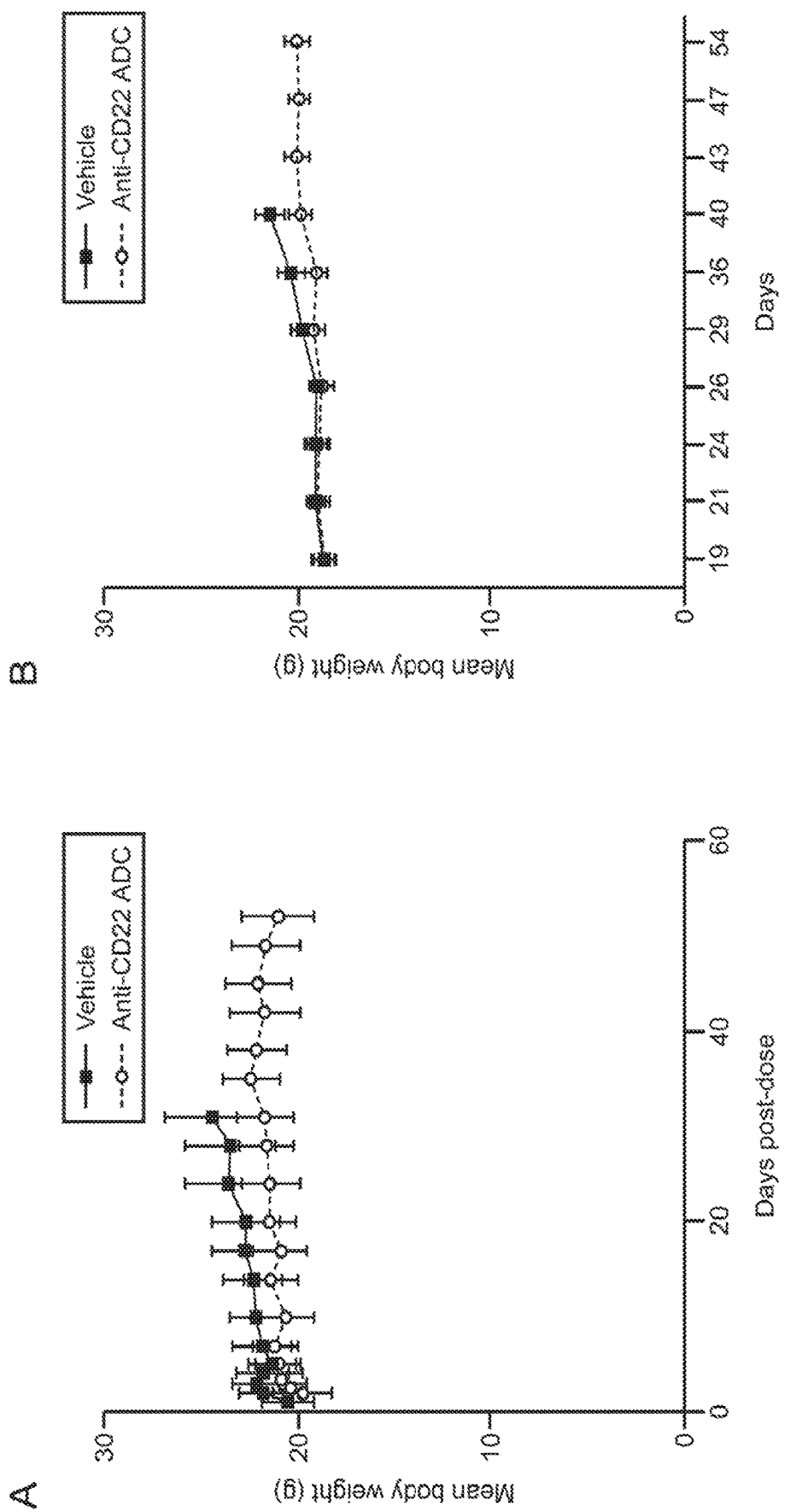
FIG. 19—Mouse body weights were not affected by treatment with an anti-CD22 ADC according to the present disclosure. Mean body weights of mice in the xenograft efficacy studies are shown.
Figure 19:
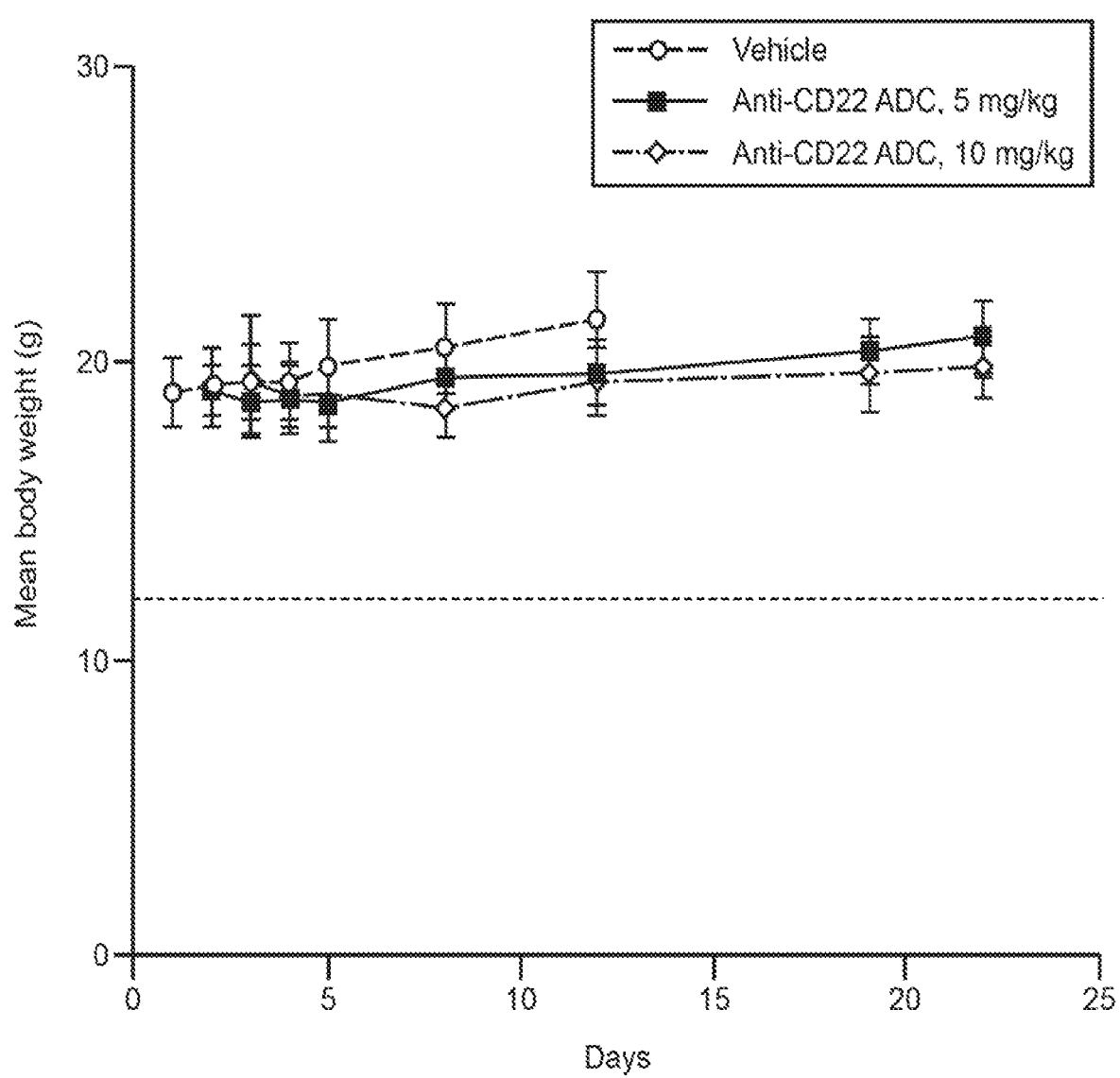

The in vivo efficacy of the anti-CD22 ADC was assessed against the WSU-DLCL2 and Ramos xenograft models (FIG. 17), which expressed relatively higher and lower amounts of CD22, respectively (FIG. 18). In a single dose study, mice bearing WSU-DLCL2 tumors were given 10 mg/kg of the anti-CD22 ADC or a vehicle control. Dosing was initiated when the tumors averaged 118 mm$^3$. Of the animals that received the ADC, 25% (2 of 8) had a partial response, with tumors that had regressed to 4 mm$^3$ by day 31. The the anti-CD22 ADC-treated and vehicle control groups had mean tumor volumes of 415 and 1783 mm$^3$, respectively, by day 31. Next, in a multidose study, mice bearing WSU-DLCL2 xenografts were treated with 10 mg/kg of the anti-CD22 ADC or a vehicle control every four days for a total of four doses. Dosing was initiated when the tumors averaged 262 mm$^3$. Of the animals that received the ADC, 75% (6 of 8) showed a complete response, with 38% of these (3 of 8) durable to the end of the study (day 59), 43 days after the last dose. By contrast, the vehicle control group reached a mean tumor volume of 2191 mm$^3$ by day 17. Finally, in a multidose study, mice bearing Ramos xenografts were treated with either 5 or 10 mg/kg of the anti-CD22 ADC or a vehicle control every four days for a total of four doses. Dosing was initiated when the tumors averaged 246 mm$^3$. As anticipated, a dose effect was observed with the groups receiving the 5 or 10 mg/kg dose demonstrating 63% or 87% tumor growth delay, respectively. Specifically, the median times to endpoint were 12, 19, and 22 days for the vehicle control, 5-, and 10 mg/kg dosing groups, respectively. In all three studies, no effect was observed on mouse body weight in the anti-CD22 ADC dosing groups (FIG. 19).

Figure 20:
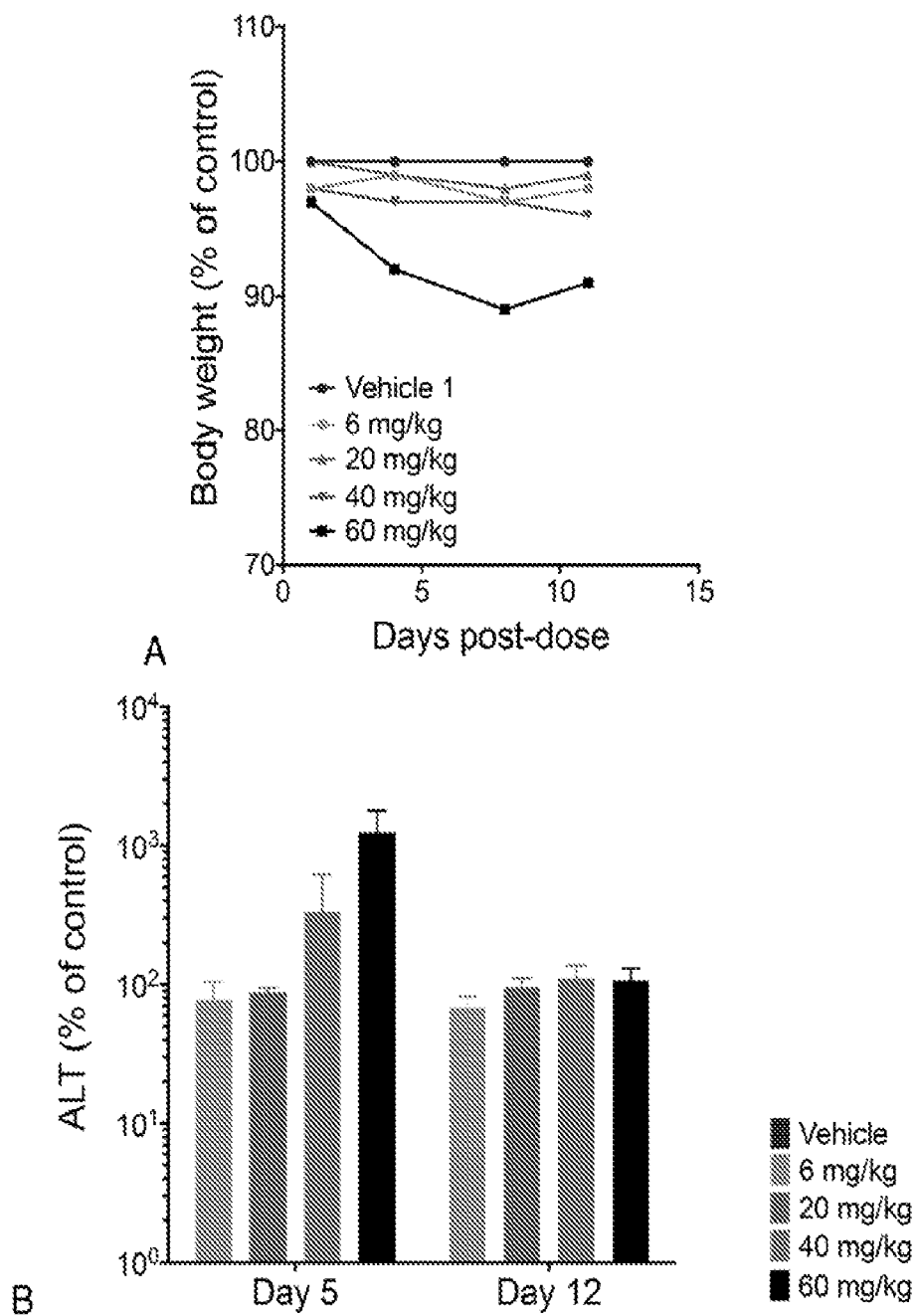
FIG. 20—an anti-CD22 ADC according to the present disclosure can be dosed in rats up to 60 mg/kg with minimal effects. Sprague-Dawley rats (5/group) received a 6, 20, 40, or 60 mg/kg dose of CAT-02-106 followed by a 12 day observation period.

The Anti-CD22 ADC was Well Tolerated at Up to 60 mg/kg in Rats and Cynomolgus Monkeys The anti-CD22 ADC did not bind to rodent CD22, however, dosing the ADC in these animals provided information related to off-target toxicity and safety of the linker-payload. As mentioned above, in mouse xenograft studies no effect of dosing was observed on body weight or clinical observations. In an exploratory rat toxicity study (FIG. 20), animals (5 per group) were given a single intravenous dose of the anti-CD22 ADC at 6, 20, 40, or 60 mg/kg and observed for 12 days post-dose. All animals survived until the end of the study. Animals dosed at 60 mg/kg experienced a 10% decrease in body weight relative to the vehicle control group. Clinical chemistry changes compatible with minimal to mild hepatobiliary injury occurred on Day 5 in animals given ≥40 mg/kg and included increased activities of alanine aminotransferase (ALT), aspartate transaminase (AST), and alkaline phosphatase (ALP). Most changes had reversed by Day 12. With respect to hematology, moderately to markedly decreased platelet counts occurred on Day 5 in animals given ≥40 mg/kg and had completely reversed by Day 12. Changes compatible with inflammation occurred on Days 5 and 12 in animals given ≥40 mg/kg and included slightly to moderately increased neutrophil and monocyte counts, slightly increased globulin concentrations, and decreased albumin globulin ratio.

Figure 21:
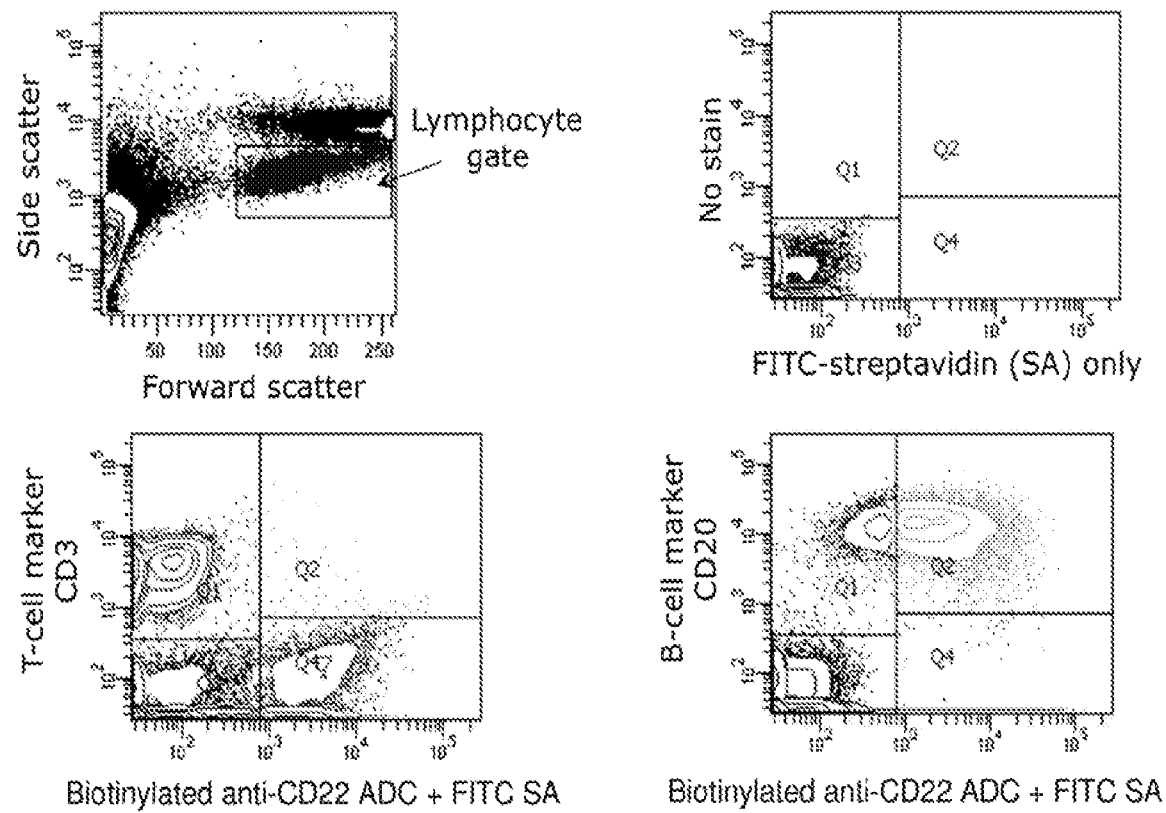
FIG. 21—an anti-CD22 ADC according to the present disclosure bound specifically to cynomolgus monkey B cells. Cynomolgus peripheral blood lymphocytes were gated according to their forward and side scatter profiles (upper left). Cells were incubated with either fluorescein-isothiocyanate (FITC)-conjugated streptavidin (SA) alone (upper right), or with biotinylated anti-CD22 ADC followed by FITC SA. Coincubation with antibodies recognizing T cells (CD3, lower left) or B cells (CD20, lower right) demonstrated specificity of CAT-02-106 binding to a B-cell population.
Figure 22:
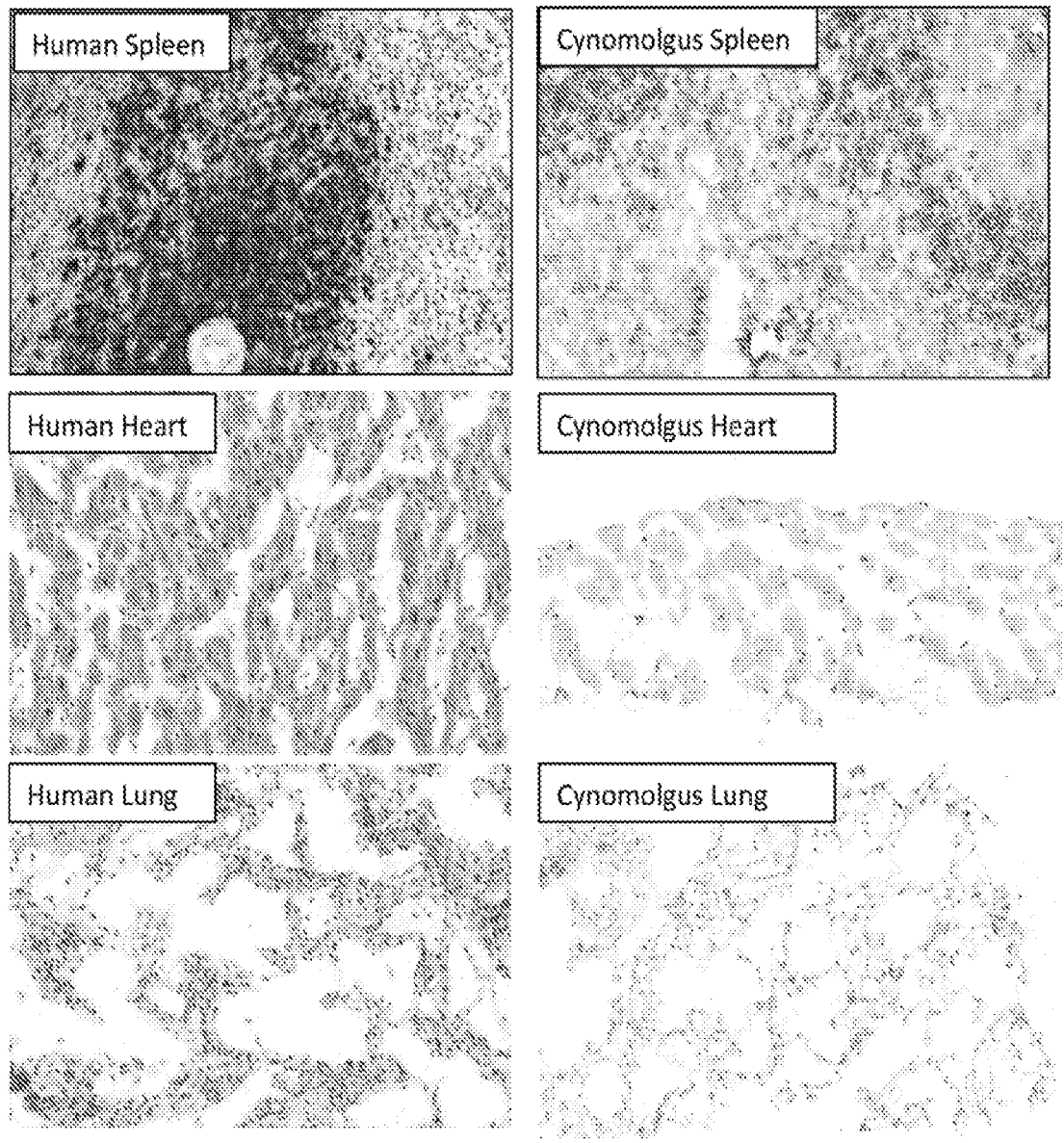
FIG. 22—an anti-CD22 ADC according to the present disclosure demonstrated B cell-specific reactivity in human and cynomolgus monkey tissues. The anti-CD22 ADC bound to B-cell rich regions of the spleen (top). Heart tissues were negative for staining (middle). Lung sections were negative with the exception of scattered leukocytes (bottom).
Figure 23:
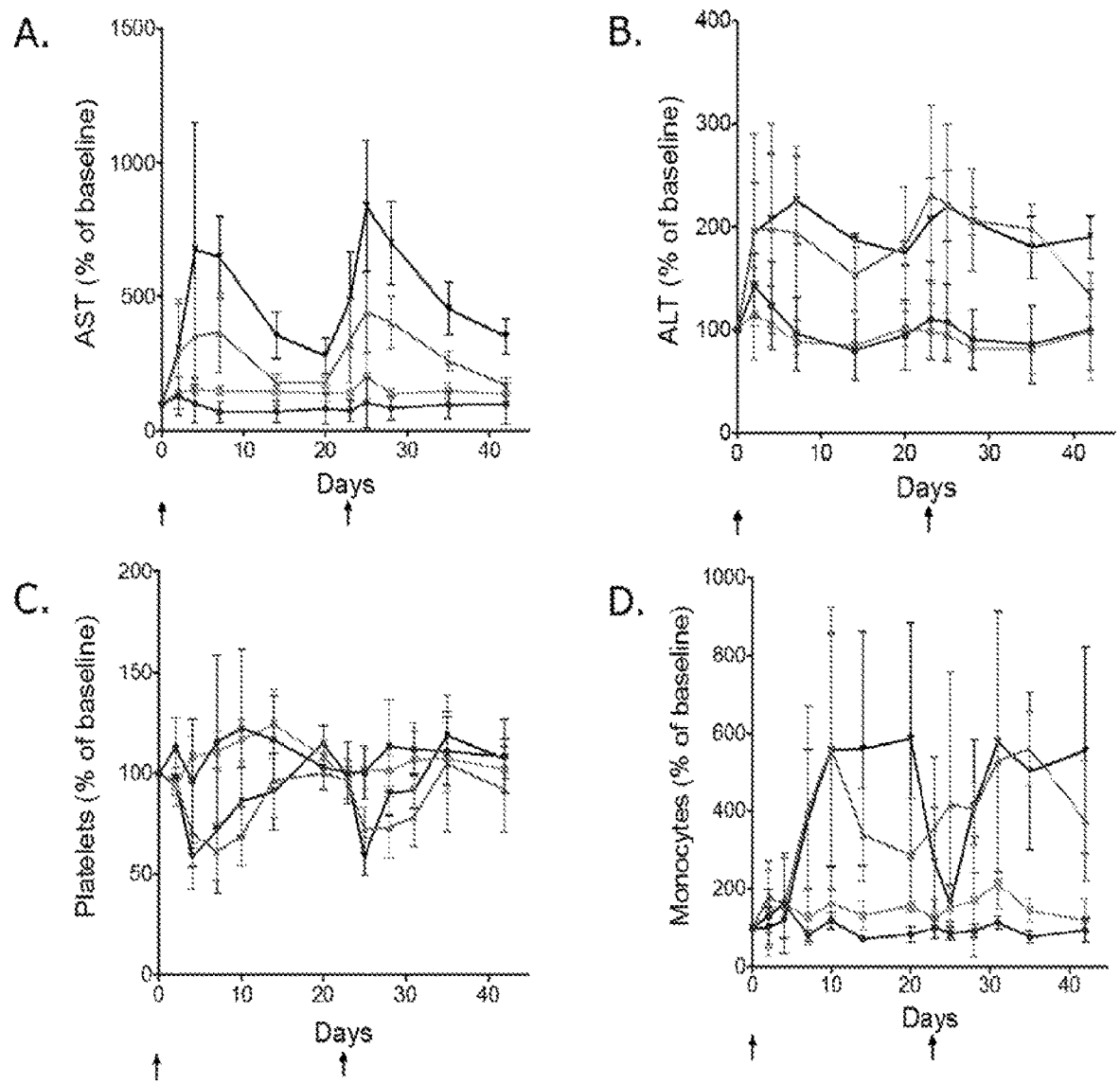
FIG. 23—Cynomolgus monkeys display no observed adverse effects with a repeat 60 mg/kg dose of an anti-CD22 ADC according to the present disclosure. Cynomolgus monkeys (2/sex/group) were given 10, 30, or 60 mg/kg of the anti-CD22 ADC once every three weeks for a total of two doses followed by a 21 day observation period.

The anti-CD22 ADC did bind to cynomolgus CD22 (FIG. 21) and had a similar tissue cross-reactivity profile in monkeys as compared to humans (FIG. 22). Therefore, cynomolgus monkeys represented an appropriate model in which to test both the on-target and off-target toxicities of this ADC. In an exploratory repeat dose study, monkeys (2/sex/group) were given 10, 30, or 60 mg/kg of the anti-CD22 ADC once every three weeks for a total of two doses followed by a 21 day observation period. All animals survived until study termination. No anti-CD22 ADC-related changes in clinical observations, body weights, or food consumption occurred. Clinical pathology changes occurred mostly in animals given ≥30 mg/kg, and were consistent with minimal liver injury, increased platelet consumption and/or sequestration, and inflammation (FIG. 23). These changes were similar at 30 and 60 mg/kg and after the first and second dose, and were of a magnitude that would not be expected to be associated with microscopic changes or clinical effects. Changes compatible with minimal liver injury in animals given ≥30 mg/kg consisted of increased ALT, AST, and ALP activities that had partially reversed by days 21 and 42. Slightly to moderately decreased platelet counts observed within a week of dosing had mostly reversed by days 21 and 42. Changes compatible with inflammation consisted of minimally to moderately increased neutrophil and monocyte counts, slightly to moderately increased globulin concentrations, and minimally decreased albumin concentrations.

Administration of the Anti-CD22 ADC LED to B-Cell Depletion in Cynomolgus Monkeys In order to assess the pharmacodynamic effects of the anti-CD22 ADC in a cross-reactive species, peripheral blood mononuclear cell populations was monitored in samples taken from cynomolgus monkeys enrolled in the repeat dose toxicity study. Specifically, flow cytometry was used to detect the ratio of B cells (CD20+), T cells (CD3+), and NK cells (CD20–/CD3–) observed in animals pre-dose and at days 7, 14, 28, and 35 (FIG. 5). In pre-dose anti-CD22 ADC-treated animals, B cells included an average of 11.6% of total lymphocytes; this value dropped to an average of 3.8% by day 35, representing an average decrease of 68% in the measured B cell populations relative to baseline levels (FIG. 24). B cell depletion was similar across all dosing groups, from 10 to 60 mg/kg, indicating that the lowest dose was sufficient to obtain the effect. Meanwhile, B cells in vehicle control-treated animals, and T cells and NK cells (not shown) in all groups were largely unchanged over the course of the treatment. The results indicated that the anti-CD22 ADC was able to selectively mediate the depletion of cynomolgus CD22+ cells in vivo without leading to adverse off-target toxicities.

Figure 25:
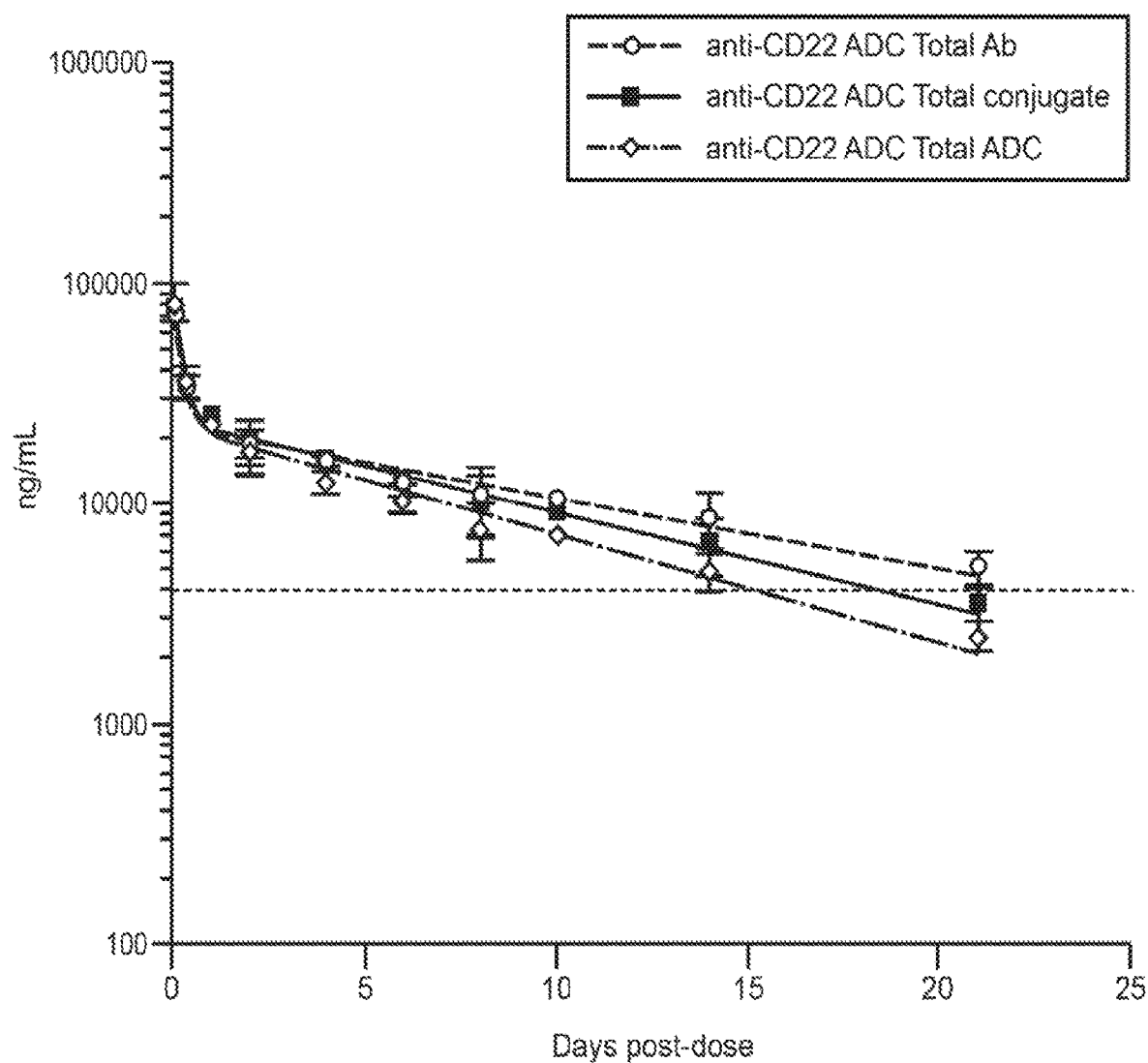
FIG. 25—an anti-CD22 ADC according to the present disclosure displayed very high in vivo stability as shown by a rat pharmacokinetic study. Sprague-Dawley rats (3/group) were given a single i.v. bolus dose of 3 mg/kg anti-CD22 ADC. Plasma samples were collected at the designated times and were analyzed (as shown in FIG. 10) for total antibody, total conjugate, and total ADC concentrations.

Pharmaco- and Toxicokinetics of the Anti-CD22 ADC in Mice, Rats, and Cynomolgus Monkeys In order to evaluate the in vivo stability of the anti-CD22 ADC, a pharmacokinetic (PK) study in rats was conducted. The concentrations of total antibody, total ADC, and total conjugate was monitored in the peripheral blood of animals (3/group) for 21 days after receiving a single 3 mg/kg dose of the anti-CD22 ADC (Table 2 and FIG. 25). As shown in FIG. 10, the total ADC and total conjugate assays employed DAR-sensitive and DAR-insensitive measurements, respectively. The PK parameters obtained for all three analytes were similar, indicating that the conjugate was largely stable in circulation. For example, the elimination half-lives of total antibody, total ADC, and total conjugate were 9.48, 6.13, and 7.22 days, respectively.

Next, the anti-CD22 ADC analyte concentrations was measured over time in the peripheral blood of mice from the Ramos multidose efficacy study described above. The purpose of this analysis was to determine the total ADC exposure level achieved at an efficacious dose in xenograft studies (FIG. 26). For this benchmark, recall that 10 mg/kg×4 doses over 22 days led to an 87% tumor growth delay in the Ramos model, and that 10 mg/kg×4 doses over 28 days led to 75% of the animals exhibiting a complete response (no palpable tumor remaining) in the WSU-DLCL2 model. The mean area under the concentration versus time curve from time 0 to infinity ($AUC_{0-inf}$) for the 10 mg/kg×4 dose in the mouse was 2530±131 (S.D.) day·μg/mL.

Finally, the anti-CD22 ADC analyte concentrations in toxicokinetic plasma samples from animals dosed in the previously described rat and cynomolgus monkey toxicity studies was assessed (FIG. 26). The purpose of these analyses was to determine the total ADC exposure levels achieved at doses correlated to the presence or absence of observed toxicities. With respect to the rat study, the $C_{max}$ and $AUC_{0-inf}$ values were generally proportional to the dose. The mean $AUC_{0-inf}$ for the 60 mg/kg dose was 5201±273 day·μg/mL. With respect to the monkey study, the $C_{max}$ and $AUC_{0-inf}$ values were generally proportional to the dose. The mean $AUC_{0-inf}$ for the first 60 mg/kg dose was 6140±667 day·μg/mL. The antibody bound to antigen in the cynomolgus model, however, clearance (not shown) was similar among all dosing groups. This indicated that the low (10 mg/kg) dose was sufficient to saturate target-mediated clearance mechanisms, and therefore that antigen-mediated clearance did not significantly affect the results of this study. This observation was consistent with the pharmacodynamic effect of the anti-CD22 ADC treatment on B-cell depletion, the extent of which was similar across all dosing groups.

Conclusions

A CD22-targeted ADC site-specifically conjugated to a maytansine payload that was resistant to efflux by MDR1- expressing cells was produced. The ADC had a DAR of 1.8, displayed good biophysical characteristics, and mediated efficacy ranging from significant (87%) tumor growth delay to complete response in vivo against two NHL xenograft models. This efficacy was achieved at exposure levels well below those associated with toxicity; indeed, in the repeat dose cynomolgus toxicity study, no observed adverse effects were noted even at the highest dose of 60 mg/kg, indicating that higher doses may be used. The anti-CD22 ADC had a combination of efficacy and safety. As an added advantage, a number of the underlying components, including the target antigen, parental antibody, and the maytansine-based cytotoxic payload have been used in humans and have been well-studied regarding safety and toxicity. Based on the cynomolgus monkey, which is a reasonable model for projecting human pharmacokinetic and toxicity profiles, the results of these studies indicated that the anti-CD22 ADC is of therapeutic use for NHL patients, such as those who have developed refractory disease due to the upregulation of MDR1.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

SEQUENCE LISTING

```
<160> NUMBER OF SEQ ID NOS: 163

<210> SEQ ID NO 1
<211> LENGTH: 123
<212> TYPE: PRT
<213> ORGANISM: Artificial sequence
<220> FEATURE:
<223> OTHER INFORMATION: Synthetic polypeptide
<220> FEATURE:
<221> NAME/KEY: MISC_FEATURE
<222> LOCATION: (19)..(19)
<223> OTHER INFORMATION: Xaa may be Lys or Arg
<220> FEATURE:
<221> NAME/KEY: MISC_FEATURE
<222> LOCATION: (78)..(78)
<223> OTHER INFORMATION: Xaa may be Ser or Thr
<220> FEATURE:
<221> NAME/KEY: MISC_FEATURE
<222> LOCATION: (84)..(84)
<223> OTHER INFORMATION: Xaa may be Asn or Ser

<400> SEQUENCE: 1

Glu Val Gln Leu Val Glu Ser Gly Gly Gly Leu Val Lys Pro Gly Gly
1               5                   10                  15

Ser Leu Xaa Leu Ser Cys Ala Ala Ser Gly Phe Ala Phe Ser Ile Tyr
            20                  25                  30

Asp Met Ser Trp Val Arg Gln Ala Pro Gly Lys Gly Leu Glu Trp Val
        35                  40                  45

Ala Tyr Ile Ser Ser Gly Gly Gly Thr Thr Tyr Tyr Pro Asp Thr Val
    50                  55                  60

Lys Gly Arg Phe Thr Ile Ser Arg Asp Asn Ala Lys Asn Xaa Leu Tyr
65                  70                  75                  80

Leu Gln Met Xaa Ser Leu Arg Ala Glu Asp Thr Ala Met Tyr Tyr Cys
                85                  90                  95

Ala Arg His Ser Gly Tyr Gly Ser Ser Tyr Gly Val Leu Phe Ala Tyr
            100                 105                 110

Trp Gly Gln Gly Thr Leu Val Thr Val Ser Ser
        115                 120

<210> SEQ ID NO 2
<211> LENGTH: 107
<212> TYPE: PRT
<213> ORGANISM: Artificial sequence
<220> FEATURE:
<223> OTHER INFORMATION: Synthetic polypeptide
<220> FEATURE:
<221> NAME/KEY: MISC_FEATURE
<222> LOCATION: (11)..(11)
<223> OTHER INFORMATION: Xaa may be Leu or Val
```

```
<220> FEATURE:
<221> NAME/KEY: MISC_FEATURE
<222> LOCATION: (44)..(44)
<223> OTHER INFORMATION: Xaa may be Val or Pro
<220> FEATURE:
<221> NAME/KEY: MISC_FEATURE
<222> LOCATION: (80)..(80)
<223> OTHER INFORMATION: Xaa may be Gln or Pro

<400> SEQUENCE: 2

Asp Ile Gln Met Thr Gln Ser Pro Ser Ser Xaa Ser Ala Ser Val Gly
1               5                   10                  15

Asp Arg Val Thr Ile Thr Cys Arg Ala Ser Gln Asp Ile Ser Asn Tyr
            20                  25                  30

Leu Asn Trp Tyr Gln Gln Lys Pro Gly Lys Ala Xaa Lys Leu Leu Ile
        35                  40                  45

Tyr Tyr Thr Ser Ile Leu His Ser Gly Val Pro Ser Arg Phe Ser Gly
50                  55                  60

Ser Gly Ser Gly Thr Asp Tyr Thr Leu Thr Ile Ser Ser Leu Gln Xaa
65                  70                  75                  80

Glu Asp Phe Ala Thr Tyr Phe Cys Gln Gln Gly Asn Thr Leu Pro Trp
                85                  90                  95

Thr Phe Gly Gly Gly Thr Lys Val Glu Ile Lys
            100                 105

<210> SEQ ID NO 3
<211> LENGTH: 123
<212> TYPE: PRT
<213> ORGANISM: Artificial sequence
<220> FEATURE:
<223> OTHER INFORMATION: Synthetic polypeptide

<400> SEQUENCE: 3

Glu Val Gln Leu Val Glu Ser Gly Gly Gly Leu Val Lys Pro Gly Gly
1               5                   10                  15

Ser Leu Lys Leu Ser Cys Ala Ala Ser Gly Phe Ala Phe Ser Ile Tyr
            20                  25                  30

Asp Met Ser Trp Val Arg Gln Ala Pro Gly Lys Gly Leu Glu Trp Val
        35                  40                  45

Ala Tyr Ile Ser Ser Gly Gly Gly Thr Thr Tyr Tyr Pro Asp Thr Val
50                  55                  60

Lys Gly Arg Phe Thr Ile Ser Arg Asp Asn Ala Lys Asn Thr Leu Tyr
65                  70                  75                  80

Leu Gln Met Ser Ser Leu Arg Ala Glu Asp Thr Ala Met Tyr Tyr Cys
                85                  90                  95

Ala Arg His Ser Gly Tyr Gly Ser Ser Tyr Gly Val Leu Phe Ala Tyr
            100                 105                 110

Trp Gly Gln Gly Thr Leu Val Thr Val Ser Ser
        115                 120

<210> SEQ ID NO 4
<211> LENGTH: 123
<212> TYPE: PRT
<213> ORGANISM: Artificial sequence
<220> FEATURE:
<223> OTHER INFORMATION: Synthetic polypeptide

<400> SEQUENCE: 4

Glu Val Gln Leu Val Glu Ser Gly Gly Gly Leu Val Lys Pro Gly Gly
1               5                   10                  15
```

```
Ser Leu Arg Leu Ser Cys Ala Ala Ser Gly Phe Ala Phe Ser Ile Tyr
            20                  25                  30

Asp Met Ser Trp Val Arg Gln Ala Pro Gly Lys Gly Leu Glu Trp Val
            35                  40                  45

Ala Tyr Ile Ser Ser Gly Gly Gly Thr Thr Tyr Tyr Pro Asp Thr Val
        50                  55                  60

Lys Gly Arg Phe Thr Ile Ser Arg Asp Asn Ala Lys Asn Ser Leu Tyr
65                  70                  75                  80

Leu Gln Met Ser Ser Leu Arg Ala Glu Asp Thr Ala Met Tyr Tyr Cys
                85                  90                  95

Ala Arg His Ser Gly Tyr Gly Ser Tyr Gly Val Leu Phe Ala Tyr
                100                 105                 110

Trp Gly Gln Gly Thr Leu Val Thr Val Ser Ser
        115                 120
```

<210> SEQ ID NO 5
<211> LENGTH: 123
<212> TYPE: PRT
<213> ORGANISM: Artificial sequence
<220> FEATURE:
<223> OTHER INFORMATION: Synthetic polypeptide

<400> SEQUENCE: 5

```
Glu Val Gln Leu Val Glu Ser Gly Gly Gly Leu Val Lys Pro Gly Gly
1               5                   10                  15

Ser Leu Lys Leu Ser Cys Ala Ala Ser Gly Phe Ala Phe Ser Ile Tyr
            20                  25                  30

Asp Met Ser Trp Val Arg Gln Ala Pro Gly Lys Gly Leu Glu Trp Val
            35                  40                  45

Ala Tyr Ile Ser Ser Gly Gly Gly Thr Thr Tyr Tyr Pro Asp Thr Val
        50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Met Tyr Tyr Cys
                85                  90                  95

Ala Arg His Ser Gly Tyr Gly Ser Tyr Gly Val Leu Phe Ala Tyr
                100                 105                 110

Trp Gly Gln Gly Thr Leu Val Thr Val Ser Ser
        115                 120
```

<210> SEQ ID NO 6
<211> LENGTH: 123
<212> TYPE: PRT
<213> ORGANISM: Artificial sequence
<220> FEATURE:
<223> OTHER INFORMATION: Synthetic polypeptide

<400> SEQUENCE: 6

```
Glu Val Gln Leu Val Glu Ser Gly Gly Gly Leu Val Lys Pro Gly Gly
1               5                   10                  15

Ser Leu Lys Leu Ser Cys Ala Ala Ser Gly Phe Ala Phe Ser Ile Tyr
            20                  25                  30

Asp Met Ser Trp Val Arg Gln Ala Pro Gly Lys Gly Leu Glu Trp Val
            35                  40                  45

Ala Tyr Ile Ser Ser Gly Gly Gly Thr Thr Tyr Tyr Pro Asp Thr Val
        50                  55                  60

Lys Gly Arg Phe Thr Ile Ser Arg Asp Asn Ala Lys Asn Ser Leu Tyr
65                  70                  75                  80
```

```
Leu Gln Met Ser Ser Leu Arg Ala Glu Asp Thr Ala Met Tyr Tyr Cys
                85                  90                  95

Ala Arg His Ser Gly Tyr Gly Ser Ser Tyr Gly Val Leu Phe Ala Tyr
            100                 105                 110

Trp Gly Gln Gly Thr Leu Val Thr Val Ser Ser
        115                 120

<210> SEQ ID NO 7
<211> LENGTH: 108
<212> TYPE: PRT
<213> ORGANISM: Artificial sequence
<220> FEATURE:
<223> OTHER INFORMATION: Synthetic polypeptide

<400> SEQUENCE: 7

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Ser Asn Tyr
            20                  25                  30

Leu Asn Trp Tyr Gln Gln Lys Pro Gly Lys Ala Val Lys Leu Leu Ile
        35                  40                  45

Tyr Tyr Thr Ser Ile Leu His Ser Gly Val Pro Ser Arg Phe Ser Gly
    50                  55                  60

Ser Gly Ser Gly Thr Asp Tyr Thr Leu Thr Ile Ser Ser Leu Gln Gln
65                  70                  75                  80

Glu Asp Phe Ala Thr Tyr Phe Cys Gln Gln Gly Asn Thr Leu Pro Trp
                85                  90                  95

Thr Phe Gly Gly Gly Thr Lys Val Glu Ile Lys Arg
            100                 105

<210> SEQ ID NO 8
<211> LENGTH: 108
<212> TYPE: PRT
<213> ORGANISM: Artificial sequence
<220> FEATURE:
<223> OTHER INFORMATION: Synthetic polypeptide

<400> SEQUENCE: 8

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Ser Asn Tyr
            20                  25                  30

Leu Asn Trp Tyr Gln Gln Lys Pro Gly Lys Ala Val Lys Leu Leu Ile
        35                  40                  45

Tyr Tyr Thr Ser Ile Leu His Ser Gly Val Pro Ser Arg Phe Ser Gly
    50                  55                  60

Ser Gly Ser Gly Thr Asp Tyr Thr Leu Thr Ile Ser Ser Leu Gln Pro
65                  70                  75                  80

Glu Asp Phe Ala Thr Tyr Phe Cys Gln Gln Gly Asn Thr Leu Pro Trp
                85                  90                  95

Thr Phe Gly Gly Gly Thr Lys Val Glu Ile Lys Arg
            100                 105

<210> SEQ ID NO 9
<211> LENGTH: 108
<212> TYPE: PRT
<213> ORGANISM: Artificial sequence
<220> FEATURE:
<223> OTHER INFORMATION: Synthetic polypeptide
```

<400> SEQUENCE: 9

```
Asp Ile Gln Met Thr Gln Ser Pro Ser Ser Val Ser Ala Ser Val Gly
1               5                   10                  15

Asp Arg Val Thr Ile Thr Cys Arg Ala Ser Gln Asp Ile Ser Asn Tyr
            20                  25                  30

Leu Asn Trp Tyr Gln Gln Lys Pro Gly Lys Ala Pro Lys Leu Leu Ile
        35                  40                  45

Tyr Tyr Thr Ser Ile Leu His Ser Gly Val Pro Ser Arg Phe Ser Gly
    50                  55                  60

Ser Gly Ser Gly Thr Asp Tyr Thr Leu Thr Ile Ser Ser Leu Gln Pro
65                  70                  75                  80

Glu Asp Phe Ala Thr Tyr Phe Cys Gln Gln Gly Asn Thr Leu Pro Trp
                85                  90                  95

Thr Phe Gly Gly Gly Thr Lys Val Glu Ile Lys Arg
            100                 105
```

<210> SEQ ID NO 10
<211> LENGTH: 6
<212> TYPE: PRT
<213> ORGANISM: Artificial sequence
<220> FEATURE:
<223> OTHER INFORMATION: Synthetic polypeptide
<220> FEATURE:
<221> NAME/KEY: MISC_FEATURE
<222> LOCATION: (1)..(1)
<223> OTHER INFORMATION: Xaa may be present or absent, when present, may
      be any amino acid, with the proviso that when the sequence is at
      the N-terminus of the conjugate, Xaa is present
<220> FEATURE:
<221> NAME/KEY: MISC_FEATURE
<222> LOCATION: (2)..(2)
<223> OTHER INFORMATION: Xaa is the modified amino acid residue of
      formula (I), FGly'
<220> FEATURE:
<221> NAME/KEY: MISC_FEATURE
<222> LOCATION: (3)..(3)
<223> OTHER INFORMATION: Xaa may be any amino acid
<220> FEATURE:
<221> NAME/KEY: MISC_FEATURE
<222> LOCATION: (4)..(4)
<223> OTHER INFORMATION: Xaa may be Pro or Ala
<220> FEATURE:
<221> NAME/KEY: MISC_FEATURE
<222> LOCATION: (5)..(5)
<223> OTHER INFORMATION: Xaa may be any amino acid
<220> FEATURE:
<221> NAME/KEY: MISC_FEATURE
<222> LOCATION: (6)..(6)
<223> OTHER INFORMATION: Xaa may be a basic or an aliphatic amino acid

<400> SEQUENCE: 10

```
Xaa Xaa Xaa Xaa Xaa Xaa
1               5
```

<210> SEQ ID NO 11
<211> LENGTH: 6
<212> TYPE: PRT
<213> ORGANISM: Artificial sequence
<220> FEATURE:
<223> OTHER INFORMATION: Synthetic polypeptide
<220> FEATURE:
<221> NAME/KEY: MISC_FEATURE
<222> LOCATION: (2)..(2)
<223> OTHER INFORMATION: Xaa is the modified amino acid residue of
      formula (I), FGly'

<400> SEQUENCE: 11

```
Leu Xaa Thr Pro Ser Arg
1               5
```

<210> SEQ ID NO 12
<211> LENGTH: 7
<212> TYPE: PRT
<213> ORGANISM: Artificial sequence
<220> FEATURE:
<223> OTHER INFORMATION: Synthetic polypeptide

<400> SEQUENCE: 12

```
Ser Leu Ser Leu Ser Pro Gly
1               5
```

<210> SEQ ID NO 13
<211> LENGTH: 12
<212> TYPE: PRT
<213> ORGANISM: Artificial sequence
<220> FEATURE:
<223> OTHER INFORMATION: Synthetic polypeptide
<220> FEATURE:
<221> NAME/KEY: MISC_FEATURE
<222> LOCATION: (6)..(6)
<223> OTHER INFORMATION: Xaa is the modified amino acid residue of
      formula (I), FGly'

<400> SEQUENCE: 13

```
Ser Pro Gly Ser Leu Xaa Thr Pro Ser Arg Gly Ser
1               5                   10
```

<210> SEQ ID NO 14
<211> LENGTH: 6
<212> TYPE: PRT
<213> ORGANISM: Artificial sequence
<220> FEATURE:
<223> OTHER INFORMATION: Synthetic polypeptide

<400> SEQUENCE: 14

```
Lys Val Asp Asn Ala Leu
1               5
```

<210> SEQ ID NO 15
<211> LENGTH: 6
<212> TYPE: PRT
<213> ORGANISM: Artificial sequence
<220> FEATURE:
<223> OTHER INFORMATION: Synthetic polypeptide

<400> SEQUENCE: 15

```
Gln Ser Gly Asn Ser Gln
1               5
```

<210> SEQ ID NO 16
<211> LENGTH: 17
<212> TYPE: PRT
<213> ORGANISM: Artificial sequence
<220> FEATURE:
<223> OTHER INFORMATION: Synthetic polypeptide
<220> FEATURE:
<221> NAME/KEY: MISC_FEATURE
<222> LOCATION: (7)..(7)
<223> OTHER INFORMATION: Xaa is the modified amino acid residue of
      formula (I), FGly'

<400> SEQUENCE: 16

```
Lys Val Asp Asn Ala Leu Xaa Thr Pro Ser Arg Gln Ser Gly Asn Ser
1               5                   10                  15

Gln
```

```
<210> SEQ ID NO 17
<211> LENGTH: 6
<212> TYPE: PRT
<213> ORGANISM: Artificial sequence
<220> FEATURE:
<223> OTHER INFORMATION: Synthetic polypeptide

<400> SEQUENCE: 17

Ser Trp Asn Ser Gly Ala
1               5

<210> SEQ ID NO 18
<211> LENGTH: 6
<212> TYPE: PRT
<213> ORGANISM: Artificial sequence
<220> FEATURE:
<223> OTHER INFORMATION: Synthetic polypeptide

<400> SEQUENCE: 18

Gly Val His Thr Phe Pro
1               5

<210> SEQ ID NO 19
<211> LENGTH: 18
<212> TYPE: PRT
<213> ORGANISM: Artificial sequence
<220> FEATURE:
<223> OTHER INFORMATION: Synthetic polypeptide
<220> FEATURE:
<221> NAME/KEY: MISC_FEATURE
<222> LOCATION: (8)..(8)
<223> OTHER INFORMATION: Xaa is the modified amino acid residue of
      formula (I), FGly'

<400> SEQUENCE: 19

Ser Trp Asn Ser Gly Ala Leu Xaa Thr Pro Ser Arg Gly Val His Thr
1               5                   10                  15

Phe Pro

<210> SEQ ID NO 20
<211> LENGTH: 5
<212> TYPE: PRT
<213> ORGANISM: Artificial sequence
<220> FEATURE:
<223> OTHER INFORMATION: Synthetic polypeptide
<220> FEATURE:
<221> NAME/KEY: MISC_FEATURE
<222> LOCATION: (2)..(2)
<223> OTHER INFORMATION: Xaa may be Ser, Thr, Ala or Gly.
<220> FEATURE:
<221> NAME/KEY: MISC_FEATURE
<222> LOCATION: (4)..(4)
<223> OTHER INFORMATION: Xaa may be Ser, Thr, Ala or Gly.

<400> SEQUENCE: 20

Cys Xaa Pro Xaa Arg
1               5

<210> SEQ ID NO 21
<211> LENGTH: 759
<212> TYPE: PRT
<213> ORGANISM: Homo sapiens

<400> SEQUENCE: 21

Met His Leu Leu Gly Pro Trp Leu Leu Leu Val Leu Glu Tyr Leu
1               5                   10                  15
```

```
Ala Phe Ser Asp Ser Ser Lys Trp Val Phe Glu His Pro Glu Thr Leu
                20                  25                  30

Tyr Ala Trp Glu Gly Ala Cys Val Trp Ile Pro Cys Thr Tyr Arg Ala
            35                  40                  45

Leu Asp Gly Asp Leu Glu Ser Phe Ile Leu Phe His Asn Pro Glu Tyr
        50                  55                  60

Asn Lys Asn Thr Ser Lys Phe Asp Gly Thr Arg Leu Tyr Glu Ser Thr
 65                  70                  75                  80

Lys Asp Gly Lys Val Pro Ser Glu Gln Lys Arg Val Gln Phe Leu Gly
                85                  90                  95

Asp Lys Asn Lys Asn Cys Thr Leu Ser Ile His Pro Val His Leu Asn
            100                 105                 110

Asp Ser Gly Gln Leu Gly Leu Arg Met Glu Ser Lys Thr Glu Lys Trp
        115                 120                 125

Met Glu Arg Ile His Leu Asn Val Ser Glu Arg Pro Phe Pro Pro His
130                 135                 140

Ile Gln Leu Pro Pro Glu Ile Gln Glu Ser Gln Glu Val Thr Leu Thr
145                 150                 155                 160

Cys Leu Leu Asn Phe Ser Cys Tyr Gly Tyr Pro Ile Gln Leu Gln Trp
                165                 170                 175

Leu Leu Glu Gly Val Pro Met Arg Gln Ala Ala Val Thr Ser Thr Ser
            180                 185                 190

Leu Thr Ile Lys Ser Val Phe Thr Arg Ser Glu Leu Lys Phe Ser Pro
        195                 200                 205

Gln Trp Ser His His Gly Lys Ile Val Thr Cys Gln Leu Gln Asp Ala
210                 215                 220

Asp Gly Lys Phe Leu Ser Asn Asp Thr Val Gln Leu Asn Val Lys His
225                 230                 235                 240

Thr Pro Lys Leu Glu Ile Lys Val Thr Pro Ser Asp Ala Ile Val Arg
                245                 250                 255

Glu Gly Asp Ser Val Thr Met Thr Cys Glu Val Ser Ser Ser Asn Pro
            260                 265                 270

Glu Tyr Thr Thr Val Ser Trp Leu Lys Asp Gly Thr Ser Leu Lys Lys
        275                 280                 285

Gln Asn Thr Phe Thr Leu Asn Leu Arg Glu Val Thr Lys Asp Gln Ser
290                 295                 300

Gly Lys Tyr Cys Cys Gln Val Ser Asn Asp Val Gly Pro Gly Arg Ser
305                 310                 315                 320

Glu Glu Val Phe Leu Gln Val Gln Tyr Pro Pro Lys Lys Val Thr Thr
                325                 330                 335

Val Ile Gln Asn Pro Met Pro Ile Arg Glu Gly Asp Thr Val Thr Leu
            340                 345                 350

Ser Cys Asn Tyr Asn Ser Ser Asn Pro Ser Val Thr Arg Tyr Glu Trp
        355                 360                 365

Lys Pro His Gly Ala Trp Glu Glu Pro Ser Leu Gly Val Leu Lys Ile
370                 375                 380

Gln Asn Val Gly Trp Asp Asn Thr Thr Ile Ala Cys Ala Ala Cys Asn
385                 390                 395                 400

Ser Trp Cys Ser Trp Ala Ser Pro Val Ala Leu Asn Val Gln Tyr Ala
                405                 410                 415

Pro Arg Asp Val Arg Val Arg Lys Ile Lys Pro Leu Ser Glu Ile His
            420                 425                 430

Ser Gly Asn Ser Val Ser Leu Gln Cys Asp Phe Ser Ser Ser His Pro
```

-continued

```
                435                 440                 445
Lys Glu Val Gln Phe Phe Trp Glu Lys Asn Gly Arg Leu Leu Gly Lys
450                 455                 460

Glu Ser Gln Leu Asn Phe Asp Ser Ile Ser Pro Glu Asp Ala Gly Ser
465                 470                 475                 480

Tyr Ser Cys Trp Val Asn Asn Ser Ile Gly Gln Thr Ala Ser Lys Ala
                485                 490                 495

Trp Thr Leu Glu Val Leu Tyr Ala Pro Arg Arg Leu Arg Val Ser Met
                500                 505                 510

Ser Pro Gly Asp Gln Val Met Glu Gly Lys Ser Ala Thr Leu Thr Cys
                515                 520                 525

Glu Ser Asp Ala Asn Pro Pro Val Ser His Tyr Thr Trp Phe Asp Trp
530                 535                 540

Asn Asn Gln Ser Leu Pro Tyr His Ser Gln Lys Leu Arg Leu Glu Pro
545                 550                 555                 560

Val Lys Val Gln His Ser Gly Ala Tyr Trp Cys Gln Gly Thr Asn Ser
                565                 570                 575

Val Gly Lys Gly Arg Ser Pro Leu Ser Thr Leu Thr Val Tyr Tyr Ser
                580                 585                 590

Pro Glu Thr Ile Gly Arg Arg Val Ala Val Gly Leu Gly Ser Cys Leu
                595                 600                 605

Ala Ile Leu Ile Leu Ala Ile Cys Gly Leu Lys Leu Gln Arg Arg Trp
610                 615                 620

Lys Arg Thr Gln Ser Gln Gln Gly Leu Gln Glu Asn Ser Ser Gly Gln
625                 630                 635                 640

Ser Phe Phe Val Arg Asn Lys Lys Val Arg Arg Ala Pro Leu Ser Glu
                645                 650                 655

Gly Pro His Ser Leu Gly Cys Tyr Asn Pro Met Met Glu Asp Gly Ile
                660                 665                 670

Ser Tyr Thr Thr Leu Arg Phe Pro Glu Met Asn Ile Pro Arg Thr Gly
                675                 680                 685

Asp Ala Glu Ser Ser Glu Met Gln Arg Pro Pro Asp Cys Asp Asp
690                 695                 700

Thr Val Thr Tyr Ser Ala Leu His Lys Arg Gln Val Gly Asp Tyr Glu
705                 710                 715                 720

Asn Val Ile Pro Asp Phe Pro Glu Asp Glu Gly Ile His Tyr Ser Glu
                725                 730                 735

Leu Ile Gln Phe Gly Val Gly Glu Arg Pro Gln Ala Gln Glu Asn Val
                740                 745                 750

Asp Tyr Val Ile Leu Lys His
                755

<210> SEQ ID NO 22
<211> LENGTH: 670
<212> TYPE: PRT
<213> ORGANISM: Homo sapiens

<400> SEQUENCE: 22

Met His Leu Leu Gly Pro Trp Leu Leu Leu Val Leu Glu Tyr Leu
1               5                   10                  15

Ala Phe Ser Asp Ser Ser Lys Trp Val Phe Glu His Pro Glu Thr Leu
                20                  25                  30

Tyr Ala Trp Glu Gly Ala Cys Val Trp Ile Pro Cys Thr Tyr Arg Ala
                35                  40                  45
```

```
Leu Asp Gly Asp Leu Glu Ser Phe Ile Leu Phe His Asn Pro Glu Tyr
 50                  55                  60

Asn Lys Asn Thr Ser Lys Phe Asp Gly Thr Arg Leu Tyr Glu Ser Thr
 65                  70                  75                  80

Lys Asp Gly Lys Val Pro Ser Glu Gln Lys Arg Val Gln Phe Leu Gly
                 85                  90                  95

Asp Lys Asn Lys Asn Cys Thr Leu Ser Ile His Pro Val His Leu Asn
                100                 105                 110

Asp Ser Gly Gln Leu Gly Leu Arg Met Glu Ser Lys Thr Glu Lys Trp
                115                 120                 125

Met Glu Arg Ile His Leu Asn Val Ser Glu Arg Pro Phe Pro Pro His
130                 135                 140

Ile Gln Leu Pro Pro Glu Ile Gln Glu Ser Gln Glu Val Thr Leu Thr
145                 150                 155                 160

Cys Leu Leu Asn Phe Ser Cys Tyr Gly Tyr Pro Ile Gln Leu Gln Trp
                165                 170                 175

Leu Leu Glu Gly Val Pro Met Arg Gln Ala Ala Val Thr Ser Thr Ser
                180                 185                 190

Leu Thr Ile Lys Ser Val Phe Thr Arg Ser Glu Leu Lys Phe Ser Pro
                195                 200                 205

Gln Trp Ser His His Gly Lys Ile Val Thr Cys Gln Leu Gln Asp Ala
210                 215                 220

Asp Gly Lys Phe Leu Ser Asn Asp Thr Val Gln Leu Asn Val Lys His
225                 230                 235                 240

Pro Pro Lys Lys Val Thr Thr Val Ile Gln Asn Pro Met Pro Ile Arg
                245                 250                 255

Glu Gly Asp Thr Val Thr Leu Ser Cys Asn Tyr Asn Ser Ser Asn Pro
                260                 265                 270

Ser Val Thr Arg Tyr Glu Trp Lys Pro His Gly Ala Trp Glu Glu Pro
                275                 280                 285

Ser Leu Gly Val Leu Lys Ile Gln Asn Val Gly Trp Asp Asn Thr Thr
                290                 295                 300

Ile Ala Cys Ala Ala Cys Asn Ser Trp Cys Ser Trp Ala Ser Pro Val
305                 310                 315                 320

Ala Leu Asn Val Gln Tyr Ala Pro Arg Asp Val Arg Val Arg Lys Ile
                325                 330                 335

Lys Pro Leu Ser Glu Ile His Ser Gly Asn Ser Val Ser Leu Gln Cys
                340                 345                 350

Asp Phe Ser Ser Ser His Pro Lys Glu Val Gln Phe Phe Trp Glu Lys
                355                 360                 365

Asn Gly Arg Leu Leu Gly Lys Glu Ser Gln Leu Asn Phe Asp Ser Ile
370                 375                 380

Ser Pro Glu Asp Ala Gly Ser Tyr Ser Cys Trp Val Asn Asn Ser Ile
385                 390                 395                 400

Gly Gln Thr Ala Ser Lys Ala Trp Thr Leu Glu Val Leu Tyr Ala Pro
                405                 410                 415

Arg Arg Leu Arg Val Ser Met Ser Pro Gly Asp Gln Val Met Glu Gly
                420                 425                 430

Lys Ser Ala Thr Leu Thr Cys Glu Ser Asp Ala Asn Pro Pro Val Ser
                435                 440                 445

His Tyr Thr Trp Phe Asp Trp Asn Asn Gln Ser Leu Pro Tyr His Ser
450                 455                 460

Gln Lys Leu Arg Leu Glu Pro Val Lys Val Gln His Ser Gly Ala Tyr
```

```
            465                 470                 475                 480
        Trp Cys Gln Gly Thr Asn Ser Val Gly Lys Gly Arg Ser Pro Leu Ser
                        485                 490                 495
        Thr Leu Thr Val Tyr Tyr Ser Pro Glu Thr Ile Gly Arg Arg Val Ala
                        500                 505                 510
        Val Gly Leu Gly Ser Cys Leu Ala Ile Leu Ile Leu Ala Ile Cys Gly
                        515                 520                 525
        Leu Lys Leu Gln Arg Arg Trp Lys Arg Thr Gln Ser Gln Gln Gly Leu
                        530                 535                 540
        Gln Glu Asn Ser Ser Gly Gln Ser Phe Phe Val Arg Asn Lys Lys Val
        545                 550                 555                 560
        Arg Arg Ala Pro Leu Ser Glu Gly Pro His Ser Leu Gly Cys Tyr Asn
                        565                 570                 575
        Pro Met Met Glu Asp Gly Ile Ser Tyr Thr Thr Leu Arg Phe Pro Glu
                        580                 585                 590
        Met Asn Ile Pro Arg Thr Gly Asp Ala Glu Ser Ser Glu Met Gln Arg
                        595                 600                 605
        Pro Pro Pro Asp Cys Asp Asp Thr Val Thr Tyr Ser Ala Leu His Lys
        610                 615                 620
        Arg Gln Val Gly Asp Tyr Glu Asn Val Ile Pro Asp Phe Pro Glu Asp
        625                 630                 635                 640
        Glu Gly Ile His Tyr Ser Glu Leu Ile Gln Phe Gly Val Gly Glu Arg
                        645                 650                 655
        Pro Gln Ala Gln Glu Asn Val Asp Tyr Val Ile Leu Lys His
                        660                 665                 670

<210> SEQ ID NO 23
<211> LENGTH: 846
<212> TYPE: PRT
<213> ORGANISM: Homo sapiens

<400> SEQUENCE: 23

Met His Leu Leu Gly Pro Trp Leu Leu Leu Val Leu Glu Tyr Leu
1               5                   10                  15

Ala Phe Ser Asp Ser Ser Lys Trp Val Phe Glu His Pro Glu Thr Leu
                20                  25                  30

Tyr Ala Trp Glu Gly Ala Cys Val Trp Ile Pro Cys Thr Tyr Arg Ala
                35                  40                  45

Leu Asp Gly Asp Leu Glu Ser Phe Ile Leu Phe His Asn Pro Glu Tyr
            50                  55                  60

Asn Lys Asn Thr Ser Lys Phe Asp Gly Thr Arg Leu Tyr Glu Ser Thr
65                  70                  75                  80

Lys Asp Gly Lys Val Pro Ser Glu Gln Lys Arg Val Gln Phe Leu Gly
                85                  90                  95

Asp Lys Asn Lys Asn Cys Thr Leu Ser Ile His Pro Val His Leu Asn
                100                 105                 110

Asp Ser Gly Gln Leu Gly Leu Arg Met Glu Ser Lys Thr Glu Lys Trp
            115                 120                 125

Met Glu Arg Ile His Leu Asn Val Ser Glu Arg Pro Phe Pro Pro His
        130                 135                 140

Ile Gln Leu Pro Pro Glu Ile Gln Glu Ser Gln Glu Val Thr Leu Thr
145                 150                 155                 160

Cys Leu Leu Asn Phe Ser Cys Tyr Gly Tyr Pro Ile Gln Leu Gln Trp
                165                 170                 175
```

-continued

Leu Leu Glu Gly Val Pro Met Arg Gln Ala Ala Val Thr Ser Thr Ser
            180                 185                 190

Leu Thr Ile Lys Ser Val Phe Thr Arg Ser Glu Leu Lys Phe Ser Pro
            195                 200             205

Gln Trp Ser His His Gly Lys Ile Val Thr Cys Gln Leu Gln Asp Ala
            210                 215                 220

Asp Gly Lys Phe Leu Ser Asn Asp Thr Val Gln Leu Asn Val Lys His
225                 230                 235                 240

Thr Pro Lys Leu Glu Ile Lys Val Thr Pro Ser Asp Ala Ile Val Arg
                        245                 250                 255

Glu Gly Asp Ser Val Thr Met Thr Cys Glu Val Ser Ser Ser Asn Pro
                260                 265                 270

Glu Tyr Thr Thr Val Ser Trp Leu Lys Asp Gly Thr Ser Leu Lys Lys
            275                 280                 285

Gln Asn Thr Phe Thr Leu Asn Leu Arg Glu Val Thr Lys Asp Gln Ser
290                 295                 300

Gly Lys Tyr Cys Cys Gln Val Ser Asn Asp Val Gly Pro Gly Arg Ser
305                 310                 315                 320

Glu Glu Val Phe Leu Gln Val Gln Tyr Ala Pro Glu Pro Ser Thr Val
                        325                 330                 335

Gln Ile Leu His Ser Pro Ala Val Glu Gly Ser Gln Val Glu Phe Leu
                340                 345                 350

Cys Met Ser Leu Ala Asn Pro Leu Pro Thr Asn Tyr Thr Trp Tyr His
            355                 360                 365

Asn Gly Lys Glu Met Gln Gly Arg Thr Glu Glu Lys Val His Ile Pro
370                 375                 380

Lys Ile Leu Pro Trp His Ala Gly Thr Tyr Ser Cys Val Ala Glu Asn
385                 390                 395                 400

Ile Leu Gly Thr Gly Gln Arg Gly Pro Gly Ala Glu Leu Asp Val Gln
                        405                 410                 415

Tyr Pro Pro Lys Lys Val Thr Thr Val Ile Gln Asn Pro Met Pro Ile
                420                 425                 430

Arg Glu Gly Asp Thr Val Thr Leu Ser Cys Asn Tyr Asn Ser Ser Asn
            435                 440                 445

Pro Ser Val Thr Arg Tyr Glu Trp Lys Pro His Gly Ala Trp Glu Glu
450                 455                 460

Pro Ser Leu Gly Val Leu Lys Ile Gln Asn Val Gly Trp Asp Asn Thr
465                 470                 475                 480

Thr Ile Ala Cys Ala Ala Cys Asn Ser Trp Cys Ser Trp Ala Ser Pro
                        485                 490                 495

Val Ala Leu Asn Val Gln Tyr Ala Pro Arg Asp Val Arg Val Arg Lys
                500                 505                 510

Ile Lys Pro Leu Ser Glu Ile His Ser Gly Asn Ser Val Ser Leu Gln
            515                 520                 525

Cys Asp Phe Ser Ser Ser His Pro Lys Glu Val Gln Phe Phe Trp Glu
530                 535                 540

Lys Asn Gly Arg Leu Leu Gly Lys Glu Ser Gln Leu Asn Phe Asp Ser
545                 550                 555                 560

Ile Ser Pro Glu Asp Ala Gly Ser Tyr Ser Cys Trp Val Asn Asn Ser
                        565                 570                 575

Ile Gly Gln Thr Ala Ser Lys Ala Trp Thr Leu Glu Val Leu Tyr Ala
                580                 585                 590

Pro Arg Arg Leu Arg Val Ser Met Ser Pro Gly Asp Gln Val Met Glu

```
                    595                 600                 605
Gly Lys Ser Ala Thr Leu Thr Cys Glu Ser Asp Ala Asn Pro Pro Val
    610                 615                 620

Ser His Tyr Thr Trp Phe Asp Trp Asn Asn Gln Ser Leu Pro Tyr His
625                 630                 635                 640

Ser Gln Lys Leu Arg Leu Glu Pro Val Lys Val Gln His Ser Gly Ala
            645                 650                 655

Tyr Trp Cys Gln Gly Thr Asn Ser Val Gly Lys Gly Arg Ser Pro Leu
                660                 665                 670

Ser Thr Leu Thr Val Tyr Tyr Ser Pro Glu Thr Ile Gly Arg Arg Val
            675                 680                 685

Ala Val Gly Leu Gly Ser Cys Leu Ala Ile Leu Ile Leu Ala Ile Cys
    690                 695                 700

Gly Leu Lys Leu Gln Arg Arg Trp Lys Arg Thr Gln Ser Gln Gln Gly
705                 710                 715                 720

Leu Gln Glu Asn Ser Ser Gly Gln Ser Phe Phe Val Arg Asn Lys Lys
                725                 730                 735

Val Arg Arg Ala Pro Leu Ser Glu Gly Pro His Ser Leu Gly Cys Tyr
            740                 745                 750

Asn Pro Met Met Glu Asp Gly Ile Ser Tyr Thr Thr Leu Arg Phe Pro
                755                 760                 765

Glu Met Asn Ile Pro Arg Thr Gly Asp Ala Glu Ser Ser Glu Met Gln
770                 775                 780

Arg Pro Pro Pro Asp Cys Asp Asp Thr Val Thr Tyr Ser Ala Leu His
785                 790                 795                 800

Lys Arg Gln Val Gly Asp Tyr Glu Asn Val Ile Pro Asp Phe Pro Glu
            805                 810                 815

Asp Glu Gly Ile His Tyr Ser Glu Leu Ile Gln Phe Gly Val Gly Glu
                820                 825                 830

Arg Pro Gln Ala Gln Glu Asn Val Asp Tyr Val Ile Leu Lys
            835                 840                 845

<210> SEQ ID NO 24
<211> LENGTH: 751
<212> TYPE: PRT
<213> ORGANISM: Homo sapiens

<400> SEQUENCE: 24

Met His Leu Leu Gly Pro Trp Leu Leu Leu Leu Val Leu Glu Tyr Leu
1               5                   10                  15

Ala Phe Ser Asp Ser Ser Lys Trp Val Phe Glu His Pro Glu Thr Leu
            20                  25                  30

Tyr Ala Trp Glu Gly Ala Cys Val Trp Ile Pro Cys Thr Tyr Arg Ala
        35                  40                  45

Leu Asp Gly Asp Leu Glu Ser Phe Ile Leu Phe His Asn Pro Glu Tyr
    50                  55                  60

Asn Lys Asn Thr Ser Lys Phe Asp Gly Thr Arg Leu Tyr Glu Ser Thr
65                  70                  75                  80

Lys Asp Gly Lys Val Pro Ser Glu Gln Lys Arg Val Gln Phe Leu Gly
                85                  90                  95

Asp Lys Asn Lys Asn Cys Thr Leu Ser Ile His Pro Val His Leu Asn
            100                 105                 110

Asp Ser Gly Gln Leu Gly Leu Arg Met Glu Ser Lys Thr Glu Lys Trp
        115                 120                 125
```

```
Met Glu Arg Ile His Leu Asn Val Ser Glu Arg Pro Phe Pro His
        130                 135                 140

Ile Gln Leu Pro Pro Glu Ile Gln Glu Ser Gln Glu Val Thr Leu Thr
145                 150                 155                 160

Cys Leu Leu Asn Phe Ser Cys Tyr Gly Tyr Pro Ile Gln Leu Gln Trp
                165                 170                 175

Leu Leu Glu Gly Val Pro Met Arg Gln Ala Ala Val Thr Ser Thr Ser
            180                 185                 190

Leu Thr Ile Lys Ser Val Phe Thr Arg Ser Glu Leu Lys Phe Ser Pro
        195                 200                 205

Gln Trp Ser His His Gly Lys Ile Val Thr Cys Gln Leu Gln Asp Ala
210                 215                 220

Asp Gly Lys Phe Leu Ser Asn Asp Thr Val Gln Leu Asn Val Lys His
225                 230                 235                 240

Thr Pro Lys Leu Glu Ile Lys Val Thr Pro Ser Asp Ala Ile Val Arg
                245                 250                 255

Glu Gly Asp Ser Val Thr Met Thr Cys Glu Val Ser Ser Ser Asn Pro
            260                 265                 270

Glu Tyr Thr Thr Val Ser Trp Leu Lys Asp Gly Thr Ser Leu Lys Lys
        275                 280                 285

Gln Asn Thr Phe Thr Leu Asn Leu Arg Glu Val Thr Lys Asp Gln Ser
290                 295                 300

Gly Lys Tyr Cys Cys Gln Val Ser Asn Asp Val Gly Pro Gly Arg Ser
305                 310                 315                 320

Glu Glu Val Phe Leu Gln Val Gln Tyr Ala Pro Glu Pro Ser Thr Val
                325                 330                 335

Gln Ile Leu His Ser Pro Ala Val Glu Gly Ser Gln Val Glu Phe Leu
            340                 345                 350

Cys Met Ser Leu Ala Asn Pro Leu Pro Thr Asn Tyr Thr Trp Tyr His
        355                 360                 365

Asn Gly Lys Glu Met Gln Gly Arg Thr Glu Glu Lys Val His Ile Pro
370                 375                 380

Lys Ile Leu Pro Trp His Ala Gly Thr Tyr Ser Cys Val Ala Glu Asn
385                 390                 395                 400

Ile Leu Gly Thr Gly Gln Arg Gly Pro Gly Ala Glu Leu Asp Val Gln
                405                 410                 415

Tyr Pro Pro Lys Lys Val Thr Thr Val Ile Gln Asn Pro Met Pro Ile
            420                 425                 430

Arg Glu Gly Asp Thr Val Thr Leu Ser Cys Asn Tyr Asn Ser Ser Asn
        435                 440                 445

Pro Ser Val Thr Arg Tyr Glu Trp Lys Pro His Gly Ala Trp Glu Glu
450                 455                 460

Pro Ser Leu Gly Val Leu Lys Ile Gln Asn Val Gly Trp Asp Asn Thr
465                 470                 475                 480

Thr Ile Ala Cys Ala Ala Cys Asn Ser Trp Cys Ser Trp Ala Ser Pro
                485                 490                 495

Val Ala Leu Asn Val Gln Tyr Ala Pro Arg Asp Val Arg Val Arg Lys
            500                 505                 510

Ile Lys Pro Leu Ser Glu Ile His Ser Gly Asn Ser Val Ser Leu Gln
        515                 520                 525

Cys Asp Phe Ser Ser Ser His Pro Lys Glu Val Gln Phe Phe Trp Glu
530                 535                 540

Lys Asn Gly Arg Leu Leu Gly Lys Glu Ser Gln Leu Asn Phe Asp Ser
```

```
                545                 550                 555                 560
            Ile Ser Pro Glu Asp Ala Gly Ser Tyr Ser Cys Trp Val Asn Asn Ser
                            565                 570                 575

Ile Gly Gln Thr Ala Ser Lys Ala Trp Thr Leu Glu Val Leu Tyr Ala
                        580                 585                 590

Pro Arg Arg Leu Arg Val Ser Met Ser Pro Gly Asp Gln Val Met Glu
                        595                 600                 605

Gly Lys Ser Ala Thr Leu Thr Cys Glu Ser Asp Ala Asn Pro Pro Val
                        610                 615                 620

Ser His Tyr Thr Trp Phe Asp Trp Asn Asn Gln Ser Leu Pro Tyr His
            625                 630                 635                 640

Ser Gln Lys Leu Arg Leu Glu Pro Val Lys Val Gln His Ser Gly Ala
                            645                 650                 655

Tyr Trp Cys Gln Gly Thr Asn Ser Val Gly Lys Gly Arg Ser Pro Leu
                        660                 665                 670

Ser Thr Leu Thr Val Tyr Tyr Ser Pro Glu Thr Ile Gly Arg Arg Val
                        675                 680                 685

Ala Val Gly Leu Gly Ser Cys Leu Ala Ile Leu Ile Leu Ala Ile Cys
                        690                 695                 700

Gly Leu Lys Leu Gln Arg Arg Trp Lys Arg Thr Gln Ser Gln Gln Gly
            705                 710                 715                 720

Leu Gln Glu Asn Ser Ser Gly Gln Ser Phe Phe Val Arg Asn Lys Lys
                            725                 730                 735

Arg Cys Arg Val Leu Arg Asp Ala Glu Thr Ser Pro Gly Leu Arg
                        740                 745                 750

<210> SEQ ID NO 25
<211> LENGTH: 107
<212> TYPE: PRT
<213> ORGANISM: Homo sapiens

<400> SEQUENCE: 25

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105

<210> SEQ ID NO 26
<211> LENGTH: 330
<212> TYPE: PRT
<213> ORGANISM: Homo sapiens

<400> SEQUENCE: 26

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
```

```
                   20                  25                  30

Phe Pro Glu Pro Val Thr Val Ser Trp Asn Ser Gly Ala Leu Thr Ser
                35                  40                  45

Gly Val His Thr Phe Pro Ala Val Leu Gln Ser Ser Gly Leu Tyr Ser
            50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 27
<211> LENGTH: 330
<212> TYPE: PRT
<213> ORGANISM: Homo sapiens

<400> SEQUENCE: 27

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60
```

-continued

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
            85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
            115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
            165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
            195                 200                 205

Lys Ala Leu Pro Ala Pro Ile Glu Lys Thr Ile Ser Lys Ala Lys Gly
            210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
            245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
            275                 280                 285

Leu Tyr Ser Lys Leu Thr Val Asp Lys Ser Arg Trp Gln Gln Gly Asn
290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
            325                 330

<210> SEQ ID NO 28
<211> LENGTH: 326
<212> TYPE: PRT
<213> ORGANISM: Homo sapiens

<400> SEQUENCE: 28

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
            50                  55                  60

Leu Ser Ser Val Val Thr Val Pro Ser Ser Asn Phe Gly Thr Gln Thr
65                  70                  75                  80

Tyr Thr Cys Asn Val Asp His Lys Pro Ser Asn Thr Lys Val Asp Lys
            85                  90                  95

Thr Val Glu Arg Lys Cys Cys Val Glu Cys Pro Pro Cys Pro Ala Pro
            100                 105                 110

```
Pro Val Ala Gly Pro Ser Val Phe Leu Phe Pro Pro Lys Pro Lys Asp
            115                 120                 125

Thr Leu Met Ile Ser Arg Thr Pro Glu Val Thr Cys Val Val Val Asp
130                 135                 140

Val Ser His Glu Asp Pro Glu Val Gln Phe Asn Trp Tyr Val Asp Gly
145                 150                 155                 160

Val Glu Val His Asn Ala Lys Thr Lys Pro Arg Glu Glu Gln Phe Asn
                165                 170                 175

Ser Thr Phe Arg Val Val Ser Val Leu Thr Val Val His Gln Asp Trp
            180                 185                 190

Leu Asn Gly Lys Glu Tyr Lys Cys Lys Val Ser Asn Lys Gly Leu Pro
        195                 200                 205

Ala Pro Ile Glu Lys Thr Ile Ser Lys Thr Lys Gly Gln Pro Arg Glu
    210                 215                 220

Pro Gln Val Tyr Thr Leu Pro Pro Ser Arg Glu Glu Met Thr Lys Asn
225                 230                 235                 240

Gln Val Ser Leu Thr Cys Leu Val Lys Gly Phe Tyr Pro Ser Asp Ile
                245                 250                 255

Ser Val Glu Trp Glu Ser Asn Gly Gln Pro Glu Asn Asn Tyr Lys Thr
            260                 265                 270

Thr Pro Pro Met Leu Asp Ser Asp Gly Ser Phe Phe Leu Tyr Ser Lys
        275                 280                 285

Leu Thr Val Asp Lys Ser Arg Trp Gln Gln Gly Asn Val Phe Ser Cys
    290                 295                 300

Ser Val Met His Glu Ala Leu His Asn His Tyr Thr Gln Lys Ser Leu
305                 310                 315                 320

Ser Leu Ser Pro Gly Lys
                325

<210> SEQ ID NO 29
<211> LENGTH: 377
<212> TYPE: PRT
<213> ORGANISM: Homo sapiens

<400> SEQUENCE: 29

Ala Ser Thr Lys Gly Pro Ser Val Phe Pro Leu Ala Pro Cys Ser Arg
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Thr Cys Asn Val Asn His Lys Pro Ser Asn Thr Lys Val Asp Lys
                85                  90                  95

Arg Val Glu Leu Lys Thr Pro Leu Gly Asp Thr Thr His Thr Cys Pro
            100                 105                 110

Arg Cys Pro Glu Pro Lys Ser Cys Asp Thr Pro Pro Cys Pro Arg
        115                 120                 125

Cys Pro Glu Pro Lys Ser Cys Asp Thr Pro Pro Cys Pro Arg Cys
    130                 135                 140

Pro Glu Pro Lys Ser Cys Asp Thr Pro Pro Cys Pro Arg Cys Pro
```

```
145                 150                 155                 160
Ala Pro Glu Leu Leu Gly Gly Pro Ser Val Phe Leu Phe Pro Pro Lys
                    165                 170                 175

Pro Lys Asp Thr Leu Met Ile Ser Arg Thr Pro Glu Val Thr Cys Val
            180                 185                 190

Val Val Asp Val Ser His Glu Asp Pro Glu Val Gln Phe Lys Trp Tyr
        195                 200                 205

Val Asp Gly Val Glu Val His Asn Ala Lys Thr Lys Pro Arg Glu Glu
    210                 215                 220

Gln Tyr Asn Ser Thr Phe Arg Val Val Ser Val Leu Thr Val Leu His
225                 230                 235                 240

Gln Asp Trp Leu Asn Gly Lys Glu Tyr Lys Cys Lys Val Ser Asn Lys
                245                 250                 255

Ala Leu Pro Ala Pro Ile Glu Lys Thr Ile Ser Lys Thr Lys Gly Gln
            260                 265                 270

Pro Arg Glu Pro Gln Val Tyr Thr Leu Pro Pro Ser Arg Glu Glu Met
        275                 280                 285

Thr Lys Asn Gln Val Ser Leu Thr Cys Leu Val Lys Gly Phe Tyr Pro
    290                 295                 300

Ser Asp Ile Ala Val Glu Trp Glu Ser Ser Gly Gln Pro Glu Asn Asn
305                 310                 315                 320

Tyr Asn Thr Thr Pro Pro Met Leu Asp Ser Asp Gly Ser Phe Phe Leu
                325                 330                 335

Tyr Ser Lys Leu Thr Val Asp Lys Ser Arg Trp Gln Gln Gly Asn Ile
            340                 345                 350

Phe Ser Cys Ser Val Met His Glu Ala Leu His Asn Arg Phe Thr Gln
        355                 360                 365

Lys Ser Leu Ser Leu Ser Pro Gly Lys
    370                 375

<210> SEQ ID NO 30
<211> LENGTH: 326
<212> TYPE: PRT
<213> ORGANISM: Homo sapiens

<400> SEQUENCE: 30

Ser Thr Lys Gly Pro Ser Val Phe Pro Leu Ala Pro Cys Ser Arg Ser
1               5                   10                  15

Thr Ser Glu Ser Thr Ala Ala Leu Gly Cys Leu Val Lys Asp Tyr Phe
            20                  25                  30

Pro Glu Pro Val Thr Val Ser Trp Asn Ser Gly Ala Leu Thr Ser Gly
        35                  40                  45

Val His Thr Phe Pro Ala Val Leu Gln Ser Ser Gly Leu Tyr Ser Leu
    50                  55                  60

Ser Ser Val Val Thr Val Pro Ser Ser Ser Leu Gly Thr Lys Thr Tyr
65                  70                  75                  80

Thr Cys Asn Val Asp His Lys Pro Ser Asn Thr Lys Val Asp Lys Arg
                85                  90                  95

Val Glu Ser Lys Tyr Gly Pro Pro Cys Pro Ser Cys Pro Ala Pro Glu
            100                 105                 110

Phe Leu Gly Gly Pro Ser Val Phe Leu Phe Pro Pro Lys Pro Lys Asp
        115                 120                 125

Thr Leu Met Ile Ser Arg Thr Pro Glu Val Thr Cys Val Val Val Asp
    130                 135                 140
```

```
Val Ser Gln Glu Asp Pro Glu Val Gln Phe Asn Trp Tyr Val Asp Gly
145                 150                 155                 160

Val Glu Val His Asn Ala Lys Thr Lys Pro Arg Glu Glu Gln Phe Asn
            165                 170                 175

Ser Thr Tyr Arg Val Val Ser Val Leu Thr Val Leu His Gln Asp Trp
            180                 185                 190

Leu Asn Gly Lys Glu Tyr Lys Cys Lys Val Ser Asn Lys Gly Leu Pro
            195                 200                 205

Ser Ser Ile Glu Lys Thr Ile Ser Lys Ala Lys Gly Gln Pro Arg Glu
            210                 215                 220

Pro Gln Val Tyr Thr Leu Pro Pro Ser Gln Glu Glu Met Thr Lys Asn
225                 230                 235                 240

Gln Val Ser Leu Thr Cys Leu Val Lys Gly Phe Tyr Pro Ser Asp Ile
            245                 250                 255

Ala Val Glu Trp Glu Ser Asn Gly Gln Pro Glu Asn Asn Tyr Lys Thr
            260                 265                 270

Thr Pro Pro Val Leu Asp Ser Asp Gly Ser Phe Phe Leu Tyr Ser Arg
            275                 280                 285

Leu Thr Val Asp Lys Ser Arg Trp Gln Glu Gly Asn Val Phe Ser Cys
290                 295                 300

Ser Val Met His Glu Ala Leu His Asn His Tyr Thr Gln Lys Ser Leu
305                 310                 315                 320

Ser Leu Ser Leu Gly Lys
            325

<210> SEQ ID NO 31
<211> LENGTH: 353
<212> TYPE: PRT
<213> ORGANISM: Homo sapiens

<400> SEQUENCE: 31

Ala Ser Pro Thr Ser Pro Lys Val Phe Pro Leu Ser Leu Cys Ser Thr
1               5                   10                  15

Gln Pro Asp Gly Asn Val Val Ile Ala Cys Leu Val Gln Gly Phe Phe
            20                  25                  30

Pro Gln Glu Pro Leu Ser Val Thr Trp Ser Glu Ser Gly Gln Gly Val
            35                  40                  45

Thr Ala Arg Asn Phe Pro Pro Ser Gln Asp Ala Ser Gly Asp Leu Tyr
        50                  55                  60

Thr Thr Ser Ser Gln Leu Thr Leu Pro Ala Thr Gln Cys Leu Ala Gly
65                  70                  75                  80

Lys Ser Val Thr Cys His Val Lys His Tyr Thr Asn Pro Ser Gln Asp
                85                  90                  95

Val Thr Val Pro Cys Pro Val Pro Ser Thr Pro Pro Thr Pro Ser Pro
            100                 105                 110

Ser Thr Pro Pro Thr Pro Ser Pro Ser Cys Cys His Pro Arg Leu Ser
            115                 120                 125

Leu His Arg Pro Ala Leu Glu Asp Leu Leu Leu Gly Ser Glu Ala Asn
        130                 135                 140

Leu Thr Cys Thr Leu Thr Gly Leu Arg Asp Ala Ser Gly Val Thr Phe
145                 150                 155                 160

Thr Trp Thr Pro Ser Ser Gly Lys Ser Ala Val Gln Gly Pro Pro Asp
            165                 170                 175

Arg Asp Leu Cys Gly Cys Tyr Ser Val Ser Ser Val Leu Ser Gly Cys
            180                 185                 190
```

```
Ala Glu Pro Trp Asn His Gly Lys Thr Phe Thr Cys Thr Ala Ala Tyr
            195                 200                 205

Pro Glu Ser Lys Thr Pro Leu Thr Ala Thr Leu Ser Lys Ser Gly Asn
    210                 215                 220

Thr Phe Arg Pro Glu Val His Leu Leu Pro Pro Ser Glu Glu Leu
225                 230                 235             240

Ala Leu Asn Glu Leu Val Thr Leu Thr Cys Leu Ala Arg Gly Phe Ser
            245                 250                 255

Pro Lys Asp Val Leu Val Arg Trp Leu Gln Gly Ser Gln Glu Leu Pro
                260                 265                 270

Arg Glu Lys Tyr Leu Thr Trp Ala Ser Arg Gln Glu Pro Ser Gln Gly
            275                 280                 285

Thr Thr Thr Phe Ala Val Thr Ser Ile Leu Arg Val Ala Ala Glu Asp
            290                 295                 300

Trp Lys Lys Gly Asp Thr Phe Ser Cys Met Val Gly His Glu Ala Leu
305                 310                 315                 320

Pro Leu Ala Phe Thr Gln Lys Thr Ile Asp Arg Leu Ala Gly Lys Pro
                325                 330                 335

Thr His Val Asn Val Ser Val Val Met Ala Glu Val Asp Gly Thr Cys
            340                 345                 350

Tyr

<210> SEQ ID NO 32
<211> LENGTH: 107
<212> TYPE: PRT
<213> ORGANISM: Homo sapiens

<400> SEQUENCE: 32

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105

<210> SEQ ID NO 33
<211> LENGTH: 107
<212> TYPE: PRT
<213> ORGANISM: Homo sapiens

<400> SEQUENCE: 33

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45
```

```
Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Leu Tyr Ala Cys Glu Val Thr His Gln Gly Leu Ser Ser
                    85                  90                  95

Pro Val Thr Lys Ser Phe Asn Arg Gly Glu Cys
                100                 105
```

<210> SEQ ID NO 34
<211> LENGTH: 107
<212> TYPE: PRT
<213> ORGANISM: Homo sapiens

<400> SEQUENCE: 34

```
Arg Ala Asp Ala Ala Pro Thr Val Ser Ile Phe Pro Pro Ser Ser Glu
1               5                   10                  15

Gln Leu Thr Ser Gly Gly Ala Ser Val Val Cys Phe Leu Asn Asn Phe
            20                  25                  30

Tyr Pro Lys Asp Ile Asn Val Lys Trp Lys Ile Asp Gly Ser Glu Arg
        35                  40                  45

Gln Asn Gly Val Leu Asn Ser Trp Thr Asp Gln Asp Ser Lys Asp Ser
    50                  55                  60

Thr Tyr Ser Met Ser Ser Thr Leu Thr Leu Thr Lys Asp Glu Tyr Glu
65                  70                  75                  80

Arg His Asn Ser Tyr Thr Cys Glu Ala Thr His Lys Thr Ser Thr Ser
                    85                  90                  95

Pro Ile Val Lys Ser Phe Asn Arg Gly Glu Cys
                100                 105
```

<210> SEQ ID NO 35
<211> LENGTH: 107
<212> TYPE: PRT
<213> ORGANISM: Mus musculus

<400> SEQUENCE: 35

```
Arg Ala Asp Ala Ala Pro Thr Val Ser Ile Phe Pro Pro Ser Met Glu
1               5                   10                  15

Gln Leu Thr Ser Gly Gly Ala Thr Val Val Cys Phe Val Asn Asn Phe
            20                  25                  30

Tyr Pro Arg Asp Ile Ser Val Lys Trp Lys Ile Asp Gly Ser Glu Gln
        35                  40                  45

Arg Asp Gly Val Leu Asp Ser Val Thr Asp Gln Asp Ser Lys Asp Ser
    50                  55                  60

Thr Tyr Ser Met Ser Ser Thr Leu Ser Leu Thr Lys Val Glu Tyr Glu
65                  70                  75                  80

Arg His Asn Leu Tyr Thr Cys Glu Val Val His Lys Thr Ser Ser Ser
                    85                  90                  95

Pro Val Val Lys Ser Phe Asn Arg Asn Glu Cys
                100                 105
```

<210> SEQ ID NO 36
<211> LENGTH: 105
<212> TYPE: PRT
<213> ORGANISM: Rattus norvegicus

<400> SEQUENCE: 36

```
Gln Pro Lys Ala Ala Pro Ser Val Thr Leu Phe Pro Pro Ser Ser Glu
```

-continued

```
                1               5                   10                  15
            Glu Leu Gln Ala Asn Lys Ala Thr Leu Val Cys Leu Ile Ser Asp Phe
                                20                  25                  30

Tyr Pro Gly Ala Val Thr Val Ala Trp Lys Ala Asp Ser Ser Pro Val
                        35                  40                  45

Lys Ala Gly Val Glu Thr Thr Thr Pro Ser Lys Gln Ser Asn Asn Lys
                    50                  55                  60

Tyr Ala Ala Ser Ser Tyr Leu Ser Leu Thr Pro Glu Gln Trp Lys Ser
            65                  70                  75                  80

His Lys Ser Tyr Ser Cys Gln Val Thr His Glu Gly Ser Thr Val Glu
                            85                  90                  95

Lys Thr Val Ala Pro Thr Glu Cys Ser
                        100                 105

<210> SEQ ID NO 37
<211> LENGTH: 6
<212> TYPE: PRT
<213> ORGANISM: Artificial sequence
<220> FEATURE:
<223> OTHER INFORMATION: Synthetic polypeptide
<220> FEATURE:
<221> NAME/KEY: MISC_FEATURE
<222> LOCATION: (2)..(2)
<223> OTHER INFORMATION: Xaa may be Cys or Ser

<400> SEQUENCE: 37

Leu Xaa Thr Pro Ser Arg
1               5

<210> SEQ ID NO 38
<211> LENGTH: 6
<212> TYPE: PRT
<213> ORGANISM: Artificial sequence
<220> FEATURE:
<223> OTHER INFORMATION: Synthetic polypeptide
<220> FEATURE:
<221> NAME/KEY: MISC_FEATURE
<222> LOCATION: (2)..(2)
<223> OTHER INFORMATION: Xaa is the formylglycine residue, FGly

<400> SEQUENCE: 38

Leu Xaa Thr Pro Ser Arg
1               5

<210> SEQ ID NO 39
<211> LENGTH: 5
<212> TYPE: PRT
<213> ORGANISM: Artificial sequence
<220> FEATURE:
<223> OTHER INFORMATION: Synthetic polypeptide

<400> SEQUENCE: 39

Ile Tyr Asp Met Ser
1               5

<210> SEQ ID NO 40
<211> LENGTH: 17
<212> TYPE: PRT
<213> ORGANISM: Artificial sequence
<220> FEATURE:
<223> OTHER INFORMATION: Synthetic polypeptide

<400> SEQUENCE: 40

Tyr Ile Ser Ser Gly Gly Gly Thr Tyr Tyr Pro Asp Thr Val Lys
1               5                   10                  15
```

Gly

<210> SEQ ID NO 41
<211> LENGTH: 14
<212> TYPE: PRT
<213> ORGANISM: Artificial sequence
<220> FEATURE:
<223> OTHER INFORMATION: Synthetic polypeptide

<400> SEQUENCE: 41

His Ser Gly Tyr Gly Ser Ser Tyr Gly Val Leu Phe Ala Tyr
1               5                   10

<210> SEQ ID NO 42
<211> LENGTH: 11
<212> TYPE: PRT
<213> ORGANISM: Artificial sequence
<220> FEATURE:
<223> OTHER INFORMATION: Synthetic polypeptide

<400> SEQUENCE: 42

Arg Ala Ser Gln Asp Ile Ser Asn Tyr Leu Asn
1               5                   10

<210> SEQ ID NO 43
<211> LENGTH: 7
<212> TYPE: PRT
<213> ORGANISM: Artificial sequence
<220> FEATURE:
<223> OTHER INFORMATION: Synthetic polypeptide

<400> SEQUENCE: 43

Tyr Thr Ser Ile Leu His Ser
1               5

<210> SEQ ID NO 44
<211> LENGTH: 9
<212> TYPE: PRT
<213> ORGANISM: Artificial sequence
<220> FEATURE:
<223> OTHER INFORMATION: Synthetic polypeptide

<400> SEQUENCE: 44

Gln Gln Gly Asn Thr Leu Pro Trp Thr
1               5

<210> SEQ ID NO 45
<211> LENGTH: 6
<212> TYPE: PRT
<213> ORGANISM: Artificial sequence
<220> FEATURE:
<223> OTHER INFORMATION: Synthetic polypeptide
<220> FEATURE:
<221> NAME/KEY: MISC_FEATURE
<222> LOCATION: (1)..(1)
<223> OTHER INFORMATION: Xaa may be present or absent and, when present,
      may be any amino acid, with the proviso that when the sulfatase
      motif is at the N-terminus of the target polypeptide, Xaa is
      present
<220> FEATURE:
<221> NAME/KEY: MISC_FEATURE
<222> LOCATION: (2)..(2)
<223> OTHER INFORMATION: Xaa may be Cys or Ser
<220> FEATURE:
<221> NAME/KEY: MISC_FEATURE
<222> LOCATION: (3)..(3)
<223> OTHER INFORMATION: Xaa may be any amino acid
<220> FEATURE:
<221> NAME/KEY: MISC_FEATURE

```
<222> LOCATION: (4)..(4)
<223> OTHER INFORMATION: Xaa may be Pro or Ala
<220> FEATURE:
<221> NAME/KEY: MISC_FEATURE
<222> LOCATION: (5)..(5)
<223> OTHER INFORMATION: Xaa may be any amino acid
<220> FEATURE:
<221> NAME/KEY: MISC_FEATURE
<222> LOCATION: (6)..(6)
<223> OTHER INFORMATION: Xaa may be a basic or an aliphatic amino acid

<400> SEQUENCE: 45

Xaa Xaa Xaa Xaa Xaa Xaa
1               5

<210> SEQ ID NO 46
<211> LENGTH: 6
<212> TYPE: PRT
<213> ORGANISM: Artificial sequence
<220> FEATURE:
<223> OTHER INFORMATION: Synthetic polypeptide
<220> FEATURE:
<221> NAME/KEY: MISC_FEATURE
<222> LOCATION: (1)..(1)
<223> OTHER INFORMATION: Xaa may be present or absent and, when present,
      may be any amino acid, with the proviso that when the sulfatase
      motif is at the N-terminus of the target polypeptide, Xaa is
      present
<220> FEATURE:
<221> NAME/KEY: MISC_FEATURE
<222> LOCATION: (3)..(3)
<223> OTHER INFORMATION: Xaa may be any amino acid
<220> FEATURE:
<221> NAME/KEY: MISC_FEATURE
<222> LOCATION: (5)..(5)
<223> OTHER INFORMATION: Xaa may be any amino acid
<220> FEATURE:
<221> NAME/KEY: MISC_FEATURE
<222> LOCATION: (6)..(6)
<223> OTHER INFORMATION: Xaa may be a basic or an aliphatic amino acid

<400> SEQUENCE: 46

Xaa Cys Xaa Pro Xaa Xaa
1               5

<210> SEQ ID NO 47
<211> LENGTH: 6
<212> TYPE: PRT
<213> ORGANISM: Artificial sequence
<220> FEATURE:
<223> OTHER INFORMATION: Synthetic polypeptide

<400> SEQUENCE: 47

Leu Cys Thr Pro Ser Arg
1               5

<210> SEQ ID NO 48
<211> LENGTH: 6
<212> TYPE: PRT
<213> ORGANISM: Artificial sequence
<220> FEATURE:
<223> OTHER INFORMATION: Synthetic polypeptide

<400> SEQUENCE: 48

Met Cys Thr Pro Ser Arg
1               5

<210> SEQ ID NO 49
<211> LENGTH: 6
<212> TYPE: PRT
<213> ORGANISM: Artificial sequence
```

```
<220> FEATURE:
<223> OTHER INFORMATION: Synthetic polypeptide

<400> SEQUENCE: 49

Val Cys Thr Pro Ser Arg
1               5

<210> SEQ ID NO 50
<211> LENGTH: 6
<212> TYPE: PRT
<213> ORGANISM: Artificial sequence
<220> FEATURE:
<223> OTHER INFORMATION: Synthetic polypeptide

<400> SEQUENCE: 50

Leu Cys Ser Pro Ser Arg
1               5

<210> SEQ ID NO 51
<211> LENGTH: 6
<212> TYPE: PRT
<213> ORGANISM: Artificial sequence
<220> FEATURE:
<223> OTHER INFORMATION: Synthetic polypeptide

<400> SEQUENCE: 51

Leu Cys Ala Pro Ser Arg
1               5

<210> SEQ ID NO 52
<211> LENGTH: 6
<212> TYPE: PRT
<213> ORGANISM: Artificial sequence
<220> FEATURE:
<223> OTHER INFORMATION: Synthetic polypeptide

<400> SEQUENCE: 52

Leu Cys Val Pro Ser Arg
1               5

<210> SEQ ID NO 53
<211> LENGTH: 6
<212> TYPE: PRT
<213> ORGANISM: Artificial sequence
<220> FEATURE:
<223> OTHER INFORMATION: Synthetic polypeptide

<400> SEQUENCE: 53

Leu Cys Gly Pro Ser Arg
1               5

<210> SEQ ID NO 54
<211> LENGTH: 6
<212> TYPE: PRT
<213> ORGANISM: Artificial sequence
<220> FEATURE:
<223> OTHER INFORMATION: Synthetic polypeptide

<400> SEQUENCE: 54

Ile Cys Thr Pro Ala Arg
1               5

<210> SEQ ID NO 55
<211> LENGTH: 6
<212> TYPE: PRT
<213> ORGANISM: Artificial sequence
<220> FEATURE:
```

```
<223> OTHER INFORMATION: Synthetic polypeptide

<400> SEQUENCE: 55

Leu Cys Thr Pro Ser Lys
1               5

<210> SEQ ID NO 56
<211> LENGTH: 6
<212> TYPE: PRT
<213> ORGANISM: Artificial sequence
<220> FEATURE:
<223> OTHER INFORMATION: Synthetic polypeptide

<400> SEQUENCE: 56

Met Cys Thr Pro Ser Lys
1               5

<210> SEQ ID NO 57
<211> LENGTH: 6
<212> TYPE: PRT
<213> ORGANISM: Artificial sequence
<220> FEATURE:
<223> OTHER INFORMATION: Synthetic polypeptide

<400> SEQUENCE: 57

Val Cys Thr Pro Ser Lys
1               5

<210> SEQ ID NO 58
<211> LENGTH: 6
<212> TYPE: PRT
<213> ORGANISM: Artificial sequence
<220> FEATURE:
<223> OTHER INFORMATION: Synthetic polypeptide

<400> SEQUENCE: 58

Leu Cys Ser Pro Ser Lys
1               5

<210> SEQ ID NO 59
<211> LENGTH: 6
<212> TYPE: PRT
<213> ORGANISM: Artificial sequence
<220> FEATURE:
<223> OTHER INFORMATION: Synthetic polypeptide

<400> SEQUENCE: 59

Leu Cys Ala Pro Ser Lys
1               5

<210> SEQ ID NO 60
<211> LENGTH: 6
<212> TYPE: PRT
<213> ORGANISM: Artificial sequence
<220> FEATURE:
<223> OTHER INFORMATION: Synthetic polypeptide

<400> SEQUENCE: 60

Leu Cys Val Pro Ser Lys
1               5

<210> SEQ ID NO 61
<211> LENGTH: 6
<212> TYPE: PRT
<213> ORGANISM: Artificial sequence
<220> FEATURE:
<223> OTHER INFORMATION: Synthetic polypeptide
```

```
<400> SEQUENCE: 61

Leu Cys Gly Pro Ser Lys
1               5

<210> SEQ ID NO 62
<211> LENGTH: 6
<212> TYPE: PRT
<213> ORGANISM: Artificial sequence
<220> FEATURE:
<223> OTHER INFORMATION: Synthetic polypeptide

<400> SEQUENCE: 62

Leu Cys Thr Pro Ser Ala
1               5

<210> SEQ ID NO 63
<211> LENGTH: 6
<212> TYPE: PRT
<213> ORGANISM: Artificial sequence
<220> FEATURE:
<223> OTHER INFORMATION: Synthetic polypeptide

<400> SEQUENCE: 63

Ile Cys Thr Pro Ala Ala
1               5

<210> SEQ ID NO 64
<211> LENGTH: 6
<212> TYPE: PRT
<213> ORGANISM: Artificial sequence
<220> FEATURE:
<223> OTHER INFORMATION: Synthetic polypeptide

<400> SEQUENCE: 64

Met Cys Thr Pro Ser Ala
1               5

<210> SEQ ID NO 65
<211> LENGTH: 6
<212> TYPE: PRT
<213> ORGANISM: Artificial sequence
<220> FEATURE:
<223> OTHER INFORMATION: Synthetic polypeptide

<400> SEQUENCE: 65

Val Cys Thr Pro Ser Ala
1               5

<210> SEQ ID NO 66
<211> LENGTH: 6
<212> TYPE: PRT
<213> ORGANISM: Artificial sequence
<220> FEATURE:
<223> OTHER INFORMATION: Synthetic polypeptide

<400> SEQUENCE: 66

Leu Cys Ser Pro Ser Ala
1               5

<210> SEQ ID NO 67
<211> LENGTH: 6
<212> TYPE: PRT
<213> ORGANISM: Artificial sequence
<220> FEATURE:
<223> OTHER INFORMATION: Synthetic polypeptide
```

```
<400> SEQUENCE: 67

Leu Cys Ala Pro Ser Ala
1               5

<210> SEQ ID NO 68
<211> LENGTH: 6
<212> TYPE: PRT
<213> ORGANISM: Artificial sequence
<220> FEATURE:
<223> OTHER INFORMATION: Synthetic polypeptide

<400> SEQUENCE: 68

Leu Cys Val Pro Ser Ala
1               5

<210> SEQ ID NO 69
<211> LENGTH: 6
<212> TYPE: PRT
<213> ORGANISM: Artificial sequence
<220> FEATURE:
<223> OTHER INFORMATION: Synthetic polypeptide

<400> SEQUENCE: 69

Leu Cys Gly Pro Ser Ala
1               5

<210> SEQ ID NO 70
<211> LENGTH: 6
<212> TYPE: PRT
<213> ORGANISM: Artificial sequence
<220> FEATURE:
<223> OTHER INFORMATION: Synthetic polypeptide
<220> FEATURE:
<221> NAME/KEY: MISC_FEATURE
<222> LOCATION: (1)..(1)
<223> OTHER INFORMATION: Xaa may be present or absent and, when present,
      may be any amino acid, with the proviso that when the sulfatase
      motif is at the N-terminus of the target polypeptide, Xaa is
      present
<220> FEATURE:
<221> NAME/KEY: MISC_FEATURE
<222> LOCATION: (2)..(2)
<223> OTHER INFORMATION: Xaa is the formylglycine residue, FGly
<220> FEATURE:
<221> NAME/KEY: MISC_FEATURE
<222> LOCATION: (3)..(3)
<223> OTHER INFORMATION: Xaa may be any amino acid
<220> FEATURE:
<221> NAME/KEY: MISC_FEATURE
<222> LOCATION: (4)..(4)
<223> OTHER INFORMATION: Xaa may be Pro or Ala
<220> FEATURE:
<221> NAME/KEY: MISC_FEATURE
<222> LOCATION: (5)..(5)
<223> OTHER INFORMATION: Xaa may be any amino acid
<220> FEATURE:
<221> NAME/KEY: MISC_FEATURE
<222> LOCATION: (6)..(6)
<223> OTHER INFORMATION: Xaa may be a basic or an aliphatic amino acid

<400> SEQUENCE: 70

Xaa Xaa Xaa Xaa Xaa Xaa
1               5

<210> SEQ ID NO 71
<211> LENGTH: 10
<212> TYPE: PRT
<213> ORGANISM: Artificial sequence
<220> FEATURE:
<223> OTHER INFORMATION: Synthetic polypeptide
```

```
<400> SEQUENCE: 71

Gln Lys Ser Leu Ser Leu Ser Pro Gly Lys
1               5                   10

<210> SEQ ID NO 72
<211> LENGTH: 16
<212> TYPE: PRT
<213> ORGANISM: Artificial sequence
<220> FEATURE:
<223> OTHER INFORMATION: Synthetic polypeptide
<220> FEATURE:
<221> NAME/KEY: MISC_FEATURE
<222> LOCATION: (10)..(10)
<223> OTHER INFORMATION: Xaa is the modified amino acid residue of
      formula (I), FGly'

<400> SEQUENCE: 72

Ser Leu Ser Leu Ser Pro Gly Ser Leu Xaa Thr Pro Ser Arg Gly Ser
1               5                   10                  15

<210> SEQ ID NO 73
<211> LENGTH: 8
<212> TYPE: PRT
<213> ORGANISM: Artificial sequence
<220> FEATURE:
<223> OTHER INFORMATION: Synthetic polypeptide

<400> SEQUENCE: 73

Ser Leu Ser Leu Ser Pro Gly Lys
1               5

<210> SEQ ID NO 74
<211> LENGTH: 6
<212> TYPE: PRT
<213> ORGANISM: Artificial sequence
<220> FEATURE:
<223> OTHER INFORMATION: Synthetic polypeptide

<400> SEQUENCE: 74

Ala Ser Thr Lys Gly Pro
1               5

<210> SEQ ID NO 75
<211> LENGTH: 7
<212> TYPE: PRT
<213> ORGANISM: Artificial sequence
<220> FEATURE:
<223> OTHER INFORMATION: Synthetic polypeptide

<400> SEQUENCE: 75

Lys Ser Thr Ser Gly Gly Thr
1               5

<210> SEQ ID NO 76
<211> LENGTH: 4
<212> TYPE: PRT
<213> ORGANISM: Artificial sequence
<220> FEATURE:
<223> OTHER INFORMATION: Synthetic polypeptide

<400> SEQUENCE: 76

Pro Glu Pro Val
1

<210> SEQ ID NO 77
<211> LENGTH: 8
<212> TYPE: PRT
```

```
<213> ORGANISM: Artificial sequence
<220> FEATURE:
<223> OTHER INFORMATION: Synthetic polypeptide

<400> SEQUENCE: 77

Asn Ser Gly Ala Leu Thr Ser Gly
1               5

<210> SEQ ID NO 78
<211> LENGTH: 21
<212> TYPE: PRT
<213> ORGANISM: Artificial sequence
<220> FEATURE:
<223> OTHER INFORMATION: Synthetic polypeptide

<400> SEQUENCE: 78

Asn Ser Gly Ala Leu Thr Ser Gly Val His Thr Phe Pro Ala Val Leu
1               5                   10                  15

Gln Ser Ser Gly Leu
            20

<210> SEQ ID NO 79
<211> LENGTH: 5
<212> TYPE: PRT
<213> ORGANISM: Artificial sequence
<220> FEATURE:
<223> OTHER INFORMATION: Synthetic polypeptide

<400> SEQUENCE: 79

Gln Ser Ser Gly Leu
1               5

<210> SEQ ID NO 80
<211> LENGTH: 4
<212> TYPE: PRT
<213> ORGANISM: Artificial sequence
<220> FEATURE:
<223> OTHER INFORMATION: Synthetic polypeptide

<400> SEQUENCE: 80

Thr Gln Thr Tyr
1

<210> SEQ ID NO 81
<211> LENGTH: 5
<212> TYPE: PRT
<213> ORGANISM: Artificial sequence
<220> FEATURE:
<223> OTHER INFORMATION: Synthetic polypeptide

<400> SEQUENCE: 81

His Lys Pro Ser Asn
1               5

<210> SEQ ID NO 82
<211> LENGTH: 22
<212> TYPE: PRT
<213> ORGANISM: Artificial sequence
<220> FEATURE:
<223> OTHER INFORMATION: Synthetic polypeptide

<400> SEQUENCE: 82

Glu Pro Lys Ser Cys Asp Lys Thr His Thr Cys Pro Cys Pro Ala
1               5                   10                  15

Pro Glu Leu Leu Gly Gly
            20
```

```
<210> SEQ ID NO 83
<211> LENGTH: 5
<212> TYPE: PRT
<213> ORGANISM: Artificial sequence
<220> FEATURE:
<223> OTHER INFORMATION: Synthetic polypeptide

<400> SEQUENCE: 83

Phe Pro Pro Lys Pro
1               5

<210> SEQ ID NO 84
<211> LENGTH: 5
<212> TYPE: PRT
<213> ORGANISM: Artificial sequence
<220> FEATURE:
<223> OTHER INFORMATION: Synthetic polypeptide

<400> SEQUENCE: 84

Ile Ser Arg Thr Pro
1               5

<210> SEQ ID NO 85
<211> LENGTH: 9
<212> TYPE: PRT
<213> ORGANISM: Artificial sequence
<220> FEATURE:
<223> OTHER INFORMATION: Synthetic polypeptide

<400> SEQUENCE: 85

Asp Val Ser His Glu Asp Pro Glu Val
1               5

<210> SEQ ID NO 86
<211> LENGTH: 7
<212> TYPE: PRT
<213> ORGANISM: Artificial sequence
<220> FEATURE:
<223> OTHER INFORMATION: Synthetic polypeptide

<400> SEQUENCE: 86

Ser His Glu Asp Pro Glu Val
1               5

<210> SEQ ID NO 87
<211> LENGTH: 9
<212> TYPE: PRT
<213> ORGANISM: Artificial sequence
<220> FEATURE:
<223> OTHER INFORMATION: Synthetic polypeptide

<400> SEQUENCE: 87

Asp Gly Val Glu Val His Asn Ala Lys
1               5

<210> SEQ ID NO 88
<211> LENGTH: 5
<212> TYPE: PRT
<213> ORGANISM: Artificial sequence
<220> FEATURE:
<223> OTHER INFORMATION: Synthetic polypeptide

<400> SEQUENCE: 88

Gln Tyr Asn Ser Thr
1               5
```

<210> SEQ ID NO 89
<211> LENGTH: 5
<212> TYPE: PRT
<213> ORGANISM: Artificial sequence
<220> FEATURE:
<223> OTHER INFORMATION: Synthetic polypeptide

<400> SEQUENCE: 89

Val Leu Thr Val Leu
1               5

<210> SEQ ID NO 90
<211> LENGTH: 7
<212> TYPE: PRT
<213> ORGANISM: Artificial sequence
<220> FEATURE:
<223> OTHER INFORMATION: Synthetic polypeptide

<400> SEQUENCE: 90

Asn Lys Ala Leu Pro Ala Pro
1               5

<210> SEQ ID NO 91
<211> LENGTH: 9
<212> TYPE: PRT
<213> ORGANISM: Artificial sequence
<220> FEATURE:
<223> OTHER INFORMATION: Synthetic polypeptide

<400> SEQUENCE: 91

Ser Lys Ala Lys Gly Gln Pro Arg Glu
1               5

<210> SEQ ID NO 92
<211> LENGTH: 7
<212> TYPE: PRT
<213> ORGANISM: Artificial sequence
<220> FEATURE:
<223> OTHER INFORMATION: Synthetic polypeptide

<400> SEQUENCE: 92

Lys Ala Lys Gly Gln Pro Arg
1               5

<210> SEQ ID NO 93
<211> LENGTH: 10
<212> TYPE: PRT
<213> ORGANISM: Artificial sequence
<220> FEATURE:
<223> OTHER INFORMATION: Synthetic polypeptide

<400> SEQUENCE: 93

Pro Pro Ser Arg Lys Glu Leu Thr Lys Asn
1               5                   10

<210> SEQ ID NO 94
<211> LENGTH: 5
<212> TYPE: PRT
<213> ORGANISM: Artificial sequence
<220> FEATURE:
<223> OTHER INFORMATION: Synthetic polypeptide

<400> SEQUENCE: 94

Tyr Pro Ser Asp Ile
1               5

```
<210> SEQ ID NO 95
<211> LENGTH: 7
<212> TYPE: PRT
<213> ORGANISM: Artificial sequence
<220> FEATURE:
<223> OTHER INFORMATION: Synthetic polypeptide

<400> SEQUENCE: 95

Asn Gly Gln Pro Glu Asn Asn
1               5

<210> SEQ ID NO 96
<211> LENGTH: 10
<212> TYPE: PRT
<213> ORGANISM: Artificial sequence
<220> FEATURE:
<223> OTHER INFORMATION: Synthetic polypeptide

<400> SEQUENCE: 96

Thr Pro Pro Val Leu Asp Ser Asp Gly Ser
1               5                   10

<210> SEQ ID NO 97
<211> LENGTH: 19
<212> TYPE: PRT
<213> ORGANISM: Artificial sequence
<220> FEATURE:
<223> OTHER INFORMATION: Synthetic polypeptide

<400> SEQUENCE: 97

His Glu Ala Leu His Asn His Tyr Thr Gln Lys Ser Leu Ser Leu Ser
1               5                   10                  15

Pro Gly Lys

<210> SEQ ID NO 98
<211> LENGTH: 6
<212> TYPE: PRT
<213> ORGANISM: Artificial sequence
<220> FEATURE:
<223> OTHER INFORMATION: Synthetic polypeptide

<400> SEQUENCE: 98

Ser Leu Ser Pro Gly Lys
1               5

<210> SEQ ID NO 99
<211> LENGTH: 12
<212> TYPE: PRT
<213> ORGANISM: Artificial sequence
<220> FEATURE:
<223> OTHER INFORMATION: Synthetic polypeptide

<400> SEQUENCE: 99

Pro Cys Ser Arg Ser Thr Ser Glu Ser Thr Ala Ala
1               5                   10

<210> SEQ ID NO 100
<211> LENGTH: 5
<212> TYPE: PRT
<213> ORGANISM: Artificial sequence
<220> FEATURE:
<223> OTHER INFORMATION: Synthetic polypeptide

<400> SEQUENCE: 100

Phe Pro Glu Pro Val
1               5
```

```
<210> SEQ ID NO 101
<211> LENGTH: 12
<212> TYPE: PRT
<213> ORGANISM: Artificial sequence
<220> FEATURE:
<223> OTHER INFORMATION: Synthetic polypeptide

<400> SEQUENCE: 101

Ser Gly Ala Leu Thr Ser Gly Val His Thr Phe Pro
1               5                   10

<210> SEQ ID NO 102
<211> LENGTH: 6
<212> TYPE: PRT
<213> ORGANISM: Artificial sequence
<220> FEATURE:
<223> OTHER INFORMATION: Synthetic polypeptide

<400> SEQUENCE: 102

Gln Ser Ser Gly Leu Tyr
1               5

<210> SEQ ID NO 103
<211> LENGTH: 5
<212> TYPE: PRT
<213> ORGANISM: Artificial sequence
<220> FEATURE:
<223> OTHER INFORMATION: Synthetic polypeptide

<400> SEQUENCE: 103

Val Ala Gly Pro Ser
1               5

<210> SEQ ID NO 104
<211> LENGTH: 5
<212> TYPE: PRT
<213> ORGANISM: Artificial sequence
<220> FEATURE:
<223> OTHER INFORMATION: Synthetic polypeptide

<400> SEQUENCE: 104

Val Leu Thr Val Val
1               5

<210> SEQ ID NO 105
<211> LENGTH: 7
<212> TYPE: PRT
<213> ORGANISM: Artificial sequence
<220> FEATURE:
<223> OTHER INFORMATION: Synthetic polypeptide

<400> SEQUENCE: 105

Asn Lys Gly Leu Pro Ala Pro
1               5

<210> SEQ ID NO 106
<211> LENGTH: 9
<212> TYPE: PRT
<213> ORGANISM: Artificial sequence
<220> FEATURE:
<223> OTHER INFORMATION: Synthetic polypeptide

<400> SEQUENCE: 106

Ser Lys Thr Lys Gly Gln Pro Arg Glu
1               5
```

```
<210> SEQ ID NO 107
<211> LENGTH: 5
<212> TYPE: PRT
<213> ORGANISM: Artificial sequence
<220> FEATURE:
<223> OTHER INFORMATION: Synthetic polypeptide

<400> SEQUENCE: 107

Met Thr Lys Asn Gln
1               5

<210> SEQ ID NO 108
<211> LENGTH: 10
<212> TYPE: PRT
<213> ORGANISM: Artificial sequence
<220> FEATURE:
<223> OTHER INFORMATION: Synthetic polypeptide

<400> SEQUENCE: 108

Thr Pro Pro Met Leu Asp Ser Asp Gly Ser
1               5                   10

<210> SEQ ID NO 109
<211> LENGTH: 4
<212> TYPE: PRT
<213> ORGANISM: Artificial sequence
<220> FEATURE:
<223> OTHER INFORMATION: Synthetic polypeptide

<400> SEQUENCE: 109

Gly Asn Val Phe
1

<210> SEQ ID NO 110
<211> LENGTH: 10
<212> TYPE: PRT
<213> ORGANISM: Artificial sequence
<220> FEATURE:
<223> OTHER INFORMATION: Synthetic polypeptide

<400> SEQUENCE: 110

Pro Cys Ser Arg Ser Thr Ser Gly Gly Thr
1               5                   10

<210> SEQ ID NO 111
<211> LENGTH: 19
<212> TYPE: PRT
<213> ORGANISM: Artificial sequence
<220> FEATURE:
<223> OTHER INFORMATION: Synthetic polypeptide

<400> SEQUENCE: 111

Ser Gly Ala Leu Thr Ser Gly Val His Thr Phe Pro Ala Val Leu Gln
1               5                   10                  15

Ser Ser Gly

<210> SEQ ID NO 112
<211> LENGTH: 10
<212> TYPE: PRT
<213> ORGANISM: Artificial sequence
<220> FEATURE:
<223> OTHER INFORMATION: Synthetic polypeptide

<400> SEQUENCE: 112

Arg Val Glu Leu Lys Thr Pro Leu Gly Asp
1               5                   10
```

<210> SEQ ID NO 113
<211> LENGTH: 7
<212> TYPE: PRT
<213> ORGANISM: Artificial sequence
<220> FEATURE:
<223> OTHER INFORMATION: Synthetic polypeptide

<400> SEQUENCE: 113

Cys Pro Arg Cys Pro Lys Pro
1               5

<210> SEQ ID NO 114
<211> LENGTH: 21
<212> TYPE: PRT
<213> ORGANISM: Artificial sequence
<220> FEATURE:
<223> OTHER INFORMATION: Synthetic polypeptide

<400> SEQUENCE: 114

Pro Lys Ser Cys Asp Thr Pro Pro Cys Pro Arg Cys Pro Ala Pro
1               5                   10                  15

Glu Leu Leu Gly Gly
            20

<210> SEQ ID NO 115
<211> LENGTH: 10
<212> TYPE: PRT
<213> ORGANISM: Artificial sequence
<220> FEATURE:
<223> OTHER INFORMATION: Synthetic polypeptide

<400> SEQUENCE: 115

Pro Pro Ser Arg Glu Glu Met Thr Lys Asn
1               5                   10

<210> SEQ ID NO 116
<211> LENGTH: 8
<212> TYPE: PRT
<213> ORGANISM: Artificial sequence
<220> FEATURE:
<223> OTHER INFORMATION: Synthetic polypeptide

<400> SEQUENCE: 116

Ser Ser Gly Gln Pro Glu Asn Asn
1               5

<210> SEQ ID NO 117
<211> LENGTH: 7
<212> TYPE: PRT
<213> ORGANISM: Artificial sequence
<220> FEATURE:
<223> OTHER INFORMATION: Synthetic polypeptide

<400> SEQUENCE: 117

His Glu Ala Leu His Asn Arg
1               5

<210> SEQ ID NO 118
<211> LENGTH: 5
<212> TYPE: PRT
<213> ORGANISM: Artificial sequence
<220> FEATURE:
<223> OTHER INFORMATION: Synthetic polypeptide

<400> SEQUENCE: 118

Ser Thr Lys Gly Pro

```
1               5

<210> SEQ ID NO 119
<211> LENGTH: 11
<212> TYPE: PRT
<213> ORGANISM: Artificial sequence
<220> FEATURE:
<223> OTHER INFORMATION: Synthetic polypeptide

<400> SEQUENCE: 119

Cys Pro Ala Pro Glu Phe Leu Gly Gly Pro Ser
1               5                   10

<210> SEQ ID NO 120
<211> LENGTH: 9
<212> TYPE: PRT
<213> ORGANISM: Artificial sequence
<220> FEATURE:
<223> OTHER INFORMATION: Synthetic polypeptide

<400> SEQUENCE: 120

Asp Val Ser Gln Glu Asp Pro Glu Val
1               5

<210> SEQ ID NO 121
<211> LENGTH: 7
<212> TYPE: PRT
<213> ORGANISM: Artificial sequence
<220> FEATURE:
<223> OTHER INFORMATION: Synthetic polypeptide

<400> SEQUENCE: 121

Asn Lys Gly Leu Pro Ser Ser
1               5

<210> SEQ ID NO 122
<211> LENGTH: 10
<212> TYPE: PRT
<213> ORGANISM: Artificial sequence
<220> FEATURE:
<223> OTHER INFORMATION: Synthetic polypeptide

<400> SEQUENCE: 122

Ser Lys Ala Lys Gly Gln Pro Arg Glu Pro
1               5                   10

<210> SEQ ID NO 123
<211> LENGTH: 10
<212> TYPE: PRT
<213> ORGANISM: Artificial sequence
<220> FEATURE:
<223> OTHER INFORMATION: Synthetic polypeptide

<400> SEQUENCE: 123

Pro Pro Ser Gln Glu Glu Met Thr Lys Asn
1               5                   10

<210> SEQ ID NO 124
<211> LENGTH: 19
<212> TYPE: PRT
<213> ORGANISM: Artificial sequence
<220> FEATURE:
<223> OTHER INFORMATION: Synthetic polypeptide

<400> SEQUENCE: 124

His Glu Ala Leu His Asn His Tyr Thr Gln Lys Ser Leu Ser Leu Ser
1               5                   10                  15
```

```
Leu Gly Lys

<210> SEQ ID NO 125
<211> LENGTH: 13
<212> TYPE: PRT
<213> ORGANISM: Artificial sequence
<220> FEATURE:
<223> OTHER INFORMATION: Synthetic polypeptide

<400> SEQUENCE: 125

Ala Ser Pro Thr Ser Pro Lys Val Phe Pro Leu Ser Leu
1               5                   10

<210> SEQ ID NO 126
<211> LENGTH: 5
<212> TYPE: PRT
<213> ORGANISM: Artificial sequence
<220> FEATURE:
<223> OTHER INFORMATION: Synthetic polypeptide

<400> SEQUENCE: 126

Gln Pro Asp Gly Asn
1               5

<210> SEQ ID NO 127
<211> LENGTH: 10
<212> TYPE: PRT
<213> ORGANISM: Artificial sequence
<220> FEATURE:
<223> OTHER INFORMATION: Synthetic polypeptide

<400> SEQUENCE: 127

Val Gln Gly Phe Phe Pro Gln Glu Pro Leu
1               5                   10

<210> SEQ ID NO 128
<211> LENGTH: 11
<212> TYPE: PRT
<213> ORGANISM: Artificial sequence
<220> FEATURE:
<223> OTHER INFORMATION: Synthetic polypeptide

<400> SEQUENCE: 128

Ser Gly Gln Gly Val Thr Ala Arg Asn Phe Pro
1               5                   10

<210> SEQ ID NO 129
<211> LENGTH: 7
<212> TYPE: PRT
<213> ORGANISM: Artificial sequence
<220> FEATURE:
<223> OTHER INFORMATION: Synthetic polypeptide

<400> SEQUENCE: 129

Ser Gly Asp Leu Tyr Thr Thr
1               5

<210> SEQ ID NO 130
<211> LENGTH: 4
<212> TYPE: PRT
<213> ORGANISM: Artificial sequence
<220> FEATURE:
<223> OTHER INFORMATION: Synthetic polypeptide

<400> SEQUENCE: 130

Pro Ala Thr Gln
```

```
<210> SEQ ID NO 131
<211> LENGTH: 4
<212> TYPE: PRT
<213> ORGANISM: Artificial sequence
<220> FEATURE:
<223> OTHER INFORMATION: Synthetic polypeptide

<400> SEQUENCE: 131

His Arg Pro Ala
1

<210> SEQ ID NO 132
<211> LENGTH: 5
<212> TYPE: PRT
<213> ORGANISM: Artificial sequence
<220> FEATURE:
<223> OTHER INFORMATION: Synthetic polypeptide

<400> SEQUENCE: 132

Leu Leu Gly Ser Glu
1               5

<210> SEQ ID NO 133
<211> LENGTH: 8
<212> TYPE: PRT
<213> ORGANISM: Artificial sequence
<220> FEATURE:
<223> OTHER INFORMATION: Synthetic polypeptide

<400> SEQUENCE: 133

Gly Leu Arg Asp Ala Ser Gly Val
1               5

<210> SEQ ID NO 134
<211> LENGTH: 10
<212> TYPE: PRT
<213> ORGANISM: Artificial sequence
<220> FEATURE:
<223> OTHER INFORMATION: Synthetic polypeptide

<400> SEQUENCE: 134

Ser Ser Gly Lys Ser Ala Val Gln Gly Pro
1               5                   10

<210> SEQ ID NO 135
<211> LENGTH: 4
<212> TYPE: PRT
<213> ORGANISM: Artificial sequence
<220> FEATURE:
<223> OTHER INFORMATION: Synthetic polypeptide

<400> SEQUENCE: 135

Gly Cys Tyr Ser
1

<210> SEQ ID NO 136
<211> LENGTH: 4
<212> TYPE: PRT
<213> ORGANISM: Artificial sequence
<220> FEATURE:
<223> OTHER INFORMATION: Synthetic polypeptide

<400> SEQUENCE: 136

Cys Ala Glu Pro
1
```

<210> SEQ ID NO 137
<211> LENGTH: 24
<212> TYPE: PRT
<213> ORGANISM: Artificial sequence
<220> FEATURE:
<223> OTHER INFORMATION: Synthetic polypeptide

<400> SEQUENCE: 137

Ser Gly Asn Thr Phe Arg Pro Glu Val His Leu Leu Pro Pro Pro Ser
1               5                   10                  15

Glu Glu Leu Ala Leu Asn Glu Leu
            20

<210> SEQ ID NO 138
<211> LENGTH: 5
<212> TYPE: PRT
<213> ORGANISM: Artificial sequence
<220> FEATURE:
<223> OTHER INFORMATION: Synthetic polypeptide

<400> SEQUENCE: 138

Ala Arg Gly Phe Ser
1               5

<210> SEQ ID NO 139
<211> LENGTH: 11
<212> TYPE: PRT
<213> ORGANISM: Artificial sequence
<220> FEATURE:
<223> OTHER INFORMATION: Synthetic polypeptide

<400> SEQUENCE: 139

Gln Gly Ser Gln Glu Leu Pro Arg Glu Lys Tyr
1               5                   10

<210> SEQ ID NO 140
<211> LENGTH: 4
<212> TYPE: PRT
<213> ORGANISM: Artificial sequence
<220> FEATURE:
<223> OTHER INFORMATION: Synthetic polypeptide

<400> SEQUENCE: 140

Ala Ala Glu Asp
1

<210> SEQ ID NO 141
<211> LENGTH: 4
<212> TYPE: PRT
<213> ORGANISM: Artificial sequence
<220> FEATURE:
<223> OTHER INFORMATION: Synthetic polypeptide

<400> SEQUENCE: 141

His Glu Ala Leu
1

<210> SEQ ID NO 142
<211> LENGTH: 25
<212> TYPE: PRT
<213> ORGANISM: Artificial sequence
<220> FEATURE:
<223> OTHER INFORMATION: Synthetic polypeptide

<400> SEQUENCE: 142

```
Ile Asp Arg Leu Ala Gly Lys Pro Thr His Val Asn Val Ser Val Val
1               5                   10                  15

Met Ala Glu Val Asp Gly Thr Cys Tyr
            20                  25

<210> SEQ ID NO 143
<211> LENGTH: 11
<212> TYPE: PRT
<213> ORGANISM: Artificial sequence
<220> FEATURE:
<223> OTHER INFORMATION: Synthetic polypeptide

<400> SEQUENCE: 143

Asn Ser Gly Ala Leu Cys Thr Pro Ser Arg Gly
1               5                   10

<210> SEQ ID NO 144
<211> LENGTH: 5
<212> TYPE: PRT
<213> ORGANISM: Artificial sequence
<220> FEATURE:
<223> OTHER INFORMATION: Synthetic polypeptide

<400> SEQUENCE: 144

Cys Thr Pro Ser Arg
1               5

<210> SEQ ID NO 145
<211> LENGTH: 9
<212> TYPE: PRT
<213> ORGANISM: Artificial sequence
<220> FEATURE:
<223> OTHER INFORMATION: Synthetic polypeptide

<400> SEQUENCE: 145

Asn Leu Cys Thr Pro Ser Arg Ala Pro
1               5

<210> SEQ ID NO 146
<211> LENGTH: 10
<212> TYPE: PRT
<213> ORGANISM: Artificial sequence
<220> FEATURE:
<223> OTHER INFORMATION: Synthetic polypeptide

<400> SEQUENCE: 146

Lys Ala Lys Gly Leu Cys Thr Pro Ser Arg
1               5                   10

<210> SEQ ID NO 147
<211> LENGTH: 5
<212> TYPE: PRT
<213> ORGANISM: Artificial sequence
<220> FEATURE:
<223> OTHER INFORMATION: Synthetic polypeptide

<400> SEQUENCE: 147

Leu Cys Thr Pro Ser
1               5

<210> SEQ ID NO 148
<211> LENGTH: 6
<212> TYPE: PRT
<213> ORGANISM: Artificial sequence
<220> FEATURE:
<223> OTHER INFORMATION: Synthetic polypeptide
```

```
<400> SEQUENCE: 148

Arg Thr Val Ala Ala Pro
1               5

<210> SEQ ID NO 149
<211> LENGTH: 5
<212> TYPE: PRT
<213> ORGANISM: Artificial sequence
<220> FEATURE:
<223> OTHER INFORMATION: Synthetic polypeptide

<400> SEQUENCE: 149

Tyr Pro Arg Glu Ala
1               5

<210> SEQ ID NO 150
<211> LENGTH: 4
<212> TYPE: PRT
<213> ORGANISM: Artificial sequence
<220> FEATURE:
<223> OTHER INFORMATION: Synthetic polypeptide

<400> SEQUENCE: 150

Pro Arg Glu Ala
1

<210> SEQ ID NO 151
<211> LENGTH: 8
<212> TYPE: PRT
<213> ORGANISM: Artificial sequence
<220> FEATURE:
<223> OTHER INFORMATION: Synthetic polypeptide

<400> SEQUENCE: 151

Asp Asn Ala Leu Gln Ser Gly Asn
1               5

<210> SEQ ID NO 152
<211> LENGTH: 9
<212> TYPE: PRT
<213> ORGANISM: Artificial sequence
<220> FEATURE:
<223> OTHER INFORMATION: Synthetic polypeptide

<400> SEQUENCE: 152

Thr Glu Gln Asp Ser Lys Asp Ser Thr
1               5

<210> SEQ ID NO 153
<211> LENGTH: 6
<212> TYPE: PRT
<213> ORGANISM: Artificial sequence
<220> FEATURE:
<223> OTHER INFORMATION: Synthetic polypeptide

<400> SEQUENCE: 153

His Gln Gly Leu Ser Ser
1               5

<210> SEQ ID NO 154
<211> LENGTH: 4
<212> TYPE: PRT
<213> ORGANISM: Artificial sequence
<220> FEATURE:
<223> OTHER INFORMATION: Synthetic polypeptide

<400> SEQUENCE: 154
```

```
Arg Gly Glu Cys
1

<210> SEQ ID NO 155
<211> LENGTH: 6
<212> TYPE: PRT
<213> ORGANISM: Artificial sequence
<220> FEATURE:
<223> OTHER INFORMATION: Synthetic polypeptide

<400> SEQUENCE: 155

Gln Pro Lys Ala Ala Pro
1               5

<210> SEQ ID NO 156
<211> LENGTH: 7
<212> TYPE: PRT
<213> ORGANISM: Artificial sequence
<220> FEATURE:
<223> OTHER INFORMATION: Synthetic polypeptide

<400> SEQUENCE: 156

Asp Phe Tyr Pro Gly Ala Val
1               5

<210> SEQ ID NO 157
<211> LENGTH: 8
<212> TYPE: PRT
<213> ORGANISM: Artificial sequence
<220> FEATURE:
<223> OTHER INFORMATION: Synthetic polypeptide

<400> SEQUENCE: 157

Asp Ser Ser Pro Val Lys Ala Gly
1               5

<210> SEQ ID NO 158
<211> LENGTH: 6
<212> TYPE: PRT
<213> ORGANISM: Artificial sequence
<220> FEATURE:
<223> OTHER INFORMATION: Synthetic polypeptide

<400> SEQUENCE: 158

Ala Pro Thr Glu Cys Ser
1               5

<210> SEQ ID NO 159
<211> LENGTH: 99
<212> TYPE: PRT
<213> ORGANISM: Homo sapiens

<400> SEQUENCE: 159

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45
```

Gly Val His Thr Phe Pro Ala Val Leu Gln Ser Ser Gly Leu Tyr Ser
        50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu

<210> SEQ ID NO 160
<211> LENGTH: 8
<212> TYPE: PRT
<213> ORGANISM: Artificial sequence
<220> FEATURE:
<223> OTHER INFORMATION: Synthetic polypeptide

<400> SEQUENCE: 160

Gly Ala Leu Thr Ser Gly Val His
1               5

<210> SEQ ID NO 161
<211> LENGTH: 11
<212> TYPE: PRT
<213> ORGANISM: Artificial sequence
<220> FEATURE:
<223> OTHER INFORMATION: Synthetic polypeptide

<400> SEQUENCE: 161

Gly Ala Leu Cys Thr Pro Ser Arg Gly Val His
1               5                   10

<210> SEQ ID NO 162
<211> LENGTH: 9
<212> TYPE: PRT
<213> ORGANISM: Artificial sequence
<220> FEATURE:
<223> OTHER INFORMATION: Synthetic polypeptide

<400> SEQUENCE: 162

Ser Leu Cys Thr Pro Ser Arg Gly Ser
1               5

<210> SEQ ID NO 163
<211> LENGTH: 18
<212> TYPE: PRT
<213> ORGANISM: Artificial sequence
<220> FEATURE:
<223> OTHER INFORMATION: Synthetic polypeptide

<400> SEQUENCE: 163

Lys Val Asp Asn Ala Leu Leu Cys Thr Pro Ser Arg Gln Ser Gly Asn
1               5                   10                  15

Ser Gln

What is claimed is:

1. A conjugate that includes at least one modified amino acid residue with a side chain of formula (I):

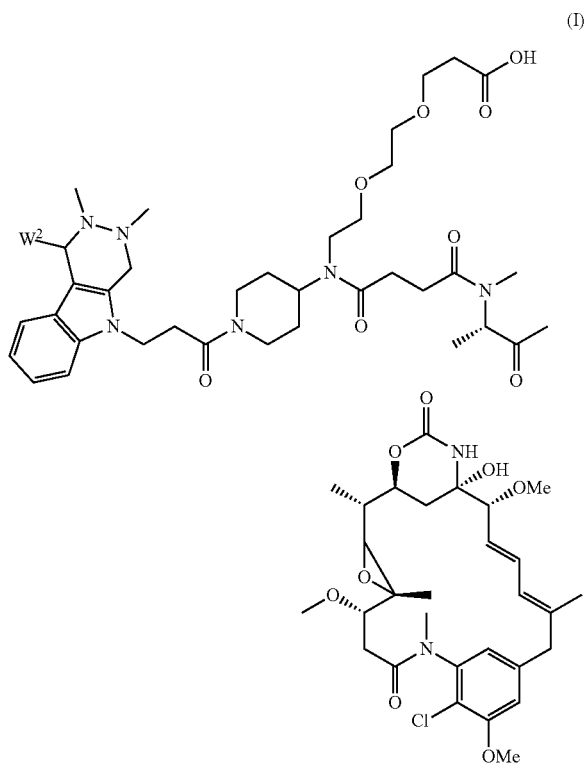

(I)

wherein
W$^2$ is an anti-CD22 antibody.

2. The conjugate of claim 1, wherein the anti-CD22 antibody constant region comprises a sequence of the formula (II):

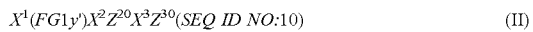

(II)

wherein
FG1y' is the modified amino acid residue of formula (I);
Z$^{20}$ is either a proline or alanine residue;
Z$^{30}$ is a basic amino acid or an aliphatic amino acid;
X$^1$ may be present or absent and, when present, can be any amino acid, with the proviso that when the sequence is at the N-terminus of the conjugate, X$^1$ is present; and
X$^2$ and X$^3$ are each independently any amino acid.

3. The conjugate of claim 2, wherein the sequence is L(FG1y')TPSR (SEQ ID NO: 11).

4. The conjugate of claim 2, wherein
Z$^{30}$ is selected from R, K, H, A, G, L, V, I, and P;
X$^1$ is selected from L, M, S, and V; and
X$^2$ and X$^3$ are each independently selected from S, T, A, V, G, and C.

5. The conjugate of claim 1, wherein the modified amino acid residue is positioned at a C-terminus of a heavy chain constant region of the anti-CD22 antibody.

6. The conjugate of claim 5, wherein the heavy chain constant region comprises a sequence of the formula (II):

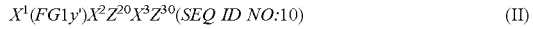

(II)

wherein
FG1y' is the modified amino acid residue of formula (I);
Z$^{20}$ is either a proline or alanine residue;
Z$^{30}$ is a basic amino acid or an aliphatic amino acid;
X$^1$ may be present or absent and, when present, can be any amino acid, with the proviso that when the sequence is at the N-terminus of the conjugate, X$^1$ is present; and
X$^2$ and X$^3$ are each independently any amino acid, and wherein the sequence is C-terminal to the amino acid sequence SLSLSPG (SEQ ID NO: 12).

7. The conjugate of claim 6, wherein the heavy chain constant region comprises the sequence SPGSL(FG1y')TPSRGS (SEQ ID NO: 13).

8. The conjugate of claim 6, wherein
Z$^{30}$ is selected from R, K, H, A, G, L, V, I, and P;
X$^1$ is selected from L, M, S, and V; and
X$^2$ and X$^3$ are each independently selected from S, T, A, V, G, and C.

9. The conjugate of claim 1, wherein the modified amino acid residue is positioned in a light chain constant region of the anti-CD22 antibody.

10. The conjugate of claim 9, wherein the light chain constant region comprises a sequence of the formula (II):

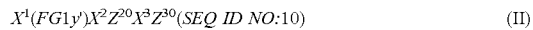

(II)

wherein
FG1y' is the modified amino acid residue of formula (I);
Z$^{20}$ is either a proline or alanine residue;
Z$^{30}$ is a basic amino acid or an aliphatic amino acid;
X$^1$ may be present or absent and, when present, can be any amino acid, with the proviso that when the sequence is at the N-terminus of the conjugate, X$^1$ is present; and
X$^2$ and X$^3$ are each independently any amino acid, and wherein the sequence is C-terminal to the sequence KVDNAL (SEQ ID NO: 14), and/or is N-terminal to the sequence QSGNSQ (SEQ ID NO: 15).

11. The conjugate of claim 10, wherein the light chain constant region comprises the sequence KVDNAL(FG1y')TPSRQSGNSQ (SEQ ID NO: 16).

12. The conjugate of claim 10, wherein
Z$^{30}$ is selected from R, K, H, A, G, L, V, I, and P;
X$^1$ is selected from L, M, S, and V; and
X$^2$ and X$^3$ are each independently selected from S, T, A, V, G, and C.

13. The conjugate of claim 1, wherein the modified amino acid residue is positioned in a heavy chain CH$_1$ region of the anti-CD22 antibody.

14. The conjugate of claim 13, wherein the heavy chain CH$_1$ region comprises a sequence of the formula (II):

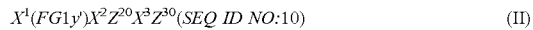

(II)

wherein
FG1y' is the modified amino acid residue of formula (I);
Z$^{20}$ is either a proline or alanine residue;
Z$^{30}$ is a basic amino acid or an aliphatic amino acid;
X$^1$ may be present or absent and, when present, can be any amino acid, with the proviso that when the sequence is at the N-terminus of the conjugate, X$^1$ is present; and
X$^2$ and X$^3$ are each independently any amino acid, and wherein the sequence is C-terminal to the amino acid sequence SWNSGA (SEQ ID NO: 17) and/or is N-terminal to the amino acid sequence GVHTFP (SEQ ID NO: 18).

15. The conjugate of claim 14, wherein the heavy chain CH$_1$ region comprises the sequence SWNSGAL(FG1y')TPSRGVHTFP (SEQ ID NO: 19).

16. The conjugate of claim 14, wherein
Z$^{30}$ is selected from R, K, H, A, G, L, V, I, and P;
X$^1$ is selected from L, M, S, and V; and $X^2$ and $X^3$ are each independently selected from S, T, A, V, G, and C.

17. The conjugate of claim 1, wherein the modified amino acid residue is positioned in a heavy chain CH2 region of the anti-CD22 antibody.

18. The conjugate of claim 1, wherein the modified amino acid residue is positioned in a heavy chain CH3 region of the anti-CD22 antibody.

19. A pharmaceutical composition comprising:
a conjugate of claim 1; and
a pharmaceutically acceptable excipient.

20. A method comprising:
administering to a subject an effective amount of a conjugate of claim 1.

21. A method of treating a leukemia or a lymphoma in a subject, the method comprising: administering to the subject a therapeutically effective amount of a pharmaceutical composition comprising a conjugate of claim 1, wherein the administering is effective to treat the leukemia or the lymphoma in the subject.

22. A method of delivering a drug to a target site in a subject, the method comprising:
administering to the subject a pharmaceutical composition comprising a conjugate of claim 1, wherein the administering is effective to release a therapeutically effective amount of the drug from the conjugate at the target site in the subject.

23. The conjugate of claim 1, wherein the modified amino acid residue is positioned at a C-terminus of a heavy chain CH3 region of the anti-CD22 antibody.

24. The conjugate of claim 5, wherein the heavy chain constant region comprises a sequence of the formula (II):

$$X^1(FG1y')X^2Z^{20}X^3Z^{30} (SEQ\ ID\ NO{:}10) \qquad (II)$$

wherein
FG1y' is the modified amino acid residue of formula (I);
$Z^{20}$ is either a proline or alanine residue;
$Z^{30}$ is a basic amino acid or an aliphatic amino acid;
$X^1$ may be present or absent and, when present, can be any amino acid, with the proviso that when the sequence is at the N-terminus of the conjugate, $X^1$ is present; and
$X^2$ and $X^3$ are each independently any amino acid, and
wherein the sequence is C-terminal to the amino acid sequence SLSLSPG (SEQ ID NO: 12).

25. The conjugate of claim 6, wherein the heavy chain CH3 region comprises the sequence SPGSL(FG1y')TPSRGS (SEQ ID NO: 13).

26. The conjugate of claim 6, wherein
$Z^{30}$ is selected from R, K, H, A, G, L, V, I, and P;
$X^1$ is selected from L, M, S, and V; and
$X^2$ and $X^3$ are each independently selected from S, T, A, V, G, and C.

27. The method of claim 21, comprising treating the leukemia.

28. The method of claim 27, wherein the leukemia is a B-cell derived leukemia.

29. The method of claim 27, wherein the leukemia is hairy cell leukemia, B-cell acute lymphoblastic leukemia, acute lymphoblastic leukemia, or chronic lymphocytic leukemia.

30. The method of claim 21, comprising treating the lymphoma.

31. The method of claim 30, wherein the lymphoma is a B-cell derived lymphoma.

32. The method of claim 30, wherein the lymphoma is Burkitt's lymphoma, Hodgkin's lymphoma, non-Hodgkin's B cell lymphoma, follicular lymphoma, diffuse large B-cell lymphoma, mantle cell lymphoma, or marginal zone lymphoma.

* * * * *